United States Patent
Zhou et al.

(10) Patent No.: US 12,084,443 B2
(45) Date of Patent: Sep. 10, 2024

(54) PROCESS OF PREPARING A PD-1/PD-L1 INHIBITOR

(71) Applicant: Incyte Corporation, Wilmington, DE (US)

(72) Inventors: Jiacheng Zhou, Newark, DE (US); Zhongjiang Jia, Kennett Square, PA (US); Qiyan Lin, Newark, DE (US); Pingli Liu, Wilmington, DE (US); Yongchun Pan, Wilmington, DE (US); Timothy Martin, Hockessin, DE (US); Bo Shen, Garnet Valley, PA (US); Naijing Su, Hockessin, DE (US); Yongzhong Wu, Glen Mills, PA (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 18/240,805

(22) Filed: Aug. 31, 2023

(65) Prior Publication Data

US 2023/0406852 A1    Dec. 21, 2023

Related U.S. Application Data

(62) Division of application No. 17/520,060, filed on Nov. 5, 2021, now Pat. No. 11,780,836.

(60) Provisional application No. 63/110,779, filed on Nov. 6, 2020.

(51) Int. Cl.
   C07D 471/04    (2006.01)
(52) U.S. Cl.
   CPC .................... C07D 471/04 (2013.01)
(58) Field of Classification Search
   CPC .................................. C07D 471/04
   USPC ....................................... 546/122
   See application file for complete search history.

(56) References Cited

U.S. PATENT DOCUMENTS

| | | | |
|---|---|---|---|
| 3,272,781 A | 9/1966 | Goodrow | |
| 4,208,328 A | 6/1980 | Lavallee et al. | |
| 4,789,711 A | 12/1988 | Monnier et al. | |
| 5,077,164 A | 12/1991 | Ueda et al. | |
| 6,114,497 A | 9/2000 | Tada et al. | |
| 6,297,351 B1 | 10/2001 | Murayama et al. | |
| 6,372,907 B1 | 4/2002 | Lee et al. | |
| 6,521,618 B2 | 2/2003 | Boschelli et al. | |
| 6,867,200 B1 | 3/2005 | Allen et al. | |
| 7,320,989 B2 | 1/2008 | Anderson et al. | |
| 7,417,065 B2 | 8/2008 | Mi et al. | |
| 7,488,802 B2 | 2/2009 | Collins et al. | |
| 7,491,245 B2 | 2/2009 | Glenn et al. | |
| 7,691,870 B2 | 4/2010 | Buchstaller et al. | |
| 7,851,489 B2 | 12/2010 | Borzilleri et al. | |
| 7,906,522 B2 | 3/2011 | Kishikawa et al. | |
| 7,943,743 B2 | 5/2011 | Korman et al. | |
| 8,008,449 B2 | 8/2011 | Korman et al. | |
| 8,163,743 B2 | 4/2012 | Baldwin et al. | |
| 8,168,757 B2 | 5/2012 | Finnefrock et al. | |
| 8,217,149 B2 | 7/2012 | Irving et al. | |
| 8,541,424 B2 | 9/2013 | DeGoey et al. | |
| 8,993,604 B2 | 3/2015 | Byrd et al. | |
| 9,085,576 B2 | 7/2015 | Minatti et al. | |
| 9,163,017 B2 | 10/2015 | DeGoey et al. | |
| 9,394,365 B1 | 7/2016 | Eisenbach-Schwartz et al. | |
| 9,540,322 B2 | 1/2017 | Jorgensen et al. | |
| 9,603,950 B1 | 3/2017 | Li et al. | |
| 9,611,261 B2 | 4/2017 | Minatti et al. | |
| 9,643,922 B2 | 5/2017 | Jorgensen et al. | |
| 10,017,520 B2 | 7/2018 | Koehler et al. | |
| 10,202,343 B2 | 2/2019 | Jorgensen et al. | |
| 10,308,644 B2 * | 6/2019 | Wu ..................... | C07D 413/14 |
| 10,618,916 B2 | 4/2020 | Wu et al. | |
| 10,669,271 B2 | 6/2020 | Wu et al. | |
| 10,793,565 B2 | 10/2020 | Wu et al. | |
| 10,800,768 B2 | 10/2020 | Wu et al. | |
| 10,806,785 B2 | 10/2020 | Liu et al. | |
| 10,906,920 B2 | 2/2021 | Wu et al. | |
| 11,124,511 B2 | 9/2021 | Wu et al. | |
| 11,339,149 B2 | 5/2022 | Wu et al. | |
| 11,401,279 B2 | 8/2022 | Li et al. | |
| 11,407,749 B2 | 8/2022 | Wu et al. | |
| 11,414,433 B2 | 8/2022 | Wu et al. | |
| 11,465,981 B2 | 10/2022 | Wu et al. | |
| 11,535,615 B2 | 12/2022 | Lajkiewicz et al. | |
| 11,566,026 B2 | 1/2023 | Wu et al. | |

(Continued)

FOREIGN PATENT DOCUMENTS

| CA | 2355249 | 6/2000 |
|---|---|---|
| CA | 3099994 | 11/2019 |

(Continued)

OTHER PUBLICATIONS

Abdellaoui et al., "Palladium-catalyzed non-directed C-H bond arylation of difluorobenzenes and dichlorobenzenes bearing benzoxazole or benzothiazole," Catalysis Communications, 2015, 71:13-16.
Ahmed et al., "Enantioselective Polymerization of Epoxides Using Biaryl-Linked Bimetallic Cobalt Catalysts: A Mechanistic Study," J Am Chem Soc., 2013, 135(50):18901-18911.
Alverez et al., "Structure—Activity Study of Bioisosteric Trifluoromethyl and Pentafluorosulfanyl Indole Inhibitors of the AAA ATPase p97," ACS Med Chem., 2015, 6(12):1225-1230.
Amaya et al., "Synthesis of three-dimensionally arranged bis-biphenol ligand on hexaaryl benzene scaffold and its application for cross-pinacol coupling reaction," Tetrahedron Letters, 2011, 52(35):4567-4569.
Anyika et al., "Point-to-Axial Chirality Transfer—A New Probe for "Sensing" the Absolute Configurations of Monoamines," J Am Chem Soc., 2014, 136(2):550-553.

(Continued)

Primary Examiner — Niloofar Rahmani
(74) Attorney, Agent, or Firm — Fish & Richardson P.C.

(57) ABSTRACT

The present invention relates to processes of preparing PD-1/PD-L1 inhibitor (R)-1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl) pyrrolidine-3-carboxylic acid, or salts thereof, related synthetic intermediates, and salts of the intermediates, where the PD-1/PD-L1 inhibitor is useful in the treatment of various diseases including infectious diseases and cancer.

9 Claims, No Drawings

(56) References Cited

U.S. PATENT DOCUMENTS

| | | |
|---|---|---|
| 11,572,366 B2 | 2/2023 | Li et al. |
| 11,596,692 B1 | 3/2023 | Wu et al. |
| 11,608,337 B2 | 3/2023 | Li et al. |
| 11,613,536 B2 | 3/2023 | Wu et al. |
| 11,673,883 B2 | 6/2023 | Lu et al. |
| 11,718,605 B2 | 8/2023 | Yu et al. |
| 11,753,406 B2 | 9/2023 | Jia et al. |
| 11,760,756 B2 | 9/2023 | Jia et al. |
| 11,780,836 B2 | 10/2023 | Zhou et al. |
| 11,787,793 B2 | 10/2023 | Wu et al. |
| 11,866,434 B2 | 1/2024 | Wang et al. |
| 11,866,435 B2 | 1/2024 | Lajkiewicz et al. |
| 11,866,451 B2 | 1/2024 | Jia et al. |
| 11,879,309 B2 | 1/2024 | Xiao et al. |
| 2002/0082266 A1 | 6/2002 | Gallant et al. |
| 2003/0134843 A1 | 7/2003 | Lubisch et al. |
| 2003/0191115 A1 | 10/2003 | Pinto et al. |
| 2004/0018986 A1 | 1/2004 | Pitlik et al. |
| 2004/0058938 A1 | 3/2004 | Cullmann et al. |
| 2004/0063963 A1 | 4/2004 | Ueno et al. |
| 2004/0082635 A1 | 4/2004 | Hashimoto et al. |
| 2004/0186114 A1 | 9/2004 | Cirillo et al. |
| 2004/0214040 A1 | 10/2004 | Lee et al. |
| 2005/0187230 A1 | 8/2005 | Ding et al. |
| 2005/0245536 A1 | 11/2005 | Hao et al. |
| 2005/0260126 A1 | 11/2005 | Kudo et al. |
| 2005/0288295 A1 | 12/2005 | Currie et al. |
| 2006/0004010 A1 | 1/2006 | Habashita et al. |
| 2006/0084650 A1 | 4/2006 | Dong et al. |
| 2006/0089362 A1 | 4/2006 | Seno et al. |
| 2006/0178367 A1 | 8/2006 | Currie et al. |
| 2006/0183746 A1 | 8/2006 | Currie et al. |
| 2006/0229337 A1 | 10/2006 | Brittelli et al. |
| 2006/0270686 A1 | 11/2006 | Kelly et al. |
| 2007/0099938 A1 | 5/2007 | Ohmoto et al. |
| 2007/0191395 A1 | 8/2007 | Kawakami et al. |
| 2008/0045536 A1 | 2/2008 | Vaccaro et al. |
| 2008/0139557 A1 | 6/2008 | Blomgren et al. |
| 2008/0153834 A1 | 6/2008 | Blomgren et al. |
| 2008/0280891 A1 | 11/2008 | Kelly et al. |
| 2009/0163545 A1 | 6/2009 | Goldfarb |
| 2009/0253735 A1 | 10/2009 | Almario-Garcia et al. |
| 2009/0281075 A1 | 11/2009 | Roughton et al. |
| 2009/0281120 A1 | 11/2009 | Nakai et al. |
| 2009/0304821 A1 | 12/2009 | Notoya et al. |
| 2010/0155712 A1 | 6/2010 | Kitamura |
| 2010/0160292 A1 | 6/2010 | Whitney et al. |
| 2010/0160303 A1 | 6/2010 | Liu et al. |
| 2010/0249151 A1 | 9/2010 | Klein et al. |
| 2010/0267775 A1 | 10/2010 | Negoro et al. |
| 2010/0267778 A1 | 10/2010 | Kusuda et al. |
| 2010/0273832 A1 | 10/2010 | Jung et al. |
| 2010/0292227 A1 | 11/2010 | Yoakim et al. |
| 2011/0053915 A1 | 3/2011 | Ivaschenko et al. |
| 2011/0062858 A1 | 3/2011 | Yersin et al. |
| 2011/0065699 A1 | 3/2011 | De Peretti et al. |
| 2011/0065700 A1 | 3/2011 | De Peretti et al. |
| 2011/0065745 A1 | 3/2011 | De Peretti et al. |
| 2011/0124640 A1 | 5/2011 | Liu et al. |
| 2011/0294781 A1 | 12/2011 | Yamamoto et al. |
| 2011/0301145 A1 | 12/2011 | Barbosa Jr. et al. |
| 2012/0058996 A1 | 3/2012 | Liu et al. |
| 2012/0295884 A1 | 11/2012 | Altmann et al. |
| 2012/0323002 A1 | 12/2012 | Yamamoto et al. |
| 2012/0328569 A1 | 12/2012 | McComas et al. |
| 2013/0096118 A1 | 4/2013 | Liu et al. |
| 2013/0131063 A1 | 5/2013 | Castro et al. |
| 2013/0203741 A1 | 8/2013 | Suzuki et al. |
| 2013/0203747 A1 | 8/2013 | Yoakim et al. |
| 2013/0203754 A1 | 8/2013 | Yang et al. |
| 2013/0253011 A1 | 9/2013 | Jung et al. |
| 2014/0058097 A1 | 2/2014 | Kobayashi et al. |
| 2014/0088117 A1 | 3/2014 | Burch et al. |
| 2014/0107027 A1 | 4/2014 | Kong et al. |
| 2014/0128382 A1 | 5/2014 | Wu et al. |
| 2014/0243306 A1 | 8/2014 | Heng et al. |
| 2014/0275058 A1 | 9/2014 | Minatti et al. |
| 2014/0288094 A1 | 9/2014 | Bennett et al. |
| 2014/0378447 A1 | 12/2014 | Okano et al. |
| 2015/0005279 A1 | 1/2015 | Bonafoux et al. |
| 2015/0011751 A1 | 1/2015 | Kawakami et al. |
| 2015/0073024 A1 | 3/2015 | Sasikumar et al. |
| 2015/0181880 A1 | 7/2015 | Takahashi |
| 2015/0210680 A1 | 7/2015 | Kobayashi et al. |
| 2015/0232478 A1 | 8/2015 | Ishida et al. |
| 2015/0239868 A1 | 8/2015 | Pais et al. |
| 2015/0252011 A1 | 9/2015 | Minatti et al. |
| 2015/0258505 A1 | 9/2015 | Hironaka et al. |
| 2015/0291549 A1 | 10/2015 | Chupak et al. |
| 2015/0299227 A1 | 10/2015 | Wolkenberg et al. |
| 2015/0307465 A1 | 10/2015 | Scott et al. |
| 2015/0376172 A1 | 12/2015 | Guba et al. |
| 2016/0015690 A1 | 1/2016 | Babaoglu et al. |
| 2016/0046648 A1 | 2/2016 | Petrukhin et al. |
| 2016/0130251 A1 | 5/2016 | Graupe et al. |
| 2016/0194295 A1 | 7/2016 | Sasikumar et al. |
| 2016/0229816 A1 | 8/2016 | Sato et al. |
| 2016/0280695 A1 | 9/2016 | Minatti et al. |
| 2017/0107216 A1 | 4/2017 | Wu et al. |
| 2017/0145025 A1 | 5/2017 | Li et al. |
| 2017/0174671 A1 | 6/2017 | Wu et al. |
| 2017/0174679 A1 | 6/2017 | Lajkiewicz et al. |
| 2017/0304282 A1 | 10/2017 | Rocco et al. |
| 2017/0320875 A1 | 11/2017 | Li et al. |
| 2017/0342060 A1 | 11/2017 | Lu et al. |
| 2017/0362253 A1 | 12/2017 | Xiao et al. |
| 2018/0016260 A1 | 1/2018 | Yu et al. |
| 2018/0057486 A1 | 3/2018 | Wu et al. |
| 2018/0177784 A1 | 6/2018 | Wu et al. |
| 2018/0177870 A1 | 6/2018 | Liu et al. |
| 2018/0179179 A1 | 6/2018 | Wu et al. |
| 2018/0179197 A1 | 6/2018 | Wu et al. |
| 2018/0179201 A1 | 6/2018 | Wu et al. |
| 2018/0179202 A1 | 6/2018 | Wu et al. |
| 2018/0273519 A1 | 9/2018 | Wu et al. |
| 2019/0040082 A1 | 2/2019 | Xiao et al. |
| 2019/0062345 A1 | 2/2019 | Xiao et al. |
| 2019/0071439 A1 | 3/2019 | Li et al. |
| 2019/0144439 A1 | 5/2019 | Wu et al. |
| 2019/0202824 A1 | 7/2019 | Wu et al. |
| 2019/0225601 A1 | 7/2019 | Wu et al. |
| 2019/0270706 A1 | 9/2019 | Jorgensen et al. |
| 2019/0300524 A1 | 10/2019 | Wu et al. |
| 2019/0345170 A1 | 11/2019 | Wu et al. |
| 2020/0172533 A1 | 6/2020 | Wu et al. |
| 2020/0172541 A1 | 6/2020 | Li et al. |
| 2020/0181126 A1 | 6/2020 | Lu et al. |
| 2020/0255424 A1 | 8/2020 | Wu et al. |
| 2020/0277309 A1 | 9/2020 | Wu et al. |
| 2020/0283423 A1 | 9/2020 | Yu et al. |
| 2020/0325115 A1 | 10/2020 | Wu et al. |
| 2020/0397893 A1 | 12/2020 | Liu et al. |
| 2020/0407357 A1 | 12/2020 | Lajkiewicz et al. |
| 2021/0002276 A1 | 1/2021 | Wu et al. |
| 2021/0017164 A1 | 1/2021 | Lu et al. |
| 2021/0017175 A1 | 1/2021 | Li et al. |
| 2021/0040090 A1 | 2/2021 | Jia et al. |
| 2021/0094976 A1 | 4/2021 | Li et al. |
| 2021/0107900 A1 | 4/2021 | Wu et al. |
| 2021/0115025 A1 | 4/2021 | Yu et al. |
| 2021/0115068 A1 | 4/2021 | Wu et al. |
| 2021/0139511 A1 | 5/2021 | Jia et al. |
| 2021/0221819 A1 | 7/2021 | Li et al. |
| 2021/0317139 A1 | 10/2021 | Xiao et al. |
| 2021/0347771 A1 | 11/2021 | Wu et al. |
| 2021/0363137 A1 | 11/2021 | Wu et al. |
| 2021/0380584 A1 | 12/2021 | Wu et al. |
| 2022/0089588 A1 | 3/2022 | Wu et al. |
| 2022/0144830 A1 | 5/2022 | Zhou et al. |
| 2022/0144831 A1 | 5/2022 | Wang et al. |
| 2022/0144832 A1 | 5/2022 | Jia et al. |
| 2022/0193050 A1 | 6/2022 | Yang et al. |
| 2022/0194931 A1 | 6/2022 | Wu et al. |
| 2022/0213090 A1 | 7/2022 | Wu et al. |

(56) References Cited

U.S. PATENT DOCUMENTS

| | | | |
|---|---|---|---|
| 2022/0340600 A1 | 10/2022 | Li et al. |
| 2022/0348594 A1 | 11/2022 | Wu et al. |
| 2022/0412976 A1 | 12/2022 | Lovat |
| 2023/0100875 A1 | 3/2023 | Lajkiewicz et al. |
| 2023/0181605 A1 | 6/2023 | Mohanlal et al. |
| 2023/0192689 A1 | 6/2023 | Lajkiewicz et al. |
| 2023/0226062 A1 | 7/2023 | Wu et al. |

FOREIGN PATENT DOCUMENTS

| | | |
|---|---|---|
| CL | 2018001531 | 7/2018 |
| CL | 2018003734 | 2/2019 |
| CL | 2018003701 | 4/2019 |
| CL | 2018003697 | 5/2019 |
| CL | 2019001744 | 10/2019 |
| CL | 2020002511 | 9/2020 |
| CN | 1344256 | 4/2002 |
| CN | 101891895 | 11/2010 |
| CN | 101910158 | 12/2010 |
| CN | 101993415 | 3/2011 |
| CN | 103933036 | 7/2014 |
| CN | 104045552 | 9/2014 |
| CN | 104211726 | 12/2014 |
| CN | 105073747 | 11/2015 |
| CN | 105164121 | 12/2015 |
| CN | 105705489 | 6/2016 |
| EP | 0361069 | 4/1990 |
| EP | 0644460 | 3/1995 |
| EP | 1505068 | 2/2005 |
| EP | 1644370 | 4/2006 |
| EP | 1942105 | 7/2008 |
| EP | 2233474 | 9/2010 |
| EP | 2402345 | 1/2012 |
| EP | 2871179 | 5/2015 |
| EP | 2824099 | 1/2018 |
| FR | 1425700 | 1/1966 |
| JP | H 10316853 | 12/1998 |
| JP | 2000128986 | 5/2000 |
| JP | 2000128987 | 5/2000 |
| JP | 2000212281 | 8/2000 |
| JP | 2001114893 | 4/2001 |
| JP | 2001163975 | 6/2001 |
| JP | 3461397 | 10/2003 |
| JP | 2003287634 | 10/2003 |
| JP | 2004059761 | 2/2004 |
| JP | 2004091369 | 3/2004 |
| JP | 2004294556 | 10/2004 |
| JP | 2005002330 | 1/2005 |
| JP | 2005248082 | 9/2005 |
| JP | 2005290301 | 10/2005 |
| JP | 2006290883 | 10/2006 |
| JP | 2008218327 | 9/2008 |
| JP | 2010202530 | 9/2010 |
| JP | 2010540452 | 12/2010 |
| JP | 2013084945 | 5/2013 |
| JP | 2014520866 | 8/2014 |
| JP | 2014532066 | 12/2014 |
| JP | 2015155397 | 8/2015 |
| JP | 2015193612 | 11/2015 |
| JP | 2016135778 | 7/2016 |
| JP | 2016532710 | 10/2016 |
| JP | 2019523231 | 8/2019 |
| JP | 2019530732 | 10/2019 |
| JP | 2020504737 | 2/2020 |
| JP | 2020504739 | 2/2020 |
| JP | 2020514271 | 5/2020 |
| JP | 2020514272 | 5/2020 |
| JP | 6911031 | 7/2021 |
| KR | 101653560 | 9/2016 |
| KR | 101715090 | 3/2017 |
| KR | 101717601 | 3/2017 |
| MX | 2019007651 | 2/2020 |
| TW | 103143948 | 12/2014 |
| TW | 201625527 | 7/2016 |
| WO | WO 1998/27108 | 6/1998 |
| WO | WO 1999/018096 | 4/1999 |
| WO | WO 1999/44992 A1 | 9/1999 |
| WO | WO 2000/35886 | 6/2000 |
| WO | WO 2001/07409 | 2/2001 |
| WO | WO 2001/047883 | 7/2001 |
| WO | WO 2001/74815 | 10/2001 |
| WO | WO 2002/000196 | 1/2002 |
| WO | WO 2002/14321 | 2/2002 |
| WO | WO 2002/48147 | 6/2002 |
| WO | WO 2002/066477 | 8/2002 |
| WO | WO 2002/071827 | 9/2002 |
| WO | WO 2002/078700 | 10/2002 |
| WO | WO 2002/083672 | 10/2002 |
| WO | WO 2002/088124 | 11/2002 |
| WO | WO 2003/022845 | 3/2003 |
| WO | WO 2003/030901 | 4/2003 |
| WO | WO 2003/031587 | 4/2003 |
| WO | WO 2003/042402 | 5/2003 |
| WO | WO 2004/006906 | 1/2004 |
| WO | WO 2004/033454 | 4/2004 |
| WO | WO 2004/035588 | 4/2004 |
| WO | WO 2004/085385 | 10/2004 |
| WO | WO 2004/089940 | 10/2004 |
| WO | WO 2005/000833 | 1/2005 |
| WO | WO 2005/005429 | 1/2005 |
| WO | WO 2005/014543 | 2/2005 |
| WO | WO 2005/014599 | 2/2005 |
| WO | WO 2005/023761 | 3/2005 |
| WO | WO 2005/034869 | 4/2005 |
| WO | WO 2005/047290 | 5/2005 |
| WO | WO 2005/063710 | 7/2005 |
| WO | WO 2005/077948 | 8/2005 |
| WO | WO 2005/079802 | 9/2005 |
| WO | WO 2005/080316 | 9/2005 |
| WO | WO 2005/086808 | 9/2005 |
| WO | WO 2005/086904 | 9/2005 |
| WO | WO 2005/097751 | 10/2005 |
| WO | WO 2005/103022 | 11/2005 |
| WO | WO 2005/105798 | 11/2005 |
| WO | WO 2006/034317 | 3/2006 |
| WO | WO 2006/034337 | 3/2006 |
| WO | WO 2006/050803 | 5/2006 |
| WO | WO 2006/053121 | 5/2006 |
| WO | WO 2006/094235 | 9/2006 |
| WO | WO 2006/099075 | 9/2006 |
| WO | WO 2006/125101 | 11/2006 |
| WO | WO 2007/004954 | 1/2007 |
| WO | WO 2007/034282 | 3/2007 |
| WO | WO 2007/038314 | 4/2007 |
| WO | WO 2007/061764 | 5/2007 |
| WO | WO 2007/067711 | 6/2007 |
| WO | WO 2007/069565 | 6/2007 |
| WO | WO 2007/096764 | 8/2007 |
| WO | WO 2007/113226 | 10/2007 |
| WO | WO 2007/146712 | 12/2007 |
| WO | WO 2008/011560 | 1/2008 |
| WO | WO 2008/021745 | 2/2008 |
| WO | WO 2008/027812 | 3/2008 |
| WO | WO 2008/032171 | 3/2008 |
| WO | WO 2008/033854 | 3/2008 |
| WO | WO 2008/033857 | 3/2008 |
| WO | WO 2008/033858 | 3/2008 |
| WO | WO 2008/057254 | 5/2008 |
| WO | WO 2008/062182 | 5/2008 |
| WO | WO 2008/064317 | 5/2008 |
| WO | WO 2008/064318 | 5/2008 |
| WO | WO 2008/071944 | 6/2008 |
| WO | WO 2008/079965 | 7/2008 |
| WO | WO 2008/104077 | 9/2008 |
| WO | WO 2008/104278 | 9/2008 |
| WO | WO 2008/104279 | 9/2008 |
| WO | WO 2008/111299 | 9/2008 |
| WO | WO 2008/114002 | 9/2008 |
| WO | WO 2008/118122 | 10/2008 |
| WO | WO 2008/133274 | 11/2008 |
| WO | WO 2008/134553 | 11/2008 |
| WO | WO 2008/141249 | 11/2008 |
| WO | WO 2008/156712 | 12/2008 |
| WO | WO 2009/027733 | 3/2009 |

(56) References Cited

FOREIGN PATENT DOCUMENTS

| | | |
|---|---|---|
| WO | WO 2009/038759 | 3/2009 |
| WO | WO 2009/039397 | 3/2009 |
| WO | WO 2009/059162 | 5/2009 |
| WO | WO 2009/062059 | 5/2009 |
| WO | WO 2009/075830 | 6/2009 |
| WO | WO 2009/077197 | 6/2009 |
| WO | WO 2009/079683 | 7/2009 |
| WO | WO 2009/106539 | 9/2009 |
| WO | WO 2009/106597 | 9/2009 |
| WO | WO 2009/123986 | 10/2009 |
| WO | WO 2009/139576 | 11/2009 |
| WO | WO 2009/143156 | 11/2009 |
| WO | WO 2009/146358 | 12/2009 |
| WO | WO 2010/011837 | 1/2010 |
| WO | WO 2010/029950 | 3/2010 |
| WO | WO 2010/036959 | 4/2010 |
| WO | WO 2010/056875 | 5/2010 |
| WO | WO 2010/064020 | 6/2010 |
| WO | WO 2010/071885 | 6/2010 |
| WO | WO 2010/075376 | 7/2010 |
| WO | WO 2010/080474 | 7/2010 |
| WO | WO 2010/089411 | 8/2010 |
| WO | WO 2010/104306 | 9/2010 |
| WO | WO 2010/115736 | 10/2010 |
| WO | WO 2010/119264 | 10/2010 |
| WO | WO 2010/130034 | 11/2010 |
| WO | WO 2011/002635 | 1/2011 |
| WO | WO 2011/008709 | 1/2011 |
| WO | WO 2011/018170 | 2/2011 |
| WO | WO 2011/044181 | 4/2011 |
| WO | WO 2011/047129 | 4/2011 |
| WO | WO 2011/047319 | 4/2011 |
| WO | WO 2011/050245 | 4/2011 |
| WO | WO 2009/096202 | 5/2011 |
| WO | WO 2011/066342 | 6/2011 |
| WO | WO 2011/082400 | 7/2011 |
| WO | WO 2011/097607 | 8/2011 |
| WO | WO 2011/113606 | 9/2011 |
| WO | WO 2011/117264 | 9/2011 |
| WO | WO 2011/140202 | 11/2011 |
| WO | WO 2011/159877 | 12/2011 |
| WO | WO 2011/161699 | 12/2011 |
| WO | WO 2012/016133 | 2/2012 |
| WO | WO 2012/033735 | 3/2012 |
| WO | WO 2012/034363 | 3/2012 |
| WO | WO 2012/047856 | 4/2012 |
| WO | WO 2012/052730 | 4/2012 |
| WO | WO 2012/052745 | 4/2012 |
| WO | WO 2012/068406 | 5/2012 |
| WO | WO 2012/080376 | 6/2012 |
| WO | WO 2012/088411 | 6/2012 |
| WO | WO 2012/100342 | 8/2012 |
| WO | WO 2012/125886 | 9/2012 |
| WO | WO 2012/129562 | 9/2012 |
| WO | WO 2012/139425 | 10/2012 |
| WO | WO 2012/159565 | 11/2012 |
| WO | WO 2012/166951 | 12/2012 |
| WO | WO 2012/168733 | 12/2012 |
| WO | WO 2012/175991 | 12/2012 |
| WO | WO 2013/008095 | 1/2013 |
| WO | WO 2013/033901 | 3/2013 |
| WO | WO 2013/040528 | 3/2013 |
| WO | WO 2013/057650 | 4/2013 |
| WO | WO 2013/059594 | 4/2013 |
| WO | WO 2013/120040 | 8/2013 |
| WO | WO 2013/134113 | 9/2013 |
| WO | WO 2013/157021 | 10/2013 |
| WO | WO 2013/163404 | 10/2013 |
| WO | WO 2014/009295 | 1/2014 |
| WO | WO 2014/009296 | 1/2014 |
| WO | WO 2014/017087 | 1/2014 |
| WO | WO 2014/039595 | 3/2014 |
| WO | WO 2014/061693 | 4/2014 |
| WO | WO 2014/081878 | 5/2014 |
| WO | WO 2014/113388 | 7/2014 |
| WO | WO 2014/114532 | 7/2014 |
| WO | WO 2014/121085 | 8/2014 |
| WO | WO 2014/133046 | 9/2014 |
| WO | WO 2014/138484 | 9/2014 |
| WO | WO 2014/138791 | 9/2014 |
| WO | WO 2014/151634 | 9/2014 |
| WO | WO 2014/152536 | 9/2014 |
| WO | WO 2014/159959 | 10/2014 |
| WO | WO 2014/181287 | 11/2014 |
| WO | WO 2014/186035 | 11/2014 |
| WO | WO 2014/210255 | 12/2014 |
| WO | WO 2015/000715 | 1/2015 |
| WO | WO 2015/013635 | 1/2015 |
| WO | WO 2015/018940 | 2/2015 |
| WO | WO 2015/033299 | 3/2015 |
| WO | WO 2015/033301 | 3/2015 |
| WO | WO 2015/034820 | 3/2015 |
| WO | WO 2015/036927 | 3/2015 |
| WO | WO 2015/086498 | 6/2015 |
| WO | WO 2015/086499 | 6/2015 |
| WO | WO 2015/086502 | 6/2015 |
| WO | WO 2015/086512 | 6/2015 |
| WO | WO 2015/095337 | 6/2015 |
| WO | WO 2015/101622 | 7/2015 |
| WO | WO 2015/120364 | 8/2015 |
| WO | WO 2015/150097 | 10/2015 |
| WO | WO 2015/160641 | 10/2015 |
| WO | WO 2015/175678 | 11/2015 |
| WO | WO 2015/197028 | 12/2015 |
| WO | WO 2016/044604 | 3/2016 |
| WO | WO 2016/094688 | 6/2016 |
| WO | WO 2016/116525 | 7/2016 |
| WO | WO 2016/118404 | 7/2016 |
| WO | WO 2016/156282 | 10/2016 |
| WO | WO 2017/035405 | 3/2017 |
| WO | WO 2017/066227 | 4/2017 |
| WO | WO 2017/070089 | 4/2017 |
| WO | WO 2017/070320 | 4/2017 |
| WO | WO 2017/087777 | 5/2017 |
| WO | WO 2017/106634 | 6/2017 |
| WO | WO 2017/108569 | 6/2017 |
| WO | WO 2017/109041 | 6/2017 |
| WO | WO 2017/112617 | 6/2017 |
| WO | WO 2017/112730 | 6/2017 |
| WO | WO 2017/192961 | 11/2017 |
| WO | WO 2017/205464 | 11/2017 |
| WO | WO 2017/222976 | 12/2017 |
| WO | WO 2017/223239 | 12/2017 |
| WO | WO 2018/013789 | 1/2018 |
| WO | WO 2018/026971 | 2/2018 |
| WO | WO 2018/044783 | 3/2018 |
| WO | WO 2018/045084 | 3/2018 |
| WO | WO 2016/057500 | 4/2018 |
| WO | WO 2018/116259 | 6/2018 |
| WO | WO 2018/119036 | 6/2018 |
| WO | WO 2018/119221 | 6/2018 |
| WO | WO 2018/119224 | 6/2018 |
| WO | WO 2018/119236 | 6/2018 |
| WO | WO 2018/119263 | 6/2018 |
| WO | WO 2018/119266 | 6/2018 |
| WO | WO 2018/119286 | 6/2018 |
| WO | WO 2018/195321 | 10/2018 |
| WO | WO 2019/023575 | 1/2019 |
| WO | WO 2019/032547 | 2/2019 |
| WO | WO 2019/034172 | 2/2019 |
| WO | WO 2019/160882 | 8/2019 |
| WO | WO 2019/191707 | 10/2019 |
| WO | WO 2019/192506 | 10/2019 |
| WO | WO 2019/204609 | 10/2019 |
| WO | WO 2020/086556 | 4/2020 |
| WO | WO 2020/088357 | 5/2020 |
| WO | WO 2020/156323 | 8/2020 |

(56) References Cited

FOREIGN PATENT DOCUMENTS

| | | |
|---|---|---|
| WO | WO 2021/030162 | 2/2021 |
| WO | WO 2021/053207 | 3/2021 |

OTHER PUBLICATIONS

Argentina Office Action in Argentina Application No. 20170103634, dated Jan. 27, 2022, 7 pages.
Arkin et al., "Small-Molecule Inhibitors of Protein-Protein Interactions: Progressing toward the Reality," Chemistry & Biology, Sep. 2014, 21:1102-1114.
Arkin et al., "Small-Molecule Inhibitors of Protein-Protein Interactions: Progressing Towards the Dream," Nature Reviews, Apr. 2004, 3:301-317.
Artz et al., "Host-guest complexation. 28. Hemispherands with four self-organizing units," J Am Chem Soc., 1984, 106(7):2160-2171.
Atzrodt et al., "The Renaissance of H/D Exchange," Angew Chem Int Ed., 2007, 7744-7765.
Australian Notice of Allowance in Australian Application No. 2017382870, dated Mar. 15, 2022, 4 pages.
Australian Office Action in Australian Application No. 2016358100, dated May 8, 2020, 5 pages.
Azuma et al., "B7-H1 is a ubiquitous antiapoptotic receptor on cancer cells," Blood, Apr. 1, 2018, 111(7):3635-3643.
Barakat, "Do We Need Small Molecule Inhibitors for the Immune Checkpoints?" J. Pharma. Care Health Sys., 2014, 1(4):1000e119.
Barber et al., "Restoring function in exhausted CD8 T cells during chronic viral infection," Nature, Feb. 2006, 439:682-687.
Bastin et al., "Salt Selection and Optimisation for Pharmaceutical New Chemical Entities," Org Proc Res Dev., dated Jan. 1, 2000, pp. 4(5):427-435.
Bentley et al., "Antenna Biphenols: Development of Extended Wavelength Chiroptical Reporters," J Org Chem., 2016, 81(3):1185-1191.
Berg, "Modulation of Protein-Protein Interactions with Small Organic Molecules," Angew. Chem. Int. Ed., 2003, 42:2462-2481.
Berge et al., "Pharmaceutical Salts," J. Pharm. Sci., Jan. 1977, 66(1):1-19.
Blank et al., "PD-L1/B7H-1 Inhibits the Effector Phase of Tumor Rejection by T Cell Receptor (TCR) Transgenic CD8+ T Cells," Cancer Res., Feb. 2004, 64(3):1140-5.
Blom et al., "Optimizing Preparative LC-MS Configurations and Methods for Parallel Synthesis Purification", J. Combi. Chem., 2003, 5:670-83.
Blom et al., "Preparative LC-MS Purification: Improved Compound Specific Method Optimization", J. Combi. Chem., Nov. 2004, 6:874-883.
Blom, "Two-Pump at Column Dilution Configuration for Preparative LC-MS", K. Blom, J. Combi. Chem., 2002, 4:295-301.
Brazilian Office Action in Brazilian Application No. BR112018012756-6, dated Jan. 5, 2021, 6 pages.
Bross et al., "Radiation damage to 2-(2'-hydroxyphenyl)benzothiazoles," Radiation Physics and Chemistry, Jul. 1992, 41:379-387.
Buisman et al., "Chiral Cooperativity in Diastereomeric Diphosphite Ligands: Effects on the Rhodium-Catalyzed Enantioselective Hydroformylation of Styrene," Organometallics, 1997, 16(13):2929-2939.
Caira, "Crystalline Polymorphism of Organic Compounds," Topics in Current Chemistry, Jan. 1, 1998, 198:163-208.
Camara et al., "Multiple dermatofibromas: Dermoscopic patterns," Indian journal of dermatology, 2013, 58(3):243.
Canadian Office Action in Canadian Application No. 3,009,474, dated Oct. 16, 2023, 4 pages.
Canadian Office Action in Canadian Application No. 3005727, dated Nov. 3, 2023, 3 pages.
Canadian Office Action in Canadian Application No. 3047986, dated Feb. 15, 2024, 3 pages.
Carter et al., "PD-1:PD-L inhibitory pathway affects both CD4+ and CD8+ T cells and is overcome by IL-2," Eur. J. Immunol., 2002, 32(3):634-643.
Chang et al., "Blocking of the PD-1/PD-L1 Interaction by a d-Peptide Antagonist for Cancer Immunotherapy" Angew. Chem. Int. Ed., 2015, 26 pages; Supporting Information for 127(40):11926-11930.
Chang et al., "Blocking of the PD-1/PD-L1 Interaction by a d-Peptide Antagonist for Cancer Immunotherapy," Angew. Chem. Int. Ed., 2015, 127(40):11926-11930.
Chen et al., "Anti-PD-1/PD-L1 therapy of human cancer: past, present, and future," J. Clin. Invest., Sep. 2015, 125(9):3384-3391.
Cheng et al., "Cancer-associated fibroblasts induce PDL1+ neutrophils through the IL6-STAT3 pathway that foster immune suppression in hepatocellular carcinoma," Cell Death and Disease, 2018, 9:422.
Cheng et al., "Recent Advances in Small Molecule Based Cancer Immunotherapy," Eur J Med Chem., 2018, 157:582-598.
Cheng et al., "Structure and Interactions of the Human Programmed Cell Death 1 Receptor," J. Bio. Chem., Apr. 2013, 288(17):11771-11785.
Cheng et al., "Synthetic connections to the aromatic directed metalation reaction. Iterative ortho metalation-cross coupling tactics for the construction of polyphenyls," Tetrahedron Letters, 1978, 28(43):5097-5098.
Chilean Notice of Allowance in Chilean Application No. 2019-1744, dated Oct. 4, 2023, 4 pages (with Machine Translation).
Chilean Office Action in Chilean Application No. 201801685, dated Aug. 20, 2019, 18 pages.
Chilean Office Action in Chilean Application No. 201803701, dated Nov. 22, 2019, 18 pages.
Chilean Office Action in Chilean Application No. 201901744, dated Apr. 14, 2020, 19 pages.
Chilean Office Action in Chilean Application No. 2922-2020, dated Dec. 8, 2021, 21 pages.
Chinese Notice of Allowance in Chinese Application No. 2017800869894, dated Dec. 12, 2023, 8 pages (with English Translation).
Chinese Office Action in Chinese Application No. 201680077700.8, dated Jul. 2, 2021, 23 pages.
Chinese Office Action in Chinese Application No. 201780086989, dated Aug. 25, 2023, 6 pages (with English translation).
Chinese Search Report in Chinese Application No. 201780049752.9, dated Dec. 28, 2020, 5 pages.
Clayden et al., "Conformational Preference and Remote (1,10) Stereocontrol in Biphenyl-2,2'-dicarboxamides," Org. Lett., 2001, 3(26):4133-4136.
Colombian Office Action in Colombian Application No. NC2019/0000386, dated Sep. 25, 2020, 18 pages.
Costa Rican Office Action in Costa Rican Application No. 2018-0374, dated Sep. 4, 2023, 21 pages (with Machine Translation).
Costa Rican Office Action in Costa Rican Application No. 2019-0318, dated Sep. 13, 2023, 15 pages (with Machine Translation).
Cram et al., "Host-guest complexation. 29. Expanded hemispherands," J Am Chem Soc., 1984, 106(11):6386-3292.
Cram et al., "Host-guest complexation. 32. Spherands composed of cyclic urea and anisyl units," J Am Chem Soc., 1984, 106(23):7150-7167.
Cram et al., "Host-guest complexation. 26. Cavitands composed of fluorobenzene units bonded in their 2,6-positions to form macrocycles," J Am Chem Soc., 1984, 106(3):695-701.
Cram et al., "Spherand hosts containing cyclic urea units," J Am Chem Soc., 1982, 104(24):6828-6830.
Curis, "Overview and Path for Growth," Aurigene Strategic Collaboration, Jan. 21, 2015, 13 slides.
Database accession No. 1478989-52-4 abstract, Nov. 22, 2013, 1 page.
Database Accession No. 1568738-04-4 abstract, Mar. 14, 2014, 1 page.
Database Accession No. 1580823-55-7 abstract, Apr. 6, 2014, 1 page.
Database Accession No. 1581556-71-9 abstract, Apr. 8, 2014, 1 page.
Database Accession No. 1590700-72-3 abstract, Apr. 27, 2014, 1 page.

(56) References Cited

OTHER PUBLICATIONS

Database accession No. 2013:447446 abstract, 2013, 1 page.
De Lucca et al., "Small Molecule Reversible Inhibitors of Bruton's Tyrosine Kinase (BTK): Structure-Activity Relationships Leading to the Identification of 7-(2-Hydroxypropan-2-y1)-4-[2-methyl-3-(4-oxo-3,4-dihydroquinazolin-3-yl)phenyl]-9H- carbazole-1-carboxamide (BMS-935177)," Journal of Medicinal Chemistry, 2016, 59(17):7915-7935.
Dhanunjayarao et al., "Synthesis and Optical Properties of Salicylaldimine-Based Diboron Complexes, " Eur J Inorg Chem., 2014, 3:539-545.
Differding, "AUNP-12—A Novel Peptide Therapeutic Targeting PD-1 Immune Checkpoint Pathway for Cancer Immunotherapy—Structure Activity Relationships & Peptide / Peptidomimetic Analogs," Differding Consulting s.p.r.l. (Belgium), Feb. 26, 2014, 12 pages.
Dolan et al., "PD-1 Pathway Inhibitors: Changing the Landscape of Cancer Immunotherapy," Cancer Control, Jul. 2014, 21(3):231-237.
Domling et al., "Programmed Death-1: Therapeutic Success after More than 100 Years of Cancer Immunotherapy, " Angew. Chem. Int. Ed., 2014, 53:2283-2288.
Dong et al., "Tumor-associated B7-H1 promotes T-cell apoptosis: a potential mechanism of immune evasion," Nature Medicine, Aug. 2002, 8(8):793-800.
Ecuador Opposition in Ecuador Application No. SENADI-2019-3773, dated Oct. 10, 2019, 29 pages.
El Salvador Office Action in El Salvador Application No. 20190025391, dated Feb. 21, 2024, 4 pages (with English Translation).
Escarcega-Bobadilla et al., "A Recyclable Trinuclear Bifunctional Catalyst Derived from a Tetraoxo Bis-Zn(salphen) Metalloligand," Chemistry—A European Journal., 2013, 19(8):2641-2648.
Escarcega-Bobadilla et al., "Metal-directed assembly of chiral bis-Zn(II) Schiff base structures," Dalton Transactions, 2012, 41(32):9766-9772.
Escarcega-Bobadilla et al., "Versatile Switching in Substrate Topicity: Supramolecular Chirality Induction in Di- and Trinuclear Host Complexes," Chemistry—A European Journal, 2012:8(22):6805-6810.
Eurasian Office Action in Eurasian Application No. 201990074/28, dated Oct. 3, 2019, 5 pages.
European Communication in European Application No. 16805690.1, dated Jan. 22, 2020, 5 pages.
European Communication in European Application No. 16805690.1, dated Jul. 10, 2018, 6 pages.
European Communication in European Application No. 16805690.1, dated Nov. 5, 2020, 4 pages.
European Communication in European Application No. 17743174.9, dated Jan. 31, 2020, 5 pages.
European Communication in European Application No. 20202254.7, dated Apr. 1, 2022, 4 pages.
European Communication in European Application No. 23189545.9, dated Aug. 28, 2023, 1 page.
Extended European Search Report in European Application No. 23189545.9, dated Jan. 26, 2024, 8 pages.
Fabris et al., "Central to Axial Transfer of Chirality in Menthone or Camphor-Derived 2,2'-Biphenols," J Org Chem., 1997, 62(21):7156-7164.
FDA Report, "22 Case Studies Where Phase 2 and Phase 3 Trials Had Divergent Results," U.S. Food and Drug Administration, Jan. 2017, 44 pages.
Francisco et al., "The PD-1 Pathway in Tolerance and Autoimmunity," Immunol. Rev., Jul. 2010, 236:219-242.
Freeman et al., "Engagement of the Pd-1 Immunoinhibitory Receptor by a Novel B7 Family Member Leads to Negative Regulation of Lymphocyte Activation," J. Exp. Med., Oct. 2000, 192(7):1027-34.
Freeman, "Structures of PD-1 with its ligands: Sideways and dancing cheek to cheek," PNAS, Jul. 2008, 105(30): 10275-10276.
Freindorf, M., "Vibronic couplings in an excited state of hydrogen bond dimeric systems," Acta Physica Polonica, 1990, A78(6):825-839.
Gong et al., "Rhodium(I)-catalyzed regiospecific dimerization of aromatic acids: two direct C-H bond activations in water," Angewandte Chemie, 2015, 54(19):5718-5721.
Goswami et al., "A turn on ESIPT probe for rapid and ratiometric fluorogenic detection of homocysteine and cysteine in water with live cell-imaging, " Tetrahedron Letters, 2014, 55(2):490-494.
Gould et al. "Salt selection for basic drugs," Int J Pharma., 1986, 33(1-3):201-217.
Green et al., "Synthesis and investigation of the configurational stability of some dimethylammonium borate salts," J. Chem. Soc., Perkin Trans. 1, 2000, 24:4403- 4408.
Greenwald et al., "The B7 Family Revisited," Annu. Rev. Immunol., 2005, 23:515-548.
Gu et al., "Undo the brake of tumour immune tolerance with antibodies, peptide mimetics and small molecule compounds targeting PD-1/PD-L1 checkpoint at different locations for acceleration of cytotoxic immunity to cancer cells," Clinical and Experimental Pharmacology and Physiology, 2019, 46(2):105-115.
Han et al., "Synthesis of binuclear phenoxyimino organoaluminum complexes and their use as the catalyst precursors for efficient ring-opening polymerisation of E-caprolactone," Dalton Transactions, 2013, 41:12346-12353.
Helgeson et al., "Host-guest complexation. 66. 18-Membered-ring spherands containing five anisyl groups," J Am Chem Soc., 1993, 1115(24):11506-11511.
Highlights Prescribing Information, "Keytruda," Revised Feb. 2019, 66 pages.
Highlights Prescribing Information, "Opdivo," Revised Apr. 2019, 90 pages.
Hilfiker "Relevance of Solid-state Properties for Pharmaceutical Products," Polymorphism in the Pharmaceutical Industry, Jan. 1, 2006, pp. 1-19.
Hu et al., "Novel highly active binuclear neutral nickel and palladium complexes as precatalysts for norbornene polymerization," Journal of Molecular Catalysis A: Chemical 253, 2006, 155-164.
Hu et al., "Syntheses and Ethylene Polymerization Behavior of Supported Salicylaldimine-Based Neutral Nickel(II) Catalysts," Organometallics, 2007, 26(10):2609-2615.
Hu et al., "Synthesis and Ethylene Polymerization Activity of a Novel, Highly Active Single-Component Binuclear Neutral Nickel(II) Catalyst," Organometallics, 2005, 24(11):2628-2632.
Huang et al., "The prognostic significance of PD-L1 in bladder cancer," Oncol. Rep., 2015, 33:3075-3084.
Huang et al., "Pharmacological treatment for keloids," Expert opinion on pharmacotherapy, 2013, 14(15):2087-2100.
Huddle et al., "Reactions of alkyl-lithium compounds with aryl halides," J Chem Soc., Perkin I, 1980, 12:2617-2625.
HuGEMM™ and HuCELL™ Models, "FactSheet," CrownBio, Oct. 2016, 8 pages.
Indian Office Action in Indian Application No. 202017053661, dated Jun. 3, 2022, 5 pages.
Indian Office Action with Indian Application No. 201817026809, dated Apr. 29, 2020, 6 pages.
Indian Office Action with Indian Application No. 201917001998, dated Nov. 24, 2020, 7 pages.
Indian Office Action with Indian Application No. 201917028273, dated Feb. 15, 2021, 5 pages.
International Preliminary Report on Patentability in International Application No. PCT/US2017/041899, dated Jan. 15, 2019, 7 pages.
International Preliminary Report on Patentability in International Application No. PCT/US2016/057487, dated May 3, 2018, 7 pages.
International Preliminary Report on Patentability in International Application No. PCT/US2016/062730, dated May 31, 2018, 7 pages.
International Preliminary Report on Patentability in International Application No. PCT/US2016/067155, dated Jun. 19, 2018, 10 pages.
International Preliminary Report on Patentability in International Application No. PCT/US2016/067925, dated Jun. 26, 2018, 8 pages.
International Preliminary Report on Patentability in International Application No. PCT/US2017/031242, dated Nov. 6, 2018, 7 pages.

(56) References Cited

OTHER PUBLICATIONS

International Preliminary Report on Patentability in International Application No. PCT/US2017/034173, dated Nov. 27, 2018, 8 pages.
International Preliminary Report on Patentability in International Application No. PCT/US2017/038120, dated Dec. 25, 2018, 6 pages.
International Preliminary Report on Patentability in International Application No. PCT/US2017/048880, dated March, 5, 2019, 9 pages.
International Preliminary Report on Patentability in International Application No. PCT/US2017/067880, dated Jun. 25, 2019, 7 pages.
International Preliminary Report on Patentability in International Application No. PCT/US2017/067886, dated Jun. 25, 2019, 9 pages.
International Preliminary Report on Patentability in International Application No. PCT/US2017/067904, dated Jun. 25, 2019, 7 pages.
International Preliminary Report on Patentability in International Application No. PCT/US2017/067946, dated Jun. 25, 2019, 9 pages.
International Preliminary Report on Patentability in International Application No. PCT/US2017/067951, dated Jun. 25, 2019, 8 pages.
International Preliminary Report on Patentability in International Application No. PCT/US2017/067984, dated Jun. 25, 2019, 7 pages.
International Preliminary Report on Patentability in International Application No. PCT/US2019/025036, dated Oct. 15, 2020, 7 pages.
International Preliminary Report on Patentability in International Application No. PCT/US2019/031728, dated Nov. 17, 2020, 7 pages.
International Preliminary Report on Patentability in International Application No. PCT/US2020/045311, dated Feb. 17, 2022, 8 pages.
International Preliminary Report on Patentability in International Application No. PCT/US2020/053190, dated Apr. 5, 2022, 7 pages.
International Preliminary Report on Patentability in International Application No. PCT/US2020/059817, dated May 17, 2022, 12 pages.
International Search Report and Written Opinion in International Application No. PCT/US2016/057487, dated Dec. 8, 2016, 11 pages.
International Search Report and Written Opinion in International Application No. PCT/US2016/062730, dated Feb. 9, 2017, 12 pages.
International Search Report and Written Opinion in International Application No. PCT/US2016/067155, dated Apr. 24, 2017, 26 pages.
International Search Report and Written Opinion in International Application No. PCT/US2016/067925, dated Mar. 27, 2017, 13 pages.
International Search Report and Written Opinion in International Application No. PCT/US2017/031242, dated Jun. 20, 2017, 22 pages.
International Search Report and Written Opinion in International Application No. PCT/US2017/034173, dated Aug. 8, 2017, 15 pages.
International Search Report and Written Opinion in International Application No. PCT/US2017/038120, dated Aug. 1, 2017, 14 pages.
International Search Report and Written Opinion in International Application No. PCT/US2017/041899, dated Sep. 5, 2017, 12 pages.
International Search Report and Written Opinion in International Application No. PCT/US2017/048880, dated Oct. 23, 2017, 15 pages.
International Search Report and Written Opinion in International Application No. PCT/US2017/067880, dated Mar. 21, 2018, 13 pages.
International Search Report and Written Opinion in International Application No. PCT/US2017/067886, dated Mar. 23, 2018, 24 pages.
International Search Report and Written Opinion in International Application No. PCT/US2017/067904, dated Mar. 22, 2018, 14 pages.
International Search Report and Written Opinion in International Application No. PCT/US2017/067946, dated May 22, 2018, 16 pages.
International Search Report and Written Opinion in International Application No. PCT/US2017/067951, dated Mar. 27, 2018, 15 pages.
International Search Report and Written Opinion in International Application No. PCT/US2017/067984, dated Mar. 22, 2018, 14 pages.
International Search Report and Written Opinion in International Application No. PCT/US2019/025036, dated Jul. 3, 2019, 12 pages.
International Search Report and Written Opinion in International Application No. PCT/US2019/031728, dated Jun. 25, 2019, 12 pages.
International Search Report and Written Opinion in International Application No. PCT/US2020/045311, dated Oct. 2, 2020, 14 pages.
International Search Report and Written Opinion in International Application No. PCT/US2020/053190, dated Jan. 29, 2021, 13 pages.
International Search Report and Written Opinion in International Application No. PCT/US2020/059817, dated Mar. 29, 2021, 19 pages.
International Search Report and Written Opinion in International Application No. PCT/US2021/058268, dated Apr. 21, 2022, 22 pages.
International Search Report and Written Opinion in International Application No. PCT/US2021/058334, dated Apr. 25, 2022, 23 pages.
International Search Report and Written Opinion in International Application No. PCT/US2021/058338, dated Feb. 9, 2022, 15 pages.
International Search Report and Written Opinion in International Application No. PCT/US2021/063965, dated Apr. 12, 2022, 20 pages.
Invitation to Pay Fee's in International Application No. PCT/US2021/058268, dated Jan. 31, 2022, 16 pages.
Invitation to Pay Fee's in International Application No. PCT/US2021/058334, dated Feb. 3, 2022, 12 pages.
Israeli Office Action in Israeli Application No. 259,406, dated Mar. 11, 2020, 10 pages.
Israeli Office Action in Israeli Application No. 260, 166, dated Jun. 2, 2020, 13 pages.
Israeli Office Action in Israeli Application No. 287,267, dated Feb. 15, 2022, 4 pages.
Israeli Office Action in Israeli Application No. 288,232, dated Oct. 11, 2023, 5 pages.
Iwai et al., "Involvement of PD-L1 on tumor cells in the escape from host immune system and tumor immunotherapy by PD-L1 blockade," PNAS, Sep. 2002, 99(19):12293-12297.
Japanese Office Action in Japanese Application No. 2018526213, dated Oct. 13, 2020, 10 pages.
Japanese Office Action in Japanese Application No. 2019-534122, dated Oct. 19, 2021, 10 pages.
Japanese Office Action in Japanese Application No. 2019-534195, dated Nov. 1, 2021, 8 pages.
Japanese Office Action in Japanese Application No. 2019-534196, dated Nov. 9, 2021, 8 pages.
Japanese Office Action in Japanese Application No. 2022-108265, dated Aug. 22, 2023, 3 pages (with English Translation).
Jiang et al., "Self-immobilizing binuclear neutral nickel catalyst for ethylene polymerization: Synthesis and catalytic studies," J Mol Cat., 2013, 380:139-143.

(56) References Cited

OTHER PUBLICATIONS

Kayal et al., "3,3'-Bis(triphenylsilyl)biphenoxide as a Sterically Hindered Ligand on Fe(II), Fe(III), and Cr(II)," Inorg Chem., 2002, 41(2):321-330.
Keir et al., "PD-1 and Its Ligands in Tolerance and Immunity," Annu. Rev. Immunol., 2008, 26:677-704.
Kerekes et al., "Aurora kinase inhibitors based on the imidazo[1,2-a]pyrazine core: fluorine and deuterium incorporation improve oral absorption and exposure," J Med Chem., 2011, 54(1):201-210.
Koch et al., "Nucleophilic reactions of pyridines and imidazoles with vinyl and aromatic halides, " J Org Chem., 1993, 58(6):1409-1414.
Komiyama et al., "IL-17 Plays an Important Role in the Development of Experimental Autoimmune Encephalomyelitis," J. Immunol., Jul. 2006, 177:566-73.
Korean Office Action in Korean Application No. 10-2018-7017417, dated Jan. 16, 2024, 7 pages (with English Translation).
Korean Office Action in Korean Application No. 10-2018-7021068, dated Feb. 22, 2024, 10 pages (with English Translation).
Korean Office Action in Korean Application No. 10-2019-7021307, dated Aug. 23, 2023, 7 pages (with English Translation).
Latchman et al., "PD-L2 is a second ligand for PD-1 and inhibits T cell activation," Nat. Immunol., Mar. 2001, 2(3):261-268.
Lazar-Molnar et al., "Crystal structure of the complex between programmed death-1 (PD-1) and its ligand PD-L2," PNAS, Jul. 2008, 105(30):10483-10488.
Legon'kova et al., "Interaction of o,odihalo o'-hydroxy azo compounds with metallic copper. II. Preparation of oligomeric azo compounds from monoazo compounds," Mosk Khim-Teknol Inst im Mendeleeva., 1968, 11(11):1281-1284 Machine Translation.
Legon'kova et al., "Interaction of o,o-dihalogeno o-hydroxy azo compounds with metallic copper," Trudy Instituta—Moskovskii Khimiko—Tekhnologicheskii Institut imeni D. I. Mendeleeva, 1956, 48:120-125 Machine Translation.
Lehtonen et al., "Comparison of quaternery methyl-, ethyl- and butylammonium hydroxides as alkylating reagents in pyrolysis-GC/MS studies of aquatic fulvic acid," Journal of Analytical and Applied Pyrolysis, 2003, 68-69:315-329.
Lexico.com, "Synonyms of Enhance," Oxford Dictionary, retrieved on Dec. 9, 2021, retrieved from URL <https://www.lexico.conn/synonynns/enhance>, 4 pages.
Li et al., "A 3D Mesomeric Supramolecular Structure of a CU(II) Coordination Polymer with 1,1'-Biphenyl-2,2',3,3'-tetracarboxylic Acid and 5,5'-Dimethyl-2,2'-bipyridine Ligands," J Inorg and Organomet Poly Mat., 2012, 22(6):1320-1324.
Li et al., "A Mini-Review for Cancer Immunotherapy: Molecular Underestanding of PD-1/PD-L1 Pathway & Translational Blockade of Immune Checkpoints," Int J Mol. Soc., 2016, 17:1151, 22 pages.
Li et al., "Analysis of Receptor Tyronise Kinase Internalization Using Flow Cytometry," Methods Mol. Biol., 2008, 457:305-317.
Li et al., "Asymmetric Alternating Copolymerization of Meso-expoxides and Cyclic Anhydrides: Efficient Access To Enantiopure Polyesters," J. Am. Chem. Soc., 2016, 138(36):11493-11496.
Li et al., "Discovery of peptide inhibitors targeting human programmed death 1 (PD-1) receptor," Oncotarget, Aug. 2016, 7(40):64967-64976.
Lin et al., "The PD-1/PD-L1 complex resembles the antigen-binding Fv domains of antibodies and T cell receptors," PNAS, FEb. 2008, 105(8):3011-3016.
Lipson et al., "From Discovery to Development: Blocking PD-1 and its Ligands," the Melanoma Letter, A Publication of The Skin Cancer Foundation, vol. 31, Summer 2013, 6 pages.
Liu et al., "Asymmetric Copolymerization of CO2 with meso-Epoxides Mediated by Dinuclear Cobalt(III) Complexes: Unprecedented Enantioselectivity and Activity," Angewandte Chemie, 2013, 52(44):11594-11598.
Liu et al., "Development of amino-and dimethylcarbamete-substituted resorcinol as programmed cell death-1 (PD-1) inhibitor," Eur J Pharm Sci, 2016, 88:50-58.
Mahoney et al., "The Next Immune-Checkpoint Inhibitors:PD-1/PD-L1 Blockade in Melanoma," Clin. Therapeutics, Nov. 2015, 37(4):761-782.
Maier et al., "Effects of the stationary phase and the solvent on the stereodynamics of biphep ligands quantified by dynamic three-column HPLC," Angewante Chemie, 2012, 51(12):2985-2988.
Malaysian Notice of Allowance in Malaysian Application No. PI 2018000767, dated Oct. 20, 2023, 1 page.
Malaysian Notice of Allowance in Malaysian Application No. PI 2018001065, dated Nov. 20, 2023, 1 page.
Malaysian Office Action in Malaysian Application No. PI 2018001065, dated Sep. 29, 2023, 2 pages.
Manecke et al., "Preparation and properties of chelate-forming monomeric and polymeric Schiff bases derived from salicylaldehyde and 2,5-dihydroxyterephthalaldehyde. I," Makromolekulare Chemie, 1970, 133:61-82 English Abstract.
Manecke et al., "Preparation and properties of monomeric and polymeric Schiff bases derived from salicylaldehyde and 2,5-dihydroxyterephthalaldehyde. II. Electrical conductivity," Makromolekulare Chemie, 1972, 160:111-126 English Abstract.
Mexican Office Action in Mexican Application No. MX/a/2018/007774, dated Apr. 8, 2021, 5 pages.
Mexican Office Action in Mexican Application No. MX/a/2018/016273, dated Mar. 26, 2021, 5 pages.
Miyaura and Suzuki, "Palladium-Catalyzed Cross-Coupling Reactions of Organoboron Compounds, " Chem Rev., 1995, 95:2457-2483.
Mochida et al., "Rhodium-Catalyzed Regioselective Olefination Directed by a Carboxylic Group," J Org Chem, 2011, 76(9):3024-3033.
Moneta et al., "Boron templated synthesis of macrocyclic hosts containing convergent hydroxy or methoxy groups," Bulletin de la Societe Chimique de France, 1988, 6:995-1004 (English Abstract).
Nallasivam et al., "Development of Unimolecular Tetrakis(piperidin-4-ol) as a Ligand for Suzuki-Miyaura Cross-Coupling Reactions: Synthesis of Incrustoporin and Preclamol," 2015, Eur J Org Chem., 2015(16):3558-3567.
Nero et al., "Oncogenic protein interfaces: small molecules, big challenges," Nature Reviews, Apr. 2014, 14:248-262.
New Zealand Office Action in New Zealand Application No. 743403, dated Feb. 8, 2024, 3 pages.
New Zealand Office Action in New Zealand Application No. 744392, dated Feb. 20, 2024, 4 pages.
New Zealand Office Action in New Zealand Application No. 783450, dated Feb. 27, 2024, 4 pages.
Nishimura et al., "Autoimmune Dilated Cardiomyopathy in PD-1 Receptor-Deficient Mice," Science, Jan. 2001, 291:319-322.
Nishimura et al., "Development of Lupus-like Autoimmune Diseases by Disruption of the PD-1 Gene Encoding an ITIM Motif-Carrying Immunoreceptor," Immunity, Aug. 1999, 11:141-151.
Nishimura et al., "PD-1: an inhibitory immunoreceptor involved in peripheral tolerance," Trends in Immunology, May 2001, 22(5):265-268.
Nishino et al., "Copper-Mediated C-H/C-H Biaryl Coupling of Benzoic Acid Derivatives and 1,3-Azoles," Angew. Chem. Int. Ed., 2013, 52:4457-4461.
Normand et al., "Dinuclear vs. mononuclear complexes: accelerated, metal-dependent ring-opening polymerization of lactide," Chem. Commun., 2013, 49(99):11692-11694.
Okazaki et al., "A rheostat for immune responses: the unique properties of PD-1 and their advantages for clinical application," Nature Immunology, Dec. 2013, 14(12):1212-1218.
Okazaki et al., "The PD-1-PD-L pathway in immunological tolerance," Trends Immunol., Apr. 2006, 4:195-201.
Otter et al., "The human papillomavirus as a common pathogen in oropharyngeal, anal and cervical cancers," Clin Oncol (R Coll Radiol), Feb. 2019, 31(2):81-90.
Paek et al., "Chiral host. Attempted synthesis using McMurray reaction as a final ring closure method, " Bulletin of the Korean Chemical Society, 1989, 10(6):572-577.
Paek et al.. , "Facile syntheses and multi-orthofunctionalizations of tertiary benzamides," Bulletin of the Korean Chemical Society, 1993, 14(6):732-739.

(56) References Cited

OTHER PUBLICATIONS

Pardoll, "The blockade of immune checkpoints in cancer immunotherapy," Nature, Apr. 2012, 12:252-264.
Parry et al., "CTLA-4 and PD-1 Receptors Inhibit T-Cell Activation by Distinct Mechanisms," Mol. Cell. Biol., Nov. 2005, 25(21):9543-9553.
Parsons et al., "Directed ortho metalation reactions. Expedient synthesis of 3,3'- disubstituted 1,1'-bi-(2-phenols) (BIPOLS)," Tetrahedron Letters, 1994, 35(41):7537-7540.
Pascolutti et al., "Structure and Dynamics of PD-L1 and an Ultra-High-Affinity PD-1 Receptor Mutant," Structure, Oct. 2016, 24:1719-1728.
Paulini et al., "Orthogonal Multipolar Interactions in Structural Chemistry and Biology," Angew. Chem. Int. Ed., 2005, 44:1788-1805.
Pearson et al., "The formation of complexes between aza-derivatives of crown ethers and primary alkylammonium salts. Part 5. Chiral macrocyclic diamines, " J. Chem. Soc., Perkin I, 1979, 12:3113-3126.
Pfeiffer et al., "Inner complex salts of the aldimine and azo series," Journal fuer Praktische Chemie, 1937, 149:217-296 Machine Translation.
Pierre et al., "Synthesis of a new macrobicyclic sideriphoric host molecule with six converging phenolate groups," Angewandte Chemie, 1991, 103(1):75-76 Machine Translation.
Postow et al., "Immune Checkpoint Blockade in Cancer Therapy," J. Clinical Oncology, Jun. 2015, 33(17):1974-1982.
Press Release Archive, "Boehringer Ingelheim and Yale University collaborate to investigate novel immunotherapy targets across several therapeutic areas," Boehringer Ingelheim, Jan. 13, 2015, 2 pages.
Puehlhofer et al., "SASAPOS cascades of perfluorinated aromatic carboxylic acids: low-temperature decarboxylation triggered by electrostatic effects of polycationic ligand sets," Euro J of Org Chem., 2004, 5:1002-1007.
Punniyamurthy et al., "Enantiomerically pure bicyclo[3.3.1]nona-2,6-diene as the sole source of enantioselectivity in BIPHEP-Rh asymmetric hydrogenation," Chem Comm., 2008, 41:5092-5094.
Qin et al., "The Diverse Function of PD-1/PD-L Pathway Beyond Cancer," Frontiers In Immunology, Oct. 2019, 10(2298):1-16.
Reck et al., "Pembrolizumab versus Chemotherapy for PD-L1-Positive Non-Small-Cell Lung Cancer," N Engl J Med., Nov. 10, 2016, 375(19):1823-1833.
Rowe et al., "Fumaric Acid" Handbook of pharmaceutical excipients, Jan. 1, 2009, pp. 276-277, 309-310, 393-396.
Rowe et al., "Fumaric Acid," Handbook of pharmaceutical excipients, Jan. 1, 2009, pp. 276-277, 318-321, 663-666.
Sabatier et al., "Prognostic and predictive value of PDLI expression in breast cancer," Oncotarget, Mar. 2015, 6(7):5449-5464.
Sharma et al., "Palladium-Catalyzed Decarboxylative Acylation of O-Phenyl Carbamates with Alpha-Oxocarboxylic Acids at Room Temperature," Advanced Synthesis & Catalysis, 2013, 355(4):667-672.
Sharpe et al., "The function of programmed cell death 1 and its ligands in regulating autoimmunity and infection," Nat. Immunol., Mar. 2007 8(3):239-245.
Sharpe et al., "The B7-CD28 Superfamily," Nature Reviews, Feb. 2002, 2:116-126.
Sorrell et al., "3,3'-Disubstituted 2,2'-biphenols. Synthesis of nonplanar, tetradentate chelating ligands," J Org Chem., 1985, 50(26):5765-5769.
Stahl et al., "Handbook of Pharmaceutical Salts: Properties, Selection, and Use," Wiley, 2002, p. 329-350.
STN Search Report dated Dec. 20, 2016, 117 pages.
STN Search Report dated Apr. 14, 2016, 79 pages.
STN Search Report dated Apr. 29, 2016, 69 pages.
STN Search Report dated Apr. 30, 2018, 8 pages.
STN Search Report dated Aug. 19, 2016, 23 pages.
STN Search Report dated Aug. 30, 2016, 4 pages.
STN Search Report dated Dec. 15, 2016, 4 pages.
STN Search Report dated Dec. 16, 2016, 25 pages.
STN Search Report dated Dec. 16, 2016, 4 pages.
STN Search Report dated Dec. 19, 2016, 11 pages.
STN Search Report dated Jul. 12, 2016, 4 pages.
STN Search Report dated Jun. 16, 2016, 8 pages.
STN Search Report dated Jun. 6, 2016, 115 pages.
STN Search Report dated Mar. 27, 2018, 4 pages.
STN Search Report dated May 24, 2016, 92 pages.
STN Search Report dated Sep. 12, 2016, 4 pages.
STN Search Report dated Sep. 12, 2016, 17 pages.
STN Search Report dated Sep. 2, 2016, 115 pages.
STN Search Report dated Sep. 27, 2017, 4 pages.
STN Search Report, dated May 1, 2016, 12 pages.
Storz, "Intellectual property issues of immune checkpoint inhibitors," mAbs, Jan. 2016, 8(1):10-26.
Suarez et al., "Inhibitors of TAM subfamily of tyrosine kinases: synthesis and biological evaluation," European Journal of Medicinal Chemistry, 2013, 61:2-25.
Sumrit et al., "Aluminum complexes containing salicylbenzoxazole ligands and their application in the ring-opening polymerization of rac-lactide and ε- caprolactone," Dalton Transactions (2016), 45(22), 9250-9266.
Sun et al., "Studies on Synthesis and Properties of Some New Dibenzocyclobromonium," Chemical Journal of Chinese Universities, 1998, 19(12), 6 pages (English Abstract).
Sznol et al., "Antagonist Antibodies to PD-1 and B7-H1 (PD-L1) in the Treatment of Advanced Human Cancer," Clin Cancer Res., Mar. 1, 2013, 19(5):1021-1034.
Taiwan Office Action in Taiwan Application No. 105133530, dated Oct. 15, 2020, 8 pages.
Taiwan Office Action in Taiwan Application No. 105137807, dated Nov. 12, 2020, 12 pages.
Taiwan Office Action in Taiwan Application No. 105141804, dated Nov. 9, 2020, 9 pages.
Tang et al., "Facile synthesis of enantioenriched phenol-sulfoxides and their aluminum complexes," Org Biomol Chem., 2016, 14(24):5580-5585.
Thai Office Action in Thai Application No. 1901003875, dated Aug. 9, 2023, 9 pages (with English Translation).
Thiel et al., "Small-Molecule Stabilization of Protein-Protein Interactions: An Underestimated Concept in Drug Discovery?" Angew. Chem. Int. Ed., 2012, 51:2012-2018.
Tucker et al., "Host-guest complexation. 52. Bridged and chiral hemispherands," J Org Chem., 1989, 54(23):5460-5482.
Ukraine Office Action in Ukraine Application No. a 2019 00525, dated Jan. 14, 2021, 11 pages.
Unrau et al., "Directed ortho metalation. Suzuki cross coupling connections. Convenient regiospecific routes to functionalized m- and p-teraryls and m-quinquearyls," Tetrahedron Letters, 1992, 33(20):2773-2776.
Vaddepally et al., "Review of Indications of FDA-Approved Immune Checkpoint Inhibitors per NCCN Guidelines with the Level of Evidence," Cancers, 2020, 12(3):738.
Velcheti et al., "Programmed death-1/programmed death-1 ligand axis as a therapeutic target in oncology: current insights," Journal of Receptor Ligand and Channel Research, Dec. 2014, 8(23): 1-7.
Vietnamese Notice of Allowance in Vietnamese Application No. 1-2018-03159, dated Jan. 31, 2024, 2 pages (with English Translation).
Wang et al., "The prognostic value of PD-L1 expression for non-small cell lung cancer patients: A meta-analysis," Eur. J. Surg. Oncol., 2015, 41:450-456.
Wang et al., "A binuclear Zn(II)-Zn(II) complex from a 2-hydroxybenzohydrazide-derived Schiff base for selective detection of pyrophosphate," Dalton Transactions, Oct. 2014, 43(37):14142-14146.
Wang et al., "Molecular Modeling and Functional Mapping of B7-H1 and B7-DC Uncouple Costimulatory Function from PD-1 Interaction," J. Exp. Med., Apr. 2013, 197(3):1083-1091.
Wei et al., "Strength of PD-1 signaling differentially affects T-cell effector functions," PNAS, Apr. 2013, E2480-E2489.
Weinmann, "Cancer Immunotherapy: Selected Targets and Small-Molecule Modulators," Chem. Med. Chem., 2016, 11:450-466.

(56) References Cited

OTHER PUBLICATIONS

Weiss et al., "Electrostatic activation of SNAr-reactivity by sulfonylonio substituents, " Zeitschrift fuer Naturforschung, 2001, 56(12):1360-1368 English Abstract.
Weiss et al., "Electrostatics and color: Massive electrostatic perturbation of chromophores by ion cluster ligands," J Am Chem Soc., 2007, 129(3):547-553.
Weiss et al., "First-ever per(onio) substitution of benzene: the role of the counterion," Angewandte Chemie, 1995, 34(12):1319-1321.
Weiss et al., "Massive electrostatic effects on heteropolar C-C disconnections: Transforming a phenyl anion into a potent leaving group," Euro J Org Chem., 2005, 16:3530-3535.
Weiss et al., "Poly-onio substituted quinones as strong electron acceptors," Inst Org Chem., 1986, 98(10):925-926.
Weiss et al., "SASAPOS, not Sisyphus: highly efficient 20-step one-pot synthesis of a discrete organic-inorganic ion cluster with a porphyrin core," Angewandte Chemie International Edition, 2002, 41(20):3815-3817.
Weiss et al., "Syntheses and Reactions of Polycationically Substituted Azido- and Diazidobenzenes," Eur J Org Chem., Nov. 2007, 31:5270-5276.
Wells et al., "Reaching for high-hanging fruit in drug discovery at protein-protein interfaces," Nature, Dec. 2007, 450:1001-1009.
Wu et al., "Targeting the BACE1 Active Site Flap Leads to a Potent Inhibitor That Elicits Robust Brain Aß Reduction in Rodents," ACS Medicinal Chemistry Letters, 2016, 7(3):271-276.
Wuts et al., "Protective Groups in Organic Synthesis," 4th Ed., 2007, 1111 pages.
www.medscape.com' [online]. "The 'Family Business' Behind the Flurry of PD-1 Inhibitors," Sep. 10, 2014. [Retrieved on Jan. 29, 2015]. Retrieved from the Internet: URL<http://www.medscape.com/viewarticle/831448_print>. 3 pages.
Xiong et al., "Biaryl-Bridged Salalen Ligands and Their Application in Titanium-Catalyzed Asymmetric Epoxidation of Olefins with Aqueous H2O2," Eur J Org Chem., 2011, 23:4289-4292.
Xu et al., "Design, synthesis and biological evaluation of deuterated nintedanib for improving pharmacokinetic properties," J Label Compd RadioPharm., Jun. 15, 2015, 58(7):308-312.
Xu et al., "Quantitative structure-activity relationship study on BTK inhibitors by modified multivariate adaptive regression spline and CoMSIA methods," SAR QSAR Environ Res., 2015, 26(4):279-300.
Yao et al., "PD-1 as an Immune Modulatory Receptor," Cancer J., 2014, 20(4):262-264.
Yin et al., "Strategies for Targeting Protein-Protein Interactions With Synthetic Agents," Angew. Chem. Int. Ed., 2005, 44:4130-4163.
Young et al., "Discovery of highly potent and selective Bruton's tyrosine kinase inhibitors: Pyridazinone analogs with improved metabolic stability," Bioorganic & Medicinal Chemistry Letters, 2016, 26(2):575-579.
Young et al., "Potent and selective Bruton's tyrosine kinase inhibitors: Discovery of GDC-0834," Bioorganic & Medicinal Chemistry Letters , 2015, 25(6):1333-1337
Zak et al., "Structural basis for small molecule targetign of the programmed death ligand 1 (PD-L1)" Oncotarget, Apr. 2016, 19 pages; Supplemental Material for 2016, 7(21):30323-30335.
Zak et al., "Structure of the Complex of Human Programmed Death 1, PD-1, and Its Ligand PD-L1: with Supplemental Information," Structure, Dec. 2015, 23:2341-2348.
Zang et al., "Four 2D metal-organic networks incorporation Cd-cluster SUBs: hydrothermal synthersis, structures and photoluminescent properties," CrystEngComm, 2009, 11(1):122-129.
Zarganes-Tzitzikas, "Inhibitors of programmed cell death 1 (PD-1): a new patent review (2010-2015)," Expert Opinion on Therapeutic Patents, Sep. 19, 2016, 26(9):973-977.
Zhan et al., "From monoclonal antibodies to small molecules: the development of inhibitors targeting the PD-1/PD-L1 pathway," Drug Discovery Today, Apr. 2016, 10 pages.
Zhang et al., "Biatryl-Based Macrocyclic and Polymeric Chiral (Salophen)Ni(II) Complexes: Synthesis and Spectroscopic Study," J ORg Chem., 2001, 66(2):481-487.
Zhang et al., "Electropray mass spectrum of a per(onio)-substituted benzene: retention of Coulombic charge upon collisionally activated decomposition," J Am Soc. Mass. Spectrom., 1998, 9(1):15-20.
Zhang et al., "Non-symmetrical diarylcarboxylic acids via rhodium(I)-catalyzed regiospecific cross-dehydrogenation coupling of aromatic acids: twofold direct C-H bond activations in water,"RSC Advances, 2016, 66(64):91617-91620.
Zhang et al., "Structural and Functional Analysis of teh Costimulatory Receptor Programmed Death-1," Immunity, MAr. 2004, 20:337-347.
Zhao et al., "Design, synthesis and organocatalysis of 2,2'-biphenol-based prolinamide organocatalysts in the asymmetric direct aldol reaction in water," Synlett, 2013, 24(20):2743-2747.

\* cited by examiner

PROCESS OF PREPARING A PD-1/PD-L1 INHIBITOR

CROSS-REFERENCE TO RELATED APPLICATIONS

The present application is a divisional of U.S. patent application Ser. No. 17/520,060, filed on Nov. 5, 2021, which claims the benefit of U.S. Provisional Application No. 63/110,779, filed Nov. 6, 2020, each of which is incorporated herein by reference in its entirety.

FIELD OF THE INVENTION

This application relates to process of preparing PD-1/PD-L1 inhibitor (R)-1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl) pyrrolidine-3-carboxylic acid, salts thereof, and related synthetic intermediate compounds and salts of the intermediates, where the PD-1/PD-L1 inhibitor is useful in the treatment of various diseases including infectious diseases and cancer.

BACKGROUND OF THE INVENTION

The immune system plays an important role in controlling and eradicating diseases such as cancer. However, cancer cells often develop strategies to evade or to suppress the immune system in order to favor their growth. One such mechanism is altering the expression of co-stimulatory and co-inhibitory molecules expressed on immune cells (Postow et al, J. Clinical Oncology 2015, 1-9). Blocking the signaling of an inhibitory immune checkpoint, such as PD-1, has proven to be a promising and effective treatment modality.

Programmed cell death-1 (PD-1), also known as CD279, is a cell surface receptor expressed on activated T cells, natural killer T cells, B cells, and macrophages (Greenwald et al, Annu. Rev. Immunol 2005, 23:515-548; Okazaki and Honjo, Trends Immunol 2006, (4):195-201). It functions as an intrinsic negative feedback system to prevent the activation of T-cells, which in turn reduces autoimmunity and promotes self-tolerance. In addition, PD-1 is also known to play a critical role in the suppression of antigen-specific T cell response in diseases like cancer and viral infection (Sharpe et al, *Nat Immunol* 2007 8, 239-245; Postow et al, J. Clinical Oncol 2015, 1-9).

The structure of PD-1 consists of an extracellular immunoglobulin variable-like domain followed by a transmembrane region and an intracellular domain (Parry et al, Mol Cell Biol 2005, 9543-9553). The intracellular domain contains two phosphorylation sites located in an immunoreceptor tyrosine-based inhibitory motif and an immunoreceptor tyrosine-based switch motif, which suggests that PD-1 negatively regulates T cell receptor-mediated signals. PD-1 has two ligands, PD-L1 and PD-L2 (Parry et al, Mol Cell Biol 2005, 9543-9553; Latchman et al, Nat Immunol 2001, 2, 261-268), and they differ in their expression patterns. PD-L1 protein is upregulated on macrophages and dendritic cells in response to lipopolysaccharide and GM-CSF treatment, and on T cells and B cells upon T cell receptor and B cell receptor signaling. PD-L1 is also highly expressed on almost all tumor cells, and the expression is further increased after IFN-γ treatment (Iwai et al, PNAS2002, 99(19):12293-7; Blank et al, Cancer Res 2004, 64(3):1140-5). In fact, tumor PD-L1 expression status has been shown to be prognostic in multiple tumor types (Wang et al, Eur J Surg Oncol 2015; Huang et al, Oncol Rep 2015; Sabatier et al, Oncotarget 2015, 6(7): 5449-5464). PD-L2 expression, in contrast, is more restricted and is expressed mainly by dendritic cells (Nakae et al, J Immunol 2006, 177:566-73). Ligation of PD-1 with its ligands PD-L1 and PD-L2 on T cells delivers a signal that inhibits IL-2 and IFN-γ production, as well as cell proliferation induced upon T cell receptor activation (Carter et al, Eur J Immunol 2002, 32(3):634-43; Freeman et al, J Exp Med 2000, 192(7):1027-34). The mechanism involves recruitment of SHP-2 or SHP-1 phosphatases to inhibit T cell receptor signaling such as Syk and Lck phosphorylation (Sharpe et al, Nat Immunol 2007, 8, 239-245). Activation of the PD-1 signaling axis also attenuates PKC-θ activation loop phosphorylation, which is necessary for the activation of NF-κB and AP1 pathways, and for cytokine production such as IL-2, IFN-γ and TNF (Sharpe et al, Nat Immunol 2007, 8, 239-245; Carter et al, Eur J Immunol 2002, 32(3):634-43; Freeman et al, J Exp Med 2000, 192(7):1027-34).

Several lines of evidence from preclinical animal studies indicate that PD-1 and its ligands negatively regulate immune responses. PD-1-deficient mice have been shown to develop lupus-like glomerulonephritis and dilated cardiomyopathy (Nishimura et al, Immunity 1999, 11:141-151; Nishimura et al, Science 2001, 291:319-322). Using an LCMV model of chronic infection, it has been shown that PD-1/PD-L1 interaction inhibits activation, expansion and acquisition of effector functions of virus-specific CD8 T cells (Barber et al, Nature 2006, 439, 682-7). Together, these data support the development of a therapeutic approach to block the PD-1-mediated inhibitory signaling cascade in order to augment or "rescue" T cell response. Accordingly, compounds and salts that block PD-1/PD-L1 protein/protein interaction are widely sought after. PD-1/PD-L1 inhibitor, (R)-1-((7-cyano-2-(3'-(3-(((R)-3-hydroxypyrrolidin-1-yl) methyl)-1,7-naphthyridin-8-ylamino)-2,2'-dimethylbiphenyl-3-yl)benzo[d]oxazol-5-yl)methyl)pyrrolidine-3-carboxylic acid, is reported in U.S. Pat. No. 10,308,644, which is incorporated herein by reference.

In view of the growing demand for compounds for the treatment of disorders related to the PD-1/PD-L1 inhibition, new and more efficient routes to prepare such compounds, salts thereof, and intermediates related thereto and salts of the intermediates, are needed. The processes and compounds described herein help meet these and other needs.

SUMMARY OF THE INVENTION

Provided herein are processes for preparing (R)-1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid, salts thereof, related synthetic intermediates compounds and salts of the intermediates.

In one aspect, provided herein is a process of preparing (R)-1-((7-cyano-2-(3'-((3-(((R)-3-hydroxypyrrolidin-1-yl) methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid, or a salt thereof, comprising:

reacting a compound of formula III-5:

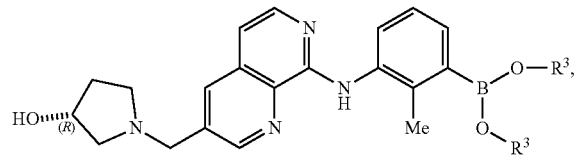

III-5 or a salt thereof, with a compound of formula III-6:

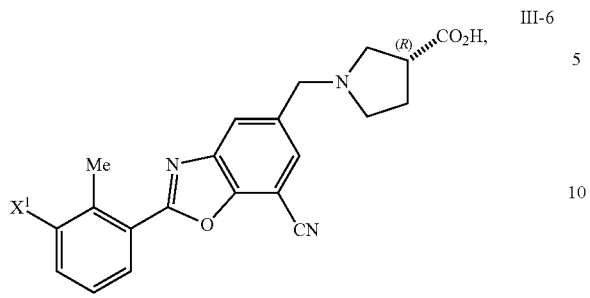

or a salt thereof, in the presence of a Suzuki catalyst and a base to form a compound of formula A-1:

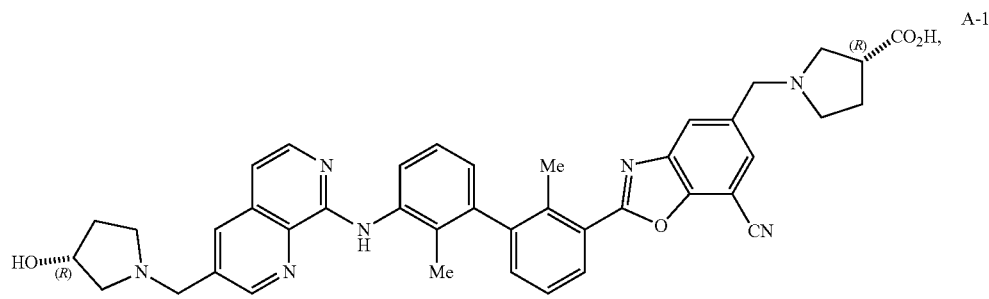

or a salt thereof; wherein:
  each $R^3$ is independently selected from H and $C_{1-6}$ alkyl; or
  each $R^3$ together form an $C_{2-3}$ alkylene linker, which is optionally substituted by 1, 2, 3, or 4 independently selected $C_{1-4}$ alkyl groups; and
  $X^1$ is halo.

In one aspect, provided herein is a process of preparing (R)-1-((7-cyano-2-(3'-((3-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid, or a salt thereof, comprising:
  reacting a compound of formula III-5:

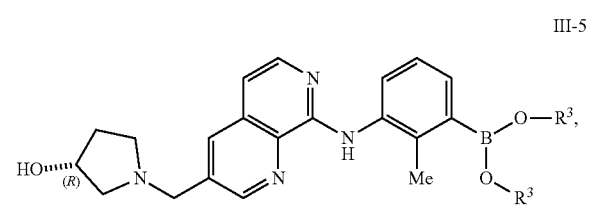

or a salt thereof, with a compound of formula IV-1:

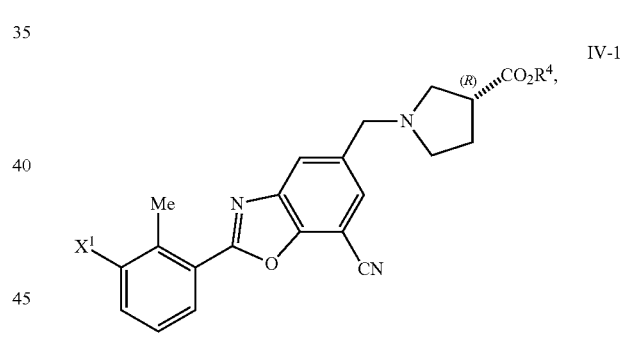

or a salt thereof, in the presence of a Suzuki catalyst and a base to form a compound of formula IV-2:

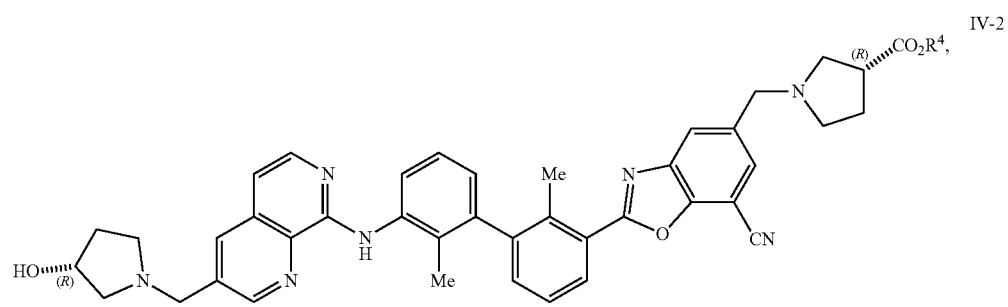

or a salt thereof, wherein:

each $R^3$ is independently selected from H and $C_{1-6}$ alkyl;
or
each $R^3$ together form an $C_{2-3}$ alkylene linker, which is optionally substituted by 1, 2, 3, or 4 independently selected $C_{1-4}$ alkyl groups; and $R^4$ is $C_{1-6}$ alkyl; and $X^1$ is halo.

In one aspect, provided herein is a process of preparing (R)-1-((7-cyano-2-(3'-((3-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid, or a salt thereof, comprising:

reacting a compound of formula V-1:

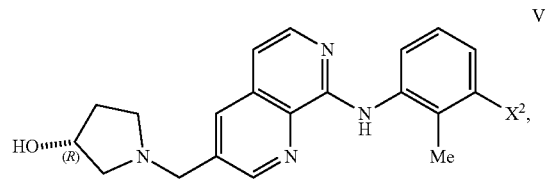

V-1 or a salt thereof, with a compound of formula V-2:

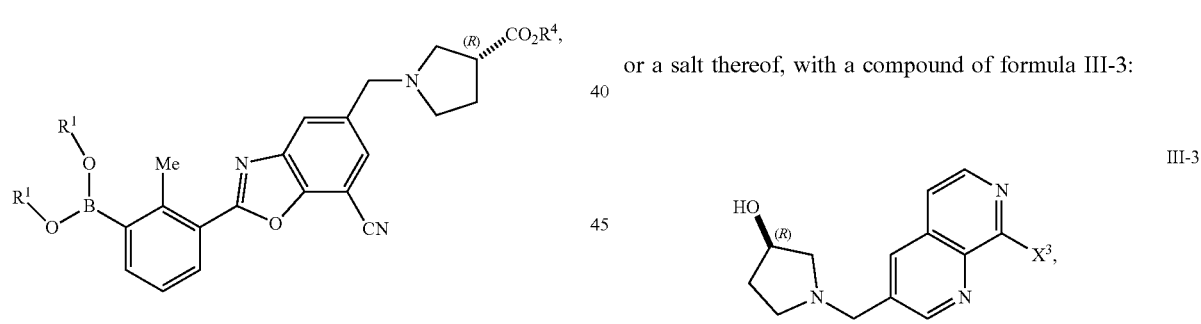

V-2 or a salt thereof, in the presence of a Suzuki catalyst and a base to form a compound of formula IV-2:

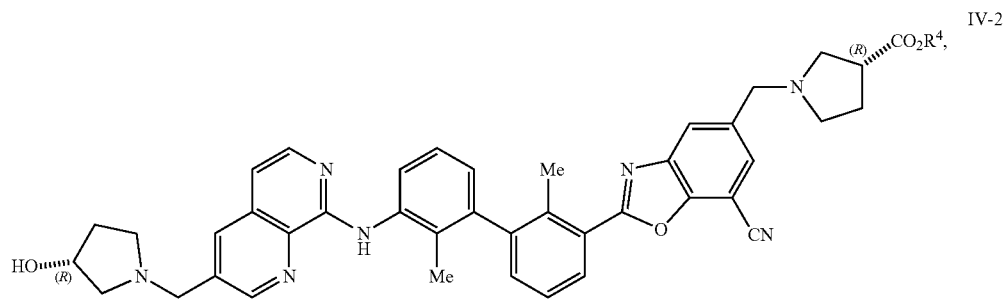

IV-2 or a salt thereof, wherein:

each $R^1$ is independently selected from H and $C_{1-6}$ alkyl;
or
each $R^1$ together form an $C_{2-3}$ alkylene linker, which is optionally substituted by 1, 2, 3, or 4 independently selected $C_{1-4}$ alkyl groups;

$X^2$ is halo; and $R^4$ is $C_{1-6}$ alkyl.

In one aspect, provided herein is a process of preparing (R)-1-((7-cyano-2-(3'-((3-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid, or a salt thereof, comprising:

reacting a compound of formula VI-1:

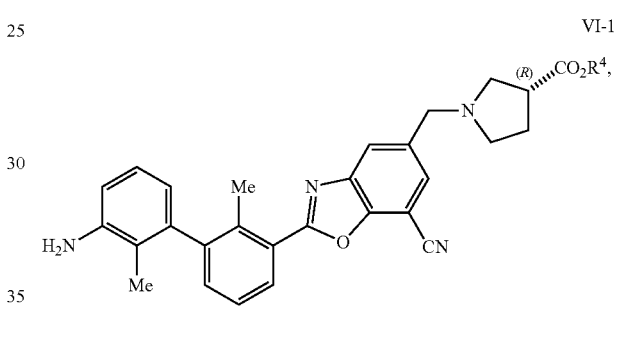

VI-1 or a salt thereof, with a compound of formula III-3:

III-3 or a salt thereof, in the presence of a catalyst to form a compound of formula IV-2:

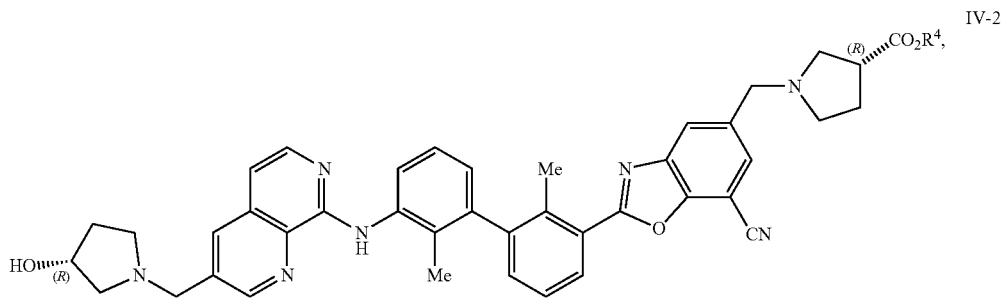

or a salt thereof, wherein $X^3$ is halo; and $R^4$ is $C_{1-6}$ alkyl.

In one aspect, provided herein is a process of preparing (R)-1-((7-cyano-2-(3'-((3-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid, or a salt thereof, comprising:

reacting a compound of formula I-2:

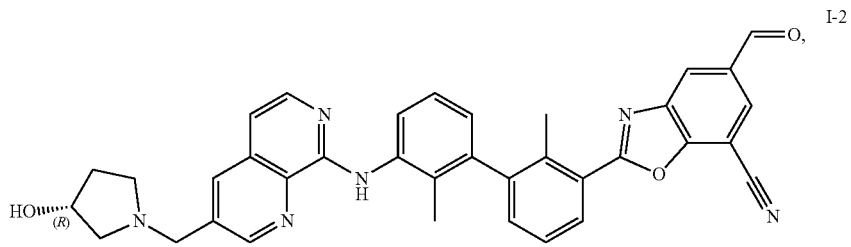

or a salt thereof, with a compound of formula XV-4:

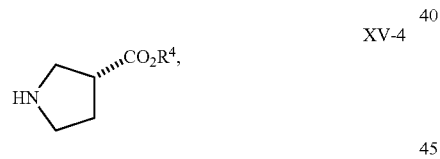

or a salt thereof, in the presence of a reducing agent to form a compound of formula IV-2:

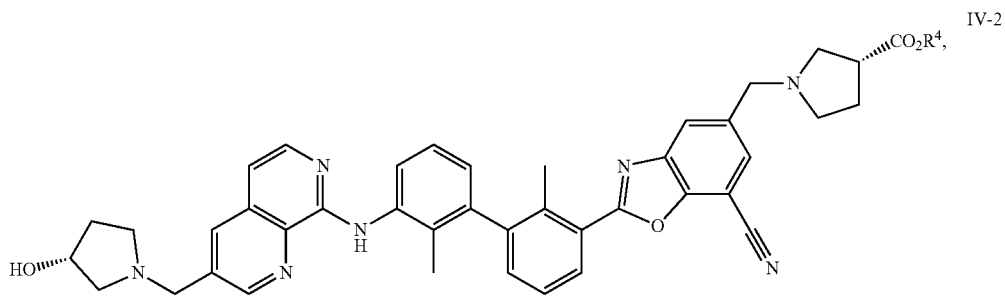

or a salt thereof, wherein $R^4$ is $C_{1-6}$ alkyl.

In one aspect, provided herein is a process of preparing (R)-1-((7-cyano-2-(3'-((3-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid, comprising:

reacting a compound of formula V-1:

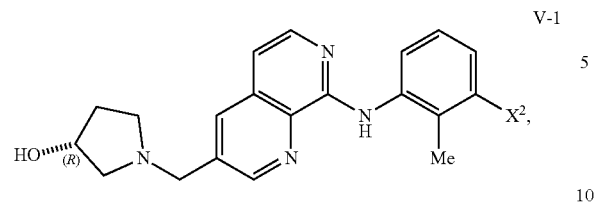

or a salt thereof, with a compound of formula I-1:

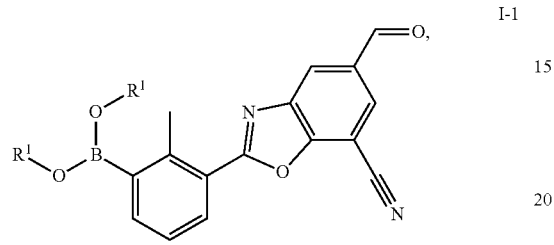

or a salt thereof, in the presence of a Suzuki catalyst and a base to form a compound of formula I-2:

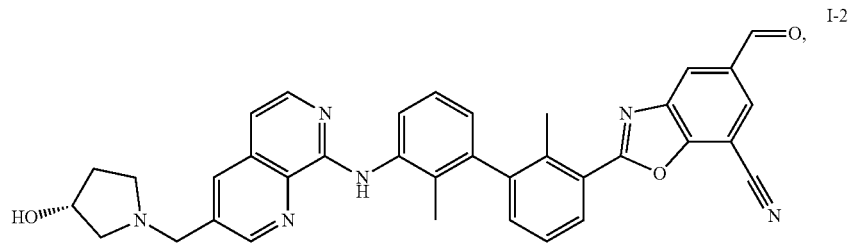 [SMILES: Cc1c(Nc2nccc3cc(CN4CC[C@@H](O)C4)cnc23)cccc1-c1cccc(-c2nc3cc(C=O)cc(C#N)c3o2)c1C]

or a salt thereof, wherein:
- each $R^1$ is independently selected from H and $C_{1-6}$ alkyl; or
- each $R^1$ together form an $C_{2-3}$ alkylene linker, which is optionally substituted by 1, 2, 3, or 4 independently selected $C_{1-4}$ alkyl groups; and
- $X^2$ is halo.

The details of one or more embodiments are set forth in the description below. Other features, objects, and advantages will be apparent from the description and from the claims.

DETAILED DESCRIPTION

The present disclosure is directed to, inter alia, processes of preparing (R)-1-((7-cyano-2-(3'-((3-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid (Compound 1):

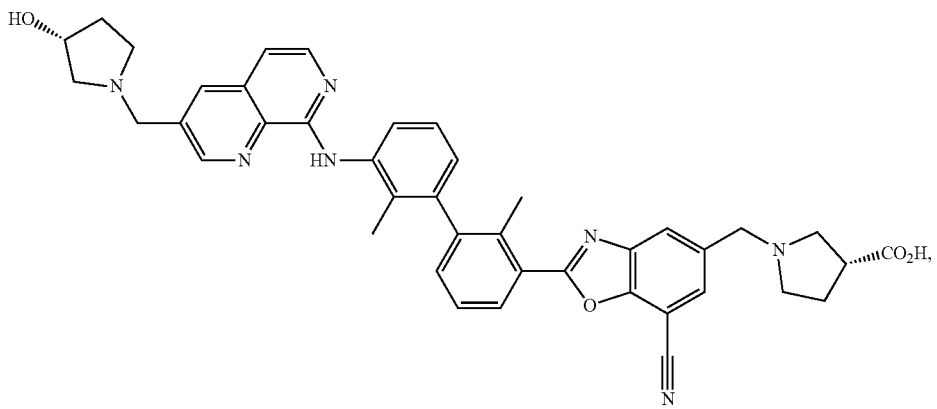

or a salt thereof, related synthetic intermediates compounds, and salts of the intermediates.

Compound 1 is described in U.S. Pat. No. 10,308,644, the entirety of which is incorporated herein by reference.

Provided herein is a process of preparing (R)-1-((7-cyano-2-(3'-((3-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid, or a salt thereof, comprising:

reacting a compound of formula III-5:

III-5 or a salt thereof, with a compound of formula III-6:

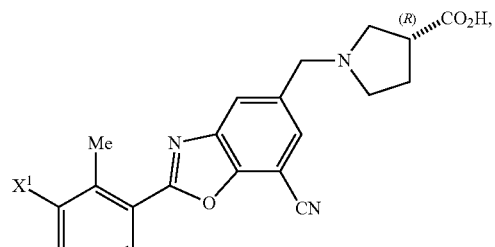

III-6 or a salt thereof, in the presence of a Suzuki catalyst and a base to form a compound of formula A-1:

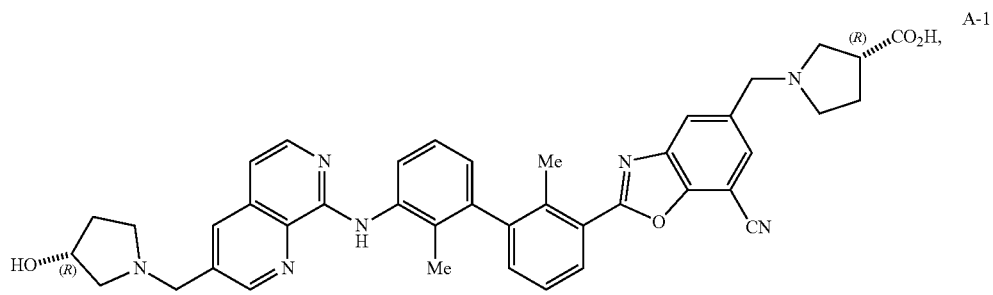

A-1 or a salt thereof; wherein:
- each $R^3$ is independently selected from H and $C_{1-6}$ alkyl; or
- each $R^3$ together form an $C_{2-3}$ alkylene linker, which is optionally substituted by 1, 2, 3, or 4 independently selected $C_{1-4}$ alkyl groups; and
- $X^1$ is halo.

In some embodiments, (R)-1-((7-cyano-2-(3'-((3-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid, or a salt thereof, is a pharmaceutically acceptable salt thereof.

In some embodiments, the compound of Formula A-1, or the salt thereof, is a salt of formula A-1a:

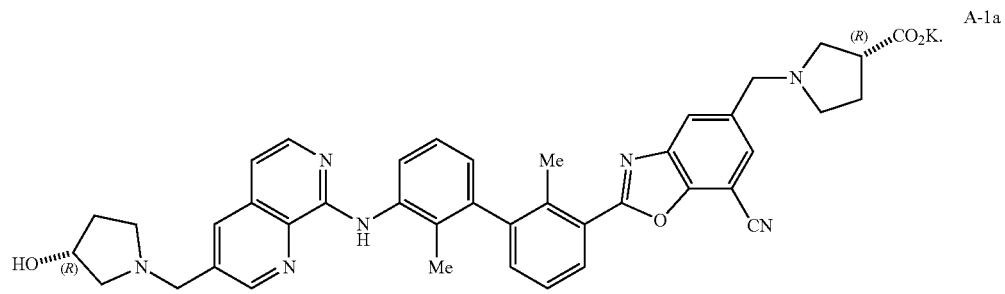

A-1a

In some embodiments, the Suzuki catalyst is a palladium catalyst. In some embodiments, the Suzuki catalyst is selected from RuPhos Pd G4, CataCXium® Pd G4, Pd(PPh$_3$)$_4$, Pd(dppf)$_2$Cl$_2$, dichlorobis[di-tert-butyl(p-dimethylaminophenyl)phosphino]palladium, and PdCl$_2$(dtbpf) (Pd-118). In some embodiments, the Suzuki catalyst is RuPhos Pd G4.

In some embodiments, the base is an alkali metal base. In some embodiments, the base is an alkali metal carbonate. In some embodiments, the base is selected from cesium carbonate, lithium carbonate, sodium carbonate, and potassium carbonate. In some embodiments, the base is potassium carbonate. In some embodiments, from about 1 to about 2 molar equivalents of the compound of formula III-6, or the salt thereof, is utilized relative to the compound of formula III-5, or the salt thereof. In some embodiments, about 1 molar equivalent of the compound of formula III-6, or the salt thereof, is utilized relative to the compound of formula III-5, or the salt thereof. In some embodiments, from about 1 to about 4 molar equivalents of the base is utilized relative to the compound of formula III-5, or the salt thereof. In some embodiments, from about 2 to about 3 molar equivalents of the base is utilized relative to the compound of formula III-5, or the salt thereof. In some embodiments, about 2.5 molar equivalents of the base is utilized relative to the compound of formula III-5, or the salt thereof. In some embodiments, from about 0.001 to about 0.1 molar equivalents of the Suzuki catalyst is utilized relative to the compound of formula III-5, or the salt thereof. In some embodiments, from about 0.001 to about 0.01 molar equivalents of the Suzuki catalyst is utilized relative to the compound of formula III-5, or the salt thereof. In some embodiments, about 0.008 molar equivalent of the Suzuki catalyst is utilized relative to the compound of formula III-5, or the salt thereof.

In some embodiments, the reacting of the compound of formula III-5, or the salt thereof, with the compound of formula III-6, or the salt thereof, is carried out at a temperature of from about 60° C. to about 120° C. In some embodiments, the reacting of the compound of formula III-5, with the compound of formula III-6, or the salt thereof, is carried out at a temperature of about 90° C.

In some embodiments, the reacting of the compound of formula III-5, with the compound of formula III-6, or the salt thereof, is carried out in a solvent component. In some embodiments, the solvent component comprises a polar protic solvent, a di-C$_{1-6}$ alkyl ether, a 4-10 membered heterocycloalkyl ether, or a mixture thereof. In some embodiments, the solvent component comprises water and 1,4-dioxane.

In some embodiments, the salt of Formula A-1a is converted to a compound of Formula A-1 by a process comprising treating the salt of Formula A-1a with a weak acid resin. In some embodiments, the weak acid resin is an ion exchange resin. In some embodiments, the ion exchange resin is Dowex MAC-3 hydrogen form. For example, Dowex MAC-3 hydrogen form can be purchased commercially (AmberLite®, Sigma-Aldrich cat. #546976).

In some embodiments, each R$^3$ is H. In some embodiments, X$^1$ is bromo.

In some embodiments, the process described herein comprises:

reacting a compound of formula III-5b:

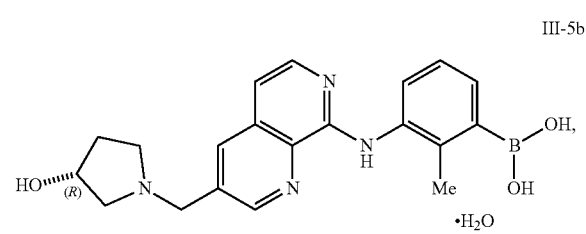

III-5b with a salt of formula III-6b:

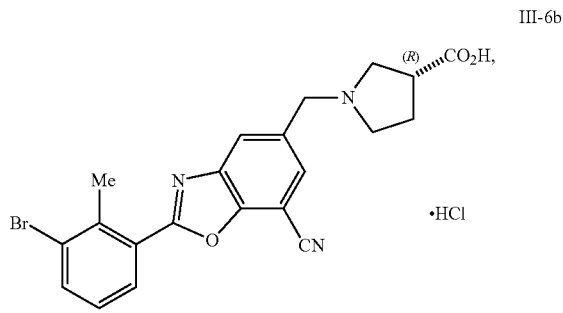

III-6b in the presence of a Suzuki catalyst and a base to form a salt of formula A-1a:

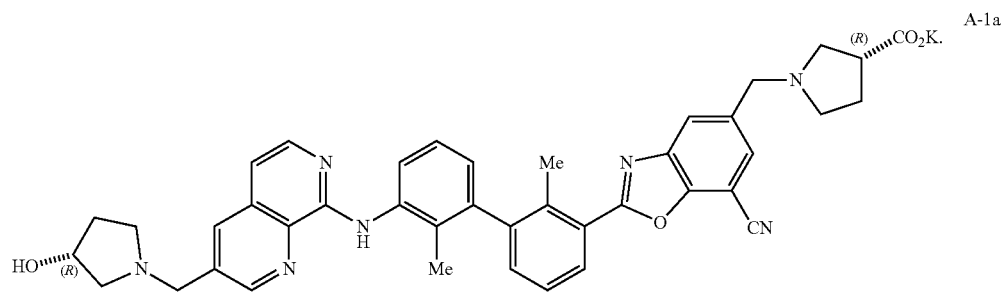

A-1a

Provided herein is a process of preparing (R)-1-((7-cyano-2-(3'-((3-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid, or a salt thereof, comprising:

reacting a compound of formula III-5:

III-5 or a salt thereof, with a compound of formula IV-1:

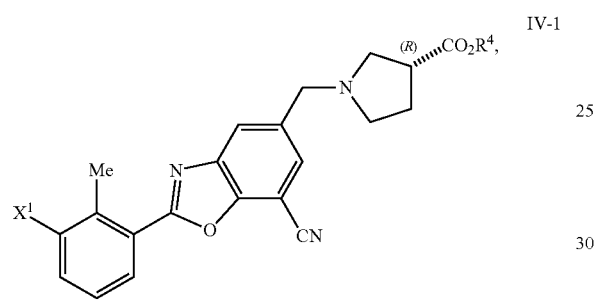

IV-1 or a salt thereof, in the presence of a Suzuki catalyst and a base to form a compound of formula IV-2:

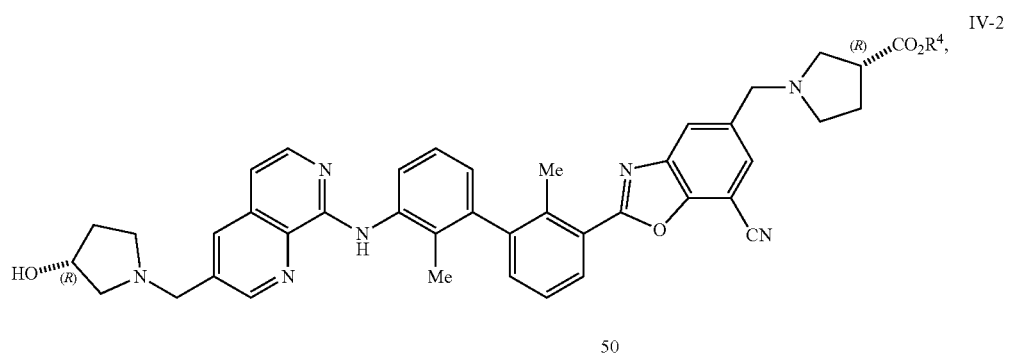

IV-2 or a salt thereof, wherein:

each $R^3$ is independently selected from H and $C_{1-6}$ alkyl; or each $R^3$ together form an $C_{2-3}$ alkylene linker, which is optionally substituted by 1, 2, 3, or 4 independently selected $C_{1-4}$ alkyl groups; and $R^4$ is $C_{1-6}$ alkyl; and $X^1$ is halo.

In some embodiments, each $R^3$ is H. In some embodiments, $R^4$ is t-butyl. In some embodiments, $X^1$ is bromo.

In some embodiments, the compound of formula IV-1, or the salt thereof, is a compound of formula IV-1a:

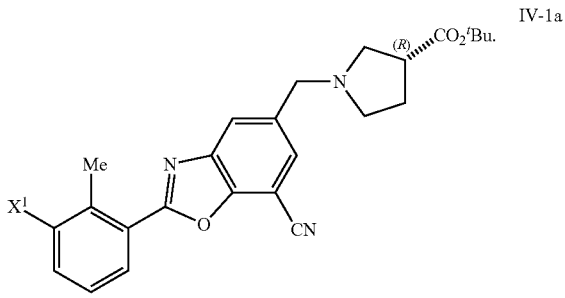

IV-1a

In some embodiments, the compound of formula IV-1, or the salt thereof, is a compound of formula IV-1b:

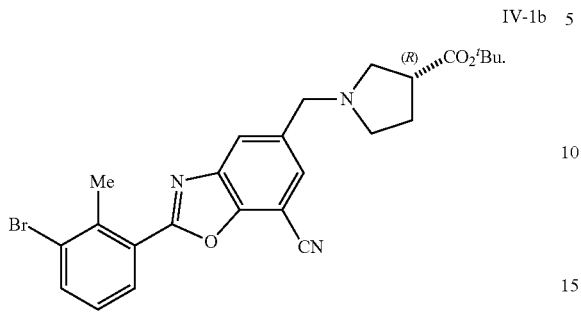

IV-1b

In some embodiments, the compound of formula IV-2, or the salt thereof, is a compound of formula IV-2a:

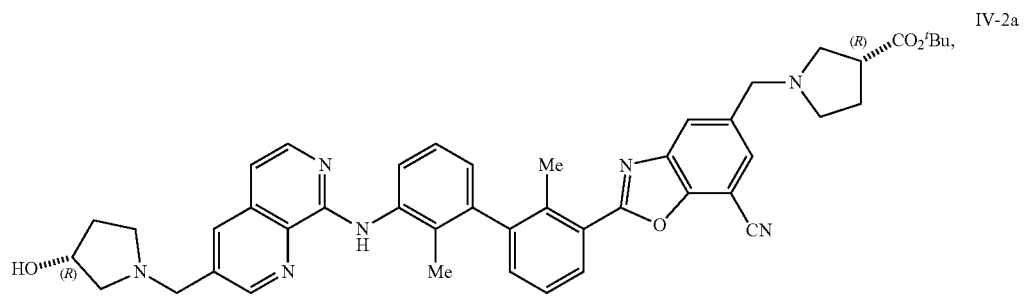

IV-2a or a salt thereof.

In some embodiments, the compound of formula III-5, or the salt thereof, is a salt of formula III-5c:

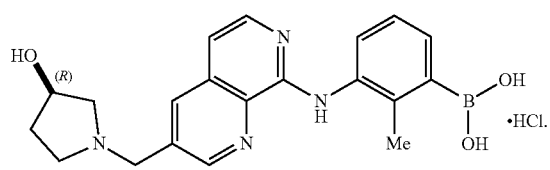

III-5c

In some embodiments, the Suzuki catalyst, present in the reacting of the compound of formula III-5, or the salt thereof, with the compound of formula IV-1, or the salt thereof, is a palladium catalyst. In some embodiments, the Suzuki catalyst, present in the reacting of the compound of formula III-5, or the salt thereof, with the compound of formula IV-1, or the salt thereof, is selected from RuPhos Pd G4, CataCXium® Pd G4, Pd(PPh₃)₄, Pd(dppf)₂Cl₂, dichlorobis[di-tert-butyl(p-dimethylaminophenyl)phosphino]palladium, and PdCl₂(dtbpf) (Pd-118). In some embodiments, the Suzuki catalyst, present in the reacting of the compound of formula III-5, or the salt thereof, with the compound of formula IV-1, or the salt thereof, is RuPhos Pd G4. In some embodiments, the base, present in the reacting of the compound of formula III-5, or the salt thereof, with the compound of formula IV-1, or the salt thereof, is an alkali metal base. In some embodiments, the base, present in the reacting of the compound of formula III-5, or the salt thereof, with the compound of formula IV-1, or the salt thereof, is an alkali metal carbonate. In some embodiments, the base, present in the reacting of the compound of formula III-5, or the salt thereof, with the compound of formula IV-1, or the salt thereof, is selected from cesium carbonate, lithium carbonate, sodium carbonate, and potassium carbonate. In some embodiments, the base, present in the reacting of the compound of formula III-5, or the salt thereof, with the compound of formula IV-1, or the salt thereof, is potassium carbonate. In some embodiments, from about 1 to about 2 molar equivalents of the compound of formula III-5, or the salt thereof, is utilized relative to the compound of formula IV-1, or the salt thereof. In some embodiments, about 1 molar equivalent of the compound of formula III-5, or the salt thereof, is utilized relative to the compound of formula IV-1, or the salt thereof. In some embodiments, from about 1 to about 4 molar equivalents of the base is utilized relative to the compound of formula IV-1, or the salt thereof. In some embodiments, from about 2 to about 4 molar equivalents of the base is utilized relative to the compound of formula IV-1, or the salt thereof. In some embodiments, about 3 molar equivalents of the base is utilized relative to the compound of formula IV-1, or the salt thereof. In some embodiments, from about 0.001 to about 0.1 molar equivalents of the Suzuki catalyst is utilized relative to the compound of formula IV-1, or the salt thereof. In some embodiments, from about 0.005 to about 0.02 molar equivalents of the Suzuki catalyst is utilized relative to the compound of formula IV-1, or the salt thereof. In some embodiments, about 0.01 molar equivalent of the Suzuki catalyst is utilized relative to the compound of formula IV-1, or the salt thereof.

In some embodiments, the reacting of the compound of formula III-5, with the compound of formula IV-1, or the salt thereof, is carried out in a solvent component. In some embodiments, the reacting of the compound of formula III-5, or the salt thereof, with the compound of formula IV-1, or the salt thereof, is carried out in a solvent component, comprising a polar protic solvent. In some embodiments, the reacting of the compound of formula III-5, or the salt thereof, with the compound of formula IV-1, or the salt thereof, is carried out in a solvent component, comprising a $C_{1-6}$ alkanol and water. In some embodiments, the reacting of the compound of formula III-5, or the salt thereof, with the compound of formula IV-1, or the salt thereof, is carried out in a solvent component, comprising water and tert-butanol.

In some embodiments, the reacting of the compound of formula III-5, or the salt thereof, with the compound of formula IV-1, or the salt thereof, is carried out at a temperature of from about 60° C. to about 100° C. In some embodiments, the reacting of the compound of formula III-5, or the salt thereof, with the compound of formula IV-1, or the salt thereof, is carried out at a temperature of about 80° C. In some embodiments, the reacting of the compound of formula III-5, or the salt thereof, with the compound of formula IV-1, or the salt thereof, is carried out at a reflux temperature of water and tert-butanol.

In some embodiments, the process further comprises deprotecting the compound of formula IV-2, or the salt thereof, to form (R)-1-((7-cyano-2-(3'-((3-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid, or the salt thereof.

In some embodiments, the deprotecting of the compound of formula IV-2, or the salt thereof, is performed in the presence of a Lewis acid. In some embodiments, the Lewis acid present in the deprotecting of the compound of formula IV-2, or the salt thereof, is trimethylsilyl triflate.

In some embodiments, the process comprises:
reacting a salt of formula III-5c:

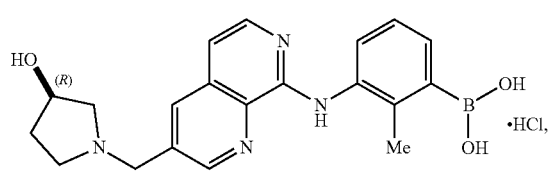

with a compound of formula IV-1:

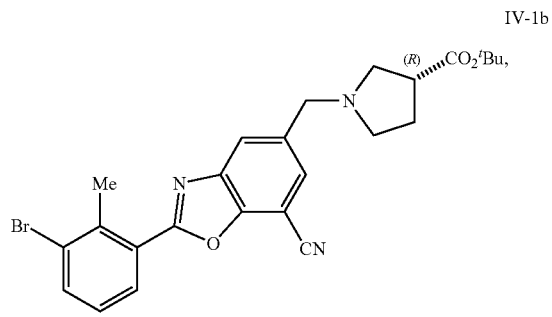

or a salt thereof, in the presence of a Suzuki catalyst and a base to form a compound of formula IV-2a:

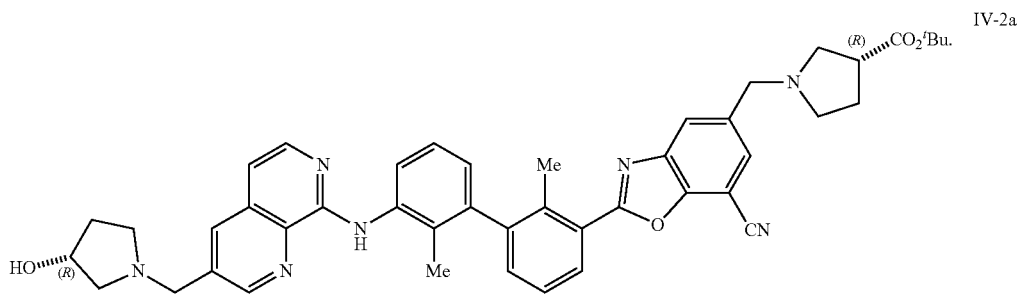

Provided herein is a process of preparing (R)-1-((7-cyano-2-(3'-((3-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid, or a salt thereof, comprising:

reacting a compound of formula V-1:

V-1 or a salt thereof, with a compound of formula V-2:

V-2 or a salt thereof, in the presence of a Suzuki catalyst and a base to form a compound of formula IV-2:

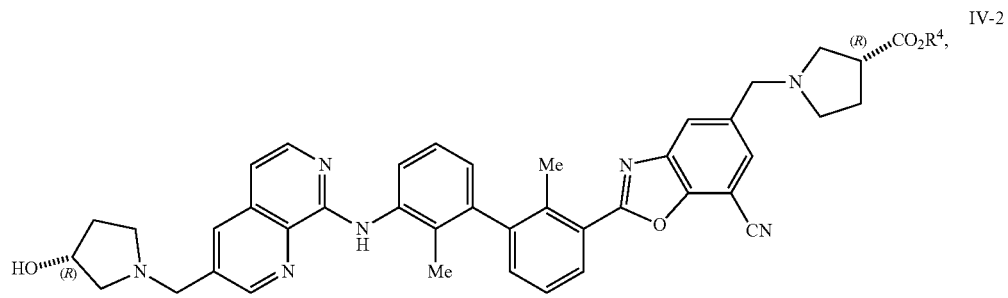

or a salt thereof, wherein:

each $R^1$ is independently selected from H and $C_{1-6}$ alkyl; or each $R^1$ together form an $C_{2-3}$ alkylene linker, which is optionally substituted by 1, 2, 3, or 4 independently selected $C_{1-4}$ alkyl groups;

$X^2$ is halo; and $R^4$ is $C_{1-6}$ alkyl.

In some embodiments, $R^4$ is t-butyl. In some embodiments, $X^2$ is bromo. In some embodiments, each $R^1$ together form a $C_2$ alkylene linker substituted with four methyl groups.

In some embodiments, the compound of formula V-1, or the salt thereof, is a compound of formula V-1a:

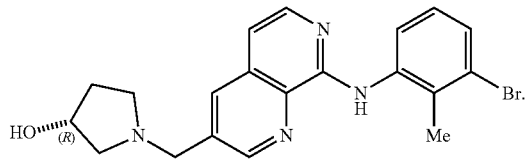

In some embodiments, the compound of formula V-2, or the salt thereof, is a compound of formula V-2a:

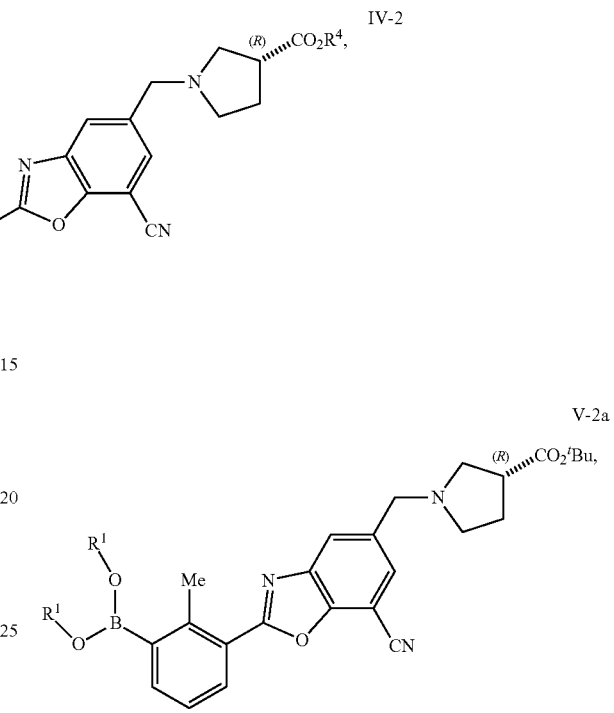

or a salt thereof.

In some embodiments, the compound of formula V-2, or the salt thereof, is a compound of formula V-2b:

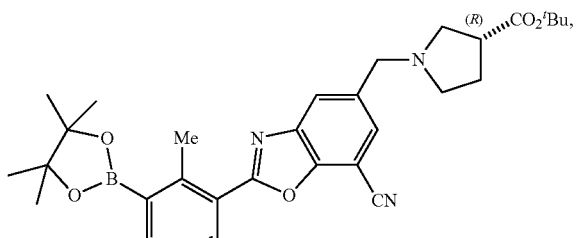

or a salt thereof.

In some embodiments, the compound of formula IV-2 is a compound of formula IV-2a:

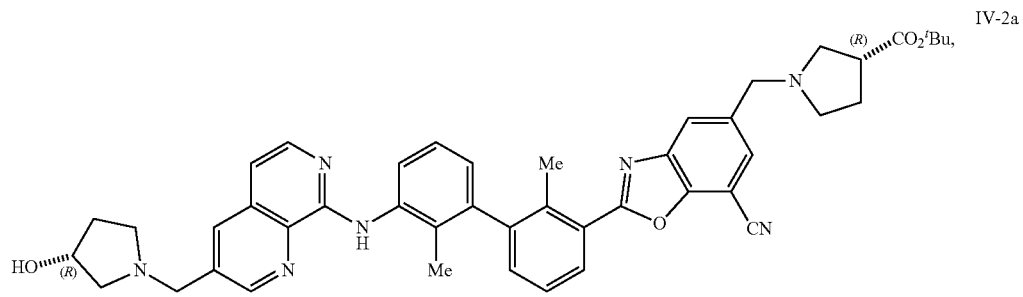

or a salt thereof.

In some embodiments, the Suzuki catalyst, present in the reacting of the compound of formula V-1, or the salt thereof, with the compound of formula V-2, or the salt thereof, is a palladium catalyst. In some embodiments, the Suzuki catalyst, present in the reacting of the compound of formula V-1, or the salt thereof, with the compound of formula V-2, or the salt thereof, is selected from RuPhos Pd G4, CataCXium® Pd G4, Pd(PPh$_3$)$_4$, Pd(dppf)$_2$Cl$_2$, dichlorobis[di-tert-butyl (p-dimethylaminophenyl)phosphino]palladium, and PdCl$_2$ (dtbpf) (Pd-118). In some embodiments, the Suzuki catalyst, present in the reacting of the compound of formula V-1, or the salt thereof, with the compound of formula V-2, or the salt thereof, is Pd(dppf)$_2$Cl$_2$. In some embodiments, the base, present in the reacting of the compound of formula V-1, or the salt thereof, with the compound of formula V-2, or the salt thereof, is an alkali metal base. In some embodiments, the base, present in the reacting of the compound of formula V-1, or the salt thereof, with the compound of formula V-2, or the salt thereof, is an alkali metal phosphate. In some embodiments, the base present in the reacting of the compound of formula V-1, or the salt thereof, with the compound of formula V-2, or the salt thereof, is selected from cesium phosphate, lithium phosphate, sodium phosphate, and potassium phosphate. In some embodiments, the base, present in the reacting of the compound of formula V-1, or the salt thereof, with the compound of formula V-2, or the salt thereof, is potassium phosphate. In some embodiments, from about 1 to about 2 molar equivalents of the compound of formula V-2, or the salt thereof, is utilized relative to the compound of formula V-1, or the salt thereof. In some embodiments, about 1 molar equivalent of the compound of formula V-2, or the salt thereof, is utilized relative to the compound of formula V-1, or the salt thereof. In some embodiments, from about 1 to about 4 molar equivalents of the base is utilized relative to the compound of formula V-1, or the salt thereof. In some embodiments, from about 2 to about 4 molar equivalents of the base is utilized relative to the compound of formula V-1, or the salt thereof. In some embodiments, about 3 molar equivalents of the base is utilized relative to the compound of formula V-1, or the salt thereof. In some embodiments, from about 0.001 to about 0.1 molar equivalents of the Suzuki catalyst is utilized relative to the compound of formula V-1, or the salt thereof. In some embodiments, from about 0.01 to about 0.03 molar equivalents of the Suzuki catalyst is utilized relative to the compound of formula V-1, or the salt thereof. In some embodiments, about 0.025 molar equivalent of the Suzuki catalyst is utilized relative to the compound of formula V-1, or the salt thereof.

In some embodiments, the reacting of the compound of formula V-1, with the compound of formula V-2, or the salt thereof, is carried out at a temperature of from about 60° C. to about 100° C. In some embodiments, the reacting of the compound of formula V-1, with the compound of formula V-2, or the salt thereof, is carried out at a temperature of about 80° C.

In some embodiments, the reacting of the compound of formula V-1, or the salt thereof, with the compound of formula V-2, or the salt thereof, is carried out in a solvent component. In some embodiments, the reacting of the compound of formula V-1, or the salt thereof, with the compound of formula V-2, or the salt thereof, is carried out in a solvent component comprising a polar protic solvent, a di-C$_{1-6}$ alkyl ether, a 4-10 membered heterocycloalkyl ether, or a mixture thereof. In some embodiments, the reacting of the compound of formula V-1, or the salt thereof, with the compound of formula V-2, or the salt thereof, is carried out in a solvent component comprising water and 1,4-dioxane.

In some embodiments, the process further comprises deprotecting the compound of formula IV-2, or the salt thereof, to form to (R)-1-((7-cyano-2-(3'-((3-(((R)-3-hydroxypyrrolidin-1-yl)methyl)-1,7-naphthyridin-8-yl) amino)-2,2'-dimethyl-[1,1'-biphenyl]-3-yl)benzo[d]oxazol-5-yl)methyl)pyrrolidine-3-carboxylic acid, or the salt thereof. In some embodiments, the deprotecting of the compound of formula IV-2, or the salt thereof, is performed in the presence of a Lewis acid. In some embodiments, the Lewis acid present in the deprotecting of the compound of formula IV-2, or the salt thereof, is trimethylsilyl triflate or trimethylsilyl iodide.

In some embodiments, the process comprises:

reacting a compound of formula V-1a:

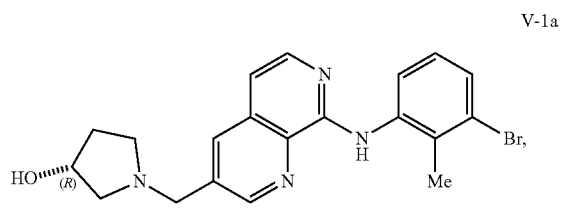

V-1a with a compound of formula V-2b:

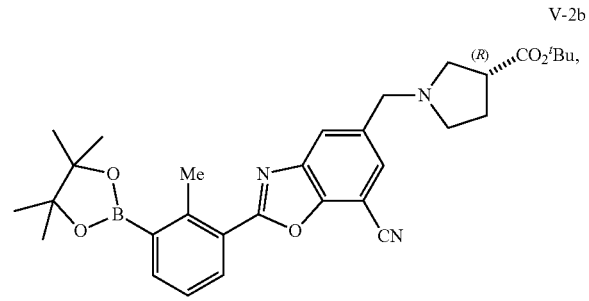

V-2b in the presence of a Suzuki catalyst and a base to form a compound of formula IV-2a:

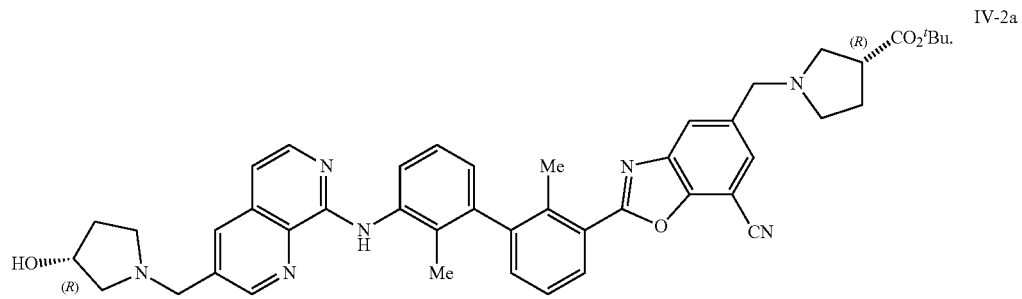

In some embodiments, the compound of formula V-2, or the salt thereof, is prepared by a process comprising:
converting a compound of formula IV-1:

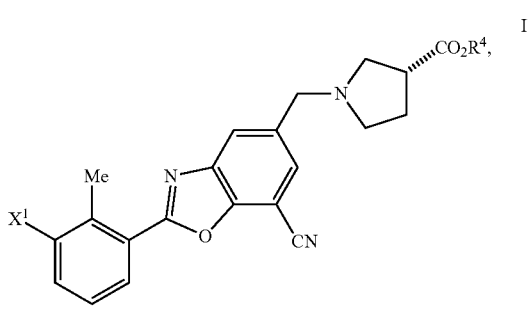

or the salt thereof, with a borylating agent to form the compound of formula V-2, or the salt thereof, wherein $X^1$ is halo; and $R^4$ is $C_{1-6}$ alkyl. In some embodiments, $X^1$ is bromo. In some embodiments, $R^4$ is t-butyl.

In some embodiments, the compound of formula V-2b, or the salt thereof, is prepared by a process comprising:
reacting a compound of formula IV-1b:

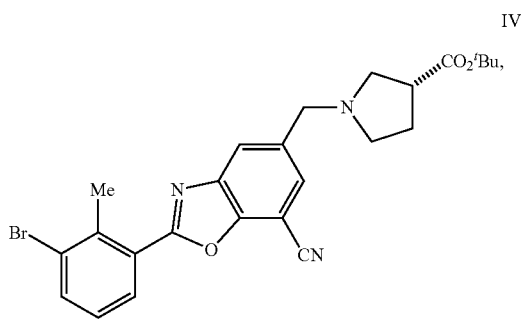

or the salt thereof, with 4,4,4',4',5,5,5',5'-octamethyl-2,2'-bi (1,3,2-dioxaborolane) to form the compound of formula V-2b. In some embodiments, the reacting of the compound of formula IV-1 or IV-1b, or the salt thereof, with the borylating agent or the 4,4,4',4',5,5,5',5'-octamethyl-2,2'-bi (1,3,2-dioxaborolane) is carried out in the presence of a catalyst and a base.

In some embodiments, the catalyst, present in the reacting of the compound of formula IV-1 or IV-1b, or the salt thereof, with the borylating agent or the 4,4,4',4',5,5,5',5'-octamethyl-2,2'-bi(1,3,2-dioxaborolane), is a palladium catalyst. In some embodiments, the catalyst, present in the reacting of the compound of formula IV-1 or IV-1b, or the salt thereof, with the borylating agent or the 4,4,4',4',5,5,5', 5'-octamethyl-2,2'-bi(1,3,2-dioxaborolane), is selected from RuPhos Pd G4, CataCXium® Pd G4, Pd(PPh$_3$)$_4$, Pd(dppf)$_2$Cl$_2$, dichlorobis[di-tert-butyl(p-dimethylaminophenyl)phosphino]palladium, and PdCl$_2$(dtbpf) (Pd-118). In some embodiments, the catalyst, present in the reacting of the compound of formula IV-1 or IV-1b, or the salt thereof, with the borylating agent or the 4,4,4',4',5,5,5',5'-octamethyl-2,2'-bi(1,3,2-dioxaborolane), is Pd(dppf)$_2$Cl$_2$. In some embodiments, the base, present in the reacting of the compound of formula IV-1 or IV-1b, or the salt thereof, with the borylating agent or the 4,4,4',4',5,5,5',5'-octamethyl-2,2'-bi (1,3,2-dioxaborolane), is an alkali metal base. In some embodiments, the base is an alkali metal acetate. In some embodiments, the base, present in the reacting of the compound of formula IV-1 or IV-1b, or the salt thereof, with the borylating agent or the 4,4,4',4',5,5,5',5'-octamethyl-2,2'-bi (1,3,2-dioxaborolane), is selected from cesium acetate, lithium acetate, sodium acetate, and potassium acetate. In some embodiments, the base, present in the reacting of the compound of formula IV-1 or IV-1b, or the salt thereof, with the borylating agent or the 4,4,4',4',5,5,5',5'-octamethyl-2, 2'-bi(1,3,2-dioxaborolane), is potassium acetate. In some embodiments, from about 1 to about 2 molar equivalents of the borylating agent or the 4,4,4',4',5,5,5',5'-octamethyl-2, 2'-bi(1,3,2-dioxaborolane) is utilized relative to the compound of formula IV-1 or IV-1b, or the salt thereof. In some embodiments, about 1 molar equivalent of the borylating agent or the 4,4,4',4',5,5,5',5'-octamethyl-2,2'-bi(1,3,2-dioxaborolane) is utilized relative to the compound of formula IV-1 or IV-1b, or the salt thereof. In some embodiments, from about 1 to about 4 molar equivalents of the base is utilized relative to the compound of formula IV-1 or IV-1b, or the salt thereof. In some embodiments, from about 2 to about 4 molar equivalents of the base is utilized relative to the compound of formula IV-1 or IV-1b, or the salt thereof. In some embodiments, about 3 molar equivalents of the base is utilized relative to the compound of formula IV-1 or IV-1b, or the salt thereof. In some embodiments, from about 0.001 to about 0.1 molar equivalents of the catalyst is utilized relative to the compound of formula IV-1 or IV-1b, or the salt thereof. In some embodiments, from about 0.01 to about 0.03 molar equivalents of the catalyst is utilized relative to the compound of formula IV-1 or IV-1b, or the salt thereof. In some embodiments, about 0.02 molar equivalent of the catalyst is utilized relative to the compound of formula IV-1 or IV-1b, or the salt thereof.

In some embodiments, the reacting of the compound of formula IV-1 or IV-1b, or the salt thereof, with the borylating agent or the 4,4,4',4',5,5,5',5'-octamethyl-2,2'-bi(1,3,2-dioxaborolane), is carried out at a temperature of from about 80° C. to about 120° C. In some embodiments, the reacting of the compound of formula IV-1 or IV-1b, or the salt thereof, with the borylating agent or the 4,4,4',4',5,5,5',5'-octamethyl-2,2'-bi(1,3,2-dioxaborolane), is carried out at a temperature of about 100° C.

In some embodiments, the reacting of the compound of formula IV-1 or IV-1b, or the salt thereof, with the borylating agent or the 4,4,4',4',5,5,5',5'-octamethyl-2,2'-bi(1,3,2-dioxaborolane), is carried out in a solvent component. In some embodiments, the reacting of the compound of formula IV-1 or IV-1b, or the salt thereof, with the borylating agent or the 4,4,4',4',5,5,5',5'-octamethyl-2,2'-bi(1,3,2-dioxaborolane), is carried out in a solvent component comprising a polar protic solvent, a di-$C_{1-6}$ alkyl ether, a 4-10 membered heterocycloalkyl ether, or a mixture thereof. In some embodiments, the reacting of the compound of formula IV-1 or IV-1b, or the salt thereof, with the borylating agent or the 4,4,4',4',5,5,5',5'-octamethyl-2,2'-bi(1,3,2-dioxaborolane), is carried out in a solvent component comprising water and 1,4-dioxane.

Provided herein is a process of preparing (R)-1-((7-cyano-2-(3'-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid, or a salt thereof, comprising:

reacting a compound of formula VI-1:

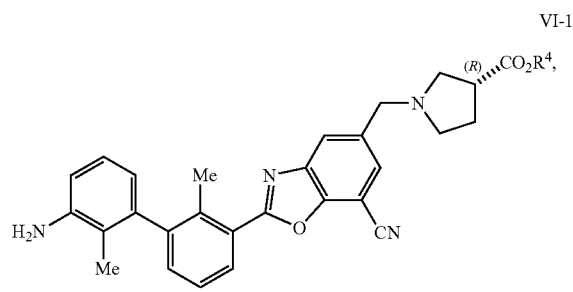

VI-1 or a salt thereof, with a compound of formula III-3:

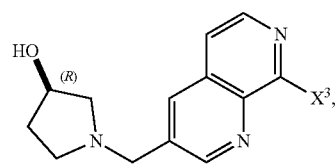

III-3 or a salt thereof,
in the presence of a catalyst to form a compound of formula IV-2:

or a salt thereof, wherein $X^3$ is halo; and $R^4$ is $C_{1-6}$ alkyl. In some embodiments, $X^3$ is chloro. In some embodiments, $R^4$ is t-butyl.

In some embodiments, the compound of formula VI-1, or the salt thereof, is a compound of formula VI-1a:

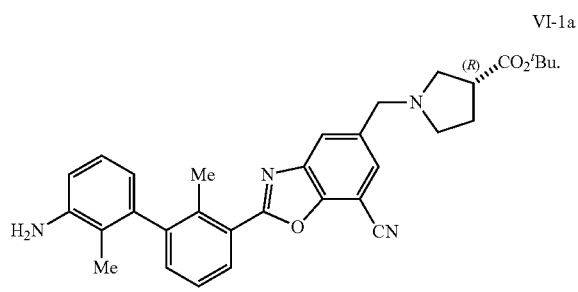

VI-1a

In some embodiments, the compound of formula III-3, or the salt thereof, is a compound of formula III-3a:

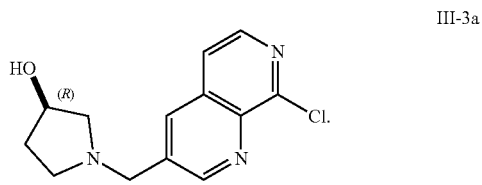

III-3a

In some embodiments, the compound of formula IV-2, or the salt thereof, is a compound of formula IV-2a:

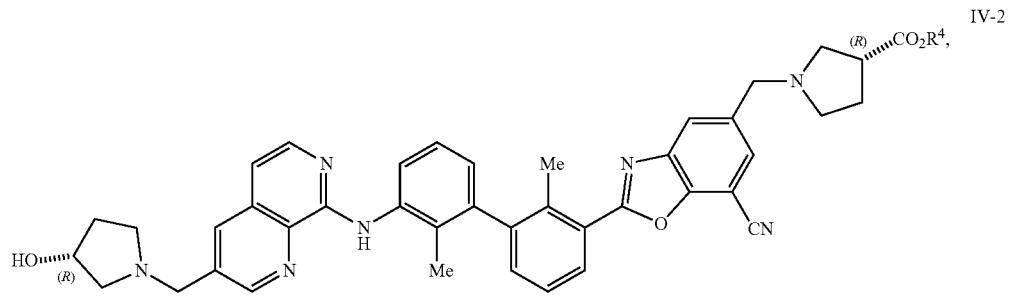

IV-2

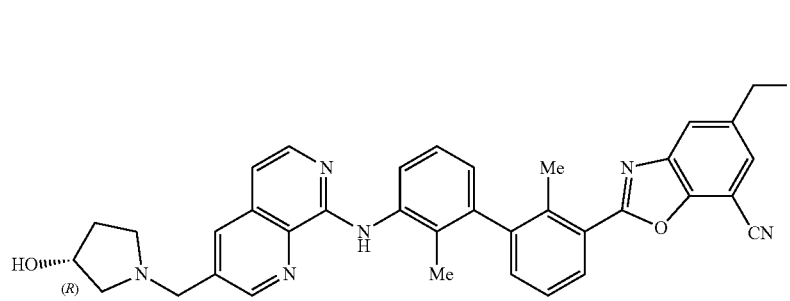

IV-2a or a salt thereof.

In some embodiments, the catalyst, present in the reacting of the compound of formula VI-1, or the salt thereof, with the compound of formula III-3, or the salt thereof, is a Lewis acid. In some embodiments, the catalyst, present in the reacting of the compound of formula VI-1, or the salt thereof, with the compound of formula III-3, or the salt thereof, is scandium triflate. In some embodiments, from about 1 to about 4 molar equivalents of the compound of formula III-3, or the salt thereof, is utilized relative to the compound of formula VI-1, or the salt thereof. In some embodiments, from about 1 to about 2 molar equivalents of the compound of formula III-3, or the salt thereof, is utilized relative to the compound of formula VI-1, or the salt thereof. In some embodiments, about 1 molar equivalent of the compound of formula III-3, or the salt thereof, is utilized relative to the compound of formula VI-1, or the salt thereof. In some embodiments, from about 1 to about 4 molar equivalents of the catalyst is utilized relative to the compound of formula VI-1, or the salt thereof. In some embodiments, from about 1 to about 2 molar equivalents of the catalyst is utilized relative to the compound of formula VI-1, or the salt thereof. In some embodiments, about 1.5 molar equivalents of the catalyst is utilized relative to the compound of formula VI-1, or the salt thereof.

In some embodiments, the reacting of the compound of formula VI-1, or the salt thereof, with the compound of formula III-3, or the salt thereof, is carried out at a temperature of from about 60° C. to about 100° C. In some embodiments, the reacting of the compound of formula VI-1, or the salt thereof, with the compound of formula III-3, or the salt thereof, is carried out at a temperature of about 100° C.

In some embodiments, the reacting of the compound of formula VI-1, or the salt thereof, with the compound of formula III-3, or the salt thereof, is carried out in a solvent component. In some embodiments, the reacting of the compound of formula VI-1, or the salt thereof, with the compound of formula III-3, or the salt thereof, is carried out in a solvent component comprising a polar protic solvent, a di-$C_{1-6}$ alkyl ether, a 4-10 membered heterocycloalkyl ether, or a mixture thereof. In some embodiments, the reacting of the compound of formula VI-1, or the salt thereof, with the compound of formula III-3, or the salt thereof, is carried out in a solvent component comprising water and 1,4-dioxane.

In some embodiments, the process further comprises deprotecting the compound of formula IV-2, or the salt thereof, process to form (R)-1-((7-cyano-2-(3'-((3-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid, or the salt thereof. In some embodiments, the deprotecting of the compound of formula IV-2, or the salt thereof, is performed in the presence of a Lewis acid. In some embodiments, the Lewis acid, present in the deprotecting of the compound of formula IV-2, or the salt thereof, is trimethylsilyl triflate or trimethylsilyl iodide.

In some embodiments, the process comprises:

reacting a compound of formula VI-1a:

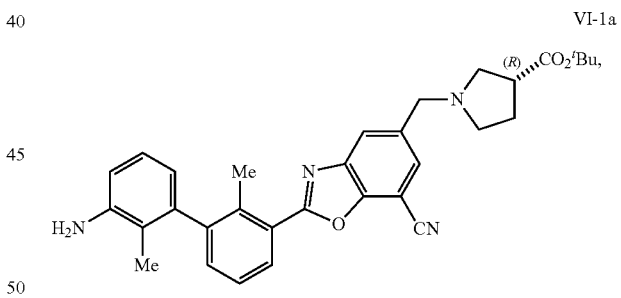

VI-1a with a salt of formula III-3b:

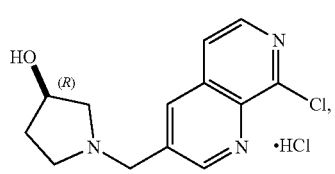

III-3b in the presence of a Lewis acid catalyst to form a compound of formula IV-2a:

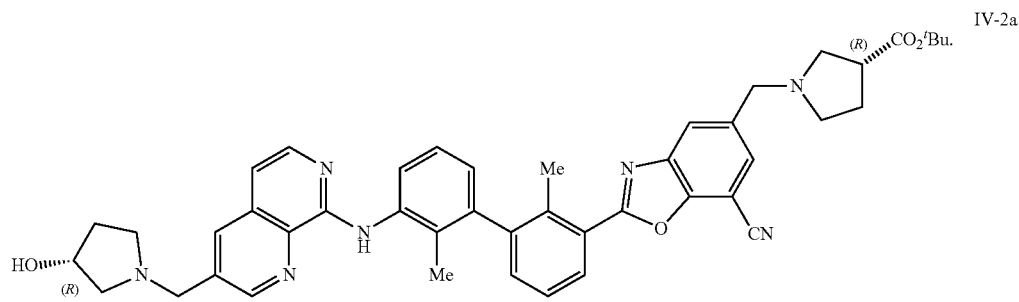

In some embodiments, the compound of formula VI-1, or the salt thereof, is prepared by a process comprising:

reacting a compound of formula IV-1:

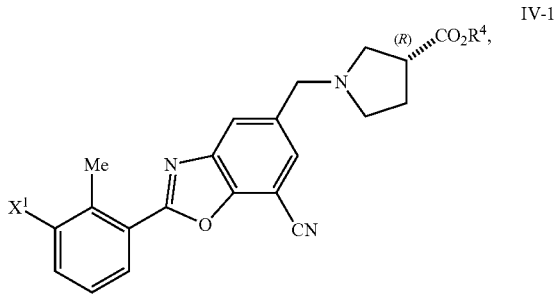

or a salt thereof, with a compound of formula III-4:

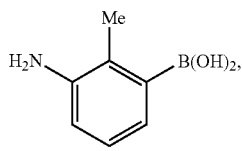

or a salt thereof, in the presence of a Suzuki catalyst and a base to form a compound of formula VI-1, or the salt thereof; wherein $X^1$ is halo; and $R^4$ is $C_{1-6}$ alkyl. In some embodiments, $X^1$ is bromo. In some embodiments, $R^4$ is t-butyl.

In some embodiments, the compound of formula IV-1, or the salt thereof, is a compound of formula IV-1b:

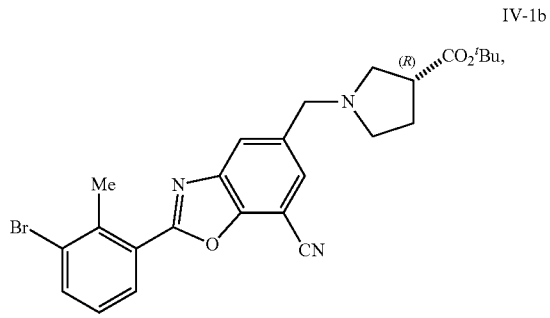 [SMILES: Cc1c(Br)cccc1-c1nc2cc(CN3CC[C@@H](C(=O)OC(C)(C)C)C3)cc(C#N)c2o1]

or a salt thereof.

In some embodiments, the Suzuki catalyst, present in the reacting of the compound formula IV-1, or the salt thereof, with the compound of formula III-4, or the salt thereof, is a palladium catalyst. In some embodiments, the Suzuki catalyst, present in the reacting of the compound formula IV-1, or the salt thereof, with the compound of formula III-4, or the salt thereof, is selected from CataCXium® Pd G4, Pd(PPh$_3$)$_4$, Pd(dppf)$_2$Cl$_2$, dichlorobis[di-tert-butyl(p-dimethylaminophenyl)phosphino]palladium, and PdCl$_2$(dtbpf) (Pd-118). In some embodiments, the Suzuki catalyst, present in the reacting of the compound formula IV-1, or the salt thereof, with the compound of formula III-4, or the salt thereof, is PdCl$_2$(dtbpf) (Pd-118). In some embodiments, the base, present in the reacting of the compound formula IV-1, or the salt thereof, with the compound of formula III-4, or the salt thereof, is an alkali metal base. In some embodiments, the base, present in the reacting of the compound formula IV-1, or the salt thereof, with the compound of formula III-4, or the salt thereof, is an alkali metal phosphate. In some embodiments, the base, present in the reacting of the compound formula IV-1, or the salt thereof, with the compound of formula III-4, or the salt thereof, is potassium phosphate dibasic. In some embodiments, from about 1 to about 2 molar equivalents of the compound of formula III-4, or the salt thereof, is utilized relative to the compound of formula IV-1, or the salt thereof. In some embodiments, from about 1 to about 1.5 molar equivalents of the compound of formula III-4, or the salt thereof, is utilized relative to the compound of formula IV-1, or the salt thereof. In some embodiments, about 1 molar equivalent of the compound of formula III-4, or the salt thereof, is utilized relative to the compound of formula IV-1, or the salt thereof. In some embodiments, from about 1 to about 9 molar equivalents of the base is utilized relative to the compound of formula IV-1, or the salt thereof. In some embodiments, from about 3 to about 5 molar equivalents of the base is utilized relative to the compound of formula IV-1, or the salt thereof. In some embodiments, about 4 molar equivalents of the base is utilized relative to the compound of formula IV-1, or the salt thereof. In some embodiments, from about 0.005 to about 0.015 molar equivalents of the Suzuki catalyst is utilized relative to the compound of formula IV-1, or the salt thereof. In some embodiments, about 0.009 molar equivalent of the Suzuki catalyst is utilized relative to the compound of formula IV-1, or the salt thereof.

In some embodiments, the reacting of the compound of formula IV-1, or the salt thereof, with a compound of formula III-4, or the salt thereof, is carried out at a temperature of from about 70° C. to about 100° C. In some embodiments, the reacting of the compound of formula IV-1, or the salt thereof, with the compound of formula III-4, or the salt thereof, is carried out at a temperature of about 80° C.

In some embodiments, the reacting of the compound of IV-1, or the salt thereof, with the compound of formula III-4, or the salt thereof, is carried out in a solvent component. In some embodiments, the reacting of the compound of IV-1, or the salt thereof, with the compound of formula III-4, or the salt thereof, is carried out in a solvent component comprising a polar protic solvent. In some embodiments, the reacting of the compound of IV-1, or the salt thereof, with the compound of formula III-4, or the salt thereof, is carried out in a solvent component comprising a $C_{1-6}$ alkanol, water, or a mixture thereof. In some embodiments, the reacting of the compound of IV-1, with the compound of formula III-4, or the salt thereof, is carried out in a solvent component comprising water and tert-butanol.

In some embodiments, the compound of Formula III-5, or the salt thereof, is a compound of formula III-5a:

III-5a

In some embodiments, the compound of Formula III-5, or the salt thereof, is a compound of formula III-5b:

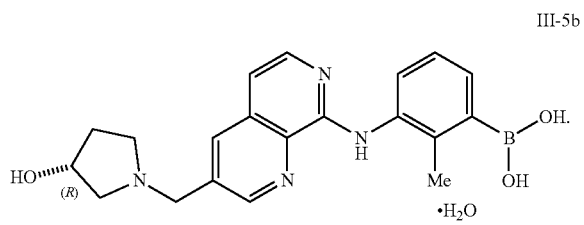

III-5b

In some embodiments, the compound of Formula III-6, or the salt thereof, is a salt of formula III-6b:

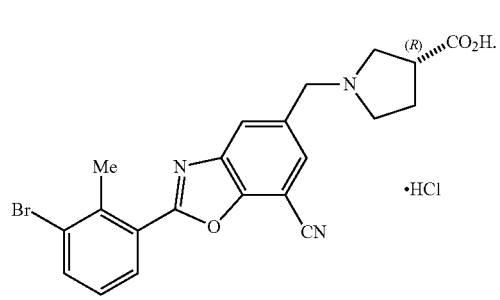

III-6b

In some embodiments, the compound of Formula III-5a is prepared by a process comprising:
reacting a compound of formula III-3:

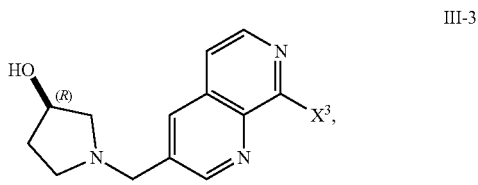

III-3 or the salt thereof, with a compound of formula III-4:

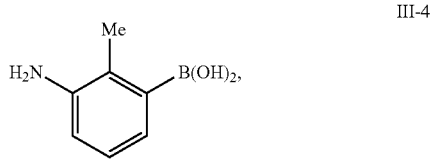 [SMILES: Cc1c(N)cccc1B(O)O]

III-4 or the salt thereof, in the presence of a base, to form the compound of formula III-5a, wherein $X^3$ is halo. In some embodiments, $X^3$ is chloro.

In some embodiments, the base, present in the reacting of the compound of formula III-3, or the salt thereof, with the compound of formula III-4, or the salt thereof, is an alkali metal base. In some embodiments, the base, present in the reacting of the compound of formula III-3, or the salt thereof, with the compound of formula III-4, or the salt thereof, is an alkali metal hydroxide. In some embodiments, the base, present in the reacting of the compound of formula III-3, or the salt thereof, with the compound of formula III-4, or the salt thereof, alkali metal hydroxide is selected from lithium hydroxide, sodium hydroxide, potassium hydroxide, rubidium hydroxide and cesium hydroxide. In some embodiments, the base, present in the reacting of the compound of formula III-3, or the salt thereof, with the compound of formula III-4, or the salt thereof, is sodium hydroxide. In some embodiments, from about 1 to about 3 molar equivalents of the compound of formula III-4, or the salt thereof, is utilized relative to the compound of formula III-3 or the salt thereof. In some embodiments, from about 1 to about 2 molar equivalents of the compound of formula III-4, or the salt thereof, is utilized relative to the compound of formula III-3 or the salt thereof. In some embodiments, about 1 molar equivalent of the compound of formula III-4, or the salt thereof, is utilized relative to the compound of formula III-3 or the salt thereof. In some embodiments, from about 1 to about 2 molar equivalents of the base is utilized relative to the compound of formula III-3 or the salt thereof. In some embodiments, about 1 molar equivalent of the base is utilized relative to the compound of formula III-3 or the salt thereof.

In some embodiments, the reacting of the compound of formula III-3, or the salt thereof, with the compound of formula III-4 or the salt thereof, is carried out at a temperature of from about 80° C. to about 120° C. In some embodiments, the reacting of the compound of formula III-3, or the salt thereof, with the compound of formula III-4, or the salt thereof, is carried out at a temperature of from about 90° C. to about 100° C.

In some embodiments, the reacting of the compound of formula III-3, or the salt thereof, with the compound of formula III-4, or the salt thereof, is carried out in a solvent component. In some embodiments, the reacting of the compound of formula III-3, or the salt thereof, with the compound of formula III-4, or the salt thereof, is carried out in a solvent component comprising a polar protic solvent. In some embodiments, the reacting of the compound of formula III-3, or the salt thereof, with the compound of formula III-4, or the salt thereof, is carried out in a solvent component comprising water.

In some embodiments, the compound of formula III-3, or the salt thereof, is a salt of formula III-3b:

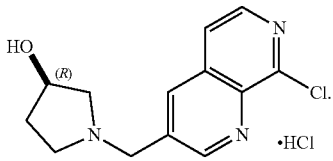

III-3b

In some embodiments, the compound of formula III-4, or the salt thereof, is a salt of formula III-4a:

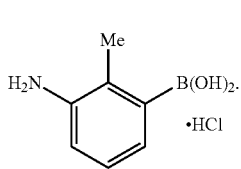

III-4a

In some embodiments, the compound of Formula III-5a is prepared by a process comprising:
reacting a salt of formula III-3a:

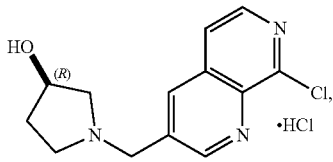

III-3a with a salt of formula III-4a:

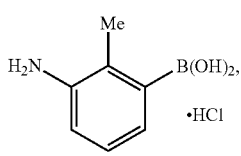

III-4a in the presence of a base to form the compound of formula III-5a.

In some embodiments, the compound of Formula III-3, or the salt thereof, is prepared by a process comprising:
reacting a compound of formula III-1:

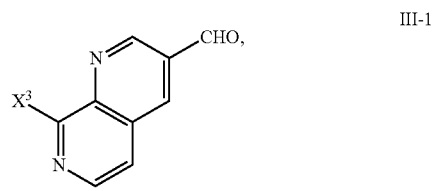

III-1 or a salt thereof, with a compound of formula III-2:

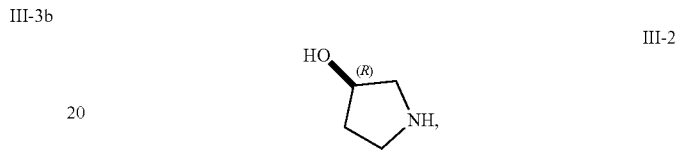

III-2 or a salt thereof, in the presence of a reducing agent to form the compound of formula III-3, or the salt thereof, wherein $X^3$ is halo. In some embodiments, $X^3$ is chloro.

In some embodiments, the compound of formula III-1, or the salt thereof, is a compound of formula III-1a:

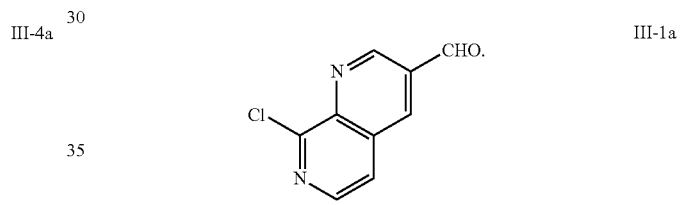

III-1a

In some embodiments, the reducing agent is selected from $NaBH_4$, $NaBH_3CN$ and $NaBH(OAc)_3$. In some embodiments, the reducing agent, present in the reacting of the compound of formula III-1, or the salt thereof, with the compound of formula III-2, or the salt thereof, is $NaBH(OAc)_3$. In some embodiments, the reacting of the compound of formula III-1, or the salt thereof, with the compound of formula III-2, or the salt thereof, is carried out in the presence of a Lewis acid. In some embodiments, the Lewis acid, present in the reacting of the compound of formula III-1, or the salt thereof, with the compound of formula III-2, or the salt thereof, is trimethyl borate. In some embodiments, from about 1 to about 2 molar equivalents of the compound of formula III-2, or the salt thereof, is utilized relative to the compound of formula III-1, or the salt thereof. In some embodiments, about 1 molar equivalent of the compound of formula III-2, or the salt thereof, is utilized relative to the compound of formula III-1, or the salt thereof. In some embodiments, from about 1 to about 2 molar equivalents of the Lewis acid is utilized relative to the compound of formula III-1, or the salt thereof. In some embodiments, about 1 molar equivalent of the Lewis acid is utilized relative to the compound of formula III-1, or the salt thereof. In some embodiments, from about 1 to about 2 molar equivalents of the reducing agent is utilized relative to the compound of formula III-1, or the salt thereof. In some embodiments, about 1 molar equivalent of the reducing agent is utilized relative to the compound of formula III-1, or the salt thereof.

In some embodiments, the reacting of the compound of formula III-1, or the salt thereof, with the compound of formula III-2, or the salt thereof, is carried out at a temperature of from about 10° C. to about 30° C. In some embodiments, the reacting of the compound of formula III-1, or the salt thereof, with the compound of formula III-2, or the salt thereof, is carried out at a temperature of from about 10° C. to about 25° C. In some embodiments, the reacting of the compound of formula III-1, or the salt thereof, with the compound of formula III-2, or the salt thereof, is carried out at a temperature of about 25° C.

In some embodiments, the reacting of the compound of formula III-1, or the salt thereof, with the compound of formula III-2, or the salt thereof, is carried out in a solvent component. In some embodiments, the reacting of the compound of formula III-1, or the salt thereof, with the compound of formula III-2, or the salt thereof, is carried out in a solvent component comprising a $C_{1-6}$ haloalkane, $C_{1-6}$ cyanoalkane, an $C_{1-6}$ alkanol, or a mixture thereof. In some embodiments, the reacting of the compound of formula III-1, or the salt thereof, with the compound of formula III-2, or the salt thereof, is carried out in a solvent component comprising dichloromethane, methanol, acetonitrile, or a mixture thereof.

In some embodiments, the compound of Formula III-2, or the salt thereof, is a salt of formula III-2a:

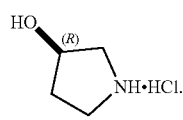

III-2a

In some embodiments, the salt of formula III-2a is reacted with a base to form the compound of formula III-2. In some embodiments, the base, present in the reacting of the salt of formula III-2a, is sodium hydroxide. In some embodiments, the base, present in the reacting of the salt of formula III-2a, is diisopropylethylamine.

In some embodiments, the compound of formula III-1, or the salt thereof, is prepared by a process comprising:

reacting a compound of formula XI-6:

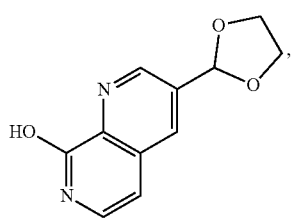

XI-6 or a salt thereof, with a Vilsmeier reagent to form a compound of formula XI-7:

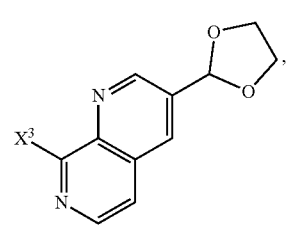

XI-7 or a salt thereof, and deprotecting the compound of formula XI-7, or the salt thereof, to form the compound of formula III-1, or the salt thereof; wherein the Vilsmeier reagent formed from dimethylformamide, wherein $X^3$ is halo. In some embodiments, $X^3$ is chloro.

In some embodiments, the compound of formula XI-7, or the salt thereof, is a compound of formula XI-7a:

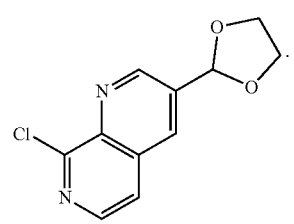

XI-7a

In some embodiments, the Vilsmeier reagent, for reacting with the compound of formula XI-6, or the salt thereof, is prepared by a process comprising reacting dimethylformamide with a chlorinating agent. In some embodiments, the chlorinating agent, for forming the Vilsmeier reagent, is selected from oxalyl chloride, phosphorus oxychloride, diphosgene, thionyl chloride, sulfuryl chloride and phosphorus pentachloride. In some embodiments, the chlorinating agent is oxalyl chloride. In some embodiments, from about 1 to about 4 molar equivalents of the chlorinating agent is utilized relative to the compound of formula XI-6, or the salt thereof. In some embodiments, about 2.5 molar equivalents of the chlorinating agent is utilized relative to the compound of formula XI-6, or the salt thereof.

In some embodiments, the reacting of the compound of formula XI-6, or the salt thereof, with the Vilsmeier reagent is carried out at a temperature of from about 50° C. to about 70° C. In some embodiments, the reacting of the compound of formula XI-6, or the salt thereof, with the Vilsmeier reagent is carried out at a temperature of from about 55° C. to about 65° C.

In some embodiments, the reacting of the compound of formula XI-6 is carried out in a solvent component. In some embodiments, the reacting of the compound of formula XI-6, or the salt thereof, with the Vilsmeier reagent is carried out in a solvent component comprising a $C_{1-6}$ haloalkane. In some embodiments, the reacting of the compound of formula XI-6, or the salt thereof, with the Vilsmeier reagent is carried out in a solvent component comprising 1,2-dichloroethane.

In some embodiments, the compound of formula XI-6, or the salt thereof, is prepared by a process comprising:
reacting a compound of formula XI-5:

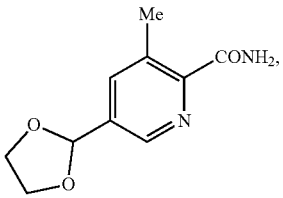

or a salt thereof, with a methylating agent, and
reacting the product of said reacting of the compound of formula XI-5, or the salt thereof, with a strong base to form the compound of formula XI-6.

In some embodiments, the methylating agent, for the reacting with the compound of formula XI-5, or the salt thereof, is N,N-dimethylformamide dimethyl acetal. In some embodiments, the strong base, for the reacting with the product of the reacting of the compound of formula XI-5, or the salt thereof, with the methylating agent, is potassium t-butoxide. In some embodiments, from about 1 to about 2 molar equivalents of the methylating agent is utilized relative to the compound of formula XI-5 or the salt thereof. In some embodiments, about 1.5 molar equivalents of the methylating agent is utilized relative to the compound of formula XI-5 or the salt thereof. In some embodiments, from about 1 to about 2 molar equivalents of the strong base is utilized relative to the compound of formula XI-5 or the salt thereof. In some embodiments, about 1.5 molar equivalents of the strong base is utilized relative to the compound of formula XI-5 or the salt thereof.

In some embodiments, the reacting of the compound of formula XI-5, or the salt thereof, with the methylating agent is carried out at a temperature of from about 50° C. to about 70° C. In some embodiments, the reacting of the compound of formula XI-5, or the salt thereof, with the methylating agent is carried out at a temperature of from about 60° C. to about 65° C.

In some embodiments, the reacting of the compound of formula XI-5, or the salt thereof, with the methylating agent is carried out in a solvent component. In some embodiments, the reacting of the compound of formula XI-5, or the salt thereof, with the methylating agent is carried out in a solvent component comprising di-$C_{1-6}$ alkyl ether or a 4-10 membered heterocycloalkyl ether. In some embodiments, the reacting of the compound of formula XI-5, or the salt thereof, with the methylating agent is carried out in a solvent component comprising tetrahydrofuran.

In some embodiments, the compound of formula XI-5, or the salt thereof, is prepared by a process comprising:
hydrolyzing a compound of formula XI-4:

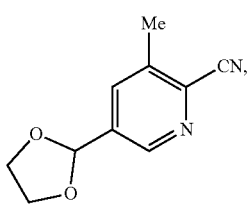

or a salt thereof, to form the compound of formula XI-5, or the salt thereof.

In some embodiments, the hydrolyzing of the compound of formula XI-4, or the salt thereof, is carried out in the presence of a base. In some embodiments, the base, present in the hydrolyzing of the compound of formula XI-4, or the salt thereof, is an alkali metal base. In some embodiments, the base, present in the hydrolyzing of the compound of formula XI-4, or the salt thereof, is an alkali metal hydroxide. In some embodiments, the base, present in the hydrolyzing of the compound of formula XI-4, or the salt thereof, alkali metal hydroxide is selected from lithium hydroxide, sodium hydroxide, potassium hydroxide, rubidium hydroxide, and cesium hydroxide. In some embodiments, the base, present in the hydrolyzing of the compound of formula XI-4, or the salt thereof, is sodium hydroxide. In some embodiments, from about 1 to about 2 molar equivalents of the base is utilized relative to the compound of formula XI-4, or the salt thereof. In some embodiments, about 1 molar equivalent of the base is utilized relative to the compound of formula XI-4, or the salt thereof.

In some embodiments, the hydrolyzing of the compound of formula XI-4, or the salt thereof, is carried out at a temperature of from about 40° C. to about 60° C. In some embodiments, the hydrolyzing of the compound of formula XI-4, or the salt thereof, is carried out at a temperature of about 50° C. In some embodiments, the hydrolyzing of the compound of formula XI-4, or the salt thereof, is carried out in a solvent component. In some embodiments, the hydrolyzing of the compound of formula XI-4, or the salt thereof, is carried out in a solvent component comprising a protic solvent. In some embodiments, the hydrolyzing of the compound of formula XI-4, or the salt thereof, is carried out in a solvent component comprising a $C_{1-6}$ alkanol. In some embodiments, the hydrolyzing of the compound of formula XI-4, or the salt thereof, is carried out in a solvent component comprising ethanol.

In some embodiments, the compound of formula XI-4, or the salt thereof, is prepared by a process comprising:
reacting a compound of formula XI-3:

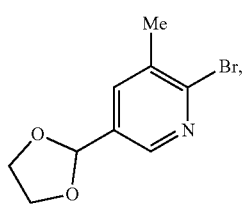

or a salt thereof, with a cyanation reagent to form the compound of formula XI-4, or the salt thereof. In some embodiments, the cyanation reagent, for the reacting of the compound of formula XI-3, or the salt thereof, is a metal nitrile. In some embodiments, the cyanation reagent, for the reacting of the compound of formula XI-3, or the salt thereof, is cuprous cyanide. In some embodiments, from about 1 to about 2 molar equivalents of the cyanation reagent is utilized relative to the compound of formula XI-3, or the salt thereof. In some embodiments, about 1 molar equivalent of the cyanation reagent is utilized relative to the compound of formula XI-3, or the salt thereof.

In some embodiments, the reacting of the compound of formula XI-3, or the salt thereof, with the cyanation reagent is carried out at a temperature of from about 100° C. to about 130° C. In some embodiments, the reacting of the compound of formula XI-3, or the salt thereof, with the cyanation reagent is carried out at a temperature of from about 110° C. to about 120° C. In some embodiments, the reacting of the compound of formula XI-3, or the salt thereof, with the cyanation reagent is carried out in a solvent component. In some embodiments, the reacting of the compound of formula XI-3, or the salt thereof, with the cyanation reagent is carried out in a solvent component comprising a polar aprotic solvent. In some embodiments, the reacting of the compound of formula XI-3, or the salt thereof, with the cyanation reagent is carried out in a solvent component comprising dimethylformamide.

In some embodiments, the compound of formula XI-3, or the salt thereof, is prepared by a process comprising:
reacting a compound of formula XI-2:

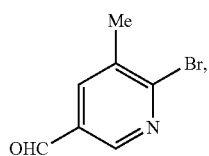

XI-2 or a salt thereof, with ethylene glycol to form the compound of formula XI-3, or the salt thereof. In some embodiments, the reacting of the compound of formula XI-2, or the salt thereof, is carried out in the presence of an acid. In some embodiments, the acid, present in the reacting of the compound of formula XI-2, or the salt thereof, with the ethylene glycol, is p-toluenesulfonic acid. In some embodiments, from about 1 to about 5 molar equivalents of the ethylene glycol is utilized relative to the compound of formula XI-2, or the salt thereof. In some embodiments, from about 2 to about 4 molar equivalents of the ethylene glycol is utilized relative to the compound of formula XI-2, or the salt thereof. In some embodiments, about 1 molar equivalent of the ethylene glycol is utilized relative to the compound of formula XI-2, or the salt thereof. In some embodiments, from about 0.01 to about 0.5 molar equivalents of the acid is utilized relative to the compound of formula XI-2, or the salt thereof. In some embodiments, from about 0.01 to about 0.1 molar equivalents of the acid is utilized relative to the compound of formula XI-2, or the salt thereof. In some embodiments, about 0.05 molar equivalent of the acid is utilized relative to the compound of formula XI-2, or the salt thereof.

In some embodiments, the reacting of the compound of formula XI-2, or the salt thereof, with the ethylene glycol is carried out at a temperature of from about 90° C. to about 130° C. In some embodiments, the reacting of the compound of formula XI-2, or the salt thereof, with the ethylene glycol is carried out at a temperature of about 110° C.

In some embodiments, the reacting of the compound of formula XI-2, or the salt thereof, with the ethylene glycol is carried out in a solvent component. In some embodiments, the reacting of the compound of formula XI-2, or the salt thereof, with the ethylene glycol is carried out in a solvent component comprising an aromatic hydrocarbon. In some embodiments, the reacting of the compound of formula XI-2 with the ethylene glycol is carried out in a solvent component comprising toluene.

In some embodiments, the compound of formula XI-2, or the salt thereof, is prepared by a process comprising:
reacting a compound of formula XI-1:

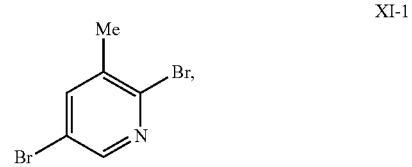

or a salt thereof, with a reagent of formula $R^{11}$—Mg—$X^{11}$; and
reacting the product of said reacting of the compound of XI-1, or the salt thereof, with dimethylformamide to form the compound of formula XI-2, or the salt thereof, wherein:
$R^{11}$ is $C_{1-6}$ alkyl; and
$X^{11}$ is Cl, Br, or I.

In some embodiments, $R^{11}$ is isopropyl. In some embodiments, $X^{11}$ is chloro. In some embodiments, the reagent of formula $R^{11}$—Mg—$X^{11}$ is isopropyl magnesium chloride. In some embodiments, from about 1 to about 2 molar equivalents of the reagent of formula $R^{11}$—Mg—$X^{11}$ is utilized relative to the compound of formula XI-1, or the salt thereof. In some embodiments, about 1.5 molar equivalents of the reagent of formula $R^{11}$—Mg—$X^{11}$ is utilized relative to the compound of formula XI-1, or the salt thereof. In some embodiments, from about 1 to about 5 molar equivalents of dimethylformamide is utilized relative to the compound of formula XI-1, or the salt thereof. In some embodiments, from about 2 to about 4 molar equivalents of dimethylformamide is utilized relative to the compound of formula XI-1, or the salt thereof. In some embodiments, about 3 molar equivalents of dimethylformamide is utilized relative to the compound of formula XI-1, or the salt thereof.

In some embodiments, the reacting of the compound of formula XI-1, or the salt thereof, with the reagent of formula $R^{11}$—Mg—$X^{11}$ is carried out at a temperature of from about 20° C. to about 30° C. In some embodiments, the reacting of the compound of formula XI-1, or the salt thereof, with the reagent of formula $R^{11}$—Mg—$X^{11}$ is carried out in a solvent component. In some embodiments, the reacting of the compound of formula XI-1, or the salt thereof, with the reagent of formula $R^{11}$—Mg—$X^{11}$ is carried out in a solvent component comprising di-$C_{1-6}$ alkyl ether or a 4-10 membered heterocycloalkyl ether. In some embodiments, the reacting of the compound of formula XI-1, or the salt thereof, with the reagent of formula $R^{11}$—Mg—$X^{11}$ is carried out in a solvent component comprising tetrahydrofuran.

In some embodiments, the compound of formula III-1, or the salt thereof, is prepared by a process comprising:
reducing a compound of formula XII-2:

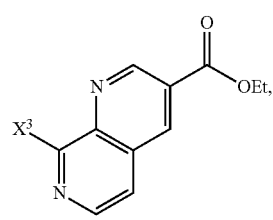

XII-2 or a salt thereof, to form the compound of formula III-1, or the salt thereof, wherein $X^3$ is halo. In some embodiments, $X^3$ is chloro.

In some embodiments, the compound of formula XII-2 is a compound of formula XII-2a:

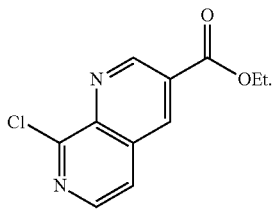

In some embodiments, the reducing of the compound of formula XII-2 is accomplished by a process comprising reacting the compound of formula XII-2 with diisobutylaluminium hydride. In some embodiments, from about 1 to about 2 molar equivalents of diisobutylaluminium hydride is utilized relative to the compound of formula XII-2. In some embodiments, about 1.5 molar equivalents of the reagent of diisobutylaluminium hydride is utilized relative to the compound of formula XII-2.

In some embodiments, the reducing of the compound of formula XII-2 is carried out at a temperature of from about −80° C. to about −70° C. In some embodiments, the reducing of the compound of formula XII-2 is carried out in a solvent component. In some embodiments the reducing of the compound of formula XII-2 is carried out in a solvent component comprising a $C_{1-6}$ haloalkane. In some embodiments, the reducing of the compound of formula XII-2 is carried out in a solvent component comprising dichloromethane.

In some embodiments, the compound of formula XII-2 is prepared by a process comprising:
reacting a compound of formula XII-1:

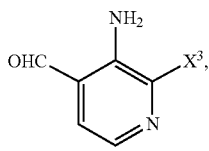

or a salt thereof, with ethyl 3,3-diethoxypropanoate in the presence of a catalyst, wherein $X^3$ is halo. In some embodiments, $X^3$ is chloro.

In some embodiments, the compound of formula XII-1, or the salt thereof, is a compound of formula XII-1a:

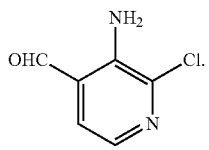

In some embodiments, the catalyst present in the reacting of the compound of formula XII-1, or the salt thereof, is lithium tetrafluoroborate. In some embodiments, from about 1 to about 2 molar equivalents of the catalyst is utilized relative to the compound of formula XII-1, or the salt thereof. In some embodiments, about 1.5 molar equivalents of the catalyst is utilized relative to the compound of formula XII-1, or the salt thereof. In some embodiments, from about 1 to about 2 molar equivalents of the ethyl 3,3-diethoxypropanoate is utilized relative to the compound of formula XII-1, or the salt thereof. In some embodiments, about 1.5 molar equivalents of the ethyl 3,3-diethoxypropanoate is utilized relative to the compound of formula XII-1, or the salt thereof.

In some embodiments, the reacting of the compound of formula XII-1, or the salt thereof, with ethyl 3,3-diethoxypropanoate is carried out at a temperature of from about 50° C. to about 80° C. In some embodiments, the reacting of the compound of formula XII-1, or the salt thereof, with ethyl 3,3-diethoxypropanoate is carried out at a temperature of about 60° C. In some embodiments, the reacting of the compound of formula XII-1, or the salt thereof, with ethyl 3,3-diethoxypropanoate is carried out in a solvent component. In some embodiments, the reacting of the compound of formula XII-1, or the salt thereof, with ethyl 3,3-diethoxypropanoate is carried out in a solvent comprising a $C_{1-6}$ cyanoalkane. In some embodiments, the reacting of the compound of formula XII-1, or the salt thereof, with ethyl 3,3-diethoxypropanoate is carried out in a solvent component comprising acetonitrile.

In some embodiments, the compound of formula XII-2 is prepared by a process comprising:
reacting a compound of formula XII-1, or a salt thereof, with N,N-dimethylaminoacrylate in the presence of a catalyst to form a compound of formula XII-2. In some embodiments, the catalyst is lithium tetrafluoroborate.

In some embodiments, the compound of formula XII-1, or the salt thereof, is prepared by a process comprising:
converting a compound of formula XIII-2:

or a salt thereof, to the compound of formula XII-1, or the salt thereof.

In some embodiments, the converting of the compound of formula XIII-2, or the salt thereof, is accomplished by a process comprising:
reacting the compound of formula XIII-2, or the salt thereof, with n-butyl lithium in the presence of tetramethylethylenediamine; and
reacting the product of said reacting of the compound of formula XIII-2, or the salt thereof, with N-formylmorpholine to form the compound of formula XII-1, or the salt thereof.

In some embodiments, from about 1 to about 2 molar equivalents of the tetramethylethylenediamine is utilized relative to the compound of formula XIII-2, or the salt thereof. In some embodiments, about 1.5 molar equivalents of the tetramethylethylenediamine is utilized relative to the compound of formula XIII-2, or the salt thereof. In some embodiments, from about 1 to about 2 molar equivalents of the N-formylmorpholine is utilized relative to the compound of formula XIII-2, or the salt thereof. In some embodiments, about 1.5 molar equivalents of the N-formylmorpholine is utilized relative to the compound of formula XIII-2, or the salt thereof.

In some embodiments, the converting of the compound of formula XIII-2, or the salt thereof, is carried out at a temperature of from about 0° C. to about 5° C. In some embodiments, the converting of the compound of formula XIII-2, or the salt thereof, is carried out in a solvent component. In some embodiments, the converting of the compound of formula XIII-2, or the salt thereof, is carried out in a solvent component comprising di-$C_{1-6}$ alkyl ether or a 4-10 membered heterocycloalkyl ether. In some embodiments, the converting of the compound of formula XIII-2, or the salt thereof, is carried out in a solvent component comprising tetrahydrofuran.

In some embodiments, the compound of formula XIII-2, or the salt thereof, is prepared by a process comprising:
reacting a compound of formula XIII-1:

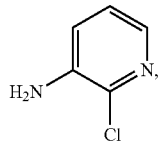

XIII-1 or a salt thereof, with isobutyl chloroformate to form the compound of formula XIII-2, or the salt thereof.

In some embodiments, the reacting of the compound of formula XIII-1, or the salt thereof, is carried out in the presence of a base. In some embodiments, the base, present in the reacting of the compound of formula XIII-1, or the salt thereof, with the isobutyl chloroformate, is an alkali metal base. In some embodiments, the base, present in the reacting of the compound of formula XIII-1, or the salt thereof, with the isobutyl chloroformate, is an alkali metal carbonate. In some embodiments, the base, present in the reacting of the compound of formula XIII-1, or the salt thereof, with the isobutyl chloroformate, is selected from cesium carbonate, lithium carbonate, sodium carbonate and potassium carbonate. In some embodiments, the base, present in the reacting of the compound of formula XIII-1, or the salt thereof, with the isobutyl chloroformate, is sodium carbonate. In some embodiments, from about 1 to about 4 molar equivalents of isobutyl chloroformate is utilized relative to the compound of formula XIII-1, or the salt thereof. In some embodiments, from about 2 to about 3 molar equivalents of isobutyl chloroformate is utilized relative to the compound of formula XIII-1, or the salt thereof. In some embodiments, about 2.5 molar equivalents of isobutyl chloroformate is utilized relative to the compound of formula XIII-1, or the salt thereof. In some embodiments, from about 1 to about 3 molar equivalents of the base is utilized relative to the compound of formula XIII-1, or the salt thereof. In some embodiments, about 2 molar equivalents of the compound of the base is utilized relative to the compound of formula XIII-1, or the salt thereof.

In some embodiments, the reacting of the compound of formula XIII-1, or the salt thereof, with the isobutyl chloroformate, is carried out at a temperature of from about 25° C. to about 35° C. In some embodiments, the reacting of the compound of formula XIII-1, or the salt thereof, with the isobutyl chloroformate, is carried out in a solvent component. In some embodiments, the reacting of the compound of formula XIII-1, or the salt thereof, with the isobutyl chloroformate, is carried out in a solvent component comprising a polar protic solvent. In some embodiments, the reacting of the compound of formula XIII-1, or the salt thereof, with the isobutyl chloroformate, is carried out in a solvent component comprising water.

In some embodiments, the compound of formula III-4, or the salt thereof, is prepared by a process comprising:
reacting a compound of formula XIV-2:

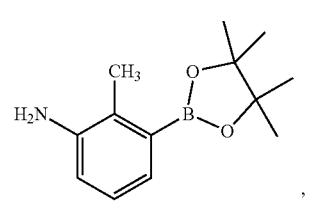

XIV-2 or a salt thereof, with hydrochloric acid to form the compound of formula III-4, or the salt thereof. In some embodiments, the compound of formula III-4 is a salt of formula III-4a. In some embodiments, the reacting of the compound of formula XIV-2, or the salt thereof, with the hydrochloric acid is carried out at a temperature of from about 80° C. to about 90° C. In some embodiments, the reacting of the compound of formula XIV-2, or the salt thereof, is carried out in a solvent component. In some embodiments, the reacting of the compound of formula XIV-2, or the salt thereof, with the hydrochloric acid is carried out in a solvent component comprising a polar protic solvent. In some embodiments, the reacting of the compound of formula XIV-2, or the salt thereof, with the hydrochloric acid is carried out in a solvent component comprising water.

In some embodiments, the compound of formula XIV-2, or the salt thereof, is prepared by a process comprising:
reacting a compound of formula XIV-1:

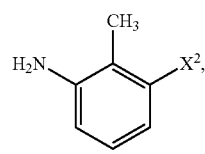

XIV-1 or a salt thereof, with 4,4,4',4',5,5,5',5'-octamethyl-2,2'-bi(1,3,2-dioxaborolane) in the presence of a catalyst to form the compound of formula XIV-2, or the salt thereof, wherein $X^2$ is halo. In some embodiments, $X^2$ is bromo.

In some embodiments, the compound of formula XIV-1 is a compound of formula XIV-1a:

XIV-1a

In some embodiments, the reacting of the compound of formula XIV-1, or the salt thereof, with 4,4,4',4',5,5,5',5'-octamethyl-2,2'-bi(1,3,2-dioxaborolane) is conducted in the presence of a base. In some embodiments, the catalyst, present in the reacting of the compound of formula XIV-1, or the salt thereof, with the 4,4,4',4',5,5,5',5'-octamethyl-2, 2'-bi(1,3,2-dioxaborolane), is a palladium catalyst. In some embodiments, the catalyst, present in the reacting of the compound of formula XIV-1, or the salt thereof, with the 4,4,4',4',5,5,5',5'-octamethyl-2,2'-bi(1,3,2-dioxaborolane), is selected from RuPhos Pd G4, CataCXium® Pd G4, Pd(PPh$_3$)$_4$, Pd(dppf)$_2$Cl$_2$, dichlorobis[di-tert-butyl(p-dimethylaminophenyl)phosphino]palladium, and PdCl$_2$(dtbpf) (Pd-118). In some embodiments, the catalyst, present in the reacting of the compound of formula XIV-1, or the salt thereof, with the 4,4,4',4',5,5,5',5'-octamethyl-2,2'-bi(1,3,2-dioxaborolane), is Pd(dppf)$_2$Cl$_2$.

In some embodiments, the base, present in the reacting of the compound of formula XIV-1, or the salt thereof, with the 4,4,4',4',5,5,5',5'-octamethyl-2,2'-bi(1,3,2-dioxaborolane), is an alkali metal base. In some embodiments, the base Z-XIV1 is an alkali metal acetate. In some embodiments, the base, present in the reacting of the compound of formula XIV-1, or the salt thereof, with the 4,4,4',4',5,5,5',5'-octamethyl-2,2'-bi(1,3,2-dioxaborolane), is selected from cesium acetate, lithium acetate, sodium acetate and potassium acetate. In some embodiments, the base, present in the reacting of the compound of formula XIV-1, or the salt thereof, with the 4,4,4',4',5,5,5',5'-octamethyl-2,2'-bi(1,3,2-dioxaborolane), is potassium acetate. In some embodiments, from about 1 to about 2 molar equivalents of the 4,4,4',4',5,5,5',5'-octamethyl-2,2'-bi(1,3,2-dioxaborolane) is utilized relative to the compound of formula XIV-1. In some embodiments, about 1.5 molar equivalents of the 4,4,4',4',5,5,5',5'-octamethyl-2,2'-bi(1,3,2-dioxaborolane) is utilized relative to the compound of formula XIV-1, or the salt thereof. In some embodiments, from about 1 to about 4 molar equivalents of the base is utilized relative to the compound of formula XIV-1, or the salt thereof. In some embodiments, from about 2 to about 4 molar equivalents of the base is utilized relative to the compound of formula XIV-1, or the salt thereof. In some embodiments, about 3 molar equivalents of the base is utilized relative to the compound of formula XIV-1, or the salt thereof. In some embodiments, from about 0.001 to about 0.1 molar equivalents of the catalyst is utilized relative to the compound of formula XIV-1, or the salt thereof. In some embodiments, from about 0.01 to about 0.03 molar equivalents of the catalyst is utilized relative to the compound of formula XIV-1, or the salt thereof. In some embodiments, about 0.02 molar equivalent of the catalyst is utilized relative to the compound of formula XIV-1.

In some embodiments, the reacting of the compound of formula XIV-1, or the salt thereof, with the 4,4,4',4',5,5,5',5'-octamethyl-2,2'-bi(1,3,2-dioxaborolane), is carried out at a temperature of from about 80° C. to about 120° C. In some embodiments, the reacting of the compound of formula XIV-1, or the salt thereof, with the 4,4,4',4',5,5,5',5'-octamethyl-2,2'-bi(1,3,2-dioxaborolane), is carried out at a temperature of from about 100° C. to about 110° C. In some embodiments, the reacting of the compound of formula XIV-1, or the salt thereof, with the 4,4,4',4',5,5,5',5'-octamethyl-2,2'-bi(1,3,2-dioxaborolane), is carried out in a solvent component. In some embodiments, the reacting of the compound of formula XIV-1, or the salt thereof, with the 4,4,4',4',5,5,5',5'-octamethyl-2,2'-bi(1,3,2-dioxaborolane), is carried out in a solvent component comprising an aromatic hydrocarbon. In some embodiments, the reacting of the compound of formula XIV-1, or the salt thereof, with the 4,4,4',4',5,5,5',5'-octamethyl-2,2'-bi(1,3,2-dioxaborolane), is carried out in a solvent component comprising toluene.

In some embodiments, the compound of formula III-6, or the salt thereof, is prepared by a process comprising: hydrolyzing the compound of formula IV-1:

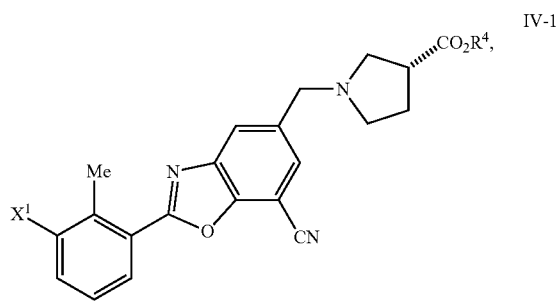

or a salt thereof, to form the compound of formula III-6, or the salt thereof, wherein $X^r$ is halo; and $R^4$ is $C_{1-6}$ alkyl. In some embodiments, $X^1$ is bromo. In some embodiments, $R^4$ is t-butyl.

In some embodiments, the compound of formula IV-1, or the salt thereof, is a compound of formula IV-1b:

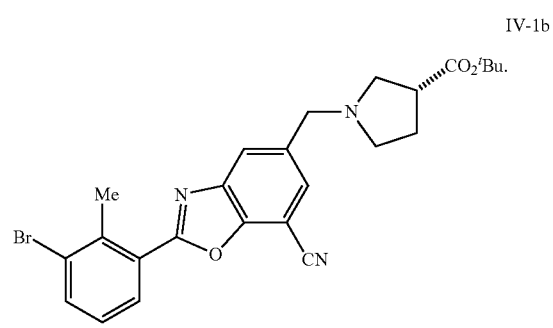 [SMILES: Cc1c(Br)cccc1-c1nc2cc(CN3CC[C@@H](C(=O)OC(C)(C)C)C3)cc(C#N)c2o1]

In some embodiments, the compound of formula III-6, or the salt thereof, is a salt of formula III-6b.

In some embodiments, the hydrolyzing of the compound of formula IV-1, or the salt thereof, is accomplished by a process comprising reacting the compound of formula IV-1 with hydrochloric acid to form the salt of formula III-6b. In some embodiments, from about 1 to about 10 molar equivalents of hydrochloric acid is utilized relative to the compound of formula IV-1, or the salt thereof. In some embodiments, from about 3 to about 7 molar equivalents of hydrochloric acid is utilized relative to the compound of formula IV-1, or the salt thereof. In some embodiments, about 5 molar equivalents of hydrochloric acid is utilized relative to the compound of formula IV-1, or the salt thereof.

In some embodiments, the hydrolyzing of the compound of formula IV-1 is carried out at a temperature of from about 30° C. to about 50° C. In some embodiments, the hydrolyzing of the compound of formula IV-1 is carried out at a temperature of from about 35° C. to about 40° C. In some embodiments, the hydrolyzing of the compound of formula IV-1, or the salt thereof, is carried out in a solvent component. In some embodiments, the hydrolyzing of the compound of formula IV-1, or the salt thereof, is carried out in a solvent component comprising a polar protic solvent, a di-$C_{1-6}$ alkyl ether, a 4-10 membered heterocycloalkyl ether, or a mixture thereof. In some embodiments, the hydrolyzing of the compound of formula IV-1, or the salt thereof, is carried out in a solvent component comprising water and 1,4-dioxane.

In some embodiments, the compound of formula IV-1, or the salt thereof, is prepared by a process comprising:
reacting the compound of formula IX-5:

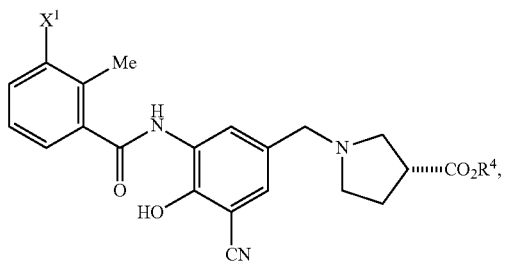

IX-5 or a salt thereof, under Mitsunobu conditions to form the compound of formula IV-1, or the salt thereof, wherein $X^1$ is halo; and $R^4$ is $C_{1-6}$ alkyl. In some embodiments, $X^1$ is bromo. In some embodiments, $R^4$ is t-butyl.

In some embodiments, the compound of formula IX-5, or the salt thereof, is a compound of formula IX-5a:

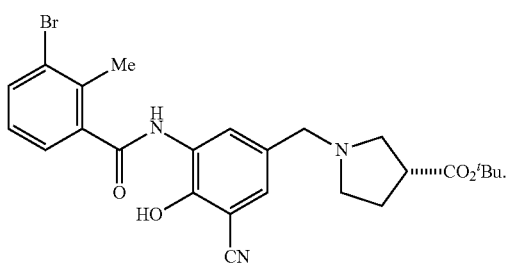

IX-5a

In some embodiments, the Mitsunobu conditions comprise treating the compound of formula IX-5, or the salt thereof, with an azodicarboxylate and a phosphine. In some embodiments, the azodicarboxylate is diethyl azodicarboxylate. In some embodiments, the phosphine is triphenyl phosphine. In some embodiments, from about 1 to about 3 molar equivalents of azodicarboxylate is utilized relative to the compound of formula IX-5, or the salt thereof. In some embodiments, about 2 molar equivalents of azodicarboxylate is utilized relative to the compound of formula IX-5, or the salt thereof. In some embodiments, from about 1 to about 3 molar equivalents of phosphine is utilized relative to the compound of formula IX-5. In some embodiments, about 2 molar equivalents of phosphine is utilized relative to the compound of formula IX-5, or the salt thereof.

In some embodiments, the reacting of the compound of formula IX-5 under the Mitsunobu conditions is carried out at a temperature of from about 40° C. to about 60° C. In some embodiments, the reacting of the compound of formula IX-5, or the salt thereof, under the Mitsunobu conditions is carried out at a temperature of from about 50° C. to about 55° C. In some embodiments, the reacting of the compound of formula IX-5, or the salt thereof, under the Mitsunobu conditions is carried out in a solvent component. In some embodiments, the reacting of the compound of formula IX-5, or the salt thereof, under the Mitsunobu conditions is carried out in a solvent component comprising di-$C_{1-6}$ alkyl ether or a 4-10 membered heterocycloalkyl ether. In some embodiments, the reacting of the compound of formula IX-5, or the salt thereof, under the Mitsunobu conditions is carried out in a solvent component comprising tetrahydrofuran.

In some embodiments, the compound of formula IX-5, or the salt thereof, is prepared by a process comprising:
reacting a compound of formula IX-4:

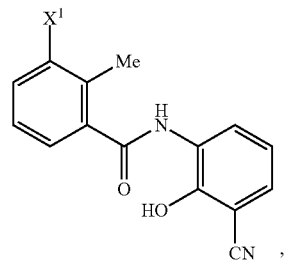

IX-4 or a salt thereof, with a compound of formula XV-4:

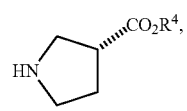

XV-4 or a salt thereof, to form a compound of formula IX-5, or the salt thereof, wherein $X^1$ is halo; and $R^4$ is $C_{1-6}$ alkyl. In some embodiments, $X^1$ is bromo. In some embodiments, $R^4$ is t-butyl.

In some embodiments, the compound of formula IX-4, or the salt thereof, is a compound of formula IX-4a:

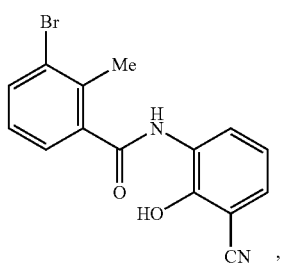

IX-4a or a salt thereof.

In some embodiments, the compound of formula XV-4, or the salt thereof, is a compound of formula XV-4a:

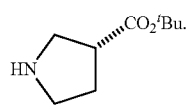

XV-4a

In some embodiments, the reacting of the compound of formula IX-4, or the salt thereof, with the compound of formula XV-4, or the salt thereof, is carried out in the presence of paraformaldehyde. In some embodiments, from about 1 to about 2 molar equivalents of the compound of formula XV-4, or the salt thereof, is utilized relative to the compound of formula IX-4, or the salt thereof. In some embodiments, about 1 molar equivalent of the compound of formula XV-4, or the salt thereof, is utilized relative to the compound of formula IX-4, or the salt thereof. In some embodiments, from about 1 to about 2 molar equivalents of paraformaldehyde is utilized relative to the compound of formula IX-4, or the salt thereof. In some embodiments, about 1 molar equivalent of paraformaldehyde is utilized relative to the compound of formula IX-4, or the salt thereof.

In some embodiments, the reacting of the compound of formula IX-4, or the salt thereof, with the compound of formula XV-4, or the salt thereof, is carried out at a temperature of from about 40° C. to about 60° C. In some embodiments, the reacting of the compound of formula IX-4, or the salt thereof, with the compound of formula XV-4, or the salt thereof, is carried out at a temperature of from about 50° C. to about 55° C. In some embodiments, the reacting of the compound of formula IX-4, or the salt thereof, with the compound of formula XV-4, or the salt thereof, is carried out in a solvent component. In some embodiments, the reacting of the compound of formula IX-4, or the salt thereof, with the compound of formula XV-4, or the salt thereof, is carried out in a solvent component comprising a $C_{1-6}$ cyanoalkane. In some embodiments, the reacting of the compound of formula IX-4, or the salt thereof, with the compound of formula XV-4, or the salt thereof, is carried out in a solvent component comprising acetonitrile.

In some embodiments, the compound of formula IX-4, or the salt thereof, is prepared by a process comprising:
reacting a compound of formula IX-3:

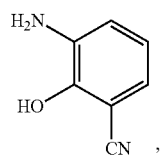

IX-3 or a salt thereof, with a compound of formula IX-3a:

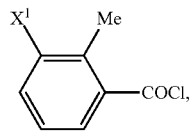

IX-3a in the presence of a tertiary amine to form the compound of formula IX-4, or the salt thereof, wherein $X^1$ is halo. In some embodiments, $X^1$ is bromo.

In some embodiments, the tertiary amine, present in the reacting of the compound of formula IX-3, or the salt thereof, with the compound of formula IX-3a, is triethylamine. In some embodiments, from about 1 to about 2 molar equivalents of the compound of formula IX-3a, is utilized relative to the compound of formula IX-3. In some embodiments, about 1 molar equivalent of the compound of formula IX-3a, is utilized relative to the compound of formula IX-3, or the salt thereof. In some embodiments, from about 1 to about 3 molar equivalents of the tertiary amine is utilized relative to the compound of formula IX-3, or the salt thereof. In some embodiments, about 2 molar equivalents of the tertiary amine is utilized relative to the compound of formula IX-3, or the salt thereof.

In some embodiments, the reacting of the compound of formula IX-3, or the salt thereof, with the compound of formula IX-3a is carried out at a temperature of from about 20° C. to about 30° C. In some embodiments, the reacting of the compound of formula IX-3, or the salt thereof, with the compound of formula IX-3a is carried out in a solvent component. In some embodiments, the reacting of the compound of formula IX-3 with the compound of formula IX-3a is carried out in a solvent component comprising di-$C_{1-6}$ alkyl ether or a 4-10 membered heterocycloalkyl ether. In some embodiments, the reacting of the compound of formula IX-3, or the salt thereof, with the compound of formula IX-3a is carried out in a solvent component comprising tetrahydrofuran.

In some embodiments, the compound of formula IX-3a is prepared by a process comprising reacting 3-halo-2-methylbenzoic acid, or a salt thereof, with thionyl chloride. In some embodiments, the reacting of the 3-halo-2-methylbenzoic acid, or the salt thereof, with the thionyl chloride is carried out in the presence of a catalyst. In some embodiments, the catalyst, present in the reacting of the 3-halo-2-methylbenzoic acid, or the salt thereof, with the thionyl chloride, is dimethylformamide. In some embodiments, from about 1 to about 5 molar equivalents of the thionyl chloride is utilized relative to the 3-halo-2-methylbenzoic acid, or the salt thereof. In some embodiments, about 2.5 molar equivalents of the thionyl chloride is utilized relative to the 3-halo-2-methylbenzoic acid, or the salt thereof.

In some embodiments, the reacting of the 3-halo-2-methylbenzoic acid, or the salt thereof, with the thionyl chloride is carried out at a temperature of from about 60° C. to about 80° C. In some embodiments, the reacting of the 3-halo-2-methylbenzoic acid, or the salt thereof, with the thionyl chloride is carried out at a temperature of from about 70° C. to about 75° C. In some embodiments, the 3-halo-2-methylbenzoic acid is 3-bromo-2-methylbenzoic acid.

In some embodiments, the compound of formula IX-3, or the salt thereof, is prepared by a process comprising:
reducing a compound of formula IX-2:

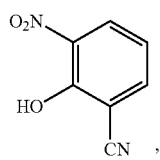

IX-2 to form the compound of formula IX-3, or the salt thereof. In some embodiments, the reducing of the compound of formula IX-2 is carried out in the presence of a reducing agent. In some embodiments, the reducing agent, present in the reducing of the compound of formula IX-2, is sodium hydrosulfite. In some embodiments, from about 1 to about 5 molar equivalents of the reducing agent is utilized relative to the compound of formula IX-2. In some embodiments, from about 3 to about 4 molar equivalents of the reducing agent is utilized relative to the compound of formula IX-2. In some embodiments, about 3.5 molar equivalents of the reducing agent is utilized relative to the compound of formula IX-2.

In some embodiments, the reducing of the compound of formula IX-2 is carried out at a temperature of from about 40° C. to about 60° C. In some embodiments, the reducing of the compound of formula IX-2 is carried out in a solvent component. In some embodiments, the reducing of the compound of formula IX-2 is carried out in a solvent component comprising a protic solvent. In some embodiments, the reducing of the compound of formula IX-2 is carried out in a solvent component comprising a $C_{1-6}$ alkanol. In some embodiments, the reducing of the compound of formula IX-2 is carried out in a solvent component comprising ethanol.

In some embodiments, the compound of formula IX-2 is prepared by a process comprising:

reacting a compound of formula IX-1:

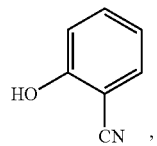

IX-1 with nitric acid to form the compound of formula IX-2. In some embodiments, from about 1.0 to about 2.0 molar equivalents of nitric acid is utilized relative to the compound of formula IX-1. In some embodiments, about 1 molar equivalent of nitric acid is utilized relative to the compound of formula IX-1.

In some embodiments, the reacting of the compound of formula IX-1 is carried out at a temperature of from about 25° C. to about 55° C. In some embodiments, the reacting of the compound of formula IX-1 is carried out at a temperature of from about 35° C. to about 45° C. In some embodiments, the reacting of the compound of formula IX-1 is carried out in a solvent component. In some embodiments, the reacting of the compound of formula IX-1 is carried out in a solvent component comprising a protic solvent. In some embodiments, the reacting of the compound of formula IX-1 is carried out in a solvent component comprising acetic acid.

Provided herein is a process of preparing (R)-1-((7-cyano-2-(3'-((3-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid, or a salt thereof, comprising:

reacting a compound of formula I-2:

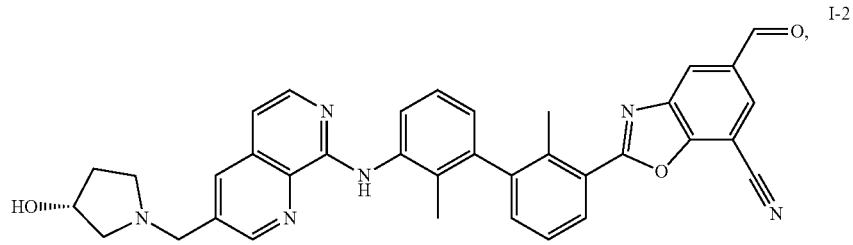 [SMILES: Cc1c(Nc2nccc3cc(CN4CC[C@@H](O)C4)cnc23)cccc1-c1cccc(-c2nc3cc(C=O)cc(C#N)c3o2)c1C]

I-2 or a salt thereof, with a compound of formula XV-4:

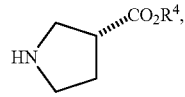

XV-4 or a salt thereof, in the presence of a reducing agent to form a compound of formula IV-2:

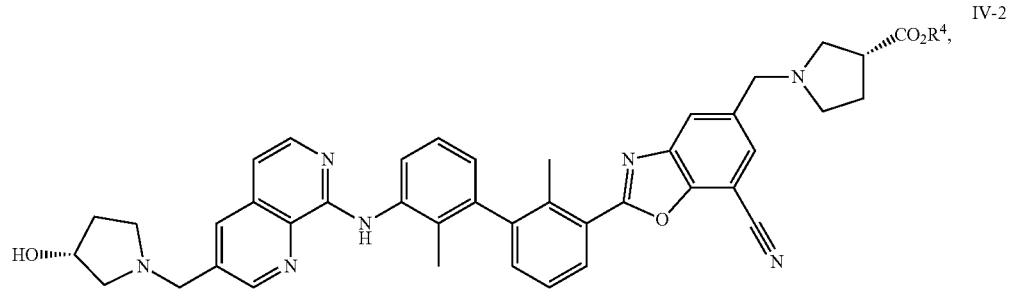

IV-2 or a salt thereof, wherein $R^4$ is $C_{1-6}$ alkyl. In some embodiments, $R^4$ is t-butyl.

In some embodiments, the compound of formula XV-4, or the salt thereof, is a compound of formula XV-4a:

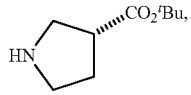

XV-4a or a salt thereof.

In some embodiments, the compound of formula IV-2 is a compound of formula IV-2a:

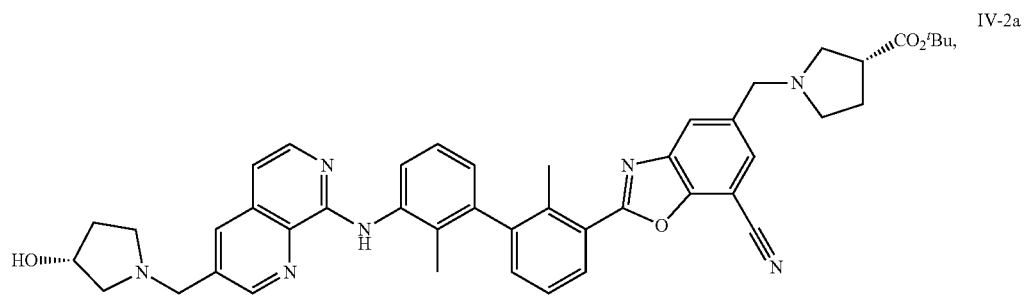 [SMILES: Cc1c(Nc2nccc3cc(CN4CC[C@@H](O)C4)cnc23)cccc1-c1cccc(-c2nc3cc(CN4CC[C@@H](C(=O)OC(C)(C)C)C4)cc(C#N)c3o2)c1C]

IV-2a or a salt thereof. In some embodiments, the reducing agent, present for the reacting of the compound of formula I-2, or the salt thereof, with the compound of formula XV-4, or the salt thereof, is a borohydride reducing agent. In some embodiments, the reducing agent, present for the reacting of the compound of formula I-2, or the salt thereof, with the compound of formula XV-4, or the salt thereof, is selected from NaBH$_4$, NaBH$_3$CN, and NaBH(OAc)$_3$. In some embodiments, the reducing agent, present for the reacting of the compound of formula I-2, or the salt thereof, with the compound of formula XV-4, or the salt thereof, is NaBH(OAc)$_3$.

In some embodiments, the reacting of the compound of formula I-2, or the salt thereof, with the compound of formula XV-4, or the salt thereof, is carried out in the presence of a tertiary amine. In some embodiments, the tertiary amine, present for the reacting of the compound of formula I-2 with the compound of formula XV-4, or the salt thereof, is triethylamine. In some embodiments, from about 1 to about 2 molar equivalents of the compound of formula XV-4, or the salt thereof, is utilized relative to the compound of formula I-2, or the salt thereof. In some embodiments, about 1 molar equivalent of the compound of formula XV-4, or the salt thereof, is utilized relative to the compound of formula I-2, or the salt thereof. In some embodiments, from about 1 to about 5 molar equivalents of the tertiary amine is utilized relative to the compound of formula I-2, or the salt thereof. In some embodiments, from about 2 to about 4 molar equivalents of the tertiary amine is utilized relative to the compound of formula I-2, or the salt thereof. In some embodiments, about 3 molar equivalents of the tertiary amine is utilized relative to the compound of formula I-2, or the salt thereof. In some embodiments, from about 1 to about 3 molar equivalents of the reducing agent is utilized relative to the compound of formula I-2, or the salt thereof. In some embodiments, about 2 molar equivalents of the reducing agent is utilized relative to the compound of formula I-2, or the salt thereof.

In some embodiments, the reacting of the compound of formula I-2, or the salt thereof, with the compound of formula XV-4, or the salt thereof, is carried out at a temperature of about room temperature. In some embodiments, the reacting of the compound of formula I-2, or the salt thereof, with the compound of formula XV-4, or the salt thereof, is carried out in a solvent component. In some embodiments, the reacting of the compound of formula I-2, or the salt thereof, with the compound of formula XV-4, or the salt thereof, is carried out in a solvent component comprising a $C_{1-6}$ haloalkane. In some embodiments, the reacting of the compound of formula I-2, or the salt thereof, with the compound of formula XV-4, or the salt thereof, is carried out in a solvent component comprising dichloromethane.

In some embodiments, the process further comprises deprotecting the compound of formula IV-2, or the salt thereof, to form (R)-1-((7-cyano-2-(3'-((3-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid, or the salt thereof. In some embodiments, the deprotecting of the compound of formula IV-2, or the salt thereof, is performed in the presence of a Lewis acid. In some embodiments, the Lewis acid, present in the deprotecting of the compound of formula IV-2, or the salt thereof, is trimethylsilyl triflate. In some embodiments, from about 1 to about 10 molar equivalents of the Lewis acid is utilized relative to the compound of formula IV-2, or the salt thereof. In some embodiments, from about 3 to about 5 molar equivalents of the Lewis acid is utilized relative to the compound of formula IV-2, or the salt thereof. In some embodiments, about 4 molar equivalents of the Lewis acid is utilized relative to the compound of formula IV-2, or the salt thereof.

In some embodiments, the deprotecting the compound of formula IV-2, or the salt thereof, is carried out at a temperature of about room temperature. In some embodiments, the deprotecting the compound of formula IV-2, or the salt thereof, is carried out in a solvent component. In some embodiments, the deprotecting the compound of formula IV-2, or the salt thereof, is carried out in a solvent component comprising a $C_{1-6}$ haloalkane. In some embodiments, the deprotecting the compound of formula IV-2, or the salt thereof, is carried out in a solvent component comprising dichloromethane.

In some embodiments, the compound of formula I-2, or the salt thereof, is prepared by a process comprising:
reacting a compound of formula V-1:

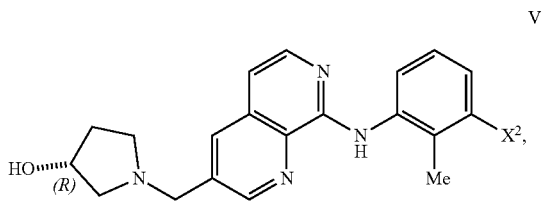

or a salt thereof, with a compound of formula I-1:

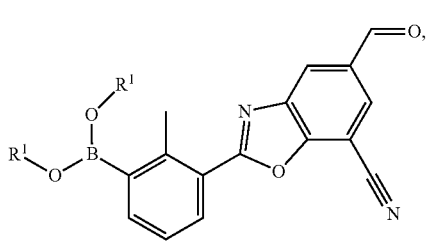

or a salt thereof, in the presence of a Suzuki catalyst and a base to form the compound of formula I-2:

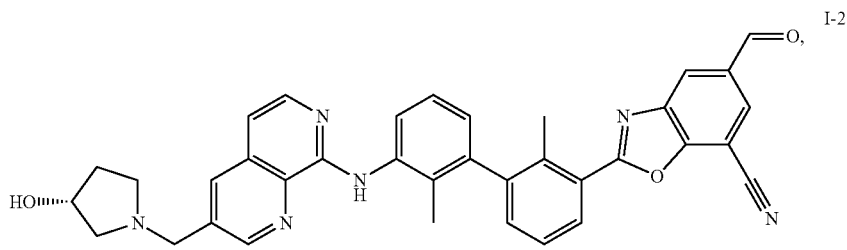 [SMILES: Cc1c(Nc2nccc3cc(CN4CC[C@@H](O)C4)cnc23)cccc1-c1cccc(-c2nc3cc(C=O)cc(C#N)c3o2)c1C]

or the salt thereof, wherein:
each $R^1$ is independently selected from H and $C_{1-6}$ alkyl; or
each $R^1$ together form an $C_{2-3}$ alkylene linker, which is optionally substituted by 1, 2, 3, or 4 independently selected $C_{1-4}$ alkyl groups; and $X^2$ is halo. In some embodiments, $X^2$ is bromo.

In some embodiments, the compound of formula V-1, or the salt thereof, is a compound of formula V-1a:

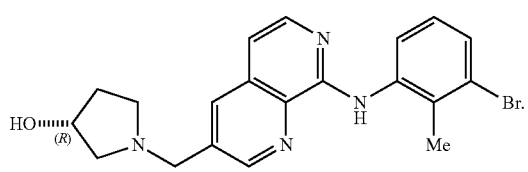

In some embodiments, the Suzuki catalyst, present in the reacting of the compound of formula V-1, or the salt thereof, with the compound of formula I-1, or the salt thereof, is a palladium catalyst. In some embodiments, the Suzuki catalyst, present in the reacting of the compound of formula V-1, or the salt thereof, with the compound of formula I-1, or the salt thereof, is selected from RuPhos Pd G4, CataCXium® Pd G4, Pd(PPh$_3$)$_4$, Pd(dppf)$_2$Cl$_2$, dichlorobis[di-tert-butyl (p-dimethylaminophenyl)phosphino]palladium, and PdCl$_2$ (dtbpf) (Pd-118). In some embodiments, the Suzuki catalyst, present in the reacting of the compound of formula V-1, or the salt thereof, with the compound of formula I-1, or the salt thereof, is Pd(dppf)$_2$Cl$_2$. In some embodiments, the base, present in the reacting of the compound of formula V-1, or the salt thereof, with the compound of formula I-1, or the salt thereof, is an alkali metal base. In some embodiments, the base, present in the reacting of the compound of formula V-1, or the salt thereof, with the compound of formula I-1, or the salt thereof, is an alkali metal phosphate. In some embodiments, the base, present in the reacting of the compound of formula V-1, or the salt thereof, with the compound of formula I-1, or the salt thereof, is selected from cesium phosphate, lithium phosphate, sodium phosphate and potassium phosphate. In some embodiments, the base, present in the reacting of the compound of formula V-1, or the salt thereof, with the compound of formula I-1, or the salt thereof, is potassium phosphate. In some embodiments, from about 1 to about 2 molar equivalents of the compound of formula I-1, or the salt thereof, is utilized relative to the compound of formula V-1, or the salt thereof. In some embodiments, about 1 molar equivalent of the compound of formula I-1, or the salt thereof, is utilized relative to the compound of formula V-1, or the salt thereof. In some embodiments, from about 1 to about 4 molar equivalents of the base is utilized relative to the compound of formula V-1, or the salt thereof. In some embodiments, from about 2 to about 4 molar equivalents of the base is utilized relative to the compound of formula V-1, or the salt thereof. In some embodiments, about 3 molar equivalents of the base is utilized relative to the compound of formula V-1, or the salt thereof. In some embodiments, from about 0.001 to about 0.1 molar equivalents of the Suzuki catalyst is utilized relative to the compound of formula V-1, or the salt thereof. In some embodiments, from about 0.01 to about 0.02 molar equivalents of the Suzuki catalyst is utilized relative to the compound of formula V-1, or the salt thereof. In some embodiments, about 0.015 molar equivalent of the Suzuki catalyst is utilized relative to the compound of formula V-1, or the salt thereof.

In some embodiments, the reacting of the compound of formula V-1, or the salt thereof, with the compound of formula I-1, or the salt thereof, is carried out at a temperature of from about 60° C. to about 100° C. In some embodiments, the reacting of the compound of formula V-1, or the salt thereof, with the compound of formula I-1, or the salt thereof, is carried out at a temperature of about 80° C. In some embodiments, the reacting of the compound of formula V-1, or the salt thereof, with the compound of formula I-1, or the salt thereof, is carried out in a solvent component. In some embodiments, the reacting of the compound of formula V-1, or the salt thereof, with the compound of formula I-1, or the salt thereof, is carried out in a solvent component comprising a polar protic solvent, a di-$C_{1-6}$ alkyl ether, a 4-10 membered heterocycloalkyl ether, or a mixture thereof. In some embodiments, the reacting of the compound of formula V-1, or the salt thereof, with the compound of formula I-1, or the salt thereof, is carried out in a solvent component comprising water and 1,4-dioxane.

In some embodiments, the compound of formula I-1, or the salt thereof, has formula I-1a:

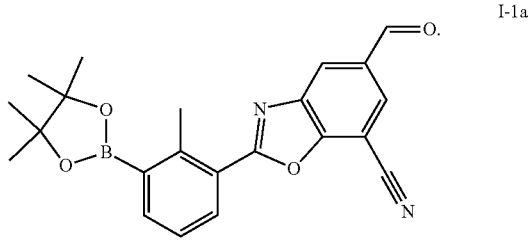 [SMILES: Cc1c(B2OC(C)(C)C(C)(C)O2)cccc1-c1nc2cc(C=O)cc(C#N)c2o1]

I-1a

Provided herein is a process of preparing (R)-1-((7-cyano-2-(3'-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid, comprising:

reacting a compound of formula V-1:

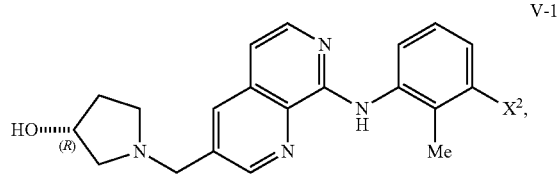

V-1 or a salt thereof, with a compound of formula I-1:

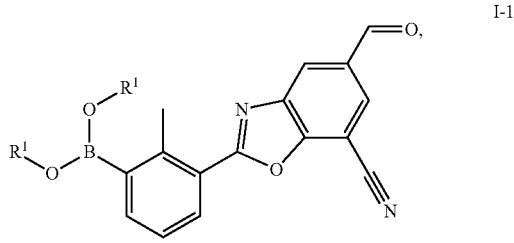

I-1 or a salt thereof, in the presence of a Suzuki catalyst and a base to form a compound of formula I-2:

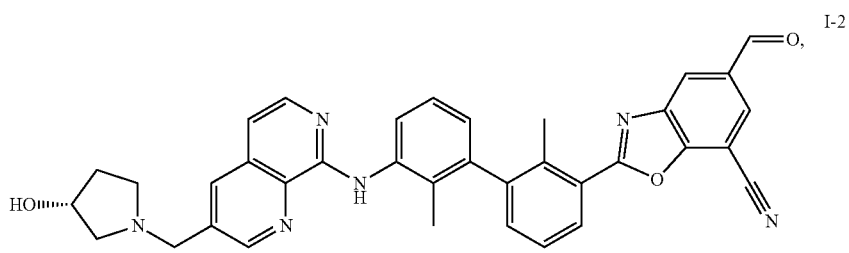 [SMILES: Cc1c(Nc2nccc3cc(CN4CC[C@@H](O)C4)cnc23)cccc1-c1cccc(-c2nc3cc(C=O)cc(C#N)c3o2)c1C]

I-2 or a salt thereof,
wherein:
each $R^1$ is independently selected from H and $C_{1-6}$ alkyl; or each $R^1$ together form an $C_{2-3}$ alkylene linker, which is optionally substituted by 1, 2, 3, or 4 independently selected $C_{1-4}$ alkyl groups; and $X^2$ is halo. In some embodiments, $X^2$ is bromo.

In some embodiments, the compound of formula V-1, or the salt thereof, is a compound of formula V-1a:

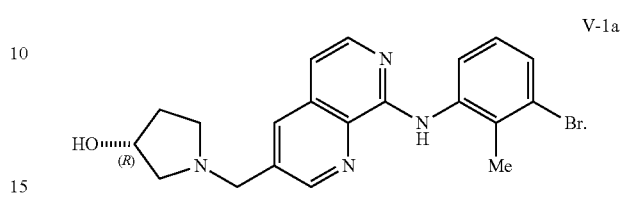

V-1a

In some embodiments, the Suzuki catalyst, present in the reacting of the compound of formula V-1, or the salt thereof, with the compound of formula I-1, or the salt thereof, is a palladium catalyst. In some embodiments, the Suzuki catalyst, present in the reacting of the compound of formula V-1, or the salt thereof, with the compound of formula I-1, or the salt thereof, is selected from RuPhos Pd G4, CataCXium® Pd G4, Pd(PPh$_3$)$_4$, Pd(dppf)$_2$Cl$_2$, dichlorobis[di-tert-butyl (p-dimethylaminophenyl)phosphino]palladium and PdCl$_2$ (dtbpf) (Pd-118). In some embodiments, the Suzuki catalyst, present in the reacting of the compound of formula V-1, or the salt thereof, with the compound of formula I-1, or the salt thereof, is Pd(dppf)$_2$Cl$_2$. In some embodiments, the base, present in the reacting of the compound of formula V-1, or the salt thereof, with the compound of formula I-1, or the salt thereof, is an alkali metal base. In some embodiments, the base, present in the reacting of the compound of formula V-1, or the salt thereof, with the compound of formula I-1, or the salt thereof, is an alkali metal phosphate. In some embodiments, the base, present in the reacting of the compound of formula V-1, or the salt thereof, with the compound of formula I-1, or the salt thereof, is selected from cesium phosphate, lithium phosphate, sodium phosphate and potassium phosphate. In some embodiments, the base, present in the reacting of the compound of formula V-1, or the salt thereof, with a compound of formula I-1, or the salt thereof, is potassium phosphate. In some embodiments, from about 1 to about 2 molar equivalents of the compound of formula I-1 is utilized relative to the compound of formula V-1, or the salt thereof. In some embodiments, about 1 molar equivalent of the compound of formula I-1, or the salt thereof, is utilized relative to the compound of formula V-1, or the salt thereof. In some embodiments, from about 1 to about 4 molar equivalents of the base is utilized relative to the compound of formula V-1, or the salt thereof. In some embodiments, from about 2 to about 4 molar equivalents of the base is utilized relative to the compound of formula V-1, or the salt thereof. In some embodiments, about 3 molar equivalents of the base is utilized relative to the compound of formula V-1, or the salt thereof. In some embodiments, from about 0.001 to about 0.1 molar equivalents of the Suzuki catalyst is utilized relative to the compound of formula V-1, or the salt thereof. In some embodiments, from about 0.01 to about 0.02 molar equivalents of the Suzuki catalyst is utilized relative to the compound of formula V-1, or the salt thereof. In some embodiments, about 0.015 molar equivalent of the Suzuki catalyst is utilized relative to the compound of formula V-1, or the salt thereof.

In some embodiments, the reacting of the compound of formula V-1, or the salt thereof, with the compound of formula I-1, or the salt thereof, is carried out at a temperature of from about 60° C. to about 100° C. In some embodiments, the reacting of the compound of formula V-1, or the salt thereof, with the compound of formula I-1, or the salt thereof, is carried out at a temperature of about 80° C. In some embodiments, the reacting of the compound of formula V-1, or the salt thereof, with the compound of formula I-1, or the salt thereof, is carried out in a solvent component. In some embodiments, the reacting of the compound of formula V-1, or the salt thereof, with the compound of formula I-1, or the salt thereof, is carried out in a solvent component comprising a polar protic solvent, a di-$C_{1-6}$ alkyl ether, a 4-10 membered heterocycloalkyl ether, or a mixture thereof. In some embodiments, the reacting of the compound of formula V-1, or the salt thereof, with the compound of formula I-1, or the salt thereof, is carried out in a solvent component comprising water and 1,4-dioxane.

In some embodiments, the compound of formula I-1, or the salt thereof, has formula I-1a:

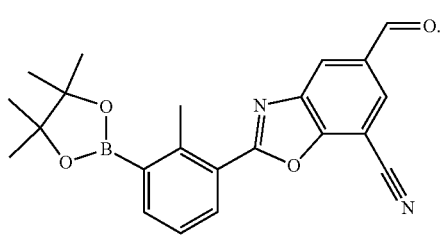

In some embodiments, the process comprises:
reacting a compound of formula V-1:

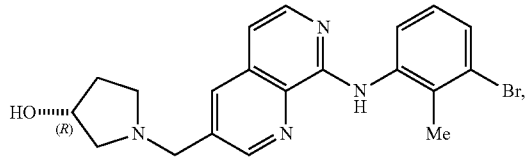

with a compound of formula I-1a:

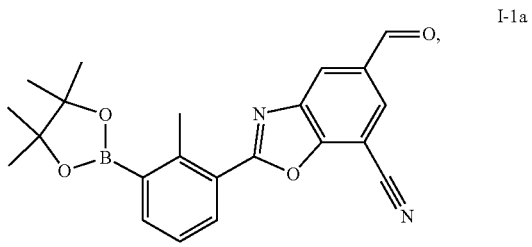 [SMILES: Cc1c(B2OC(C)(C)C(C)(C)O2)cccc1-c1nc2cc(C=O)cc(C#N)c2o1]

in the presence of a Suzuki catalyst and a base to form the compound of formula I-2, or the salt thereof.

In some embodiments, the compound of formula I-1, or the salt thereof, is prepared by a process comprising:
oxidizing a compound of formula II-3:

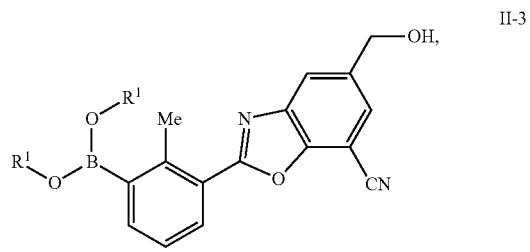

or a salt thereof, to form the compound of formula I-1, or the salt thereof;
wherein:
each $R^1$ is independently selected from H and $C_{1-6}$ alkyl; or
each $R^1$ together form an $C_{2-3}$ alkylene linker, which is optionally substituted by 1, 2, 3, or 4 independently selected $C_{1-4}$ alkyl groups.

In some embodiments, the oxidizing the compound of formula II-3, or the salt thereof, is carried out in the presence of an oxidizing agent. In some embodiments, the oxidizing agent for oxidizing the compound of formula II-3, or the salt thereof, is Dess-Martin periodinane. In some embodiments, from about 1 to about 4 molar equivalents of the oxidizing agent is utilized relative to the compound of formula II-3, or the salt thereof. In some embodiments, from about 1 to about 2 molar equivalents of the oxidizing agent is utilized relative to the compound of formula II-3, or the salt thereof. In some embodiments, about 1 molar equivalent of the oxidizing agent is utilized relative to the compound of formula II-3, or the salt thereof.

In some embodiments, the oxidizing the compound of formula II-3, or the salt thereof, is carried out at a temperature of about room temperature. In some embodiments, the oxidizing the compound of formula II-3, or the salt thereof, is carried out in a solvent component. In some embodiments, the oxidizing the compound of formula II-3, or the salt thereof, is carried out in a solvent component comprising a di-$C_{1-6}$ alkyl ether or a 4-10 membered heterocycloalkyl ether. In some embodiments, the oxidizing the compound of formula II-3, or the salt thereof, is carried out in a solvent component comprising dioxane.

In some embodiments, the compound of formula II-3, or the salt thereof, has formula II-3a:

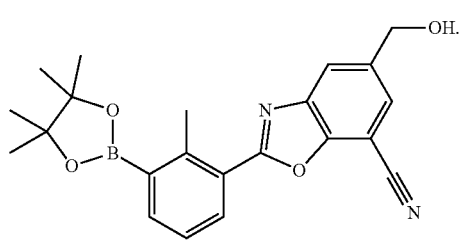

In some embodiments, the compound of formula II-3, or the salt thereof, is prepared by a process comprising:
cyanating a compound of formula II-2:

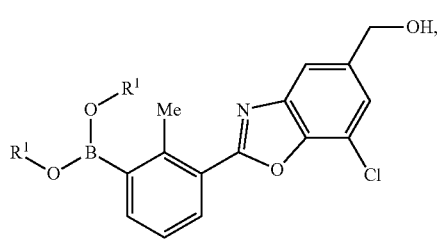

or a salt thereof, to form the compound of formula II-3, or the salt thereof.
wherein:
each $R^1$ is independently selected from H and $C_{1-6}$ alkyl; or
each $R^1$ together form an $C_{2-3}$ alkylene linker, which is optionally substituted by 1, 2, 3, or 4 independently selected $C_{1-4}$ alkyl groups.

In some embodiments, the cyanating the compound of formula II-2, or the salt thereof, is carried out in the presence of a cyanation reagent. In some embodiments, the cyanation reagent CR-II is a metal nitrile. In some embodiments, the cyanation reagent for the cyanating the compound of formula II-2 is zinc cyanide. In some embodiments, the cyanating the compound of formula II-2, or the salt thereof, is carried out in the presence of a catalyst. In some embodiments, the catalyst, present in the cyanating of the compound of formula II-2, or the salt thereof, is a palladium catalyst. In some embodiments, the catalyst, present in the cyanating of the compound of formula II-2, or the salt thereof, is ᵗBuXPhos Pd G3. In some embodiments, from about 1 to about 3 molar equivalents of the cyanation reagent is utilized relative to the compound of formula II-2, or the salt thereof. In some embodiments, about 2 molar equivalents of the cyanation reagent is utilized relative to the compound of formula II-2, or the salt thereof. In some embodiments, from about 0.01 to about 0.1 molar equivalents of the catalyst is utilized relative to the compound of formula II-2, or the salt thereof. In some embodiments, about 0.04 molar equivalent of the catalyst is utilized relative to the compound of formula II-2, or the salt thereof.

In some embodiments, the cyanating the compound of formula II-2, or the salt thereof, is carried out at a temperature of from about 80° C. to about 100° C. In some embodiments, the cyanating the compound of formula II-2, or the salt thereof, is carried out at a temperature of about 85° C. In some embodiments, the cyanating the compound of formula II-2, or the salt thereof, is carried out in a solvent component. In some embodiments, the cyanating the compound of formula II-2, or the salt thereof, is carried out in a solvent component comprising a polar aprotic solvent. In some embodiments, the cyanating the compound of formula II-2, or the salt thereof, is carried out in a solvent component comprising dimethylformamide.

In some embodiments, the compound of formula II-2, or the salt thereof, has formula II-2a:

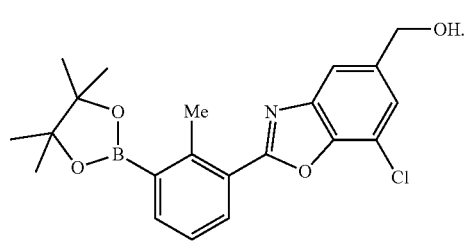

In some embodiments, the compound of formula II-2 is prepared by a process comprising:
reacting a compound of formula II-1:

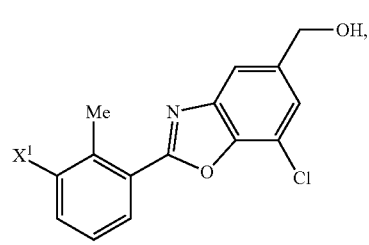

or a salt thereof, with a borylating agent in the presence of a catalyst and a base, wherein $X^1$ is halo.

In some embodiments, the compound of formula II-1, or the salt thereof, is a compound of formula II-1a:

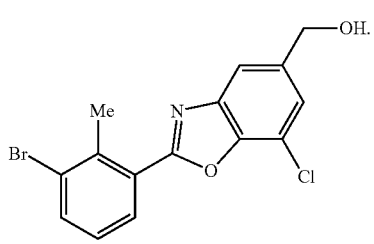

In some embodiments, the borylating agent for the reacting with the compound of formula II-1, or the salt thereof, is 4,4,4',4',5,5,5',5'-octamethyl-2,2'-bi(1,3,2-dioxaborolane). In some embodiments, the catalyst, present in the reacting of the compound of formula II-1, or the salt thereof, with a borylating agent, is a palladium catalyst. In some embodiments, the catalyst C-II1 is selected from RuPhos Pd G4, CataCXium® Pd G4, Pd(PPh₃)₄, Pd(dppf)₂Cl₂, dichlorobis[di-tert-butyl(p-dimethylaminophenyl)phosphino]palladium and PdCl₂(dtbpf) (Pd-118). In some embodiments, the catalyst, present in the reacting of the compound of formula II-1, or the salt thereof, with a borylating agent, is Pd(dppf)₂Cl₂. In some embodiments, the base, present in the reacting of the compound of formula II-1, or the salt thereof, with a borylating agent, is an alkali metal base. In some embodiments, the base, present in the reacting of the compound of formula II-1, or the salt thereof, with a borylating agent, is an alkali metal acetate. In some embodiments, the base, present in the reacting of the compound of formula II-1, or the salt thereof, with a borylating agent, is selected from cesium acetate, lithium acetate, sodium acetate and potassium acetate. In some embodiments, the base, present in the reacting of the compound of formula II-1, or the salt thereof, with a borylating agent, is potassium acetate. In some embodiments, from about 1 to about 2 molar equivalents of the borylating agent is utilized relative to the compound of formula II-1, or the salt thereof. In some embodiments, about 1.5 molar equivalents of the borylating agent is utilized relative to the compound of formula II-1, or the salt thereof. In some embodiments, from about 1 to about 4 molar equivalents of the base is utilized relative to the compound of formula II-1, or the salt thereof. In some embodiments, from about 1 to about 3 molar equivalents of the base is utilized relative to the compound of formula II-1, or the salt thereof. In some embodiments, about 2 molar equivalents of the base is utilized relative to the compound of formula II-1, or the salt thereof. In some embodiments, from about 0.001 to about 0.1 molar equivalents of the catalyst is utilized relative to the compound of formula II-1, or the salt thereof. In some embodiments, from about 0.01 to about 0.02 molar equivalents of the catalyst is utilized relative to the compound of formula II-1, or the salt thereof. In some embodiments, about 0.01 molar equivalent of the catalyst is utilized relative to the compound of formula II-1, or the salt thereof.

In some embodiments, the reacting of the compound of formula II-1, or the salt thereof, with the borylating agent is carried out at a temperature of from about 80° C. to about 120° C. In some embodiments, the reacting of the compound of formula II-1, or the salt thereof, with the borylating agent is carried out at a temperature of from about 100° C. to about 110° C. In some embodiments, the reacting of the compound of formula II-1, or the salt thereof, with the borylating agent is carried out in a solvent component. In some embodiments, the reacting of the compound of formula II-1, or the salt thereof, with the borylating agent is carried out in a solvent component comprising a di-$C_{1-6}$ alkyl ether or a 4-10 membered heterocycloalkyl ether. In some embodiments, the reacting of the compound of formula II-1, or the salt thereof, with the borylating agent is carried out in a solvent component comprising 1,4-dioxane.

In some embodiments, the compound of formula II-1, or the salt thereof, is prepared by a process comprising:
reducing a compound of formula VII-5:

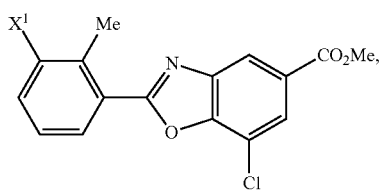

or a salt thereof, to form the compound of formula II-1, or the salt thereof, wherein $X^1$ is halo. In some embodiments, $X^1$ is bromo.

In some embodiments, the compound of formula VII-5, or the salt thereof, is a compound of formula VII-5a:

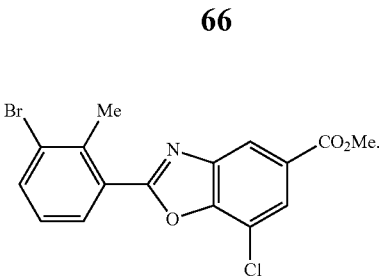

In some embodiments, the reducing of the compound of formula VII-5, or the salt thereof, is accomplished by a process comprising reacting the compound of formula VII-5, or the salt thereof, with the diisobutylaluminium hydride. In some embodiments, from about 1 to about 3 molar equivalents of the diisobutylaluminium hydride is utilized relative to the compound of formula VII-5, or the salt thereof. In some embodiments, about 2 molar equivalents of the reagent of the diisobutylaluminium hydride is utilized relative to the compound of formula VII-5, or the salt thereof.

In some embodiments, the reducing of the compound of formula VII-5, or the salt thereof, is carried out at a temperature of from about −10° C. to about 10° C. In some embodiments, the reducing of the compound of formula VII-5, or the salt thereof, is carried out at a temperature of about 0° C. In some embodiments, the reducing of the compound of formula VII-5, or the salt thereof, is carried out in a solvent component. In some embodiments, the reducing of the compound of formula VII-5, or the salt thereof, is carried out in a solvent component comprising a $C_{1-6}$ haloalkane. In some embodiments, the reducing of the compound of formula VII-5, or the salt thereof, is carried out in a solvent component comprising dichloromethane.

In some embodiments, the compound of formula VII-5, or the salt thereof, is prepared by a process comprising:
reacting a compound of formula VII-3:

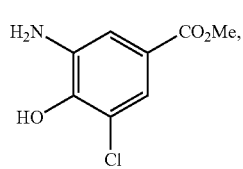

or a salt thereof, with a compound of formula VII-4:

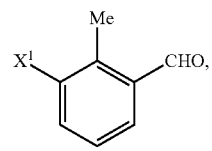

in the presence of an oxidant to form the compound of formula VII-5, or the salt thereof, wherein $X^1$ is halo. In some embodiments, $X^1$ is bromo. In some embodiments, the compound of formula VII-4 is a compound of formula VII-4a:

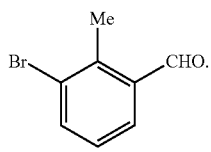

VII-4a

In some embodiments, the oxidant, for the reacting of the compound of formula VII-3, or the salt thereof, with the compound of formula VII-4, is 2,3-dichloro-5,6-dicyanobenzoquinone. In some embodiments, from about 1 to about 2 molar equivalents of the compound of formula VII-4 is utilized relative to the compound of formula VII-3, or the salt thereof. In some embodiments, about 1 molar equivalent of the compound of formula VII-4 is utilized relative to the compound of formula VII-3, or the salt thereof. In some embodiments, from about 1 to about 2 molar equivalents of the oxidant is utilized relative to the compound of formula VII-3, or the salt thereof. In some embodiments, about 1 molar equivalent of the oxidant is utilized relative to the compound of formula VII-3, or the salt thereof.

In some embodiments, the reacting of the compound of formula VII-3, or the salt thereof, with the compound of formula VII-4 is carried out at a temperature of about room temperature. In some embodiments, the reacting of the compound of formula VII-3, or the salt thereof, with the compound of formula VII-4 is carried out in a solvent component. In some embodiments, the reacting of the compound of formula VII-3, or the salt thereof, with the compound of formula VII-4 is carried out in a solvent component comprising a protic solvent. In some embodiments, the reacting of the compound of formula VII-3, or the salt thereof, with the compound of formula VII-4 is carried out in a solvent component comprising a $C_{1-6}$ alkanol. In some embodiments, the reacting of the compound of formula VII-3, or the salt thereof, with the compound of formula VII-4 is carried out in a solvent component comprising ethanol.

In some embodiments, the compound of formula VII-3, or the salt thereof, is prepared by a process comprising:

reducing a compound of formula VII-2:

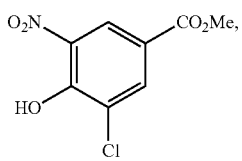

VII-2 to form the compound of formula VII-3, or the salt thereof.

In some embodiments, the reducing of the compound of formula VII-2 is carried out in the presence of hydrogen and a catalyst. In some embodiments, the catalyst, present for the reducing of the compound of formula VII-2, is a palladium catalyst. In some embodiments, the catalyst, present for the reducing of the compound of formula VII-2, is Pd/C. In some embodiments, the reducing of the compound of formula VII-2 is carried out under pressure of from about 1 atmosphere to about 2 atmospheres. In some embodiments, the reducing of the compound of formula VII-2 is carried out under pressure of about 1 atmosphere. In some embodiments, the reducing of the compound of formula VII-2 is carried out at a temperature of about room temperature. In some embodiments, the reducing of the compound of formula VII-2 is carried out in a solvent component. In some embodiments, the reducing of the compound of formula VII-2 is carried out in a solvent component comprising an aprotic polar solvent. In some embodiments, the reducing of the compound of formula VII-2 is carried out in a solvent component comprising ethyl acetate.

In some embodiments, the compound of formula VII-2 is prepared by a process comprising:

reducing a compound of formula VII-1:

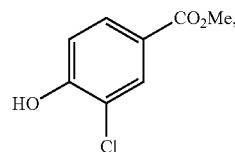

VII-1 with nitric acid to form the compound of formula VII-2. In some embodiments, from about 1 to about 3 molar equivalents of the nitric acid is utilized relative to the compound of formula VII-1. In some embodiments, about 2 molar equivalents of the nitric acid is utilized relative to the compound of formula VII-1.

In some embodiments, the reducing of the compound of formula VII-1 is carried out at a temperature of about room temperature. In some embodiments, the reducing of the compound of formula VII-1 is carried out in a solvent component. In some embodiments, the reducing of the compound of formula VII-1 is carried out in a solvent component comprising a protic solvent. In some embodiments, the reducing of the compound of formula VII-1 is carried out in a solvent component comprising acetic acid.

In some embodiments, the compound of formula V-1, or the salt thereof, is prepared by a process comprising:

reacting a compound of formula VIII-8:

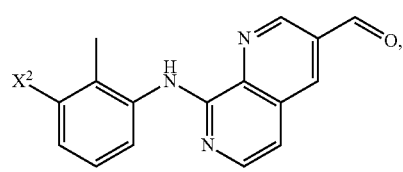

VIII-8 or a salt thereof, with a compound of formula III-2:

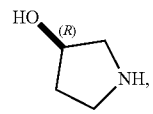

III-2 or a salt thereof, in the presence of a reducing agent to form the compound of formula V-1, or the salt thereof, wherein $X^2$ is halo. In some embodiments, $X^2$ is bromo.

In some embodiments, the compound of formula VIII-8, or the salt thereof, is a compound of formula VIII-8a:

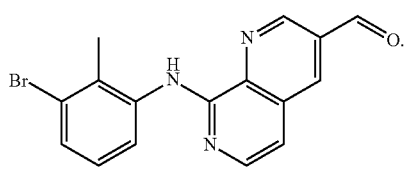

VIII-8a

In some embodiments, the reducing agent, present in the reacting of the compound of formula VIII-8, or the salt thereof, with the compound of formula III-2, or the salt thereof, is selected from NaBH$_4$, NaBH$_3$CN and NaBH(OAc)$_3$. In some embodiments, the reducing agent, present in the reacting of the compound of formula VIII-8, or the salt thereof, with the compound of formula III-2, or the salt thereof, is NaBH(OAc)$_3$. In some embodiments, the reacting of the compound of formula VIII-8, or the salt thereof, with the compound of formula III-2, or the salt thereof, is carried out in the presence of a tertiary amine. In some embodiments, the tertiary amine, present in the reacting of the compound of formula VIII-8, or the salt thereof, with the compound of formula III-2, or the salt thereof, is triethylamine. In some embodiments, from about 1 to about 2 molar equivalents of the compound of formula III-2, or the salt thereof, is utilized relative to the compound of formula VIII-8, or the salt thereof. In some embodiments, about 1.5 molar equivalents of the compound of formula III-2, or the salt thereof, is utilized relative to the compound of formula VIII-8, or the salt thereof. In some embodiments, from about 1 to about 5 molar equivalents of the reducing agent is utilized relative to the compound of formula VIII-8, or the salt thereof. In some embodiments, from about 1 to about 3 molar equivalents of the reducing agent is utilized relative to the compound of formula VIII-8, or the salt thereof. In some embodiments, about 2 molar equivalents of the reducing agent is utilized relative to the compound of formula VIII-8, or the salt thereof. In some embodiments, from about 1 to about 3 molar equivalents of the tertiary amine is utilized relative to the compound of formula VIII-8, or the salt thereof. In some embodiments, about 2 molar equivalents of the tertiary amine is utilized relative to the compound of formula VIII-8, or the salt thereof.

In some embodiments, the reacting of the compound of formula VIII-8, or the salt thereof, with the compound of formula III-2, or the salt thereof, is carried out at a temperature of from about 20° C. to about 30° C. In some embodiments, the reacting of the compound of formula VIII-8, or the salt thereof, with the compound of formula III-2, or the salt thereof, is carried out in a solvent component. In some embodiments, the reacting of the compound of formula VIII-8, or the salt thereof, with the compound of formula III-2, or the salt thereof, is carried out in a solvent component comprising an C$_{1-6}$ haloalkane. In some embodiments, the reacting of the compound of formula VIII-8, or the salt thereof, with the compound of formula III-2, or the salt thereof, is carried out in a solvent component comprising dichloromethane.

In some embodiments, the compound of formula VIII-8, or the salt thereof, is prepared by a process comprising:
oxidizing a compound of formula VIII-7:

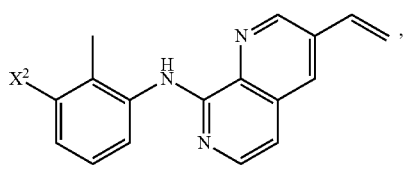

VIII-7 or a salt thereof, to form the compound of formula VIII-8, or the salt thereof, wherein X$^2$ is halo. In some embodiments, X$^2$ is bromo.

In some embodiments, the compound of formula VIII-7, or the salt thereof, is a compound of formula VIII-7a:

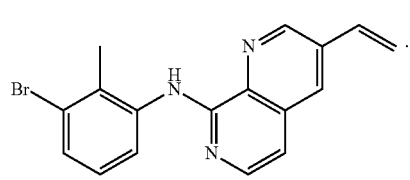

VIII-7a

In some embodiments, the oxidizing the compound of formula VIII-7, or the salt thereof, is carried out in the presence of a catalyst. In some embodiments, the catalyst, present for the oxidizing the compound of formula VIII-7, or the salt thereof, is osmium tetroxide. In some embodiments, the oxidizing the compound of formula VIII-7, or the salt thereof, is carried out in the presence of an oxidizing agent. In some embodiments, the oxidizing agent, for the oxidizing of the compound of formula VIII-7, or the salt thereof, is sodium periodate. In some embodiments, from about 0.01 to about 0.1 molar equivalents of the catalyst is utilized relative to the compound of formula VIII-7, or the salt thereof. In some embodiments, about 0.04 molar equivalent of the catalyst is utilized relative to the compound of formula VIII-7, or the salt thereof. In some embodiments, from about 1 to about 3 molar equivalents of the oxidizing agent is utilized relative to the compound of formula VIII-7, or the salt thereof. In some embodiments, about 2 molar equivalents of the oxidizing agent is utilized relative to the compound of formula VIII-7, or the salt thereof.

In some embodiments, the oxidizing of the compound of formula VIII-7, or the salt thereof, is carried out at a temperature of is carried out at a temperature of from about 30° C. to about 35° C. In some embodiments, the oxidizing of the compound of formula VIII-7, or the salt thereof, is carried out in a solvent component. In some embodiments, the oxidizing of the compound of formula VIII-7, or the salt thereof, is carried out in a solvent component comprising a di-C$_{1-6}$ alkyl ether, a 4-10 membered heterocycloalkyl ether, a polar protic solvent, or a mixture thereof. In some embodiments, the oxidizing of the compound of formula VIII-7, or the salt thereof, is carried out in a solvent component comprising tetrahydrofuran and water.

In some embodiments, the compound of formula VIII-7, or the salt thereof, is prepared by a process comprising:
reacting a compound of formula VIII-6:

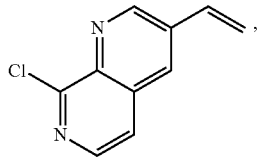

VIII-6 or a salt thereof, with a compound of formula XIV-1:

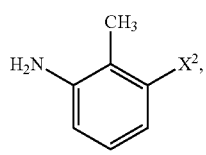

XIV-1 or a salt thereof, to form a compound of formula VIII-7, or the salt thereof, wherein $X^2$ is halo. In some embodiments, $X^2$ is bromo.

In some embodiments, the compound of formula XIV-1 is a compound of formula XIV-1a:

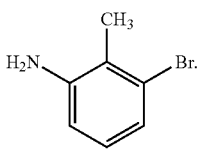

XIV-1a

In some embodiments, the reacting of the compound of formula VIII-6, or the salt thereof, with a compound of formula XIV-1, or the salt thereof, is carried out in the presence of an acid. In some embodiments, the acid, present in the reacting of the compound of formula VIII-6, or the salt thereof, with the compound of formula XIV-1, or the salt thereof, is a strong organic acid. In some embodiments, the acid, present for the reacting of the compound of formula VIII-6, or the salt thereof, with the compound of formula XIV-1, or the salt thereof, is a $C_{1-6}$alkylsulfonic acid. In some embodiments, the acid, present in the reacting of the compound of formula VIII-6, or the salt thereof, with the compound of formula XIV-1, or the salt thereof, is methanesulfonic acid. In some embodiments, from about 1 to about 2 molar equivalents of the compound of formula XIV-1, or the salt thereof, is utilized relative to the compound of formula VIII-6, or the salt thereof. In some embodiments, about 1 molar equivalent of the compound of formula XIV-1, or the salt thereof, is utilized relative to the compound of formula VIII-6, or the salt thereof. In some embodiments, from about 1 to about 2 molar equivalents of the acid is utilized relative to the compound of formula VIII-6, or the salt thereof. In some embodiments, about 1 molar equivalent of the acid is utilized relative to the compound of formula VIII-6, or the salt thereof.

In some embodiments, the reacting of the compound of formula VIII-6, or the salt thereof, with the compound of formula XIV-1, or the salt thereof, is carried out at a temperature of from about 50° C. to about 70° C. In some embodiments, the reacting of the compound of formula VIII-6, or the salt thereof, with the compound of formula XIV-1, or the salt thereof, is carried out at a temperature of about 60° C. In some embodiments, the reacting of the compound of formula VIII-6, or the salt thereof, with the compound of formula XIV-1, or the salt thereof, is carried out in a solvent component. In some embodiments, the reacting of the compound of formula VIII-6, or the salt thereof, with the compound of formula XIV-1, or the salt thereof, is carried out in a solvent component comprising a protic solvent. In some embodiments, the reacting of the compound of formula VIII-6, or the salt thereof, with the compound of formula XIV-1, or the salt thereof, is carried out in a solvent component comprising a $C_{1-6}$ alkanol. In some embodiments, the reacting of the compound of formula VIII-6, or the salt thereof, with the compound of formula XIV-1, or the salt thereof, is carried out in a solvent comprising isopropanol.

In some embodiments, the compound of formula VIII-6, or the salt thereof, is prepared by a process comprising:
reacting a compound of formula VIII-5:

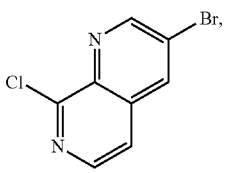

VIII-5 or a salt thereof, with 4,4,5,5-tetramethyl-2-vinyl-1,3,2-dioxaborolane in the presence of a catalyst and a base to form a compound of formula VIII-6, or the salt thereof.

In some embodiments, the catalyst, present in the reacting of the compound of formula VIII-5, or the salt thereof, with the 4,4,5,5-tetramethyl-2-vinyl-1,3,2-dioxaborolane, is a palladium catalyst. In some embodiments, the catalyst, present in the reacting of the compound of formula VIII-5, or the salt thereof, with the 4,4,5,5-tetramethyl-2-vinyl-1,3,2-dioxaborolane, is selected from RuPhos Pd G4, CataCXium® Pd G4, Pd(PPh$_3$)$_4$, Pd(dppf)$_2$Cl$_2$, dichlorobis[di-tert-butyl(p-dimethylaminophenyl)phosphino]palladium and PdCl$_2$(dtbpf) (Pd-118). In some embodiments, the catalyst, present in the reacting of the compound of formula VIII-5, or the salt thereof, with the 4,4,5,5-tetramethyl-2-vinyl-1,3,2-dioxaborolane, is Pd(dppf)$_2$Cl$_2$. In some embodiments, the base, present in the reacting of the compound of formula VIII-5, or the salt thereof, with the 4,4,5,5-tetramethyl-2-vinyl-1,3,2-dioxaborolane, is an alkali metal base. In some embodiments, the base, present in the reacting of the compound of formula VIII-5, or the salt thereof, with the 4,4,5,5-tetramethyl-2-vinyl-1,3,2-dioxaborolane, is an alkali metal carbonate. In some embodiments, the base, present in the reacting of the compound of formula VIII-5, or the salt thereof, with the 4,4,5,5-tetramethyl-2-vinyl-1,3,2-dioxaborolane, is selected from cesium carbonate, lithium carbonate, sodium carbonate and potassium carbonate. In some embodiments, the base, present in the reacting of the compound of formula VIII-5, or the salt thereof, with the 4,4,5,5-tetramethyl-2-vinyl-1,3,2-dioxaborolane, is sodium carbonate. In some embodiments, from about 1 to about 2 molar equivalents of the 4,4,5,5-tetramethyl-2-vinyl-1,3,2-dioxaborolane is utilized relative to the compound of formula VIII-5, or the salt thereof. In some embodiments, about 1.5 molar equivalents of the 4,4,5,5-tetramethyl-2-vinyl-1,3,2-dioxaborolane is utilized relative to the compound of formula VIII-5, or the salt thereof. In some embodiments, from about 1 to about 5 molar equivalents of the base is utilized relative to the compound of formula VIII-5, or the salt thereof. In some embodiments, from about 2 to about 4 molar equivalents of the base is utilized relative to the compound of formula VIII-5, or the salt thereof. In some embodiments, about 3 molar equivalents of the base is utilized relative to the compound of formula VIII-5, or the salt thereof. In some embodiments, from about 0.01 to about 0.1 molar equivalents of the catalyst is utilized relative to the compound of formula VIII-5, or the salt thereof. In some embodiments, about 0.06 molar equivalent of the catalyst is utilized relative to the compound of formula VIII-5, or the salt thereof.

In some embodiments, the reacting of the compound of formula VIII-5, or the salt thereof, and the 4,4,5,5-tetramethyl-2-vinyl-1,3,2-dioxaborolane is carried out at a temperature of from about 80° C. to about 100° C. In some embodiments, the reacting of the compound of formula VIII-5, or the salt thereof, and the 4,4,5,5-tetramethyl-2-vinyl-1,3,2-dioxaborolane is carried out at a temperature of about 90° C. In some embodiments, the reacting of the compound of formula VIII-5, or the salt thereof, and the 4,4,5,5-tetramethyl-2-vinyl-1,3,2-dioxaborolane is carried out in a solvent component. In some embodiments, the reacting of the compound of formula VIII-5, or the salt thereof, and the 4,4,5,5-tetramethyl-2-vinyl-1,3,2-dioxaborolane is carried out in a solvent component comprising a polar protic solvent, a di-$C_{1-6}$ alkyl ether, a 4-10 membered heterocycloalkyl ether, or a mixture thereof. In some embodiments, the reacting of the compound of formula VIII-5, or the salt thereof, and the 4,4,5,5-tetramethyl-2-vinyl-1,3,2-dioxaborolane is carried out in a solvent component comprising water and 1,4-dioxane.

In some embodiments, the compound of formula VIII-5, or the salt thereof, is prepared by a process comprising:
reacting a compound of formula VIII-4:

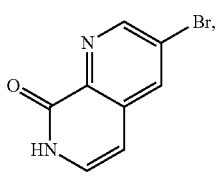

VIII-4 or a salt thereof, with a chlorinating agent to form a compound of formula VIII-5, or the salt thereof.

In some embodiments, the chlorinating agent, for reacting with the compound of formula VIII-4, or the salt thereof, is selected from oxalyl chloride, phosphorus oxychloride, diphosgene, thionyl chloride, sulfuryl chloride and phosphorus pentachloride. In some embodiments, the chlorinating agent, for reacting with the compound of formula VIII-4, or the salt thereof, is phosphorus oxychloride. In some embodiments, the reacting of the compound of formula VIII-4, or the salt thereof, with the chlorinating agent is carried out in the presence of a base. In some embodiments, the base, present in the reacting with the compound of formula VIII-4, or the salt thereof, is N,N-dimethylaniline. In some embodiments, from about 1 to about 5 molar equivalents of the chlorinating agent is utilized relative to the compound of formula VIII-4, or the salt thereof. In some embodiments, from about 2 to about 4 molar equivalents of the chlorinating agent is utilized relative to the compound of formula VIII-4, or the salt thereof. In some embodiments, about 3 molar equivalents of the chlorinating agent is utilized relative to the compound of formula VIII-4, or the salt thereof. In some embodiments, from about 1 to about 5 molar equivalents of the base is utilized relative to the compound of formula VIII-4, or the salt thereof. In some embodiments, from about 2 to about 4 molar equivalents of the base is utilized relative to the compound of formula VIII-4, or the salt thereof. In some embodiments, about 3 molar equivalents of the base is utilized relative to the compound of formula VIII-4, or the salt thereof.

In some embodiments, the reacting of the compound of formula VIII-4, or the salt thereof, with the chlorinating agent is carried out at a temperature of from about 100° C. to about 150° C. In some embodiments, the reacting of the compound of formula VIII-4, or the salt thereof, with the chlorinating agent is carried out at a temperature of about 130° C. In some embodiments, the reacting of the compound of formula VIII-4, or the salt thereof, with the chlorinating agent is carried out in a solvent component. In some embodiments, the reacting of the compound of formula VIII-4, or the salt thereof, with the chlorinating agent is carried out in a solvent component comprising an aromatic hydrocarbon. In some embodiments, the reacting of the compound of formula VIII-4, or the salt thereof, with the chlorinating agent is carried out in a solvent component comprising toluene.

In some embodiments, the compound of formula VIII-4, or the salt thereof, is prepared by a process comprising:
(i) reacting a compound of formula VIII-2:

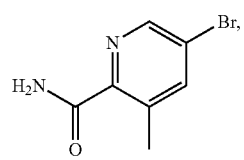

VIII-2 or a salt thereof, with N,N-dimethylformamide dimethyl acetal to form a compound of formula VIII-3:

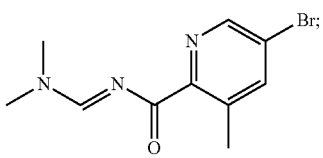

VIII-3

(ii) treating the compound of formula VIII-3 with a strong base to form the compound of formula VIII-4, or the salt thereof.

In some embodiments, the strong base, for reacting with the compound of formula VIII-3, is potassium t-butoxide. In some embodiments, from about 1 to about 2 molar equivalents of the N,N-dimethylformamide dimethyl acetal is utilized relative to the compound of formula VIII-2, or the salt thereof. In some embodiments, about 1.5 molar equivalents of the N,N-dimethylformamide dimethyl acetal is utilized relative to the compound of formula VIII-2, or the salt thereof. In some embodiments, from about 1 to about 2 molar equivalents of the strong base is utilized relative to the compound of formula VIII-2, or the salt thereof. In some embodiments, about 1.5 molar equivalents of the strong base is utilized relative to the compound of formula VIII-2, or the salt thereof.

In some embodiments, the reacting of the compound of formula VIII-2, or the salt thereof, is carried out at a temperature of from about 100° C. to about 120° C. In some embodiments, the reacting of the compound of formula VIII-2, or the salt thereof, is carried out at a temperature of about 110° C. In some embodiments, the reacting of the compound of formula VIII-2, or the salt thereof, is carried out in a solvent component. In some embodiments, the reacting of the compound of formula VIII-2, or the salt thereof, is carried out in a solvent component comprising an aromatic hydrocarbon. In some embodiments, the reacting of the compound of formula VIII-2, or the salt thereof, is carried out in a solvent component comprising toluene.

In some embodiments, the compound of formula VIII-2, or the salt thereof, is prepared by a process comprising:

(i) reacting a compound of formula VIII-1:

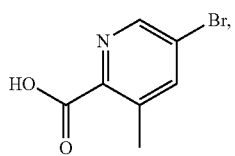

or a salt thereof, with a chlorinating agent to form a compound of formula VIII-1a:

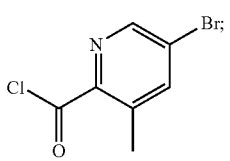

and (ii) reacting the compound of formula VIII-1a with an ammonia agent to form the compound of formula VIII-2.

In some embodiments, the reacting of the compound of formula VIII-1, or the salt thereof, is carried out in the presence of a catalyst. In some embodiments, the chlorinating agent, for reacting with the compound of formula VIII-1, or the salt thereof, is selected from oxalyl chloride, phosphorus oxychloride, diphosgene, thionyl chloride, sulfuryl chloride, and phosphorus pentachloride. In some embodiments, the chlorinating agent, for reacting with the compound of formula VIII-1, or the salt thereof, is thionyl chloride. In some embodiments, the catalyst, present in the reacting with the compound of formula VIII-1, or the salt thereof, is dimethylformamide. In some embodiments, from about 1 to about 4 molar equivalents of the chlorinating agent is utilized relative to the compound of formula VIII-1, or the salt thereof. In some embodiments, from about 1 to about 2 molar equivalents of the chlorinating agent is utilized relative to the compound of formula VIII-1, or the salt thereof. In some embodiments, about 1 molar equivalent of the chlorinating agent is utilized relative to the compound of formula VIII-1, or the salt thereof. In some embodiments, from about 0.01 to about 0.5 molar equivalents of the catalyst is utilized relative to the compound of formula VIII-1, or the salt thereof. In some embodiments, from about 0.1 to about 0.3 molar equivalents of the catalyst is utilized relative to the compound of formula VIII-1, or the salt thereof. In some embodiments, about 0.2 molar equivalent of the catalyst is utilized relative to the compound of formula VIII-1, or the salt thereof.

In some embodiments, the reacting of the compound of formula VIII-1, or the salt thereof, is carried out at a temperature of from about 100° C. to about 120° C. In some embodiments, the reacting of the compound of formula VIII-1, or the salt thereof, is carried out at a temperature of about 110° C. In some embodiments, the reacting of the compound of formula VIII-1, or the salt thereof, is carried out in a solvent component. In some embodiments, the reacting of the compound of formula VIII-1, or the salt thereof, is carried out in a solvent component comprising an aromatic hydrocarbon. In some embodiments, the reacting of the compound of formula VIII-1, or the salt thereof, is carried out in a solvent component comprising toluene.

In some embodiments, the ammonia agent, for reacting with the compound of formula VIII-1a, is ammonium hydroxide. In some embodiments, the ammonia agent, for reacting with the compound of formula VIII-1a, is aqueous ammonium hydroxide. In some embodiments, the reacting of the compound of formula VIII-1a, is carried out at a temperature of from about 0° C. to about 40° C. In some embodiments, the reacting of the compound of formula VIII-1a, is carried out at a temperature of from about 25° C. to about 40° C. In some embodiments, the reacting of the compound of formula VIII-1a, is carried out at a temperature of below 40° C. In some embodiments, the reacting of the compound of formula VIII-1a, is carried out in a solvent component. In some embodiments, the reacting of the compound of formula VIII-1a, is carried out in a solvent component comprising an aromatic hydrocarbon, a protic solvent, or a mixture thereof. In some embodiments, the reacting of the compound of formula VIII-1a, is carried out in a solvent component comprising toluene and water.

In some embodiments, the compound of formula IV-1, or the salt thereof, is prepared by a process comprising:

reacting a compound of formula X-7:

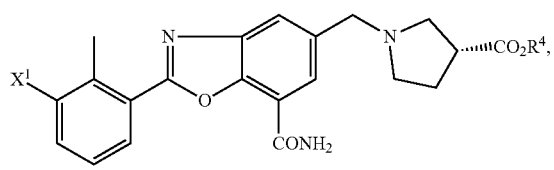

or a salt thereof, with a dehydrating agent to form the compound of formula IV-1, or the salt thereof, wherein $X^1$ is halo; and $R^4$ is $C_{1-6}$ alkyl. In some embodiments, $X^1$ is bromo. In some embodiments, $R^4$ is t-butyl.

In some embodiments, the compound of formula X-7 is a compound of formula X-7a:

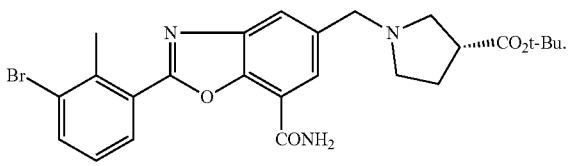

In some embodiments, the reacting of the compound of formula X-7, or the salt thereof, with the dehydrating agent is carried out in the presence of a base. In some embodiments, the base, present for the reacting of the compound of formula X-7, or the salt thereof, with the dehydrating agent, is a tertiary amine. In some embodiments, the base, present for the reacting of the compound of formula X-7, or the salt thereof, with the dehydrating agent, is triethylamine. In some embodiments, the dehydrating agent, for reacting of the compound of formula X-7, or the salt thereof, is trifluoroacetic anhydride. In some embodiments, from about 1 to about 4 molar equivalents of the dehydrating agent is utilized relative to the compound of formula X-7, or the salt thereof. In some embodiments, from about 1 to about 3 molar equivalents of the dehydrating agent is utilized relative to the compound of formula X-7, or the salt thereof. In some embodiments, about 2 molar equivalents of the dehydrating agent is utilized relative to the compound of formula X-7, or the salt thereof. In some embodiments, from about 1 to about 10 molar equivalents of the base is utilized relative to the compound of formula X-7, or the salt thereof. In some embodiments, from about 3 to about 7 molar equivalents of the base is utilized relative to the compound of formula X-7, or the salt thereof. In some embodiments, about 5 molar equivalents of the base is utilized relative to the compound of formula X-7, or the salt thereof.

In some embodiments, the reacting of the compound of formula X-7, or the salt thereof, with the dehydrating agent is carried out at a temperature of from about −10° C. to about 10° C. In some embodiments, the reacting of the compound of formula X-7, or the salt thereof, is carried out at a temperature of about 0° C. In some embodiments, the reacting of the compound of formula X-7, or the salt thereof, with the dehydrating agent is carried out in a solvent component. In some embodiments, the reacting of the compound of formula X-7, or the salt thereof, with the dehydrating agent is carried out in a solvent component comprising di-$C_{1-6}$ alkyl ether or a 4-10 membered heterocycloalkyl ether. In some embodiments, the reacting of the compound of formula X-7, or the salt thereof, with the dehydrating agent is carried out in a solvent component comprising tetrahydrofuran.

In some embodiments, the compound of formula X-7, or the salt thereof, is prepared by a process comprising:
reacting a compound of formula X-6:

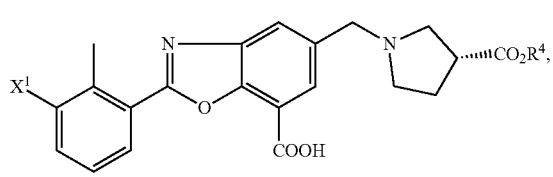

X-6 or a salt thereof, with an $C_{1-6}$ alkyl chloroformate; and
reacting the product of said reacting of the compound of formula X-6, or the salt thereof, with ammonium hydroxide to form the compound of formula X-7, or the salt thereof, wherein $X^1$ is halo; and $R^4$ is $C_{1-6}$ alkyl. In some embodiments, $X^1$ is bromo. In some embodiments, $R^4$ is t-butyl.

In some embodiments, the compound of formula X-6 is a compound of formula X-6a:

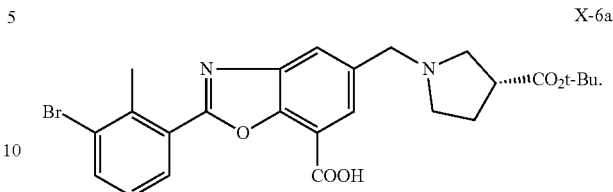

X-6a

In some embodiments, the reacting of the compound of formula X-6, or the salt thereof, with the $C_{1-6}$ alkyl chloroformate is carried out in the presence of a base. In some embodiments, the base, present for the reacting of the compound of formula X-6, or the salt thereof, with the $C_{1-6}$ alkyl chloroformate, N-methylmorpholine. In some embodiments, the $C_{1-6}$ alkyl chloroformate is isobutylchloroformate. In some embodiments, from about 1 to about 12 molar equivalents of ammonium hydroxide is utilized relative to the compound of formula X-6, or the salt thereof. In some embodiments, from about 5 to about 10 molar equivalents of ammonium hydroxide is utilized relative to the compound of formula X-6, or the salt thereof. In some embodiments, about 8 molar equivalents of ammonium hydroxide is utilized relative to the compound of formula X-6, or the salt thereof. In some embodiments, from about 1 to about 10 molar equivalents of the base is utilized relative to the compound of formula X-6, or the salt thereof. In some embodiments, from about 5 to about 7 molar equivalents of the base is utilized relative to the compound of formula X-6, or the salt thereof. In some embodiments, about 5.5 molar equivalents of the base is utilized relative to the compound of formula X-6, or the salt thereof. In some embodiments, from about 1 to about 5 molar equivalents of the $C_{1-6}$ alkyl chloroformate is utilized relative to the compound of formula X-6, or the salt thereof. In some embodiments, from about 2 to about 4 molar equivalents of the $C_{1-6}$ alkyl chloroformate is utilized relative to the compound of formula X-6, or the salt thereof. In some embodiments, about 3 molar equivalents of the $C_{1-6}$ alkyl chloroformate is utilized relative to the compound of formula X-6, or the salt thereof.

In some embodiments, the reacting of the compound of formula X-6, or the salt thereof, with the $C_{1-6}$ alkyl chloroformate is carried out at a temperature of from about −10° C. to about 10° C. In some embodiments, the reacting of the compound of formula X-6, or the salt thereof, with the $C_{1-6}$ alkyl chloroformate is carried out at a temperature of about 0° C. In some embodiments, the reacting of the compound of formula X-6, or the salt thereof, with the $C_{1-6}$ alkyl chloroformate is carried out in a solvent component. In some embodiments, the reacting of the compound of formula X-6, or the salt thereof, with the $C_{1-6}$ alkyl chloroformate is carried out in a solvent component comprising di-$C_{1-6}$ alkyl ether or a 4-10 membered heterocycloalkyl ether. In some embodiments, the reacting of the compound of formula X-6, or the salt thereof, with the $C_{1-6}$ alkyl chloroformate is carried out in a solvent component comprising tetrahydrofuran.

In some embodiments, the compound of formula X-6, or the salt thereof, is prepared by a process comprising:

reacting a compound of formula X-4:

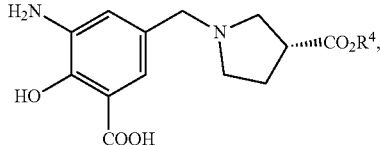

X-4 or a salt thereof, with a compound of formula X-5:

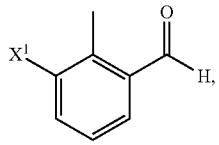

X-5 to form a compound of formula X-44:

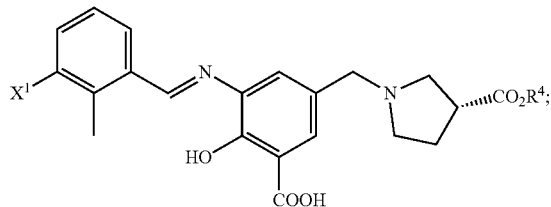

X-44 and reacting the compound of formula X-44 with a dehydrogenating agent to form the compound of formula X-6, or the salt thereof, wherein $X^1$ is halo; and $R^4$ is $C_{1-6}$ alkyl. In some embodiments, $X^1$ is bromo. In some embodiments, $R^4$ is t-butyl.

In some embodiments, the compound of formula X-4 is a compound of formula X-4a:

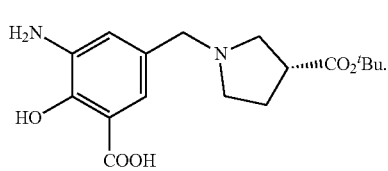

X-4a

In some embodiments, the compound of formula X-5 is a compound of formula X-5a:

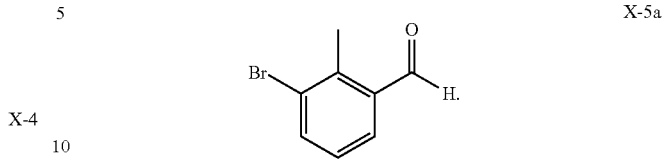

X-5a

In some embodiments, the dehydrogenating agent, for the reacting with the compound of formula X-44, is 2,3-dichloro-5,6-dicyano-1,4-benzoquinone (DDQ). In some embodiments, from about 1 to about 2 molar equivalents of the compound of formula X-5 is utilized relative to the compound of formula X-4, or the salt thereof. In some embodiments, about 1 molar equivalent of the compound of formula X-5 is utilized relative to the compound of formula X-4, or the salt thereof. In some embodiments, from about 1 to about 2 molar equivalents of the dehydrogenating agent is utilized relative to the compound of formula X-4, or the salt thereof. In some embodiments, about 1.5 molar equivalents of the dehydrogenating agent is utilized relative to the compound of formula X-4, or the salt thereof.

In some embodiments, the reacting of the compound of formula X-4, or the salt thereof, with the compound of formula X-5 is carried out at a temperature of about room temperature. In some embodiments, the reacting of the compound of formula X-4, or the salt thereof, with the compound of formula X-5 is carried out in a solvent component. In some embodiments, the reacting of the compound of formula X-4, or the salt thereof, with the compound of formula X-5 is carried out in a solvent component comprising a protic solvent. In some embodiments, the reacting of the compound of formula X-4, or the salt thereof, with the compound of formula X-5 is carried out in a solvent component comprising a $C_{1-6}$ alkanol. In some embodiments, the reacting of the compound of formula X-4, or the salt thereof, with the compound of formula X-5 is carried out in a solvent component comprising methanol. In some embodiments, the reacting of the compound of formula X-44 with the dehydrogenating agent is carried out at a temperature of about room temperature. In some embodiments, the reacting of the compound of formula X-44 with the dehydrogenating agent is carried out in a solvent component. In some embodiments, the reacting of the compound of formula X-44 with the dehydrogenating agent is carried out in a solvent component comprising a $C_{1-6}$ haloalkane. In some embodiments, the reacting of the compound of formula X-44 with the dehydrogenating agent is carried out in a solvent component comprising dichloromethane.

In some embodiments, the compound of formula X-4, or the salt thereof, is prepared by a process comprising:
reducing a compound of formula X-3:

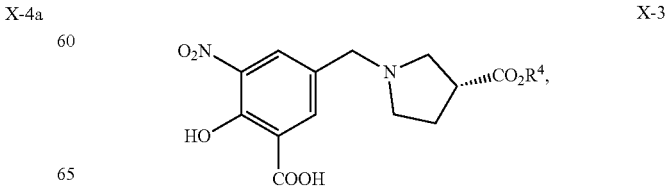

X-3 or a salt thereof, to form the compound of formula X-4, or the salt thereof, wherein R⁴ is C₁₋₆ alkyl. In some embodiments, R⁴ is t-butyl.

In some embodiments, the compound of formula X-3 is a compound of formula X-3a:

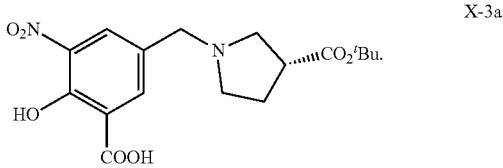 [SMILES: CC(C)(C)OC(=O)[C@@H]1CCN(Cc2cc(C(=O)O)c(O)c([N+](=O)[O-])c2)C1]

In some embodiments, the reducing of the compound of formula X-3, or a salt thereof, is carried out in the presence of hydrogen and a catalyst. In some embodiments, the catalyst, present for the reducing of the compound of formula X-3, or the salt thereof, is a palladium catalyst. In some embodiments, the catalyst, present for the reducing of the compound of formula X-3, or the salt thereof, is Pd/C. In some embodiments, the reducing of the compound of formula X-3, or a salt thereof, is carried out under pressure of from about 1 atmosphere to about 2 atmospheres. In some embodiments, the reducing of the compound of formula X-3, or a salt thereof, is carried out under pressure of about 1 atmosphere. In some embodiments, the reducing of the compound of formula X-3, or a salt thereof, is carried out at a temperature of about room temperature. In some embodiments, the reducing of the compound of formula X-3, or a salt thereof, is carried out in a solvent component. In some embodiments, the reducing of the compound of formula X-3, or a salt thereof, is carried out in a solvent component comprising a C₁₋₆ alkanol, a di-C₁₋₆ alkyl ether, a 4-10 membered heterocycloalkyl ether, or a mixture thereof. In some embodiments, the reducing of the compound of formula X-3, or a salt thereof, is carried out in a solvent component comprising methanol and tetrahydrofuran.

In some embodiments, the compound of formula X-3, or the salt thereof, is prepared by a process comprising:

reacting a compound of formula X-2:

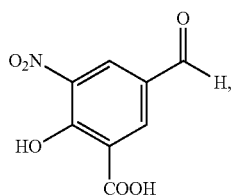

or a salt thereof, with a compound of formula XV-4:

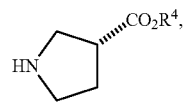

or a salt thereof, in the presence of a reducing agent to form the compound of formula X-3, or the salt thereof, wherein R⁴ is C₁₋₆ alkyl. In some embodiments, R⁴ is t-butyl.

In some embodiments, the reducing agent, present for the reacting of the compound of formula X-2, or the salt thereof, with the compound of formula XV-4, or the salt thereof, is selected from NaBH₄, NaBH₃CN and NaBH(OAc)₃. In some embodiments, the reducing agent, present for the reacting of the compound of formula X-2, or the salt thereof, with the compound of formula XV-4, or the salt thereof, is NaBH(OAc)₃. In some embodiments, the reacting of the compound of formula X-2, or the salt thereof, with the compound of formula XV-4, or the salt thereof, is carried out in the presence of a tertiary amine. In some embodiments, the tertiary amine, present for the reacting of the compound of formula X-2, or the salt thereof, with the compound of formula XV-4, or the salt thereof, is triethylamine. In some embodiments, from about 1 to about 2 molar equivalents of the compound of formula XV-4, or the salt thereof, is utilized relative to the compound of formula X-2, or the salt thereof. In some embodiments, about 1 molar equivalent of the compound of formula XV-4, or the salt thereof, is utilized relative to the compound of formula X-2, or the salt thereof. In some embodiments, from about 1 to about 5 molar equivalents of the reducing agent is utilized relative to the compound of formula X-2, or the salt thereof. In some embodiments, from about 1 to about 3 molar equivalents of the reducing agent is utilized relative to the compound of formula X-2, or the salt thereof. In some embodiments, about 2 molar equivalents of the reducing agent is utilized relative to the compound of formula X-2, or the salt thereof. In some embodiments, from about 1 to about 3 molar equivalents of the tertiary amine is utilized relative to the compound of formula X-2, or the salt thereof. In some embodiments, about 1 molar equivalent of the tertiary amine is utilized relative to the compound of formula X-2, or the salt thereof.

In some embodiments, the reacting of the compound of formula X-2, or the salt thereof, with the compound of formula XV-4, or the salt thereof, is carried out at a temperature of about room temperature. In some embodiments, the reacting of the compound of formula X-2, or the salt thereof, with the compound of formula XV-4, or the salt thereof, is carried out in a solvent component. In some embodiments, the reacting of the compound of formula X-2, or the salt thereof, with the compound of formula XV-4, or the salt thereof, is carried out in a solvent component comprising a polar aprotic solvent. In some embodiments, the reacting of the compound of formula X-2, or the salt thereof, with the compound of formula XV-4, or the salt thereof, is carried out in a solvent component comprising dimethylformamide.

In some embodiments, the compound of formula XV-4, or the salt thereof, is a compound of formula XV-4a:

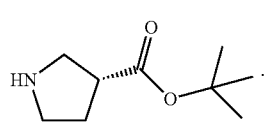

In some embodiments, the compound of formula XV-4, or the salt thereof, is a salt of formula XV-4b:

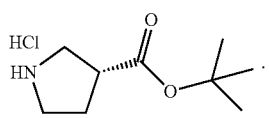

In some embodiments, the compound of formula X-2, or the salt thereof, is prepared by a process comprising:
reacting a compound of formula X-1:

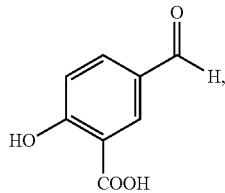

X-1 or a salt thereof, with nitric acid to form the compound of formula X-2, or the salt thereof.

In some embodiments, from about 1 to about 2 molar equivalents of the nitric acid is utilized relative to the compound of formula X-1, or the salt thereof. In some embodiments, about 1 molar equivalent of the nitric acid is utilized relative to the compound of formula X-1, or the salt thereof.

In some embodiments, the reducing of the compound of formula X-1, or the salt thereof, is carried out at a temperature of from about 0° C. to about 10° C. In some embodiments, the reducing of the compound of formula X-1, or the salt thereof, is carried out in a solvent component. In some embodiments, the reducing of the compound of formula X-1, or the salt thereof, is carried out in a solvent component comprising a protic solvent. In some embodiments, the reducing of the compound of formula X-1, or the salt thereof, is carried out in a solvent component comprising sulfuric acid.

In some embodiments, the compound of formula XV-4, or the salt thereof, is prepared by a process comprising:
reacting a chiral salt of the compound of formula XV-4:

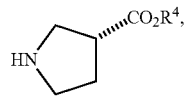

XV-4 with a base to form the compound of formula XV-4, or the salt thereof, wherein $R^4$ is $C_{1-6}$ alkyl. In some embodiments, $R^4$ is t-butyl.

In some embodiments, the base, for the reacting with the chiral salt of the compound of formula XV-4, is an alkali metal base. In some embodiments, the base, for the reacting with the chiral salt of the compound of formula XV-4, is an alkali metal carbonate. In some embodiments, the base, for the reacting with the chiral salt of the compound of formula XV-4, is selected from cesium carbonate, lithium carbonate, sodium carbonate, and potassium carbonate. In some embodiments, the base, for the reacting with the chiral salt of the compound of formula XV-4, is sodium carbonate. In some embodiments, from about 1 to about 2 molar equivalents of the base is utilized relative to the chiral salt of the compound of formula XV-4. In some embodiments, about 1.5 molar equivalents of the compound of the base is utilized relative to the chiral salt of the compound of formula XV-4.

In some embodiments, the reacting of the chiral salt of the compound of formula XV-4 with the base is carried out at a temperature of about room temperature. In some embodiments, the reacting of the chiral salt of the compound of formula XV-4 with the base is carried out in a solvent component. In some embodiments, the reacting of the chiral salt of the compound of formula XV-4 with the base is carried out in a solvent component comprising a polar protic solvent and a $C_{1-6}$ haloalkane. In some embodiments, the reacting of the chiral salt of the compound of formula XV-4 with the base is carried out in a solvent component comprising water and dichloromethane.

In some embodiments, the chiral salt of the compound of formula XV-4 is the L-tartrate salt of formula XV-3:

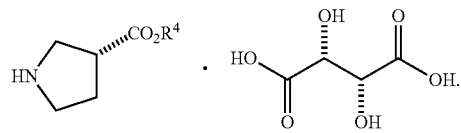

XV-3

In some embodiments, the L-tartrate salt of formula XV-3 has formula XV-3a:

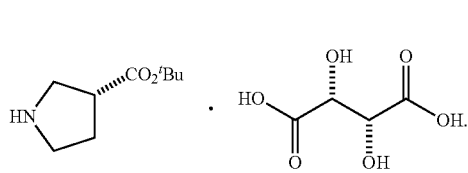

XV-3a

In some embodiments, the L-tartrate salt of formula XV-3 is prepared by a process comprising:
reacting the compound of formula XV-4 with the L-(+)-tartaric acid to form the L-tartrate salt of formula XV-3. In some embodiments, from about 1 to about 2 molar equivalents of L-(+)-tartaric acid is utilized relative to the compound of formula XV-4. In some embodiments, about 1 molar equivalent of the L-(+)-tartaric acid is utilized relative to the compound of formula XV-4.

In some embodiments, the reacting of the compound of formula XV-4 with the L-(+)-tartaric acid is carried out at a temperature of about 110° C. In some embodiments, the reacting of the compound of formula XV-4 with the L-(+)-tartaric acid is carried out in a solvent component. In some embodiments, the reacting of the compound of formula XV-4 with the L-(+)-tartaric acid is carried out in a solvent component comprising a protic solvent. In some embodiments, the reacting of the compound of formula XV-4 with the L-(+)-tartaric acid is carried out in a solvent component comprising a $C_{1-6}$ alkanol. In some embodiments, the reacting of the compound of formula XV-4 with the L-(+)-tartaric acid is carried out in a solvent component comprising ethanol.

In some embodiments, the compound of formula XV-4 is prepared by a process comprising:
reducing the compound of formula XV-2:

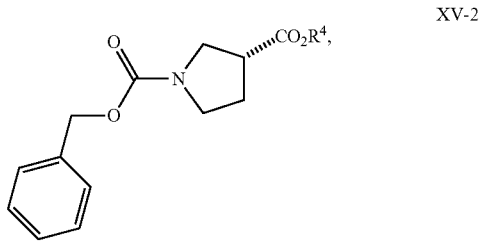

XV-2 to form the compound of formula XV-4, wherein $R^4$ is $C_{1-6}$ alkyl. In some embodiments, $R^4$ is t-butyl.

In some embodiments, the compound of formula XV-2 has formula XV-2a:

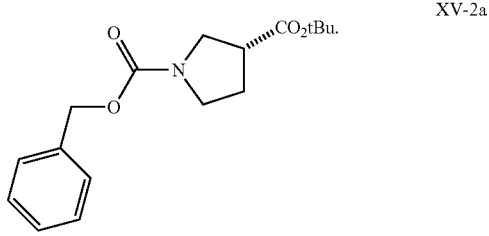 [SMILES: CC(C)(C)OC(=O)[C@@H]1CCN(C(=O)OCc2ccccc2)C1]

XV-2a

In some embodiments, the reducing of the compound of formula XV-2 is carried out in the presence of hydrogen and a catalyst. In some embodiments, the catalyst, present for the reducing of the compound of formula XV-2, is a palladium catalyst. In some embodiments, the catalyst is 10% Pd/C. In some embodiments, the reducing of the compound of formula XV-2 is carried out under pressure of from about 20 psi to about 40 psi. In some embodiments, the reducing of the compound of formula XV-2 is carried out under pressure of about 30 psi. In some embodiments, the reducing of the compound of formula XV-2 is carried out at a temperature of about room temperature. In some embodiments, the reducing of the compound of formula XV-2 is carried out in a solvent component. In some embodiments, the reducing of the compound of formula XV-2 is carried out in a solvent component comprising a protic solvent. In some embodiments, the reducing of the compound of formula XV-2 is carried out in a solvent component comprising a $C_{1-6}$ alkanol. In some embodiments, the reducing of the compound of formula XV-2 is carried out in a solvent component comprising methanol.

In some embodiments, the compound of formula XV-2 is prepared by a process comprising:
esterifying the compound of formula XV-1:

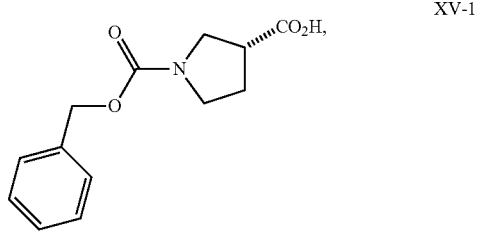 [SMILES: O=C(O)[C@@H]1CCN(C(=O)OCc2ccccc2)C1]

XV-1 to form the compound of formula XV-2.

In some embodiments, the esterifying of the compound of formula XV-1 is performed in the presence of an esterification agent. In some embodiments, the esterification agent, for the esterifying of the compound of formula XV-1, is tert-butyl 2,2,2-trichloroacetimidate. In some embodiments, the esterifying of the compound of formula XV-1 is performed in the presence of a Lewis acid. In some embodiments, the Lewis acid, present in the esterifying of the compound of formula XV-1, is boron trifluoride etherate. In some embodiments, from about 1 to about 5 molar equivalents of the esterification agent is utilized relative to the compound of formula XV-1. In some embodiments, from about 1 to about 3 molar equivalents of the esterification agent is utilized relative to the compound of formula XV-1. In some embodiments, about 2 molar equivalents of the esterification agent is utilized relative to the compound of formula XV-1. In some embodiments, from about 0.1 to about 1 molar equivalents of the Lewis acid is utilized relative to the compound of formula XV-1. In some embodiments, about 0.1 molar equivalent of the Lewis acid is utilized relative to the compound of formula XV-1.

In some embodiments, the esterifying of the compound of formula XV-1 is carried out at a temperature of about room temperature. In some embodiments, the esterifying of the compound of formula XV-1 is carried out in a solvent component. In some embodiments, the esterifying of the compound of formula XV-1 is carried out in a solvent component comprising a $C_{1-6}$ haloalkane. In some embodiments, the esterifying of the compound of formula XV-1 is carried out in a solvent component comprising dichloromethane.

In some embodiments, the compound of formula XV-1 is prepared by a process comprising:
reacting the compound of formula XV-0:

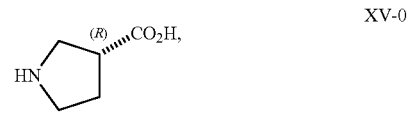

XV-0 or a salt thereof, with benzyl chloroformate to form the compound of formula XV-1.

In some embodiments, reacting of the compound of formula XV-0, or the salt thereof, with the benzyl chloroformate is carried out in the presence of a base. In some embodiments, the base, present for reacting of the compound of formula XV-0, or the salt thereof, with the benzyl chloroformate, is an alkali metal base. In some embodiments, the base, present for reacting of the compound of formula XV-0, or the salt thereof, with the benzyl chloroformate, is an alkali metal hydroxide. In some embodiments, the base, present for reacting of the compound of formula XV-0, or the salt thereof, with the benzyl chloroformate, is selected from lithium hydroxide, sodium hydroxide, potassium hydroxide, rubidium hydroxide, and cesium hydroxide. In some embodiments, the base, present for reacting of the compound of formula XV-0, or the salt thereof, with the benzyl chloroformate, is sodium hydroxide. In some embodiments, from about 1 to about 2 molar equivalents of the benzyl chloroformate is utilized relative to the compound of formula III-2, or the salt thereof. In some embodiments, about 1 molar equivalent of the benzyl chloroformate is utilized relative to the compound of formula III-2, or the salt thereof. In some embodiments, from about 1 to about 2 molar equivalents of the base is utilized relative to the compound of formula III-2, or the salt thereof. In some embodiments, about 1 molar equivalent of the base is utilized relative to the compound of formula III-2, or the salt thereof.

In some embodiments, the reacting of the compound of formula III-2, or the salt thereof, with the benzyl chloroformate is carried out at a temperature of about room temperature. In some embodiments, the reacting of the compound of formula III-2, or the salt thereof, with the benzyl chloroformate is carried out in a solvent component. In some embodiments, the reacting of the compound of formula III-2, or the salt thereof, with the benzyl chloroformate is carried out in a solvent component comprising polar protic solvent. In some embodiments, the reacting of the compound of formula III-2, or the salt thereof, with the benzyl chloroformate is carried out in a solvent component comprising water.

In some embodiments, the compound of formula XV-4, or the salt thereof, is prepared by a process comprising:
reducing the compound of formula XV-2:

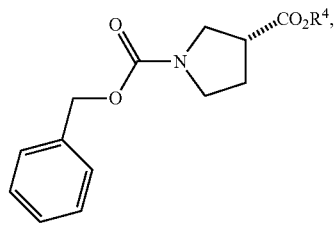

XV-2 to form the compound of formula XV-4, or the salt thereof, wherein $R^4$ is $C_{1-6}$ alkyl. In some embodiments, $R^4$ is t-butyl.

In some embodiments, the compound of formula XV-2 has formula XV-2a:

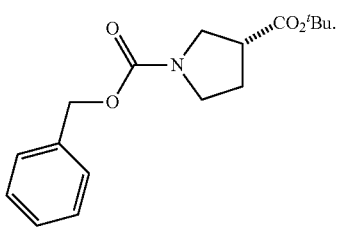

XV-2a

In some embodiments, the reducing of the compound of formula XV-2 is carried out in the presence of hydrogen and a catalyst. In some embodiments, the catalyst, present in the reducing of the compound of formula XV-2, is a palladium catalyst. In some embodiments, the catalyst, present in the reducing of the compound of formula XV-2, is 10% Pd/C. In some embodiments, the reducing of the compound of formula XV-2 is carried out under pressure of from about 20 psi to about 40 psi. In some embodiments, the reducing of the compound of formula XV-2 is carried out under pressure of about 35 psi. In some embodiments, the reducing of the compound of formula XV-2 is carried out at a temperature of about room temperature. In some embodiments, the reducing of the compound of formula XV-2 is carried out in a solvent component. In some embodiments, the reducing of the compound of formula XV-2 is carried out in a solvent component comprising a protic solvent. In some embodiments, the reducing of the compound of formula XV-2 is carried out in a solvent component comprising a $C_{1-6}$ alkanol. In some embodiments, the reducing of the compound of formula XV-2 is carried out in a solvent component comprising methanol.

In some embodiments, the compound of formula XV-2 is prepared by a process comprising:
esterifying the compound of formula XV-1:

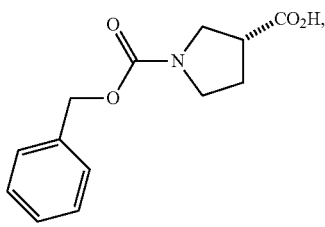

XV-1 to form the compound of formula XV-2.

In some embodiments, the esterifying of the compound of formula XV-1 is performed by reacting the compound of formula XV-2 with an esterification agent. In some embodiments, the esterification agent, for the esterifying of the compound of formula XV-1, is tert-butyl 2,2,2-trichloroacetimidate. In some embodiments, from about 1 to about 5 molar equivalents of the esterification agent is utilized relative to the compound of formula XV-1. In some embodiments, from about 1 to about 3 molar equivalents of the esterification agent is utilized relative to the compound of formula XV-1. In some embodiments, about 2 molar equivalents of the esterification agent is utilized relative to the compound of formula XV-1. In some embodiments, the esterifying of the compound of formula XV-1 is carried out at a temperature of from about 40° C. to about 60° C. In some embodiments, the esterifying of the compound of formula XV-1 is carried out at a temperature of about 50° C. In some embodiments, the esterifying of the compound of formula XV-1 is carried out in a solvent component. In some embodiments, the esterifying of the compound of formula XV-1 is carried out in a solvent component comprising an aromatic hydrocarbon. In some embodiments, the esterifying of the compound of formula XV-1 is carried out in a solvent component comprising toluene.

In some embodiments, the compound of formula XV-4 is prepared by a process comprising:
esterifying the salt of formula XV-0a:

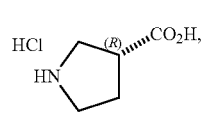

XV-0a to form the compound of formula XV-4.

In some embodiments, the esterifying of the salt of formula XV-0a is performed in the presence of an esterification agent. In some embodiments, the esterification agent, for the esterifying of the salt of formula XV-0a, is tert-butyl acetate. In some embodiments, the esterifying of the salt of formula XV-0a is performed in the presence of a Lewis acid. In some embodiments, the Lewis acid, present for the esterifying of the salt of formula XV-0a, is boron trifluoride etherate. In some embodiments, from about 1 to about 20 molar equivalents of the esterification agent is utilized relative to the salt of formula XV-0a. In some embodiments, from about 5 to about 15 molar equivalents of the esterification agent is utilized relative to the salt of formula XV-0a. In some embodiments, about 10 molar equivalents of the esterification agent is utilized relative to the salt of formula XV-0a. In some embodiments, from about 1 to about 10 molar equivalents of the Lewis acid is utilized relative to the salt of formula XV-0a. In some embodiments, about 6 molar equivalents of the Lewis acid is utilized relative to the salt of formula XV-0a. In some embodiments, the esterifying of the salt of formula XV-0a is carried out at a temperature of from about 0° C. to about 5° C.

Provided herein is a compound of formula IV-1b:

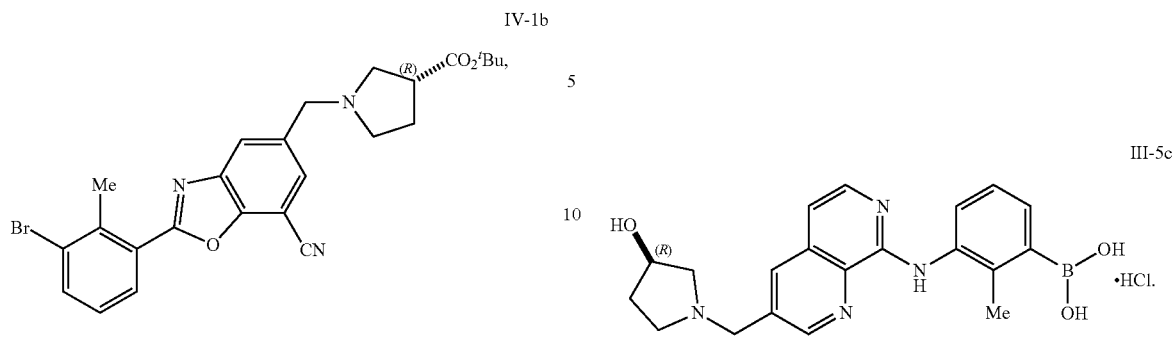

IV-1b or a salt thereof.

Provided herein is a compound of formula IV-2a:

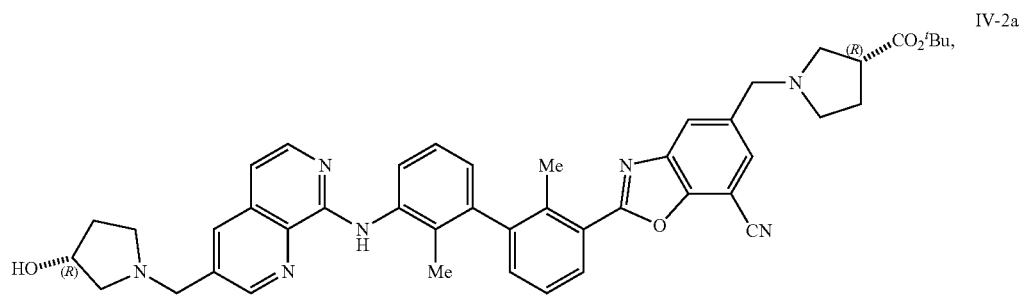

IV-2a or a salt thereof.

Provided herein is a compound of formula III-5:

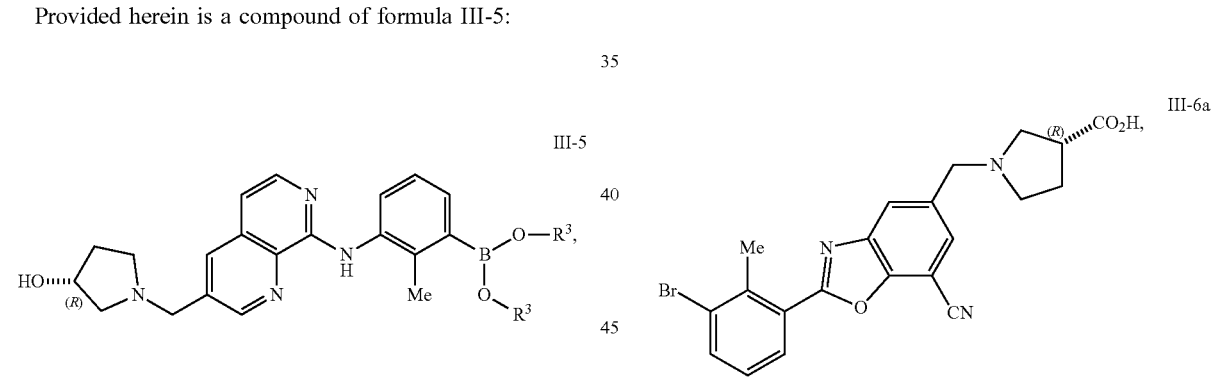

III-5 or a salt thereof, wherein:
  each R³ is independently selected from H and C₁₋₆ alkyl; or
  each R³ together form an C₂₋₃ alkylene linker, which is optionally substituted by 1, 2, 3, or 4 independently selected C₁₋₄ alkyl groups.

Provided herein is a compound of formula III-5a:

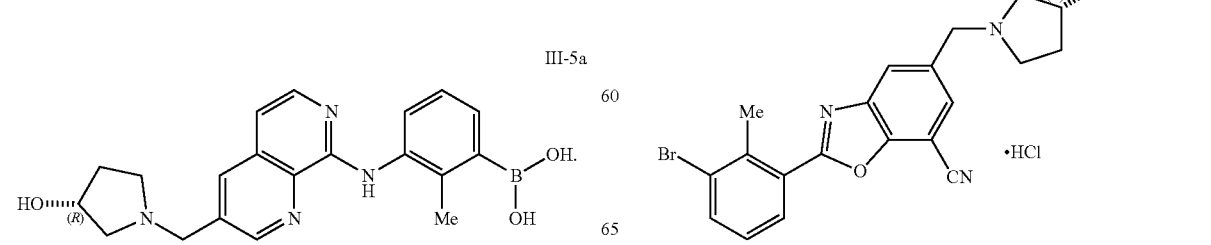

III-5a

Provided herein is a compound of formula III-5c:

III-5c

Provided herein is a compound of formula III-6a:

III-6a or a salt thereof.

Provided herein is a compound of formula III-6b:

III-6b

Provided herein is a compound of formula V-2:

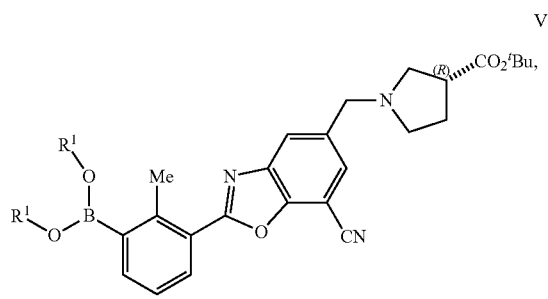

or a salt thereof, wherein:
each R¹ is independently selected from H and $C_{1-6}$ alkyl; or
each R¹ together form an $C_{2-3}$ alkylene linker, which is optionally substituted by 1, 2, 3, or 4 independently selected $C_{1-4}$ alkyl groups.

Provided herein is a compound of formula V-2b:

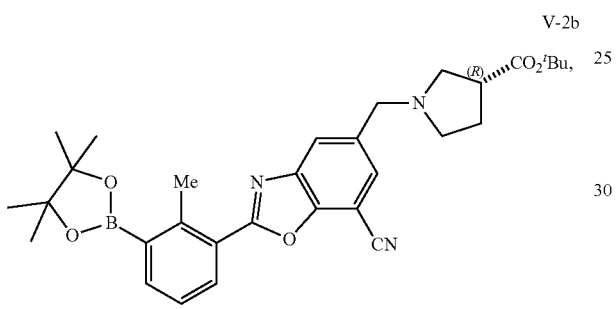

or a salt thereof.

Provided herein is a compound of formula VI-1a:

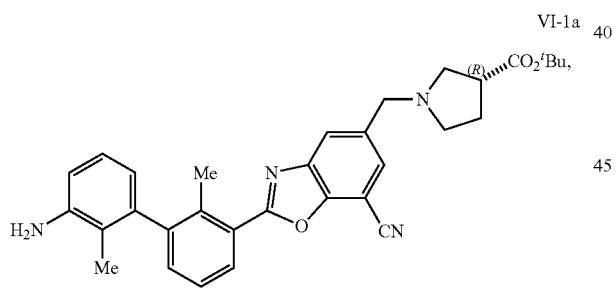

or a salt thereof.

Provided herein is a compound of formula IX-4a:

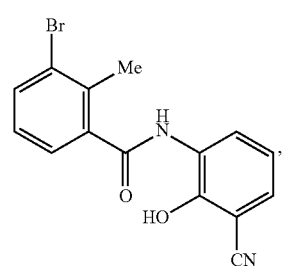

or a salt thereof.

Provided herein is a compound of formula IX-5a:

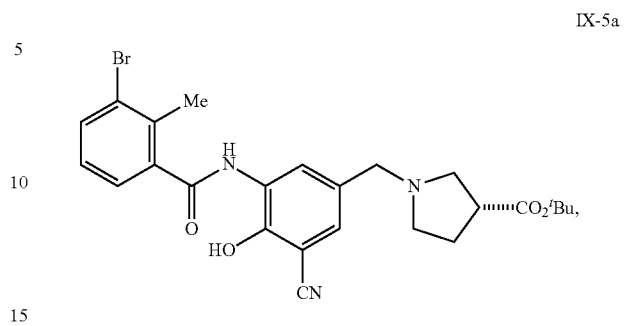

or a salt thereof.

Provided herein is a compound of formula X-3a:

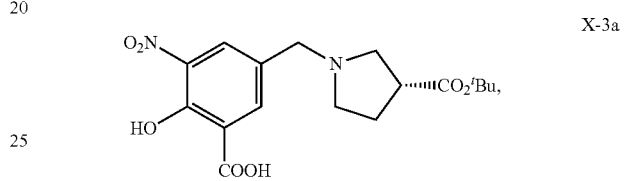

or a salt thereof.

Provided herein is a compound of formula X-4:

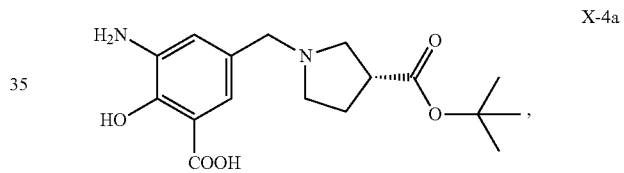

or a salt thereof.

Provided herein is a compound of formula X-44a:

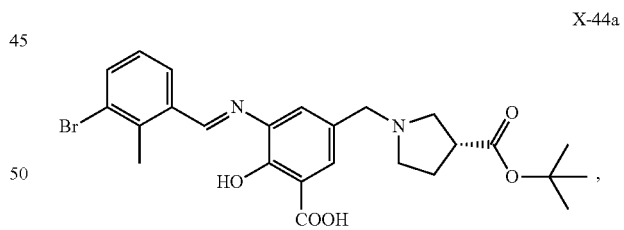

or a salt thereof.

Provided herein is a compound of formula X-6a:

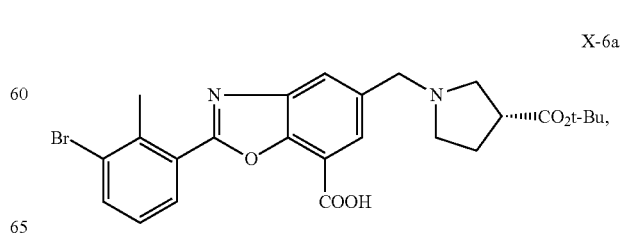

or a salt thereof.

93

Provided herein is a compound of formula X-7a:

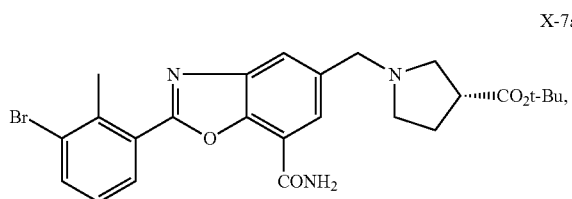

or a salt thereof.

Provided herein is a compound of formula XI-4:

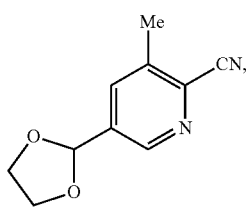

or a salt thereof.

Provided herein is a compound of formula XI-5:

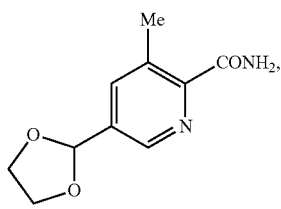

or a salt thereof.

Provided herein is a compound of formula XI-6:

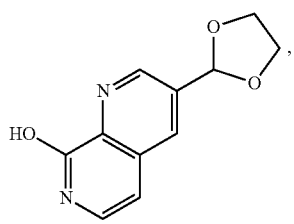

or a salt thereof.

Provided herein is a compound of formula XI-7a:

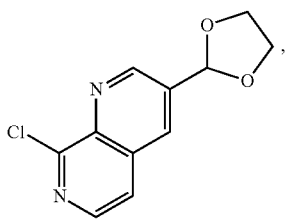

or a salt thereof.

94

Provided herein is a compound of formula XV-3a:

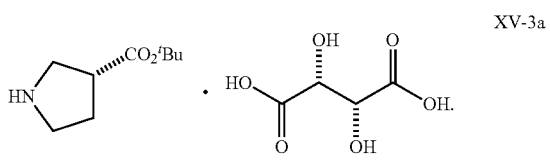 [SMILES: CC(C)(C)OC(=O)[C@@H]1CCNC1 ; O=C(O)[C@H](O)[C@@H](O)C(=O)O]

In some embodiments, the term "about" means ±10%. In some embodiments, the term "about" means ±5%.

In some embodiments, the compounds and intermediates disclosed herein can be found together with other substances such as water and solvents (e.g., hydrates and solvates) or can be isolated.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Compounds disclosed described herein also include pharmaceutically acceptable salts of the compounds. As used herein, the term "pharmaceutically acceptable salt" refers to a salt formed by the addition of a pharmaceutically acceptable acid or base to a compound disclosed herein. As used herein, the phrase "pharmaceutically acceptable" refers to a substance that is acceptable for use in pharmaceutical applications from a toxicological perspective and does not adversely interact with the active ingredient. Pharmaceutically acceptable salts, including mono- and bi-salts, include, but are not limited to, those derived from organic and inorganic acids such as, but not limited to, acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in their entireties.

The reactions described herein can be carried out at appropriate temperatures which can be readily determined by the skilled artisan. Reaction temperatures will depend on, for example, the melting and boiling points of the reagents and solvent, if present; the thermodynamics of the reaction (e.g., vigorously exothermic reactions may need to be carried out at reduced temperatures); and the kinetics of the reaction (e.g., a high activation energy barrier may need elevated temperatures).

The expressions, "ambient temperature" and "room temperature" or "rt" as used herein, are understood in the art, and refer generally to a temperature, e.g., a reaction temperature, that is about the temperature of the room in which the salt forming reaction is carried out, for example, a temperature from about 20° C. to about 30° C.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected. In some embodiments, reactions can be carried out in the absence of solvent, such as when at least one of the reagents is a liquid or gas.

Suitable solvents can include halogenated solvents such as carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, α,α,α-trifluorotoluene, 1,2-dichloroethane, 1,2-dibromoethane, hexafluorobenzene, 1,2,4-trichlorobenzene, 1,2-dichlorobenzene, chlorobenzene, fluorobenzene, mixtures thereof and the like.

Suitable solvents can include ether solvents such as: dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, anisole, t-butyl methyl ether, mixtures thereof and the like.

Suitable hydrocarbon solvents include benzene, cyclohexane, pentane, hexane, toluene, cycloheptane, methylcyclohexane, heptane (e.g., n-heptane), ethylbenzene, m-, o-, or p-xylene, octane, indane, nonane, naphthalene, mixtures thereof, and the like.

At various places in the present specification, substituents of compounds and intermediates are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

For compounds of the invention in which a variable appears more than once, each variable can be a different moiety independently selected from the group defining the variable. For example, where a structure is described having two R groups that are simultaneously present on the same compound, the two R groups can represent different moieties independently selected from the group defined for R. In another example, when an optionally multiple substituent is designated in the form:

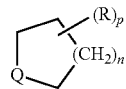

then it is understood that substituent R can occur p number of times on the ring, and R can be a different moiety at each occurrence. It is understood that each R group may replace any hydrogen atom attached to a ring atom, including one or both of the (CH2)n hydrogen atoms. Further, in the above example, should the variable Q be defined to include hydrogens, such as when Q is the to be CH2, NH, etc., any floating substituent such as R in the above example, can replace a hydrogen of the Q variable as well as a hydrogen in any other non-variable component of the ring.

As used herein, the term "alkyl", employed alone or in combination with other terms, refers to a saturated hydrocarbon group that may be straight-chain or branched. In some embodiments, the alkyl group contains 1 to 12, 1 to 8, or 1 to 6 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, n-heptyl, n-octyl, and the like. In some embodiments, the alkyl moiety is methyl, ethyl, n-propyl, isopropyl, n-butyl, isobutyl, tert-butyl, n-pentyl, isopentyl, neopentyl, n-hexyl, or 2,4,4-trimethylpentyl. In some embodiments, the alkyl moiety is methyl.

As used herein, the terms "halo" and "halogen", employed alone or in combination with other terms, refer to fluoro, chloro, bromo, and iodo.

As used herein, the term "di-$C_{1-6}$ alkyl ether" refers to two saturated hydrocarbon groups that may be straight-chain or branched, which has at least one oxygen heteroatom. Example of di-$C_{1-6}$ alkyl ether includes diethyl ether.

As used herein, the term "4-10 membered heterocycloalkyl ether" refers to a non-aromatic ring or ring system, which optionally contain one or more alkenylene groups as part of the ring structure, which has at least one oxygen heteroatom ring member and 4-10 ring members. Included within the term "heterocycloalkyl" are monocyclic 4-, 5-, 6- and 7-membered heterocycloalkyl groups. Examples of 4-10 membered heterocycloalkyl ether include tetrahydrofuran, tetrahydropyran, dioxane, and the like.

The term "$C_{1-6}$ alkanol" as used herein, refers to an alkyl group having 1 to 6 carbon atoms including one or more hydroxyl (OH) substituents. Examples of $C_{1-6}$ alcohol include, but are not limited to, methanol, ethanol, n-propanol, isopropanol, n-butanol and the like.

Suitable protic solvents can include, by way of example and without limitation, water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, glycerol, mixtures thereof, and the like.

Suitable aprotic solvents can include, by way of example and without limitation, tetrahydrofuran (THF), N,N-dimethylformamide (DMF), N,N-dimethylacetamide (DMA), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, hexamethylphosphoramide, mixtures thereof, and the like.

The term "anti-solvent" as used herein, refers to solvents in which a chemical compound is sparingly soluble. Anti-solvents may be used to achieve supersaturation and solidification by exposing a solution of a product to another solvent(s) in which the product is sparingly soluble.

The reactions described herein can be carried out in air or under an inert atmosphere. Typically, reactions containing reagents or products that are substantially reactive with air can be carried out using air-sensitive synthetic techniques that are well known to the skilled artisan.

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., Protective Groups in Organic Synthesis, 4d. Ed., Wiley & Sons, 2007, which is incorporated herein by reference in its entirety. Adjustments to the protecting groups and formation and cleavage methods described herein may be adjusted as necessary in light of the various substituents.

In some embodiments, preparation of compounds can involve the addition of acids or bases to affect, for example, catalysis of a desired reaction or formation of salt forms such as acid addition salts.

Example acids can be inorganic or organic acids. Inorganic acids include hydrochloric acid, hydrobromic acid, sulfuric acid, phosphoric acid, and nitric acid. Organic acids include formic acid, acetic acid, propionic acid, butanoic acid, benzoic acid, 4-nitrobenzoic acid, methanesulfonic acid, p-toluenesulfonic acid, benzenesulfonic acid, tartaric acid, trifluoroacetic acid, propiolic acid, butyric acid, 2-butynoic acid, vinyl acetic acid, pentanoic acid, hexanoic acid, heptanoic acid, octanoic acid, nonanoic acid and decanoic acid.

Example bases include alkali metal bases such as alkali metal hydroxides (e.g., cesium acetate, lithium acetate, sodium acetate, and potassium acetate), alkali metal carbonate (e.g., lithium carbonate, sodium carbonate, and potassium carbonate), alkali metal phosphates (e.g., cesium phosphate, lithium phosphate, sodium phosphate, potassium phosphate, and potassium phosphate dibasic), and alkali metal acetate (e.g., cesium acetate, lithium acetate, sodium acetate, and potassium acetate). Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include sodium and potassium salts of methyl, ethyl, n-propyl, i-propyl, n-butyl, t-butyl, trimethylsilyl and cyclohexyl substituted amides.

The term "Lewis acid" as used herein refers to a compound that is capable of accepting an electron pair from a Lewis base to form a Lewis adduct. Examples of Lewis acid includes trimethylsilyl triflate, scandium triflate, trimethylsilyl iodide, trimethyl borate, and boron trifluoride etherate.

The term "reducing agent" as used herein refers to a compound or element that donates an electron to an electron receptor in a redox chemical reaction. Examples of reducing agent includes $NaBH_4$, $NaBH_3CN$ and $NaBH(OAc)_3$, and sodium hydrosulfite.

The term "oxidizing agent" as used herein refers to a compound or element that accepts an electron from an electron donor in a redox chemical reaction. Examples of oxidizing agent includes Dess-Martin periodinane and sodium periodate.

The present invention also includes salt forms of the compounds described herein. Examples of salts (or salt forms) include, but are not limited to, mineral or organic acid salts of basic residues such as amines, alkali or organic salts of acidic residues such as carboxylic acids, and the like. Generally, the salt forms can be prepared by reacting the free base or acid with stoichiometric amounts or with an excess of the desired salt-forming inorganic or organic acid or base in a suitable solvent or various combinations of solvents. Lists of suitable salts are found in Remington's Pharmaceutical Sciences, 17th ed., Mack Publishing Company, Easton, Pa., 1985, p. 1418, the disclosure of which is hereby incorporated by reference in its entirety.

Upon carrying out preparation of compounds according to the processes described herein, the usual isolation and purification operations such as concentration, filtration, extraction, solid-phase extraction, recrystallization, chromatography, and the like may be used, to isolate the desired products.

In some embodiments, the compounds of the invention, and salts thereof, are substantially isolated. By "substantially isolated" is meant that the compound is at least partially or substantially separated from the environment in which it was formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or the salt thereof. Methods for isolating compounds and their salts are routine in the art.

The Suzuki coupling reactions can be initiated using a number of palladium(0) and palladium(II) catalysts and performed under conditions known in the art (see, e.g., Miyaura and Suzuki, *Chem. Rev.* 1995, 95, 2457-2483, which is hereby incorporated in its entirety). In some embodiments, the Suzuki catalyst is a palladium catalyst selected from RuPhos Pd G4, CataCXium® Pd G4, $Pd(PPh_3)_4$, $Pd(dppf)_2Cl_2$, dichlorobis[di-tert-butyl(p-dimethylaminophenyl)phosphino]palladium, $PdCl_2(dtbpf)$ (Pd-118), and tetrakis(tri(o-tolyl)phosphine)palladium(0).

The Suzuki catalyst can be purchased commercially: RuPhos Pd G4 (Sigma-Aldrich, cat. #804290), CataCXium® Pd G4 (Sigma-Aldrich, cat. #900349; (2'-(methylamino)-[1,1'-biphenyl]-2-yl)((methylsulfonyl)oxy)palladium di(1-adamantyl)-n-butylphosphine complex), and $Pd(PPh_3)_4$ (Sigma-Aldrich, cat. #697265), $Pd(dppf)_2Cl_2$ (Sigma-Aldrich, cat. #697230). Structures of exemplary catalyst are also shown below:

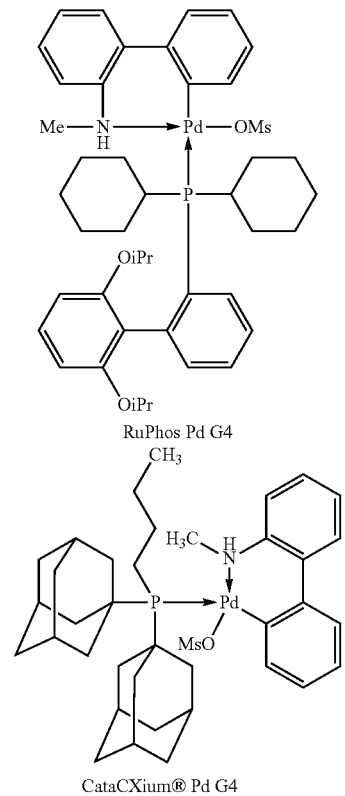

RuPhos Pd G4

CataCXium® Pd G4

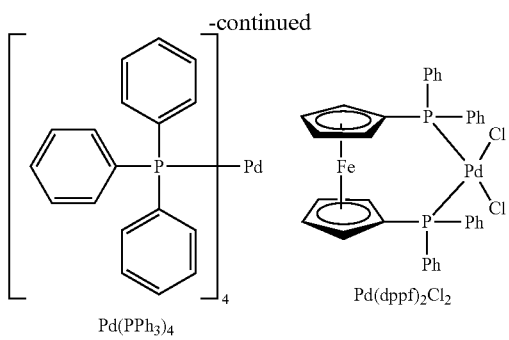

Pd(PPh₃)₄        Pd(dppf)₂Cl₂

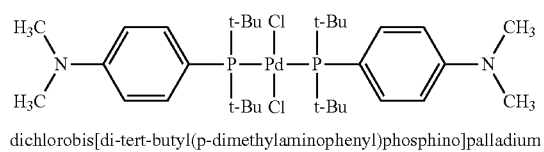

dichlorobis[di-tert-butyl(p-dimethylaminophenyl)phosphino]palladium

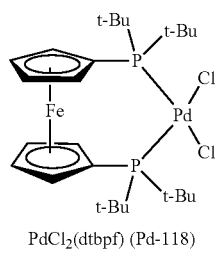

PdCl₂(dtbpf) (Pd-118)

The processes described herein can be monitored according to any suitable method known in the art. For example, product formation can be monitored by spectroscopic means, such as nuclear magnetic resonance spectroscopy (e.g., 1H or 13C), infrared spectroscopy, or spectrophotometry (e.g., UV-visible); or by chromatography such as high performance liquid chromatography (HPLC) or thin layer chromatography (TLC) or other related techniques.

The following abbreviations may be used herein: aq. (aqueous); br (broad); d (doublet); dd (doublet of doublets); DCM (dichloromethane); DMF (N, N-dimethylformamide); Et (ethyl); EtOAc (ethyl acetate); g (gram(s)); h (hour(s)); HPLC (high performance liquid chromatography); Hz (hertz); J (coupling constant); LCMS (liquid chromatography-mass spectrometry); m (multiplet); M (molar); MS (Mass spectrometry); Me (methyl); MeCN (acetonitrile); MeOH (methanol); mg (milligram(s)); min. (minutes(s)); mL (milliliter(s)); mmol (millimole(s)); nM (nanomolar); NMR (nuclear magnetic resonance spectroscopy); Ph (phenyl); r.t. (room temperature), s (singlet); t (triplet or tertiary); TBS (tert-butyldimethylsilyl); tert (tertiary); tt (triplet of triplets); TFA (trifluoroacetic acid); THF (tetrahydrofuran); μg (microgram(s)); μL (microliter(s)); μM (micromolar); wt % (weight percent).

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to inhibit the activity of PD-1/PD-L1 protein/protein interaction according to at least one assay described herein.

Embodiments

1. A process of preparing (R)-1-((7-cyano-2-(3'-((3-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid, or a salt thereof, comprising:

reacting a compound of formula III-5:

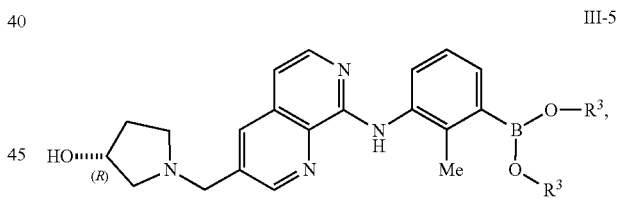

or a salt thereof, with a compound of formula III-6:

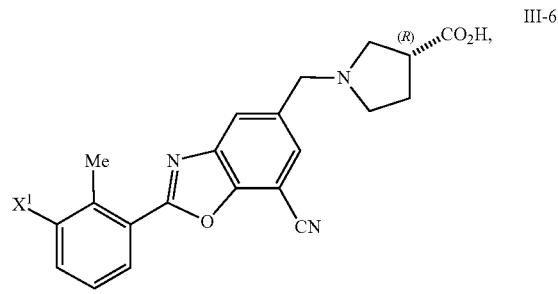

or a salt thereof, in the presence of a Suzuki catalyst and a base to form a compound of formula A-1:

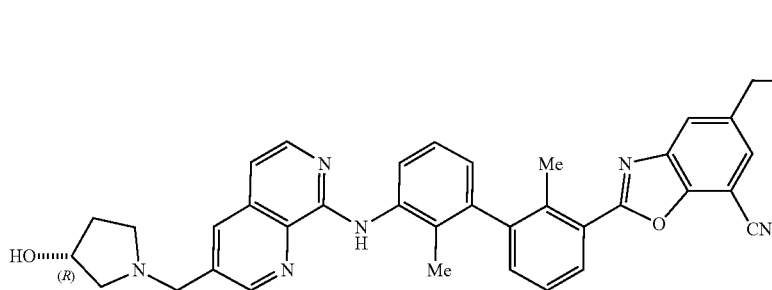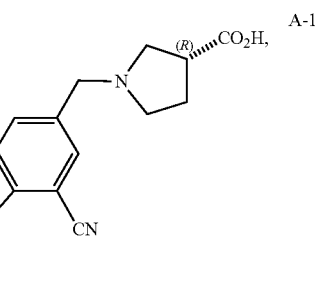

or a salt thereof; wherein:
each $R^3$ is independently selected from H and $C_{1-6}$ alkyl; or
each $R^3$ together form an $C_{2-3}$ alkylene linker, which is optionally substituted by 1, 2, 3, or 4 independently selected $C_{1-4}$ alkyl groups; and
$X^1$ is halo.

2. The process of embodiment 1, wherein the compound of Formula A-1, or the salt thereof, is a salt of formula A-1a:

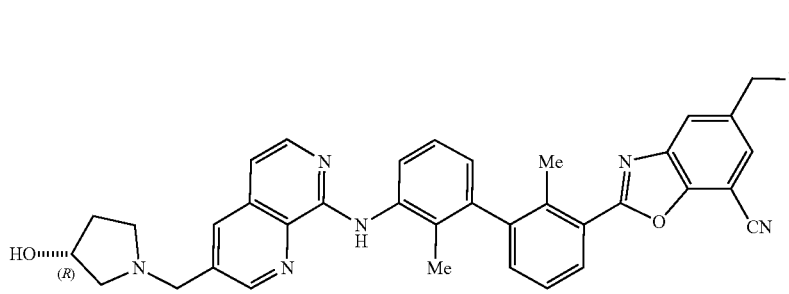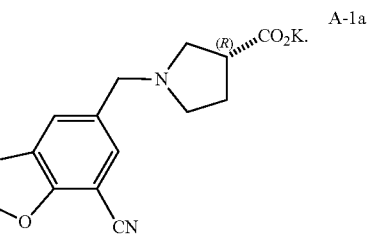

3. The process of embodiment 1 or 2, wherein the Suzuki catalyst is a palladium catalyst.
4. The process of embodiment 3, wherein the Suzuki catalyst is selected from RuPhos Pd G4, CataCXium® Pd G4 ((2'-(methylamino)-[1,1'-biphenyl]-2-yl)((methylsulfonyl)oxy)palladium di(1-adamantyl)-n-butylphosphine complex), Pd(PPh$_3$)$_4$, Pd(dppf)$_2$Cl$_2$, dichlorobis[di-tert-butyl(p-dimethylaminophenyl)phosphino]palladium, and PdCl$_2$(dtbpf) (Pd-118).
5. The process of embodiment 4, wherein the Suzuki catalyst is RuPhos Pd G4.
6. The process of any one of embodiments 1-5, wherein the base is an alkali metal base.
7. The process of embodiment 6, wherein the base is an alkali metal carbonate.
8. The process of embodiment 7, wherein the base is selected from cesium carbonate, lithium carbonate, sodium carbonate, and potassium carbonate.
9. The process of embodiment 8, wherein the base is potassium carbonate.
10. The process of any one of embodiments 1-9, wherein from about 1 to about 2 molar equivalents of the compound of formula III-6, or the salt thereof, is utilized relative to the compound of formula III-5, or the salt thereof.
11. The process of any one of embodiments 1-10, wherein from about 2 to about 3 molar equivalents of the base is utilized relative to the compound of formula III-5, or the salt thereof.
12. The process of any one of embodiments 1-11, wherein from about 0.001 to about 0.1 molar equivalents of the Suzuki catalyst is utilized relative to the compound of formula III-5, or the salt thereof.
13. The process of any one of embodiments 1-11, wherein from about 0.001 to about 0.01 molar equivalents of the Suzuki catalyst is utilized relative to the compound of formula III-5, or the salt thereof.
14. The process of any one of embodiments 1-13, wherein the reacting of the compound of formula III-5, or the salt thereof, with the compound of formula III-6, or the salt thereof, is carried out at a temperature of from about 60° C. to about 120° C.
15. The process of any one of embodiments 1-13, wherein the reacting of the compound of formula III-5, or the salt thereof, with the compound of formula III-6, or the salt thereof, is carried out at a temperature of about 90° C.
16. The process of any one of embodiments 1-15, wherein the reacting of the compound of formula III-5, or the salt thereof, with the compound of formula III-6, or the salt thereof, is carried out in a solvent component.
17. The process of embodiment 16, wherein the solvent component comprises a polar protic solvent, a di-$C_{1-6}$ alkyl ether, a 4-10 membered heterocycloalkyl ether, or a mixture thereof.
18. The process of embodiment 17, wherein the solvent component comprises water and 1,4-dioxane.
19. The process of any one of embodiments 2-18, wherein the salt of Formula A-1a is converted to a compound of Formula A-1 by a process comprising treating the salt of Formula A-1a with a weak acid resin.
20. The process of embodiment 19, wherein the weak acid resin is an ion exchange resin.
21. The process of embodiment 20, wherein the ion exchange resin is Dowex MAC-3 hydrogen form.
22. The process of any one of embodiments 1 and 3-18, wherein each $R^3$ is H.

23. The process of any one of embodiments 1, 3-18 and 22, wherein $X^1$ is bromo.

24. The process of any one of embodiments 1-23, wherein the process comprises: reacting a compound of formula III-5b:

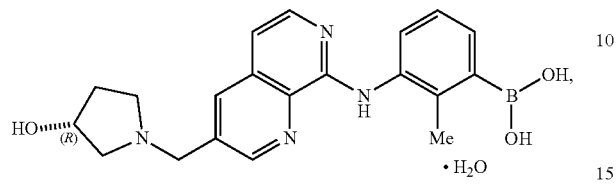
III-5b with a salt of formula III-6b:

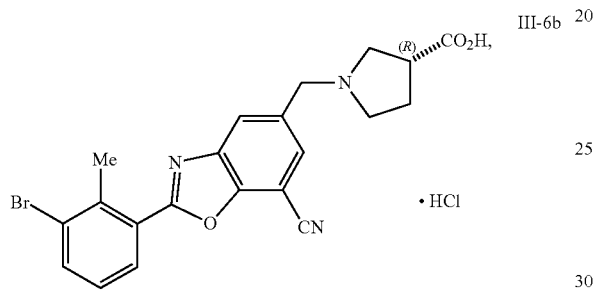
III-6b in the presence of a Suzuki catalyst and a base to form a salt of formula A-1a:

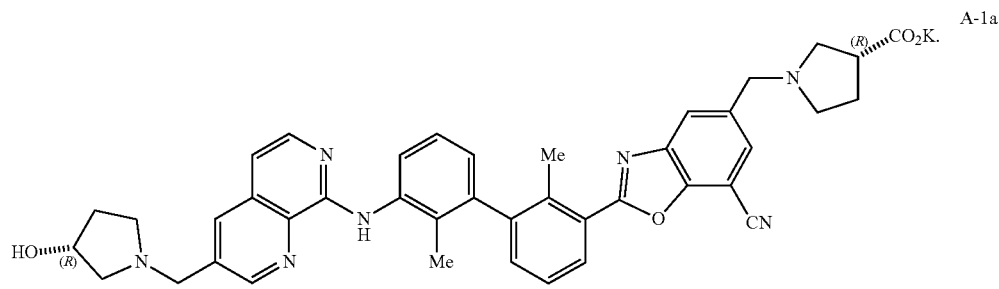
A-1a

25. A process of preparing (R)-1-((7-cyano-2-(3'-((3-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid, or a salt thereof, comprising:

reacting a compound of formula III-5:

III-5 or a salt thereof, with a compound of formula IV-1:

IV-1 or a salt thereof, in the presence of a Suzuki catalyst and a base to form a compound of formula IV-2:

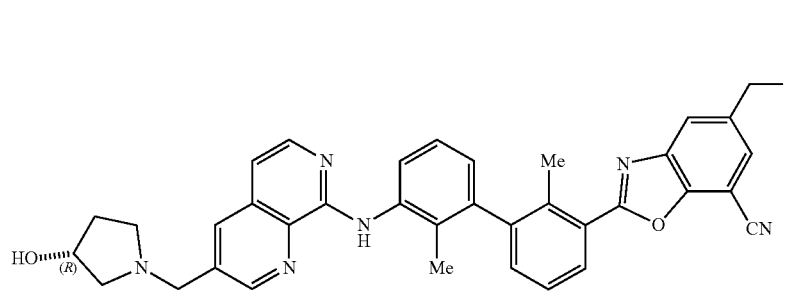

or a salt thereof, wherein:
each $R^3$ is independently selected from H and $C_{1-6}$ alkyl; or
each $R^3$ together form an $C_{2-3}$ alkylene linker, which is optionally substituted by 1, 2, 3, or 4 independently selected $C_{1-4}$ alkyl groups; and
$R^4$ is $C_{1-6}$ alkyl; and
$X^1$ is halo.

26. The process of embodiment 25, wherein each $R^3$ is H.
27. The process of embodiment 25 or 26, wherein $R^4$ is t-butyl.
28. The process of any one of embodiments 25-27, wherein $X^1$ is bromo.
29. The process of embodiment 25, wherein the compound of formula IV-1, or the salt thereof, is a compound of formula IV-1a:

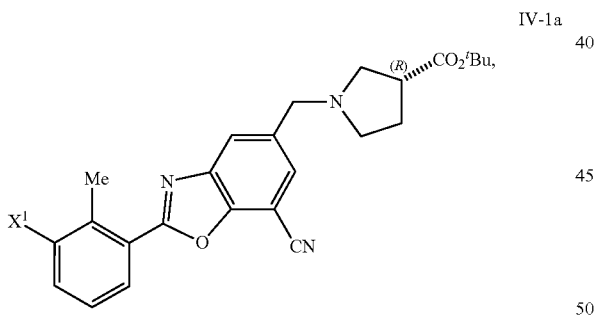

or a salt thereof.

30. The process of embodiment 25, wherein the compound of formula IV-1, or the salt thereof, is a compound of formula IV-1b:

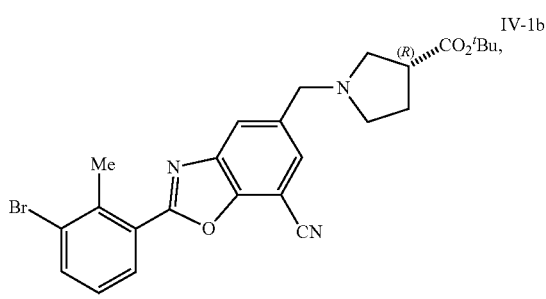

or a salt thereof.

31. The process of embodiment 25, wherein the compound of formula IV-2, or the salt thereof, is a compound of formula IV-2a:
32. The process of embodiment 25, wherein the compound of formula III-5, or the salt thereof, is a salt of formula III-5c:

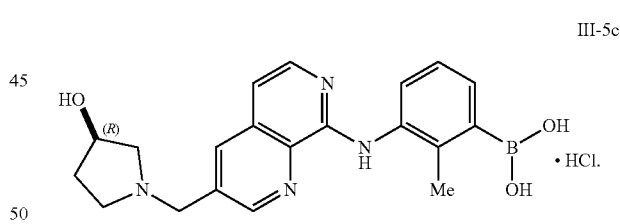

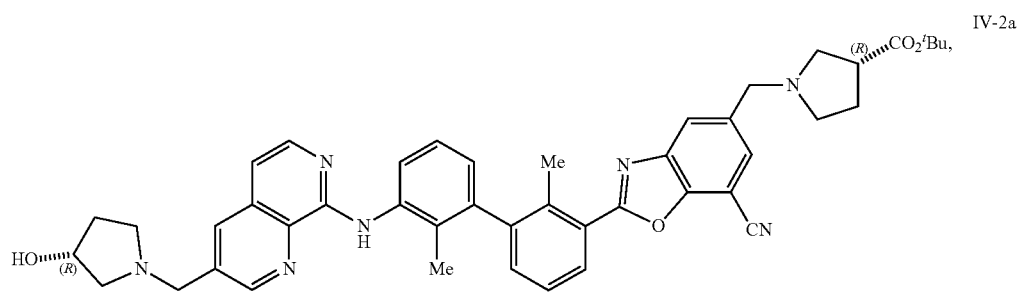

or a salt thereof.

33. The process of any one of embodiments 25-32, wherein the Suzuki catalyst, present in the reacting of the compound of formula III-5, or the salt thereof, with the compound of formula IV-1, or the salt thereof, is a palladium catalyst.

34. The process of embodiment 33, wherein the Suzuki catalyst, present in the reacting of the compound of formula III-5, or the salt thereof, with the compound of formula IV-1, or the salt thereof, is selected from RuPhos Pd G4, CataCXium® Pd G4 ((2'-(methylamino)-[1,1'-biphenyl]-2-yl)((methylsulfonyl)oxy)palladium di(1-adamantyl)-n-butylphosphine complex), Pd(PPh₃)₄, Pd(dppf)₂Cl₂, dichlorobis[di-tert-butyl(p-dimethylaminophenyl)phosphino]palladium, and PdCl₂(dtbpf) (Pd-118).

35. The process of any one of embodiments 25-34, wherein the base, present in the reacting of the compound of formula III-5, or the salt thereof, with the compound of formula IV-1, or the salt thereof, is an alkali metal carbonate.

36. The process of embodiment 35, wherein the base, present in the reacting of the compound of formula III-5, or the salt thereof, with the compound of formula IV-1, or the salt thereof, is selected from cesium carbonate, lithium carbonate, sodium carbonate, and potassium carbonate.

37. The process of embodiment 36, wherein the base, present in the reacting of the compound of formula III-5, or the salt thereof, with the compound of formula IV-1, or the salt thereof, is potassium carbonate.

38. The process of any one of embodiments 25-30 and 32-37 further comprising deprotecting the compound of formula IV-2, or the salt thereof, to form (R)-1-((7-cyano-2-(3'-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid, or the salt thereof.

39. The process of embodiment 38, wherein the deprotecting of the compound of formula IV-2, or the salt thereof, is performed in the presence of a Lewis acid.

40. The process of embodiment 39, wherein the Lewis acid present in the deprotecting of the compound of formula IV-2, or the salt thereof, is trimethylsilyl triflate.

41. The process of any one of embodiments 25-40, wherein the process comprises: reacting a salt of formula III-5c:

with a compound of formula IV-1b:

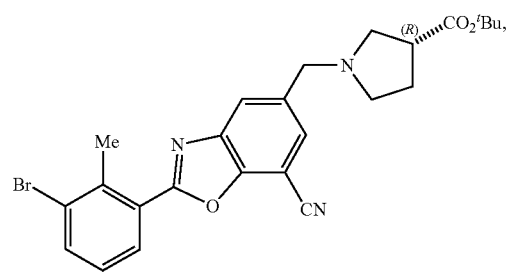

or a salt thereof, in the presence of a Suzuki catalyst and a base to form a compound of formula IV-2a:

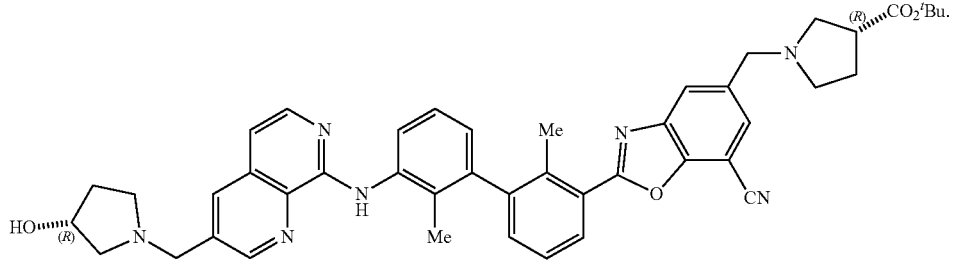

42. A process of preparing (R)-1-((7-cyano-2-(3'-((3-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid, or a salt thereof, comprising:

reacting a compound of formula V-1:

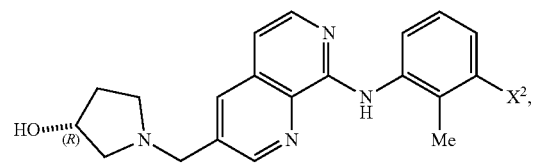

or a salt thereof, with a compound of formula V-2:

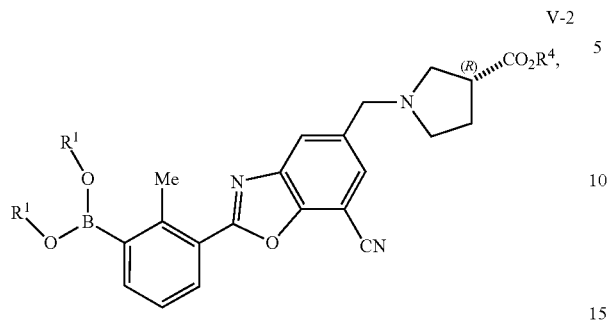

V-2 or a salt thereof, in the presence of a Suzuki catalyst and a base to form a compound of formula IV-2:

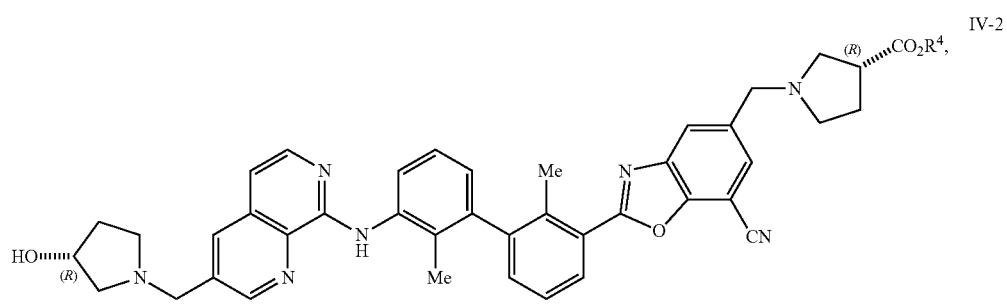

IV-2 or a salt thereof, wherein:
- each $R^1$ is independently selected from H and $C_{1-6}$ alkyl; or
- each $R^1$ together form an $C_{2-3}$ alkylene linker, which is optionally substituted by 1, 2, 3, or 4 independently selected $C_{1-4}$ alkyl groups;
- $X^2$ is halo; and
- $R^4$ is $C_{1-6}$ alkyl.

43. The process of embodiment 42, wherein $R^4$ is t-butyl.

44. The process of embodiment 42 or 43, wherein $X^2$ is bromo.

45. The process of any one of embodiments 42-44, wherein each $R^1$ together form a $C_2$ alkylene linker substituted with four methyl groups.

46. The process of embodiment 42, wherein the compound of formula V-1, or the salt thereof, is a compound of formula V-1a:

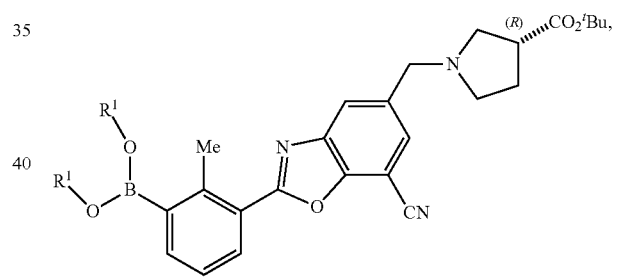

V-1a or a salt thereof.

47. The process of embodiment 42, wherein the compound of formula V-2, or the salt thereof, is a compound of formula V-2a:

V-2a or a salt thereof.

48. The process of embodiment 42, wherein the compound of formula V-2, or the salt thereof, is a compound of formula V-2b:

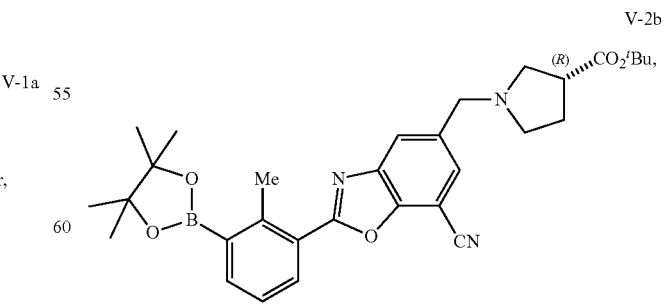

V-2b or a salt thereof.

49. The process of embodiment 42, wherein the compound of formula IV-2 is a compound of formula IV-2a:

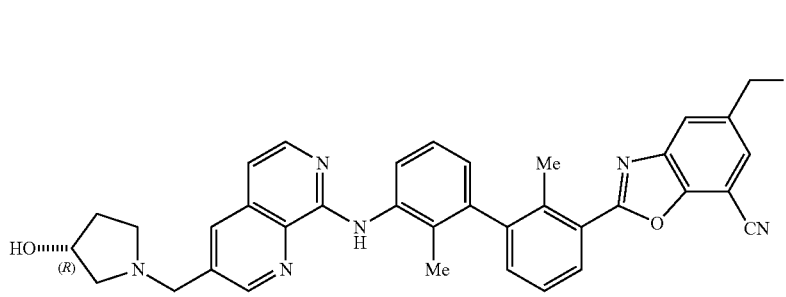
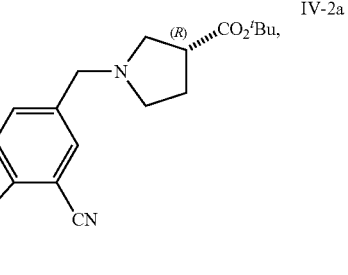

or a salt thereof.

50. The process of any one of embodiments 42-49, wherein the Suzuki catalyst, present in the reacting of the compound of formula V-1, or the salt thereof, with the compound of formula V-2, or the salt thereof, is a palladium catalyst.
51. The process of embodiment 50, wherein the Suzuki catalyst, present in the reacting of the compound of formula V-1, or the salt thereof, with the compound of formula V-2, or the salt thereof, is selected from RuPhos Pd G4, CataCXium® Pd G4 ((2'-(methylamino)-[1,1'-biphenyl]-2-yl)((methylsulfonyl)oxy)palladium di(1-adamantyl)-n-butylphosphine complex), Pd(PPh$_3$)$_4$, Pd(dppf)$_2$Cl$_2$, dichlorobis[di-tert-butyl(p-dimethylaminophenyl)phosphino]palladium, and PdCl$_2$(dtbpf) (Pd-118).
52. The process of embodiment 51, wherein the Suzuki catalyst, present in the reacting of the compound of formula V-1, or the salt thereof, with the compound of formula V-2, or the salt thereof, is Pd(dppf)$_2$Cl$_2$.
53. The process of any one of embodiments 42-52, wherein the base, present in the reacting of the compound of formula V-1, or the salt thereof, with the compound of formula V-2, or the salt thereof, is an alkali metal base.
54. The process of embodiment 53, wherein the base, present in the reacting of the compound of formula V-1, or the salt thereof, with the compound of formula V-2, or the salt thereof, is an alkali metal phosphate.
55. The process of embodiment 54, wherein the base, present in the reacting of the compound of formula V-1, or the salt thereof, with the compound of formula V-2, or the salt thereof, is selected from cesium phosphate, lithium phosphate, sodium phosphate, and potassium phosphate.
56. The process of embodiment 55, wherein the base, present in the reacting of the compound of formula V-1, or the salt thereof, with the compound of formula V-2, or the salt thereof, is potassium phosphate.
57. The process of any one of embodiments 42-56, further comprising deprotecting the compound of formula IV-2, or the salt thereof, to form (R)-1-((7-cyano-2-(3'-((3-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid, or the salt thereof.
58. The process of embodiment 57, wherein the deprotecting of the compound of formula IV-2, or the salt thereof, is performed in the presence of a Lewis acid.
59. The process of embodiment 58, wherein the Lewis acid, present in the deprotecting of the compound of formula IV-2, or the salt thereof, is trimethylsilyl triflate or trimethylsilyl iodide.
60. The process of any one of embodiments 42-59, wherein the process comprises: reacting a compound of Formula V-1a:

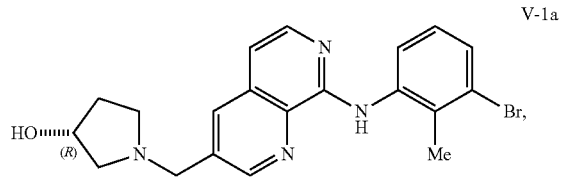

with a compound of formula V-2b:

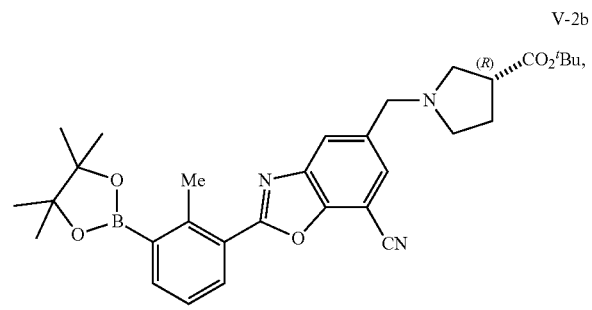

in the presence of a Suzuki catalyst and a base to form a compound of formula IV-2a:

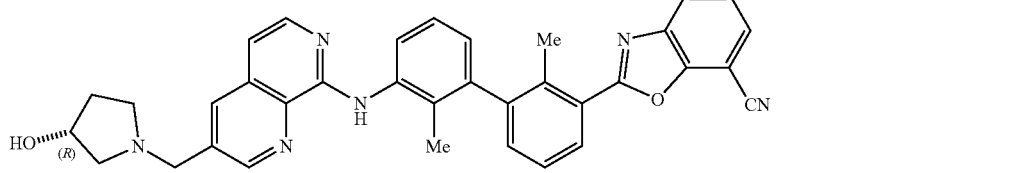

61. The process of any one of embodiments 42-59, wherein the compound of formula V-2, or the salt thereof, is prepared by a process comprising:
converting a compound of formula IV-1:

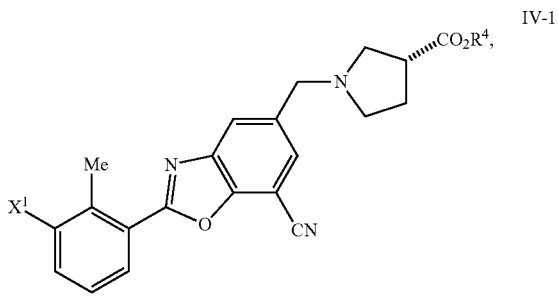

or the salt thereof, with a borylating agent to form the compound of formula V-2, or the salt thereof, wherein $X^1$ is halo; and $R^4$ is $C_{1-6}$ alkyl.

62. The process of embodiment 61, wherein $X^1$ is bromo.

63. The process of embodiment 61 or 62, wherein $R^4$ is t-butyl.

64. The process of any one of embodiments 48-60, wherein the compound of formula V-2b, or the salt thereof, is prepared by a process comprising:
reacting a compound of formula IV-1b:

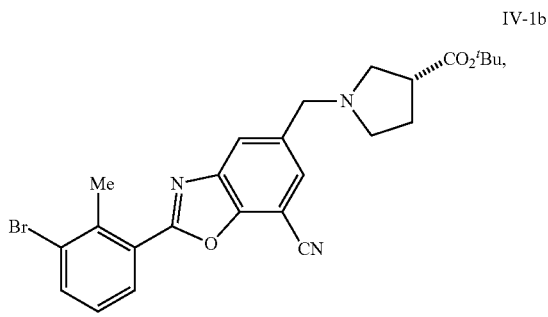 [SMILES: Cc1c(Br)cccc1-c1nc2cc(CN3CC[C@@H](C(=O)OC(C)(C)C)C3)cc(C#N)c2o1]

or the salt thereof, with 4,4,4',4',5,5,5',5'-octamethyl-2,2'-bi (1,3,2-dioxaborolane) to form the compound of formula V-2b, or the salt thereof.

65. The process of any one of embodiments 61-64, wherein the reacting of the compound of formula IV-1 or IV-1b, or the salt thereof, with the borylating agent or the 4,4,4',4',5,5,5',5'-octamethyl-2,2'-bi(1,3,2-dioxaborolane) is carried out in the presence of a catalyst and a base.

66. The process of embodiment 65, wherein the catalyst, present in the reacting of the compound of formula IV-1 or IV-1b, or the salt thereof, with the borylating agent or the 4,4,4',4',5,5,5',5'-octamethyl-2,2'-bi(1,3,2-dioxaborolane), is a palladium catalyst.

67. The process of embodiment 66, wherein the catalyst, present in the reacting of the compound of formula IV-1 or IV-1b, or the salt thereof, with the borylating agent or the 4,4,4',4',5,5,5',5'-octamethyl-2,2'-bi(1,3,2-dioxaborolane), is selected from RuPhos Pd G4, CataCXium® Pd G4 ((2'-(methylamino)-[1,1'-biphenyl]-2-yl)((methylsulfonyl)oxy)palladium di(1-adamantyl)-n-butylphosphine complex), Pd(PPh$_3$)$_4$, Pd(dppf)$_2$Cl$_2$, dichlorobis[di-tert-butyl(p-dimethylaminophenyl) phosphino]palladium, and PdCl$_2$(dtbpf) (Pd-118).

68. The process of embodiment 67, wherein the catalyst, present in the reacting of the compound of formula IV-1 or IV-1b, or the salt thereof, with the borylating agent or the 4,4,4',4',5,5,5',5'-octamethyl-2,2'-bi(1,3,2-dioxaborolane), is Pd(dppf)$_2$Cl$_2$.

69. The process of any one of embodiments 61-68, wherein the base, present in the reacting of the compound of formula IV-1 or IV-1b, or the salt thereof, with the borylating agent or the 4,4,4',4',5,5,5',5'-octamethyl-2,2'-bi(1,3,2-dioxaborolane), is an alkali metal base.

70. The process of embodiment 69, wherein the base, present in the reacting of the compound of formula IV-1 or IV-1b, or the salt thereof, with the borylating agent or the 4,4,4',4',5,5,5',5'-octamethyl-2,2'-bi(1,3,2-dioxaborolane), is an alkali metal acetate.

71. The process of embodiment 70, wherein the base, present in the reacting of the compound of formula IV-1 or IV-1b, or the salt thereof, with the borylating agent or the 4,4,4',4',5,5,5',5'-octamethyl-2,2'-bi(1,3,2-dioxaborolane), is selected from cesium acetate, lithium acetate, sodium acetate, and potassium acetate.

72. The process of embodiment 71, wherein the base, present in the reacting of the compound of formula IV-1 or IV-1b, or the salt thereof, with the borylating agent or the 4,4,4',4',5,5,5',5'-octamethyl-2,2'-bi(1,3,2-dioxaborolane), is potassium acetate.

73. A process of preparing (R)-1-((7-cyano-2-(3'-(((R)-3-hydroxypyrrolidin-1-yl)methyl)-1,7-naphthyridin-8-yl)amino)-2,2'-dimethyl-[1,1'-biphenyl]-3-yl) benzo[d]oxazol-5-yl)methyl)pyrrolidine-3-carboxylic acid, or a salt thereof, comprising:
reacting a compound of formula VI-1

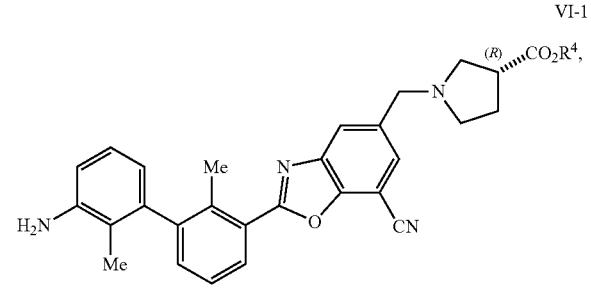

or a salt thereof, with a compound of formula III-3:

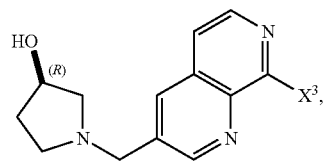

or a salt thereof, in the presence of a catalyst to form a compound of formula IV-2:

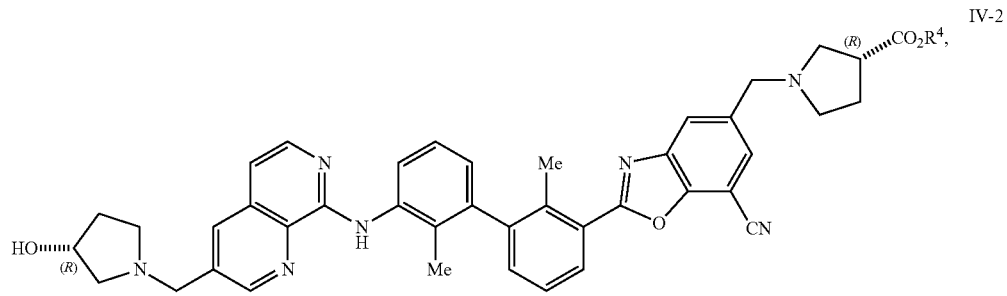

or a salt thereof, wherein $X^3$ is halo; and $R^4$ is $C_{1-6}$ alkyl.

74. The process of embodiment 73, wherein $X^3$ is chloro.

75. The process of embodiment 73 or 74, wherein $R^4$ is t-butyl.

76. The process of embodiment 73, wherein the compound of formula VI-1, or the salt thereof, is a compound of formula VI-1a:

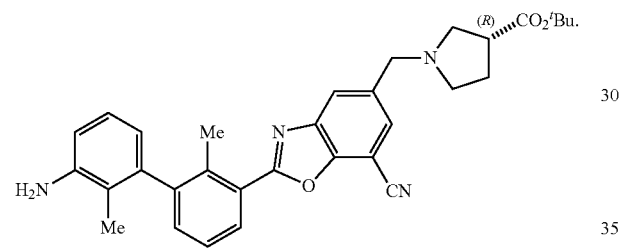

77. The process of embodiment 73, wherein the compound of formula III-3, or the salt thereof, is a compound of formula III-3a:

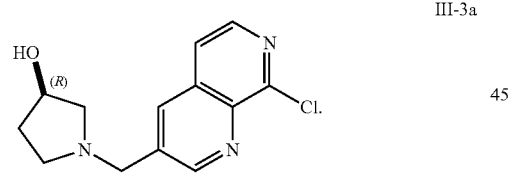

78. The process of embodiment 73, wherein the compound of formula IV-2, or the salt thereof, is a compound of formula IV-2a:

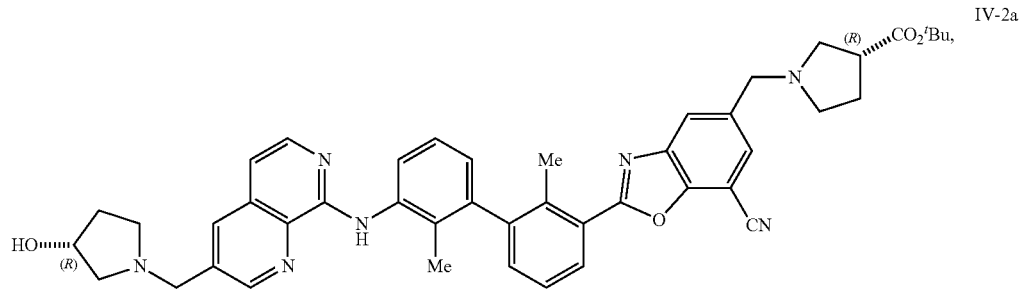

or a salt thereof.

79. The process of any one of embodiments 73-78, wherein the catalyst, present in the reacting of the compound of formula VI-1, or the salt thereof, with the compound of formula III-3, or the salt thereof, is a Lewis acid.
80. The process of embodiment 79, wherein the catalyst, present in the reacting of the compound of formula VI-1, or the salt thereof, with the compound of formula III-3, or the salt thereof, is scandium triflate.
81. The process of any one of embodiments 73-80, further comprising deprotecting the compound of formula IV-2, or the salt thereof, to form (R)-1-((7-cyano-2-(3'-((3-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid, or the salt thereof.
82. The process of embodiment 81, wherein the deprotecting of the compound of formula IV-2, or the salt thereof, is performed in the presence of a Lewis acid.
83. The process of embodiment 82, wherein the Lewis acid, present in the deprotecting the compound of formula IV-2, or the salt thereof, is trimethylsilyl triflate or trimethylsilyl iodide.
84. The process of any one of embodiments 73-83, wherein the process comprises: reacting a compound of formula VI-1a:

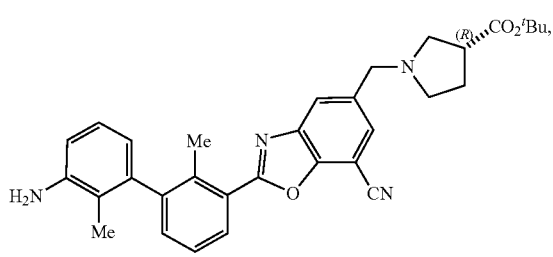

VI-1a with a salt of formula III-3b:

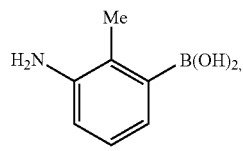

III-3b in the presence of a catalyst to form a compound of formula IV-2a:

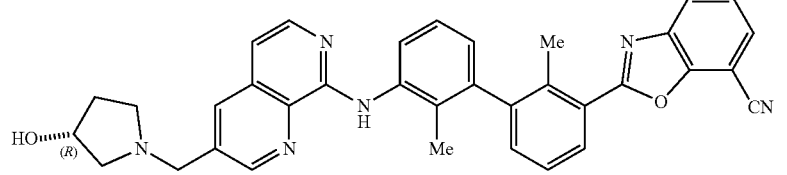

IV-2a

85. The process of any one of embodiments 73-83, wherein the compound of formula VI-1, or the salt thereof, is prepared by a process comprising: reacting a compound of formula IV-1:

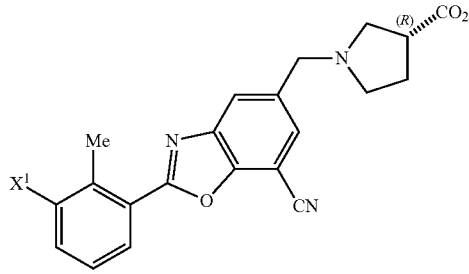

IV-1 or a salt thereof, with a compound of formula III-4:

III-4

$H_2N$  Me  $B(OH)_2$, or a salt thereof, in the presence of a Suzuki catalyst and a base to form a compound of formula VI-1, or the salt thereof; wherein $X^1$ is halo; and $R^4$ is $C_{1-6}$ alkyl.
86. The process of embodiment 85, wherein $X^1$ is bromo.
87. The process of embodiment 85 or 86, wherein $R^4$ is t-butyl.
88. The process of embodiment 85, wherein the compound of formula IV-1, or the salt thereof, is a compound of formula IV-1b:

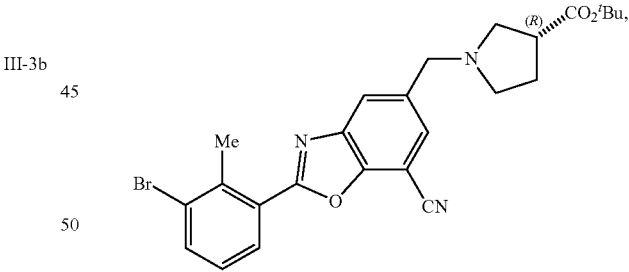

IV-1b or a salt thereof.

89. The process of any one of embodiments 85-88, wherein the Suzuki catalyst, present in the reacting of the compound formula IV-1, or the salt thereof, with the compound of formula III-4, or the salt thereof, is a palladium catalyst.
90. The process of embodiment 89, wherein the Suzuki catalyst, present in the reacting of the compound formula IV-1, or the salt thereof, with the compound of formula III-4, or the salt thereof, is selected from CataCXium® Pd G4 ((2'-(methylamino)-[1,1'-biphenyl]-2-yl)((methylsulfonyl)oxy)palladium di(1-adamantyl)-n-butylphosphine complex), Pd(PPh$_3$)$_4$, Pd(dppf)$_2$Cl$_2$, dichlorobis[di-tert-butyl(p-dimethylaminophenyl)phosphino]palladium, and PdCl$_2$(dtbpf) (Pd-118).
91. The process of embodiment 90, wherein the Suzuki catalyst, present in the reacting of the compound formula IV-1, or the salt thereof, with the compound of formula III-4, or the salt thereof, is PdCl$_2$(dtbpf) (Pd-118).
92. The process of any one of embodiments 85-91, wherein the base, present in the reacting of the compound formula IV-1, or the salt thereof, with the compound of formula III-4, or the salt thereof, is an alkali metal base.
93. The process of embodiment 92, wherein the base, present in the reacting of the compound formula IV-1, or the salt thereof, with the compound of formula III-4, or the salt thereof, is an alkali metal phosphate.
94. The process of embodiment 93, wherein the base, present in the reacting of the compound formula IV-1, or the salt thereof, with the compound of formula III-4, or the salt thereof, is potassium phosphate dibasic.
95. The process of any one of embodiments 1-23, 25-31 and 33-40, wherein the compound of Formula III-5, or the salt thereof, is a compound of formula III-5a:

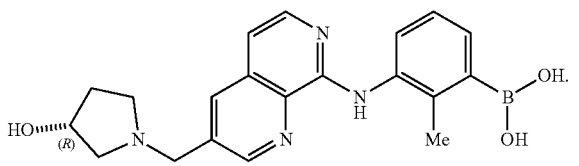

III-5a

96. The process of any one of embodiments 1-23, 25-31 and 33-40, wherein the compound of Formula III-5, or the salt thereof, is a compound of formula III-5b:

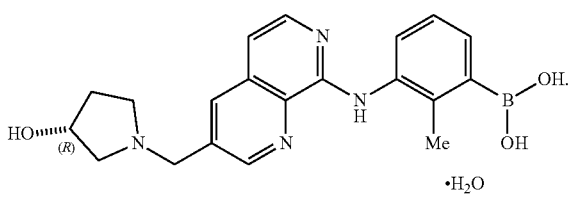

III-5b

97. The process of any one of embodiments 1-40, wherein the compound of Formula III-6, or the salt thereof, is a salt of formula III-6b:

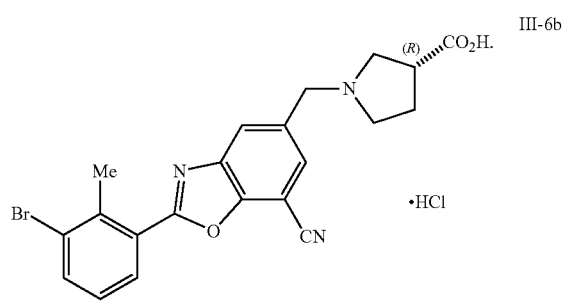

III-6b

98. The process of embodiment 95, wherein the compound of Formula III-5a is prepared by a process comprising:
reacting a compound of formula III-3:

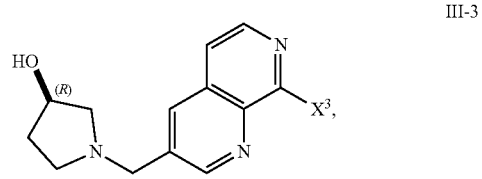

III-3 or the salt thereof, with a compound of formula III-4:

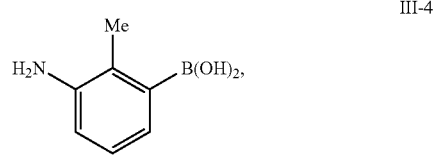

III-4 or the salt thereof, in the presence of a base to form the compound of formula III-5a, wherein X$^3$ is halo.
99. The process of embodiment 98, wherein X$^3$ is chloro.
100. The process of embodiment 98 or 99, wherein the base, present in the reacting of the compound of formula III-3, or the salt thereof, with the compound of formula III-4, or the salt thereof, is an alkali metal base.
101. The process of embodiment 100, wherein the base, present in the reacting of the compound of formula III-3, or the salt thereof, with the compound of formula III-4, or the salt thereof, is an alkali metal hydroxide.
102. The process of embodiment 101, wherein the base, present in the reacting of the compound of formula III-3, or the salt thereof, with the compound of formula III-4, or the salt thereof, alkali metal hydroxide is selected from lithium hydroxide, sodium hydroxide, potassium hydroxide, rubidium hydroxide and cesium hydroxide.
103. The process of embodiment 102, wherein the base, present in the reacting of the compound of formula III-3, or the salt thereof, with the compound of formula III-4, or the salt thereof, is sodium hydroxide.
104. The process of any one of embodiments 98-103, wherein from about 1 to about 3 molar equivalents of the compound of formula III-4, or the salt thereof, is utilized relative to the compound of formula III-3 or the salt thereof.
105. The process of embodiment 104, wherein from about 1 to about 2 molar equivalents of the compound of formula III-4, or the salt thereof, is utilized relative to the compound of formula III-3 or the salt thereof.

106. The process of any one of embodiments 98-105, wherein from about 1 to about 2 molar equivalents of the base is utilized relative to the compound of formula III-3 or the salt thereof.

107. The process of any one of embodiments 98-106, wherein the reacting of the compound of formula III-3, or the salt thereof, with the compound of formula III-4 or the salt thereof, is carried out at a temperature of from about 80° C. to about 120° C.

108. The process of embodiment 107, wherein the reacting of the compound of formula III-3, or the salt thereof, with the compound of formula III-4, or the salt thereof, is carried out at a temperature of from about 90° C. to about 100° C.

109. The process of any one of embodiments 98-108, wherein the reacting of the compound of formula III-3, or the salt thereof, with the compound of formula III-4, or the salt thereof, is carried out in a solvent component.

110. The process of embodiment 109, wherein the reacting of the compound of formula III-3, or the salt thereof, with the compound of formula III-4, or the salt thereof, is carried out in a solvent component comprising a polar protic solvent.

111. The process of embodiment 110, wherein the reacting of the compound of formula III-3, or the salt thereof, with the compound of formula III-4, or the salt thereof, is carried out in a solvent component comprising water.

112. The process of any one of embodiments 98-111, wherein the compound of formula III-3, or the salt thereof, is a salt of formula III-3b:

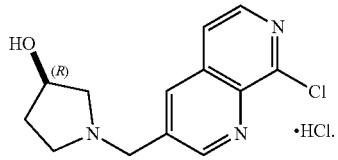

III-3b

113. The process of any one of embodiments 98-112, wherein the compound of formula III-4, or the salt thereof, is a salt of formula III-4a:

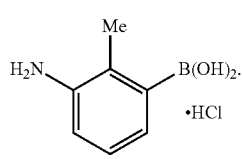

III-4a

114. The process of embodiment 113, wherein the compound of Formula III-5a is prepared by a process comprising:

reacting a salt of formula III-3a:

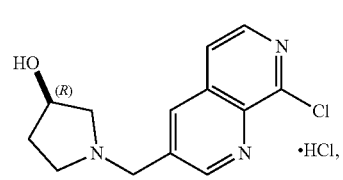

III-3a with a salt of formula III-4a:

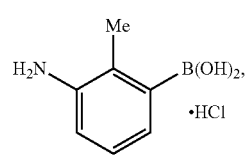

III-4a in the presence of a base to form the compound of formula III-5a.

115. The process of any one of embodiments 98-114, wherein the compound of Formula III-3, or the salt thereof, is prepared by a process comprising:

reacting a compound of formula III-1:

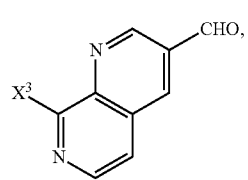

III-1 or a salt thereof, with a compound of formula III-2:

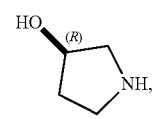

III-2 or a salt thereof, in the presence of a reducing agent to form the compound of formula III-3, or the salt thereof, wherein $X^3$ is halo.

116. The process of embodiment 115, wherein $X^3$ is chloro.

117. The process of embodiment 115, wherein the compound of formula III-1, or the salt thereof, is a compound of formula III-1a:

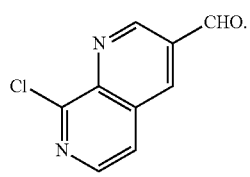

III-1a

118. The process of any one of embodiments 115-117, wherein the reducing agent, present in the reacting of the compound of formula III-1, or the salt thereof, with the compound of formula III-2, or the salt thereof, is selected from NaBH$_4$, NaBH$_3$CN and NaBH(OAc)$_3$.
119. The process of embodiment 118, wherein the reducing agent, present in the reacting of the compound of formula III-1, or the salt thereof, with the compound of formula III-2, or the salt thereof, is NaBH(OAc)$_3$.
120. The process of any one of embodiments 115-119, wherein the reacting of the compound of formula III-1, or the salt thereof, with the compound of formula III-2, or the salt thereof, is carried out in the presence of a Lewis acid.
121. The process of embodiment 120, wherein the Lewis acid, present in the reacting of the compound of formula III-1 or the salt thereof, with the compound of formula III-2, or the salt thereof, is trimethyl borate.
122. The process of any one of embodiments 115-121, wherein from about 1 to about 2 molar equivalents of the compound of formula III-2, or the salt thereof, is utilized relative to the compound of formula III-1, or the salt thereof.
123. The process of any one of embodiments 120-122, wherein from about 1 to about 2 molar equivalents of the Lewis acid is utilized relative to the compound of formula III-1, or the salt thereof.
124. The process of any one of embodiments 115-123, wherein from about 1 to about 2 molar equivalents of the reducing agent is utilized relative to the compound of formula III-1, or the salt thereof.
125. The process of any one of embodiments 115-124, wherein the reacting of the compound of formula III-1, or the salt thereof, with the compound of formula III-2, or the salt thereof, is carried out at a temperature of from about 10° C. to about 30° C.
126. The process of embodiment 125, wherein the reacting of the compound of formula III-1, or the salt thereof, with the compound of formula III-2, or the salt thereof, is carried out at a temperature of from about 10° C. to about 25° C.
127. The process of any one of embodiments 115-126, wherein the reacting of the compound of formula III-1, or the salt thereof, with the compound of formula III-2, or the salt thereof, is carried out in a solvent component.
128. The process of embodiment 127, wherein the reacting of the compound of formula III-1, or the salt thereof, with the compound of formula III-2, or the salt thereof, is carried out in a solvent component comprising a C$_{1-6}$ haloalkane, C$_{1-6}$ cyanoalkane, an C$_{1-6}$ alkanol, or a mixture thereof.
129. The process of embodiment 128, wherein the reacting of the compound of formula III-1, or the salt thereof, with the compound of formula III-2, or the salt thereof, is carried out in a solvent component comprising dichloromethane, methanol, acetonitrile, or a mixture thereof.
130. The process of any one of embodiments 115-129, wherein the compound of Formula III-2, or the salt thereof, is a salt of formula III-2a:

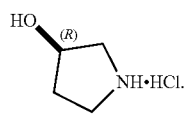

III-2a

131. The process of embodiment 130, wherein the salt of formula III-2a is reacted with a base to form the compound of formula III-2.
132. The process of embodiment 131, wherein the base, present in the reacting of the salt of formula III-2a, is sodium hydroxide.
133. The process of embodiment 131, wherein the base, present in the reacting of the salt of formula III-2a, is diisopropylethylamine.
134. The process of any one of embodiments 115-133, wherein the compound of formula III-1, or the salt thereof, is prepared by a process comprising:
reacting a compound of formula XI-6:

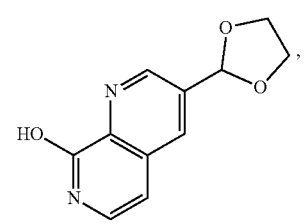

XI-6 or a salt thereof, with a Vilsmeier reagent to form a compound of formula XI-7:

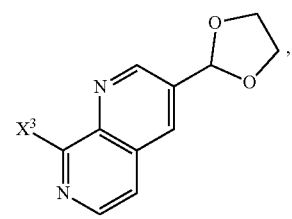

XI-7 or a salt thereof, and
deprotecting the compound of formula XI-7, or the salt thereof, to form the compound of formula III-1, or the salt thereof; wherein the Vilsmeier reagent formed from dimethylformamide, wherein X$^3$ is halo.
135. The process of embodiment 134, wherein X$^3$ is chloro.
136. The process of embodiment 134, wherein the compound of formula XI-7, or the salt thereof, is a compound of formula XI-7a:

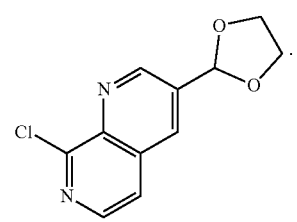

XI-7a

137. The process of any one of embodiments 134-136, wherein the Vilsmeier reagent, for reacting with the compound of formula XI-6, or the salt thereof, is prepared by a process comprising reacting dimethylformamide with a chlorinating agent.

138. The process of embodiment 137, wherein the chlorinating agent, for forming the Vilsmeier reagent, is selected from oxalyl chloride, phosphorus oxychloride, diphosgene, thionyl chloride, sulfuryl chloride and phosphorus pentachloride.
139. The process of embodiment 138, wherein the chlorinating agent is oxalyl chloride.
140. The process of any one of embodiments 137-139, wherein from about 1 to about 4 molar equivalents of the chlorinating agent is utilized relative to the compound of formula XI-6, or the salt thereof.
141. The process of any one of embodiments 134-140, wherein the reacting of the compound of formula XI-6, or the salt thereof, with the Vilsmeier reagent is carried out at a temperature of from about 50° C. to about 70° C.
142. The process of embodiment 141, wherein the reacting of the compound of formula XI-6, or the salt thereof, with the Vilsmeier reagent is carried out at a temperature of from about 55° C. to about 65° C.
143. The process of any one of embodiments 134-142, wherein the reacting of the compound of formula XI-6, or the salt thereof, with the Vilsmeier reagent is carried out in a solvent component.
144. The process of embodiment 143, wherein the reacting of the compound of formula XI-6, or the salt thereof, with the Vilsmeier reagent is carried out in a solvent component comprising a $C_{1-6}$ haloalkane.
145. The process of embodiment 144, wherein the reacting of the compound of formula XI-6, or the salt thereof, with the Vilsmeier reagent is carried out in a solvent component comprising 1,2-dichloroethane.
146. The process of any one of embodiments 134-145, wherein the compound of formula XI-6 is prepared by a process comprising:
reacting a compound of formula XI-5:

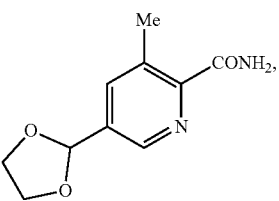

XI-5 or a salt thereof, with a methylating agent, and
reacting the product of said reacting of the compound of formula XI-5, or the salt thereof, with a strong base to form the compound of formula XI-6.
147. The process of embodiment 146, wherein the methylating agent is N,N-dimethylformamide dimethyl acetal.
148. The process of embodiment 146 or 147, wherein the strong base is potassium t-butoxide.
149. The process of any one of embodiments 146-148, wherein from about 1 to about 2 molar equivalents of the methylating agent is utilized relative to the compound of formula XI-5, or the salt thereof.
150. The process of any one of embodiments 146-149, wherein from about 1 to about 2 molar equivalents of the strong base is utilized relative to the compound of formula XI-5, or the salt thereof.
151. The process of any one of embodiments 146-150, wherein the reacting of the compound of formula XI-5,
or the salt thereof, with the methylating agent is carried out at a temperature of from about 50° C. to about 70° C.
152. The process of any one of embodiments 146-151, wherein the reacting of the compound of formula XI-5, or the salt thereof, with the methylating agent is carried out in a solvent component.
153. The process of embodiment 152, wherein the reacting of the compound of formula XI-5, or the salt thereof, with the methylating agent is carried out in a solvent component comprising di-$C_{1-6}$ alkyl ether or a 4-10 membered heterocycloalkyl ether.
154. The process of embodiment 153, wherein the reacting of the compound of formula XI-5, or the salt thereof, with the methylating agent is carried out in a solvent component comprising tetrahydrofuran.
155. The process of any one of embodiments 146-154, wherein the compound of formula XI-5, or the salt thereof, is prepared by a process comprising:
hydrolyzing a compound of formula XI-4:

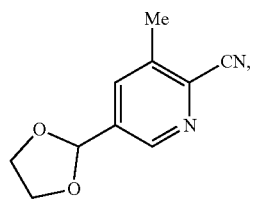

XI-4 or a salt thereof, to form the compound of formula XI-5, or the salt thereof.
156. The process of embodiment 155, wherein the hydrolyzing of the compound of formula XI-4, or the salt thereof, is carried out in the presence of a base.
157. The process of embodiment 156, wherein the base, present in the hydrolyzing of the compound of formula XI-4, or the salt thereof, is an alkali metal base.
158. The process of embodiment 157, wherein the base, present in the hydrolyzing of the compound of formula XI-4, or the salt thereof, is an alkali metal hydroxide.
159. The process of embodiment 158, wherein the base, present in the hydrolyzing of the compound of formula XI-4, or the salt thereof, alkali metal hydroxide is selected from lithium hydroxide, sodium hydroxide, potassium hydroxide, rubidium hydroxide, and cesium hydroxide.
160. The process of embodiment 159, wherein the base, present in the hydrolyzing of the compound of formula XI-4, or the salt thereof, is sodium hydroxide.
161. The process of any one of embodiments 156-160, wherein from about 1 to about 2 molar equivalents of the base is utilized relative to the compound of formula XI-4, or the salt thereof.
162. The process of any one of embodiments 155-161, wherein the hydrolyzing of the compound of formula XI-4, or the salt thereof, is carried out at a temperature of from about 40° C. to about 60° C.
163. The process of any one of embodiments 155-162, wherein the hydrolyzing of the compound of formula XI-4, or the salt thereof, is carried out in a solvent component.
164. The process of embodiment 163, wherein the hydrolyzing of the compound of formula XI-4, or the salt thereof, is carried out in a solvent component comprising a protic solvent.

165. The process of embodiment 164, wherein the hydrolyzing of the compound of formula XI-4, or the salt thereof, is carried out in a solvent component comprising a $C_{1-6}$ alkanol.

166. The process of embodiment 165, wherein the hydrolyzing of the compound of formula XI-4, or the salt thereof, is carried out in a solvent component comprising ethanol.

167. The process of any one of embodiments 155-166, wherein the compound of formula XI-4, or the salt thereof, is prepared by a process comprising:
reacting a compound of formula XI-3:

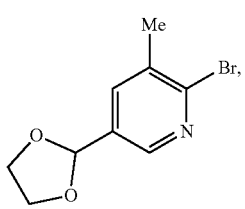

XI-3 or a salt thereof, with a cyanation reagent to form the compound of formula XI-4, or the salt thereof.

168. The process of embodiment 167, wherein the cyanation reagent, present in the reacting of the compound of formula XI-3, or the salt thereof, is a metal nitrile.

169. The process of embodiment 168, wherein the cyanation reagent, present in the reacting of the compound of formula XI-3, or the salt thereof, is cuprous cyanide.

170. The process of any one of embodiments 167-169, wherein from about 1 to about 2 molar equivalents of the cyanation reagent is utilized relative to the compound of formula XI-3, or the salt thereof.

171. The process of any one of embodiments 167-170, wherein the reacting of the compound of formula XI-3, or the salt thereof, with the cyanation reagent is carried out at a temperature of from about 100° C. to about 130° C.

172. The process of any one of embodiments 167-171, wherein the reacting of the compound of formula XI-3, or the salt thereof, with the cyanation reagent is carried out in a solvent component.

173. The process of embodiment 172, wherein the reacting of the compound of formula XI-3, or the salt thereof, with the cyanation reagent is carried out in a solvent component comprising a polar aprotic solvent.

174. The process of embodiment 173, wherein the reacting of the compound of formula XI-3, or the salt thereof, with the cyanation reagent is carried out in a solvent component comprising dimethylformamide.

175. The process of any one of embodiments 167-174, wherein the compound of formula XI-3, or the salt thereof, is prepared by a process comprising:
reacting a compound of formula XI-2:

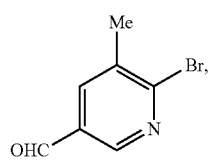

XI-2 or a salt thereof, with ethylene glycol to form the compound of formula XI-3, or the salt thereof.

176. The process of embodiment 175, wherein the reacting of the compound of formula XI-2, or the salt thereof, is carried out in the presence of an acid.

177. The process of embodiment 176, wherein the acid, present in the reacting of the compound of formula XI-2, or the salt thereof, with the ethylene glycol, is p-toluenesulfonic acid.

178. The process of any one of embodiments 175-177, wherein from about 1 to about 5 molar equivalents of the ethylene glycol is utilized relative to the compound of formula XI-2, or the salt thereof.

179. The process of embodiment 178, wherein from about 2 to about 4 molar equivalents of the ethylene glycol is utilized relative to the compound of formula XI-2, or the salt thereof.

180. The process of any one of embodiments 176-179, wherein from about 0.01 to about 0.5 molar equivalents of the acid is utilized relative to the compound of formula XI-2, or the salt thereof.

181. The process of embodiment 180, wherein from about 0.01 to about 0.1 molar equivalents of the acid is utilized relative to the compound of formula XI-2, or the salt thereof.

182. The process of any one of embodiments 175-181, wherein the reacting of the compound of formula XI-2, or the salt thereof, with the ethylene glycol is carried out at a temperature of from about 90° C. to about 130° C.

183. The process of any one of embodiments 175-182, wherein the reacting of the compound of formula XI-2, or the salt thereof, with the ethylene glycol is carried out in a solvent component.

184. The process of embodiment 183, wherein the reacting of the compound of formula XI-2, or the salt thereof, with the ethylene glycol is carried out in a solvent component comprising an aromatic hydrocarbon.

185. The process of embodiment 184, wherein the reacting of the compound of formula XI-2, or the salt thereof, with the ethylene glycol is carried out in a solvent component comprising toluene.

186. The process of any one of embodiments 175-185, wherein the compound of formula XI-2, or the salt thereof, is prepared by a process comprising:
reacting a compound of formula XI-1:

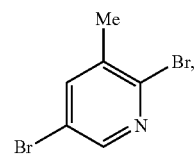

XI-1 or a salt thereof, with a reagent of formula $R^{11}$—Mg—$X^{11}$; and
reacting the product of said reacting of the compound of XI-1, or the salt thereof, with dimethylformamide to form the compound of formula XI-2, or the salt thereof, wherein:
$R^{11}$ is $C_1$-6 alkyl; and
$X^{11}$ is Cl, Br, or I.

187. The process of embodiment 186, wherein $R^{11}$ is isopropyl.

188. The process of embodiment 186 or 187, wherein $X^{11}$ is chloro.

189. The process of embodiment 186, wherein the reagent of formula $R^{11}$—Mg—$X^{11}$ is isopropyl magnesium chloride.

190. The process of any one of embodiments 186-189, wherein from about 1 to about 2 molar equivalents of the reagent of formula $R^{11}$—Mg—$X^{11}$ is utilized relative to the compound of formula XI-1, or the salt thereof.

191. The process of any one of embodiments 186-190, wherein from about 1 to about 5 molar equivalents of dimethylformamide is utilized relative to the compound of formula XI-1, or the salt thereof.

192. The process of embodiment 191, wherein from about 2 to about 4 molar equivalents of dimethylformamide is utilized relative to the compound of formula XI-1, or the salt thereof.

193. The process of any one of embodiments 186-192, wherein the reacting of the compound of formula XI-1, or the salt thereof, with the reagent of formula $R^{11}$—Mg—$X^{11}$ is carried out at a temperature of from about 20° C. to about 30° C.

194. The process of any one of embodiments 186-193, wherein the reacting of the compound of formula XI-1, or the salt thereof, with the reagent of formula $R^{11}$—Mg—$X^{11}$ is carried out in a solvent component.

195. The process of embodiment 194, wherein the reacting of the compound of formula XI-1, or the salt thereof, with the reagent of formula $R^{11}$—Mg—$X^{11}$ is carried out in a solvent component comprising di-$C_{1-6}$ alkyl ether or a 4-10 membered heterocycloalkyl ether.

196. The process of embodiment 195, wherein the reacting of the compound of formula XI-1, or the salt thereof, with the reagent of formula $R^{11}$—Mg—$X^{11}$ is carried out in a solvent component comprising tetrahydrofuran.

197. The process of any one of embodiments 115-133, wherein the compound of formula III-1, or the salt thereof, is prepared by a process comprising:
reducing a compound of formula XII-2:

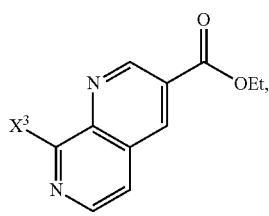

XII-2 to form the compound of formula III-1, or the salt thereof, wherein $X^3$ is halo.

198. The process of embodiment 197, wherein $X^3$ is chloro.

199. The process of embodiment 197, wherein the compound of formula XII-2 is a compound of formula XII-2a:

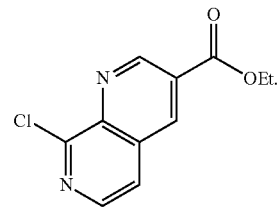

XII-2a

200. The process of any one of embodiments 197-199, wherein the reducing of the compound of formula XII-2 is accomplished by a process comprising reacting the compound of formula XII-2 with diisobutylaluminium hydride.

201. The process of any one of embodiments 197-200, wherein the compound of formula XII-2 is prepared by a process comprising:
reacting a compound of formula XII-1:

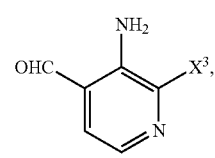

XII-1 or a salt thereof, with ethyl 3,3-diethoxypropanoate in the presence of a catalyst, wherein $X^3$ is halo.

202. The process of embodiment 201, wherein $X^3$ is chloro.

203. The process of embodiment 201, wherein the compound of formula XII-1, or the salt thereof, is a compound of formula XII-1a:

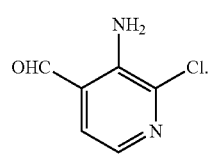

XII-1a

204. The process of any one of embodiments 197-203, wherein the compound of formula XII-2 is prepared by a process comprising:
reacting a compound of formula XII-1, or a salt thereof, with N,N-dimethylaminoacrylate in the presence of a catalyst to form a compound of formula XII-2.

205. The process of embodiment 204, wherein the compound of formula XII-1, or the salt thereof, is prepared by a process comprising:
converting a compound of formula XIII-2:

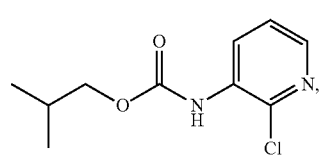

XIII-2 or a salt thereof, to the compound of formula XII-1, or the salt thereof.

206. The process of embodiment 205, wherein the converting of the compound of formula XIII-2, or the salt thereof, is accomplished by a process comprising:
reacting the compound of formula XIII-2, or the salt thereof, with n-butyl lithium in the presence of tetramethylethylenediamine; and
reacting the product of said reacting of the compound of formula XIII-2, or the salt thereof, with N-formylmorpholine to form the compound of formula XII-1, or the salt thereof.

207. The process of embodiment 205 or 206, wherein the compound of formula XIII-2, or the salt thereof, is prepared by a process comprising:
reacting a compound of formula XIII-1:

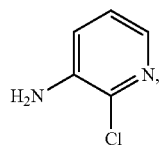

XIII-1 or a salt thereof, with isobutyl chloroformate to form the compound of formula XIII-2, or the salt thereof.

208. The process of embodiment 207, wherein the reacting of the compound of formula XIII-1, or the salt thereof, is carried out in the presence of a base.

209. The process of any one of embodiments 85-94 and 98-114, wherein the compound of formula III-4, or the salt thereof, is prepared by a process comprising:
reacting a compound of formula XIV-2:

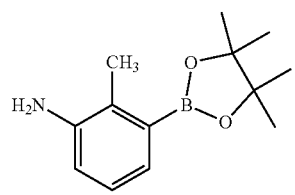

XIV-2 or a salt thereof, with hydrochloric acid to form the compound of formula III-4, or the salt thereof.

210. The process of embodiment 209, wherein the compound of formula III-4 is a salt of formula III-4a.

211. The process of embodiment 209 or 210, wherein the compound of formula XIV-2, or the salt thereof, is prepared by a process comprising:
reacting a compound of formula XIV-1:

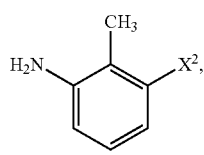

XIV-1 or a salt thereof, with 4,4,4',4',5,5,5',5'-octamethyl-2,2'-bi(1,3,2-dioxaborolane) in the presence of a catalyst to form the compound of formula XIV-2, or the salt thereof, wherein $X^2$ is halo.

212. The process of embodiment 211, wherein $X^2$ is bromo.

213. The process of embodiment 211, wherein the compound of formula XIV-1 is a compound of formula XIV-1a:

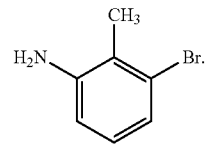

XIV-1a

214. The process of any one of embodiments 211-213, wherein the reacting of the compound of formula XIV-1, or the salt thereof, with the 4,4,4',4',5,5,5',5'-octamethyl-2,2'-bi(1,3,2-dioxaborolane) is conducted in the presence of a base.

215. The process of any one of embodiments 1-23, wherein the compound of formula III-6, or the salt thereof, is prepared by a process comprising:
hydrolyzing the compound of formula IV-1:

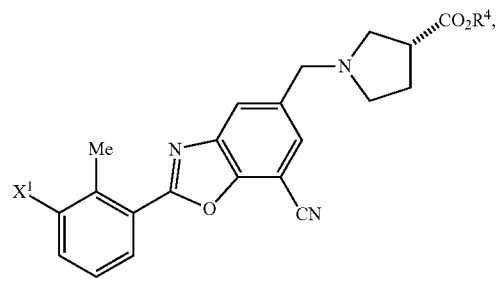

IV-1 or a salt thereof, to form the compound of formula III-6, or the salt thereof, wherein $X^1$ is halo; and $R^4$ is $C_{1-6}$ alkyl.

216. The process of embodiment 215, wherein $X^1$ is bromo.

217. The process of embodiment 215 or 216, wherein $R^4$ is t-butyl.

218. The process of embodiment 215, wherein the compound of formula IV-1, or the salt thereof, is a compound of formula IV-1b:

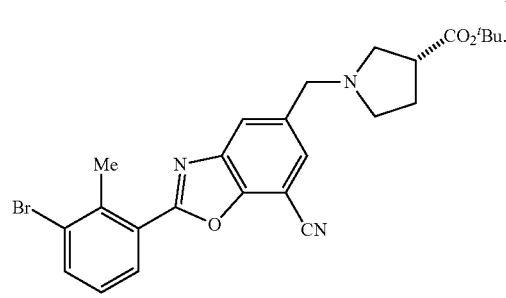

IV-1b

219. The process of any one of embodiments 215-218, wherein the compound of formula III-6, or the salt thereof, is a salt of formula III-6b.

220. The process of embodiment 219, wherein the hydrolyzing of the compound of formula IV-1, or the salt thereof, is accomplished by a process comprising reacting the compound of formula IV-1 with hydrochloric acid to form the salt of formula III-6b.

221. The process of embodiment 220, wherein from about 1 to about 10 molar equivalents of hydrochloric acid is utilized relative to the compound of formula IV-1, or the salt thereof.

222. The process of embodiment 221, wherein from about 3 to about 7 molar equivalents of hydrochloric acid is utilized relative to the compound of formula IV-1, or the salt thereof.

223. The process of any one of embodiments 220-222, wherein the hydrolyzing of the compound of formula IV-1 is carried out at a temperature of from about 30° C. to about 50° C.

224. The process of any one of embodiments 220-223, wherein the hydrolyzing of the compound of formula IV-1, or the salt thereof, is carried out in a solvent component.

225. The process of embodiment 224, wherein the hydrolyzing of the compound of formula IV-1, or the salt thereof, is carried out in a solvent component comprising a polar protic solvent, a di-$C_{1-6}$ alkyl ether, a 4-10 membered heterocycloalkyl ether, or a mixture thereof.

226. The process of embodiment 225, wherein the hydrolyzing of the compound of formula IV-1, or the salt thereof, is carried out in a solvent component comprising water and 1,4-dioxane.

227. The process of any one of embodiments 215-226, wherein the compound of formula IV-1, or the salt thereof, is prepared by a process comprising:
reacting the compound of formula IX-5:

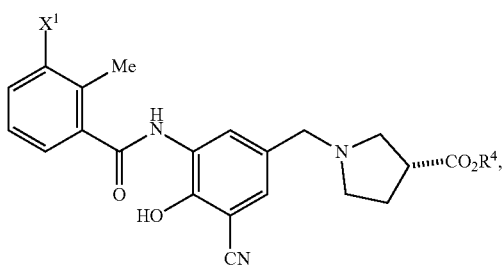

IX-5 or a salt thereof, under Mitsunobu conditions to form the compound of formula IV-1, or the salt thereof, wherein $X^1$ is halo; and $R^4$ is $C_{1-6}$ alkyl.

228. The process of embodiment 227, wherein $X^1$ is bromo.

229. The process of embodiment 227 or 228, wherein $R^4$ is t-butyl.

230. The process of embodiment 227, wherein the compound of formula IX-5, or the salt thereof, is a compound of formula IX-5a:

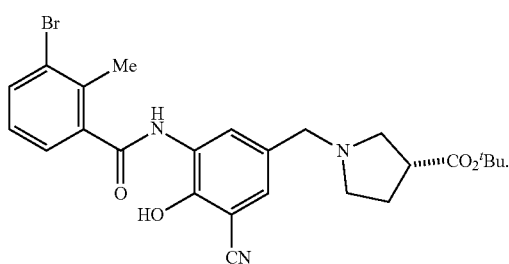

IX-5a

231. The process of any one of embodiments 227-230, wherein the Mitsunobu conditions comprise treating the compound of formula IX-5, or the salt thereof, with an azodicarboxylate and a phosphine.

232. The process of embodiment 231, wherein the azodicarboxylate is diethyl azodicarboxylate.

233. The process of embodiment 231 or 232, wherein the phosphine is triphenyl phosphine.

234. The process any one of embodiments 231-233, wherein from about 1 to about 3 molar equivalents of azodicarboxylate is utilized relative to the compound of formula IX-5, or the salt thereof.

235. The process of any one of embodiments 231-234, wherein from about 1 to about 3 molar equivalents of phosphine is utilized relative to the compound of formula IX-5, or the salt thereof.

236. The process of embodiment 235, wherein about 2 molar equivalents of phosphine is utilized relative to the compound of formula IX-5, or the salt thereof.

237. The process of any one of embodiments 227-236, wherein the reacting of the compound of formula IX-5, or the salt thereof, under the Mitsunobu conditions is carried out at a temperature of from about 40° C. to about 60° C.

238. The process of any one of embodiments 227-237, wherein the reacting of the compound of formula IX-5, or the salt thereof, under the Mitsunobu conditions is carried out in a solvent component.

239. The process of embodiment 238, wherein the reacting of the compound of formula IX-5, or the salt thereof, under the Mitsunobu conditions is carried out in a solvent component comprising di-$C_{1-6}$ alkyl ether or a 4-10 membered heterocycloalkyl ether.

240. The process of embodiment 239, wherein the reacting of the compound of formula IX-5, or the salt thereof, under the Mitsunobu conditions is carried out in a solvent component comprising tetrahydrofuran.

241. The process of any one of embodiments 227-240, wherein the compound of formula IX-5, or the salt thereof, is prepared by a process comprising:
reacting a compound of formula IX-4:

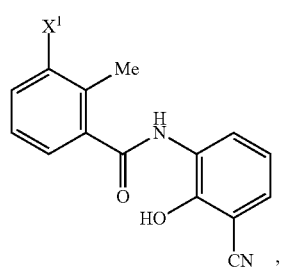

IX-4 or a salt thereof, with a compound of formula XV-4:

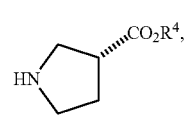

XV-4 or a salt thereof, to form a compound of formula IX-5, or the salt thereof, wherein $X^1$ is halo; and $R^4$ is $C_{1-6}$ alkyl.

242. The process of embodiment 241, wherein $X^1$ is bromo.

243. The process of embodiment 241 or 242, wherein $R^4$ is t-butyl.

244. The process of embodiment 241, wherein the compound of formula IX-4, or the salt thereof, is a compound of formula IX-4a:

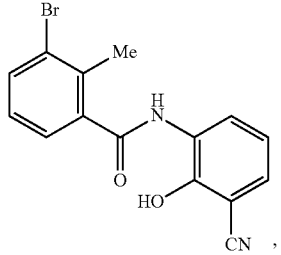

IX-4a or a salt thereof.

245. The process of embodiment 241, wherein the compound of formula XV-4, or the salt thereof, is a compound of formula XV-4a:

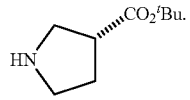

XV-4a

246. The process of any one of embodiments 241-245, wherein the reacting of the compound of formula IX-4, or the salt thereof, with the compound of formula XV-4, or the salt thereof, is carried out in the presence of paraformaldehyde.
247. The process of any one of embodiments 241-246, wherein from about 1 to about 2 molar equivalents of the compound of formula XV-4, or the salt thereof, is utilized relative to the compound of formula IX-4, or the salt thereof.
248. The process of any one of embodiments 241-247, wherein from about 1 to about 2 molar equivalents of paraformaldehyde is utilized relative to the compound of formula IX-4, or the salt thereof.
249. The process of any one of embodiments 241-248, wherein the reacting of the compound of formula IX-4, or the salt thereof, with the compound of formula XV-4, or the salt thereof, is carried out at a temperature of from about 40° C. to about 60° C.
250. The process of any one of embodiments 241-249, wherein the reacting of the compound of formula IX-4, or the salt thereof, with the compound of formula XV-4, or the salt thereof, is carried out in a solvent component.
251. The process of embodiment 250, wherein the reacting of the compound of formula IX-4, or the salt thereof, with the compound of formula XV-4, or the salt thereof, is carried out in a solvent component comprising a $C_{1-6}$ cyanoalkane.
252. The process of embodiment 251, wherein the reacting of the compound of formula IX-4, or the salt thereof, with the compound of formula XV-4, or the salt thereof, is carried out in a solvent component comprising acetonitrile.
253. The process of any one of embodiments 241-252, wherein the compound of formula IX-4, or the salt thereof, is prepared by a process comprising:

reacting a compound of formula IX-3:

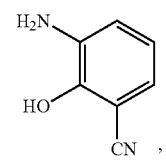

IX-3 or a salt thereof, with a compound of formula IX-3a:

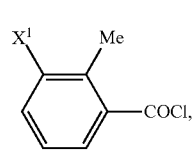

IX-3a in the presence of a tertiary amine to form the compound of formula IX-4, or the salt thereof, wherein $X^1$ is halo.

254. The process of embodiment 253, wherein $X^1$ is bromo.
255. The process of any one of embodiments 253-254, wherein the tertiary amine, present in the reacting of the compound of formula IX-3, or the salt thereof, with the compound of formula IX-3a, is triethylamine.
256. The process of any one of embodiments 253-255, wherein from about 1 to about 2 molar equivalents of the compound of formula IX-3a is utilized relative to the compound of formula IX-3, or the salt thereof.
257. The process of any one of embodiments 253-256, wherein from about 1 to about 3 molar equivalents of the tertiary amine is utilized relative to the compound of formula IX-3, or the salt thereof.
258. The process of any one of embodiments 253-257, wherein the reacting of the compound of formula IX-3, or the salt thereof, with the compound of formula IX-3a is carried out at a temperature of from about 20° C. to about 30° C.
259. The process of any one of embodiments 253-258, wherein the reacting of the compound of formula IX-3, or the salt thereof, with the compound of formula IX-3a is carried out in a solvent component.
260. The process of embodiment 259, wherein the reacting of the compound of formula IX-3, or the salt thereof, with the compound of formula IX-3a is carried out in a solvent component comprising di-$C_{1-6}$ alkyl ether or a 4-10 membered heterocycloalkyl ether.
261. The process of embodiment 260, wherein the reacting of the compound of formula IX-3, or the salt thereof, with the compound of formula IX-3a is carried out in a solvent component comprising tetrahydrofuran.
262. The process of any one of embodiments 253-261, wherein the compound of formula IX-3a, or the salt thereof, is prepared by a process comprising reacting 3-halo-2-methylbenzoic acid, or a salt thereof, with thionyl chloride.
263. The process of embodiment 262, wherein the reacting of the 3-halo-2-methylbenzoic acid, or the salt thereof, with the thionyl chloride is carried out in the presence of a catalyst.
264. The process of embodiment 263, wherein the catalyst, present in the reacting of 3-halo-2-methylbenzoic acid, or the salt thereof, with the thionyl chloride, is dimethylformamide.

265. The process of any one of embodiments 262-264, wherein from about 1 to about 5 molar equivalents of thionyl chloride is utilized relative to the 3-halo-2-methylbenzoic acid, or the salt thereof.

266. The process of any one of embodiments 262-265, wherein the reacting of the 3-halo-2-methylbenzoic acid, or the salt thereof, with the thionyl chloride is carried out at a temperature of from about 60° C. to about 80° C.

267. The process of any one of embodiments 262-266, wherein the 3-halo-2-methylbenzoic acid, or the salt thereof, is 3-bromo-2-methylbenzoic acid.

268. The process of any one of embodiments 253-267, wherein the compound of formula IX-3, or the salt thereof, is prepared by a process comprising:
reducing a compound of formula IX-2:

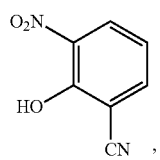

to form the compound of formula IX-3, or the salt thereof.

269. The process of embodiment 268, wherein the reducing of the compound of formula IX-2 is carried out in the presence of a reducing agent.

270. The process of embodiment 269, wherein the reducing agent, present in the reducing of the compound of formula IX-2, is sodium hydrosulfite.

271. The process of embodiment 270, wherein from about 1 to about 5 molar equivalents of the reducing agent is utilized relative to the compound of formula IX-2.

272. The process of any one of embodiments 268-271, wherein the reducing of the compound of formula IX-2 is carried out at a temperature of from about 40° C. to about 60° C.

273. The process of any one of embodiments 268-272, wherein the reducing of the compound of formula IX-2 is carried out in a solvent component.

274. The process of embodiment 273, wherein the reducing of the compound of formula IX-2 is carried out in a solvent component comprising a protic solvent.

275. The process of embodiment 274, wherein the reducing of the compound of formula IX-2 is carried out in a solvent component comprising a $C_{1-6}$ alkanol.

276. The process of embodiment 275, wherein the reducing of the compound of formula IX-2 is carried out in a solvent component comprising ethanol.

277. The process of any one of embodiments 268-276, wherein the compound of formula IX-2 is prepared by a process comprising:
reacting a compound of formula IX-1:

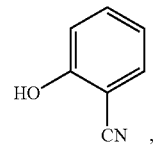

with nitric acid to form the compound of formula IX-2.

278. The process of embodiment 277, wherein from about 1.0 to about 2.0 molar equivalents of nitric acid is utilized relative to the compound of formula IX-1.

279. The process of embodiment 277 or 278, wherein the reacting of the compound of formula IX-1 is carried out at a temperature of from about 25° C. to about 55° C.

280. The process of any one of embodiments 277-279, wherein the reacting of the compound of formula IX-1 is carried out in a solvent component.

281. The process of embodiment 280, wherein the reacting of the compound of formula IX-1 is carried out in a solvent component comprising a protic solvent.

282. The process of embodiment 281, wherein the reacting of the compound of formula IX-1 is carried out in a solvent component comprising acetic acid.

283. A process of preparing (R)-1-((7-cyano-2-(3'-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid, or a salt thereof, comprising:
reacting a compound of formula I-2:

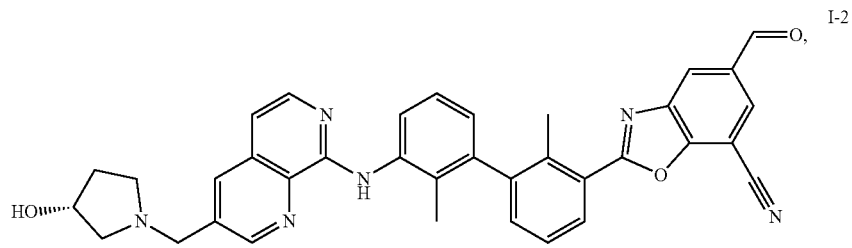 [SMILES: Cc1c(Nc2nccc3cc(CN4CC[C@@H](O)C4)cnc23)cccc1-c1cccc(-c2nc3cc(C=O)cc(C#N)c3o2)c1C]

or a salt thereof, with a compound of formula XV-4:

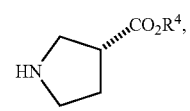

or a salt thereof, in the presence of a reducing agent to form a compound of formula IV-2:

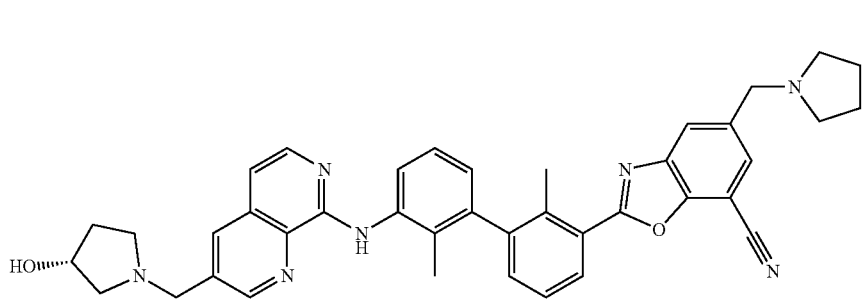

or a salt thereof, wherein R⁴ is $C_{1-6}$ alkyl.

284. The process of embodiment 283, wherein R⁴ is t-butyl.
285. The process of embodiment 283, wherein the compound of formula XV-4, or the salt thereof, is a compound of formula XV-4a:

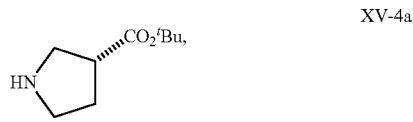 [SMILES: CC(C)(C)OC(=O)[C@@H]1CCNC1]

or a salt thereof.

286. The process of embodiment 283, wherein the compound of formula IV-2 is a compound of formula IV-2a:

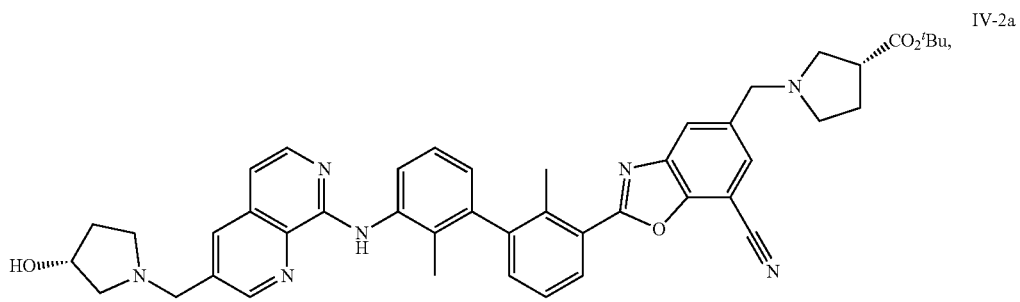 [SMILES: Cc1c(Nc2nccc3cc(CN4CC[C@@H](O)C4)cnc23)cccc1-c1cccc(-c2nc3cc(CN4CC[C@@H](C(=O)OC(C)(C)C)C4)cc(C#N)c3o2)c1C]

or a salt thereof.

287. The process of any one of embodiments 283-286, wherein the reducing agent, present for the reacting of the compound of formula I-2 with the compound of formula XV-4, or the salt thereof, is a borohydride reducing agent.
288. The process of embodiment 287, wherein the reducing agent, present for the reacting of the compound of formula I-2 with the compound of formula XV-4, or the salt thereof, is selected from $NaBH_4$, $NaBH_3CN$, and $NaBH(OAc)_3$.
289. The process of any one of embodiments 283-288, wherein the reacting of the compound of formula I-2, with the compound of formula XV-4, or the salt thereof, is carried out in the presence of a tertiary amine.
290. The process of embodiment 289, wherein the tertiary amine, present for the reacting of the compound of formula I-2 with the compound of formula XV-4, or the salt thereof, is triethylamine.
291. The process of any one of embodiments 283-290, further comprising deprotecting the compound of formula IV-2, or the salt thereof, to form (R)-1-((7-cyano-2-(3'-((3-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl) pyrrolidine-3-carboxylic acid, or the salt thereof.

292. The process of embodiment 291, wherein the deprotecting of the compound of formula IV-2, or the salt thereof, is performed in the presence of a Lewis acid.
293. The process of embodiment 292, wherein the Lewis acid, present in the deprotecting of the compound of formula IV-2, or the salt thereof, is trimethylsilyl triflate.
294. The process of any one of embodiments 283-293, wherein the compound of formula I-2, or the salt thereof, is prepared by a process comprising:

reacting a compound of formula V-1:

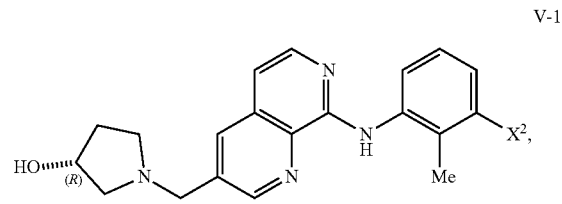

or a salt thereof, with a compound of formula I-1:

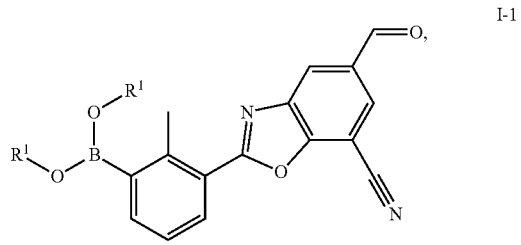

or a salt thereof, in the presence of a Suzuki catalyst and a base to form the compound of formula I-2:

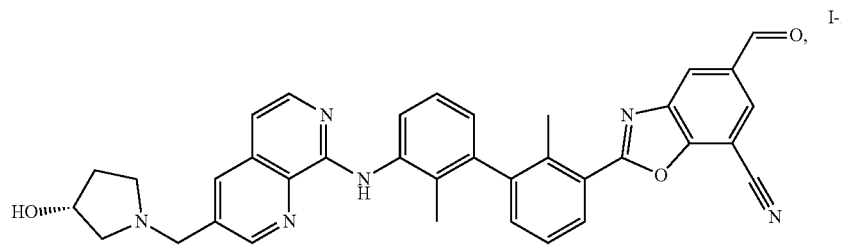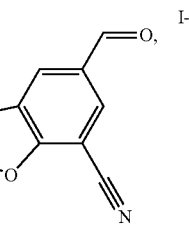

or the salt thereof, wherein:
each $R^1$ is independently selected from H and $C_{1-6}$ alkyl; or
each $R^1$ together form an $C_{2-3}$ alkylene linker, which is optionally substituted by 1, 2, 3, or 4 independently selected $C_{1-4}$ alkyl groups; and
$X^2$ is halo.

295. The process of embodiment 294, wherein $X^2$ is bromo.

296. The process of embodiment 294, wherein the compound of formula V-1, or the salt thereof, is a compound of formula V-1a:

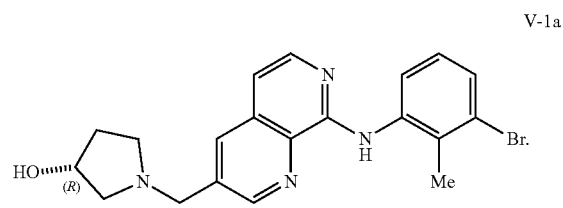

297. The process of any one of embodiments 294-296, wherein the Suzuki catalyst, present in the reacting of the compound of formula V-1, or the salt thereof, with the compound of formula I-1, or the salt thereof, is a palladium catalyst.

298. The process of embodiment 297, wherein the Suzuki catalyst, present in the reacting of the compound of formula V-1, or the salt thereof, with the compound of formula I-1, or the salt thereof, is selected from RuPhos Pd G4, CataCXium® Pd G4 ((2'-(methylamino)-[1,1'-biphenyl]-2-yl)((methylsulfonyl)oxy)palladium di(1-adamantyl)-n-butylphosphine complex), Pd(PPh₃)₄, Pd(dppf)₂Cl₂, dichlorobis[di-tert-butyl(p-dimethylaminophenyl)phosphino]palladium, and PdCl₂(dtbpf) (Pd-118).

299. The process of any one of embodiments 294-298, wherein the base, present in the reacting of the compound of formula V-1, or the salt thereof, with the compound of formula I-1, or the salt thereof, is selected from cesium phosphate, lithium phosphate, sodium phosphate and potassium phosphate.

300. The process of embodiment 299, wherein the base, present in the reacting of the compound of formula V-1, or the salt thereof, with the compound of formula I-1, or the salt thereof, is potassium phosphate.

301. The process of any one of embodiments 294-300, wherein the compound of formula I-1, or the salt thereof, has formula I-1a:

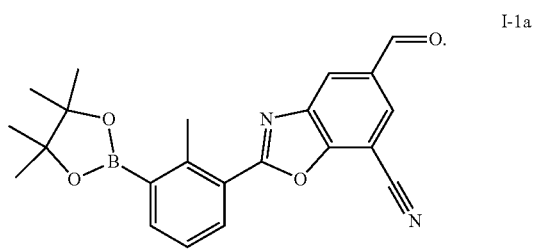 [SMILES: Cc1c(B2OC(C)(C)C(C)(C)O2)cccc1-c1nc2cc(C=O)cc(C#N)c2o1]

302. A process of preparing (R)-1-((7-cyano-2-(3'-((3-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid, comprising:
reacting a compound of formula V-1:

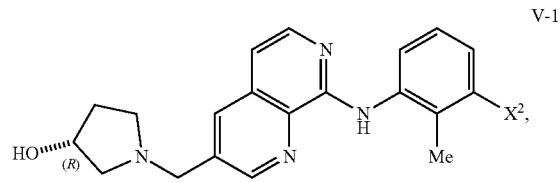

or a salt thereof, with a compound of formula I-1:

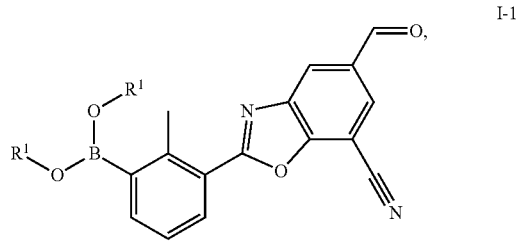

or a salt thereof, in the presence of a Suzuki catalyst and a base to form a compound of formula I-2:

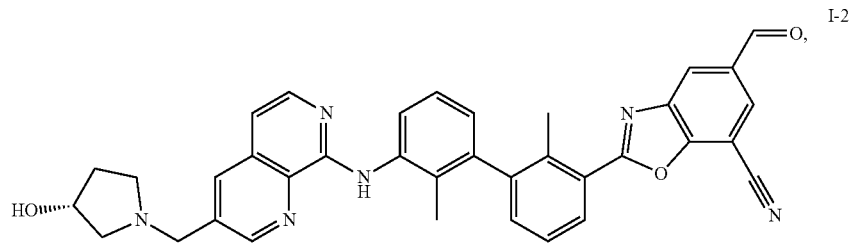 [SMILES: Cc1c(Nc2nccc3cc(CN4CC[C@@H](O)C4)cnc23)cccc1-c1cccc(-c2nc3cc(C=O)cc(C#N)c3o2)c1C]

or a salt thereof,
wherein:
  each $R^1$ is independently selected from H and $C_{1-6}$ alkyl; or
  each $R^1$ together form an $C_{2-3}$ alkylene linker, which is optionally substituted by 1, 2, 3, or 4 independently selected $C_{1-4}$ alkyl groups; and
  $X^2$ is halo.

303. The process of embodiment 302, wherein $X^2$ is bromo.

304. The process of embodiment 302, wherein the compound of formula V-1, or the salt thereof, is a compound of formula V-1a:

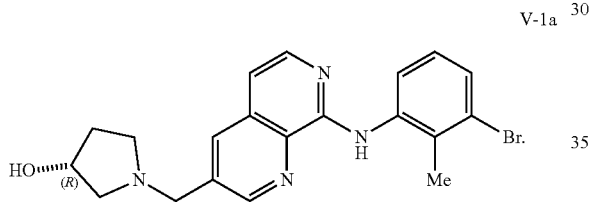

305. The process of any one of embodiments 302-304, wherein the Suzuki catalyst, present in the reacting of the compound of formula V-1, or the salt thereof, with the compound of formula I-1, or the salt thereof, is a palladium catalyst.

306. The process of embodiment 305, wherein the Suzuki catalyst, present in the reacting of the compound of formula V-1, or the salt thereof, with the compound of formula I-1, or the salt thereof, is selected from RuPhos Pd G4, CataCXium® Pd G4 ((2'-(methylamino)-[1,1'-biphenyl]-2-yl)((methylsulfonyl)oxy)palladium di(1-adamantyl)-n-butylphosphine complex), Pd(PPh$_3$)$_4$, Pd(dppf)$_2$Cl$_2$, dichlorobis[di-tert-butyl(p-dimethylaminophenyl)phosphino]palladium and PdCl$_2$(dtbpf) (Pd-118).

307. The process of any one of embodiments 302-306, wherein the base, present in the reacting of the compound of formula V-1, or the salt thereof, with the compound of formula I-1, or the salt thereof, is selected from cesium phosphate, lithium phosphate, sodium phosphate and potassium phosphate.

308. The process of any one of embodiments 302-307, wherein the compound of formula I-1, or the salt thereof, has formula I-1a:

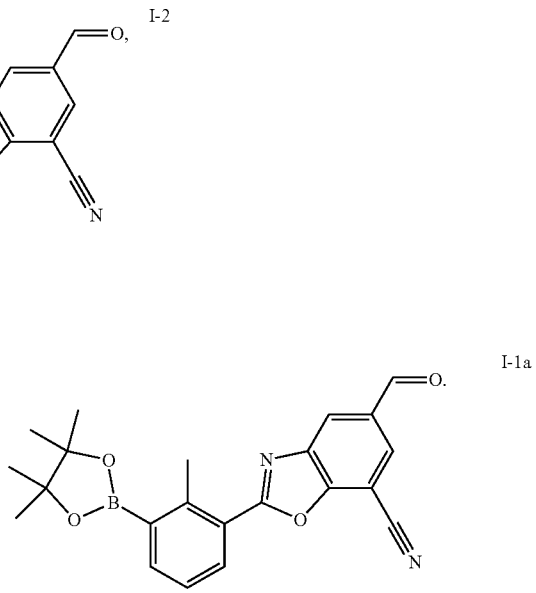

309. The process of any one of embodiments 294-308, wherein the compound of formula I-1, or the salt thereof, is prepared by a process comprising:
oxidizing a compound of formula II-3:

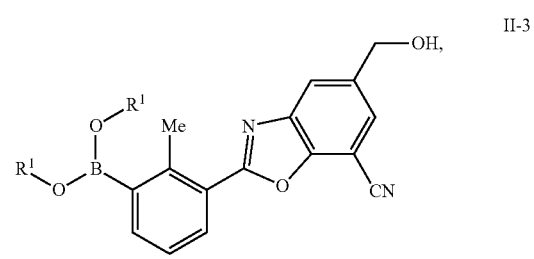

or a salt thereof, to form the compound of formula I-1, or the salt thereof; wherein:
  each $R^1$ is independently selected from H and $C_{1-6}$ alkyl; or
  each $R^1$ together form an $C_{2-3}$ alkylene linker, which is optionally substituted by 1, 2, 3, or 4 independently selected $C_{1-4}$ alkyl groups.

310. The process of embodiment 309, wherein the oxidizing the compound of formula II-3, or the salt thereof, is carried out in the presence of an oxidizing agent.

311. The process of embodiment 310, wherein the oxidizing agent for oxidizing the compound of formula II-3, or the salt thereof, is Dess-Martin periodinane.

312. The process of any one of embodiments 309-311, wherein the compound of formula II-3, or the salt thereof, has formula II-3a:

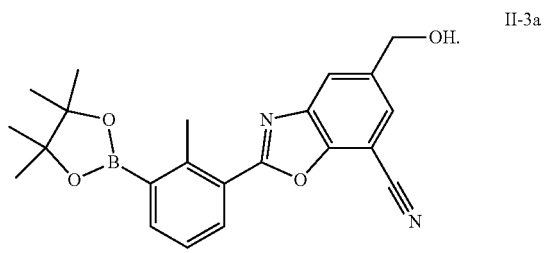 [SMILES: Cc1c(B2OC(C)(C)C(C)(C)O2)cccc1-c1nc2cc(CO)cc(C#N)c2o1]

II-3a

313. The process of any one of embodiments 309-312, wherein the compound of formula II-3, or the salt thereof, is prepared by a process comprising:
cyanating a compound of formula II-2, or a salt thereof:

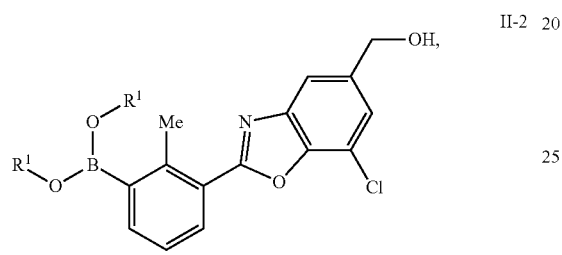

II-2 to form the compound of formula II-3, or the salt thereof,
wherein:
each $R^1$ is independently selected from H and $C_{1-6}$ alkyl; or
each $R^1$ together form an $C_{2-3}$ alkylene linker, which is optionally substituted by 1, 2, 3, or 4 independently selected $C_{1-4}$ alkyl groups.

314. The process of embodiment 313, wherein the cyanating the compound of formula II-2, or the salt thereof, is carried out in the presence of a cyanation reagent.

315. The process of embodiment 314, wherein the cyanation reagent for the cyanating of the compound of formula II-2, or the salt thereof, is a metal nitrile.

316. The process of embodiment 315, wherein the cyanation reagent, for the cyanating of the compound of formula II-2, or the salt thereof, is zinc cyanide.

317. The process of any one of embodiments 313-316, wherein the cyanating the compound of formula II-2, or the salt thereof, is carried out in the presence of a catalyst.

318. The process of embodiment 317, wherein the catalyst, present in the cyanating of the compound of formula II-2, or the salt thereof, is a palladium catalyst.

319. The process of embodiment 318, wherein the catalyst, present in the cyanating of the compound of formula II-2, or the salt thereof, is ᵗBuXPhos Pd G3.

320. The process of any one of embodiments 313-319, wherein the compound of formula II-2, or the salt thereof, has formula II-2a:

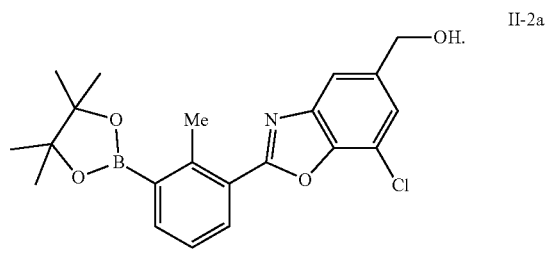 [SMILES: Cc1c(B2OC(C)(C)C(C)(C)O2)cccc1-c1nc2cc(CO)cc(Cl)c2o1]

II-2a

321. The process of any one of embodiments 313-320, wherein the compound of formula II-2, or the salt thereof, is prepared by a process comprising:
reacting a compound of formula II-1:

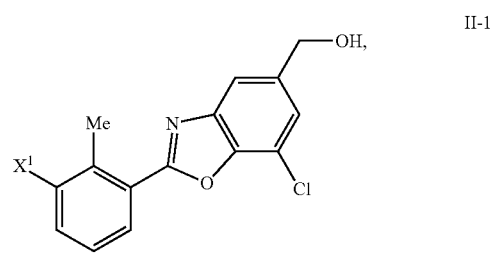

II-1 or a salt thereof, with a borylating agent in the presence of a catalyst and a base, wherein $X^1$ is halo.

322. The process of embodiment 321, wherein the compound of formula II-1, or the salt thereof, is a compound of formula II-1a:

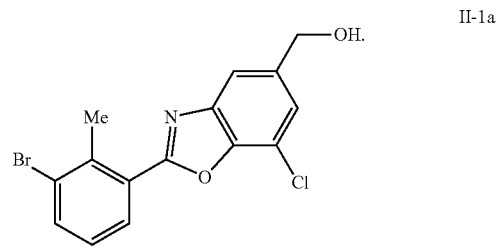 [SMILES: Cc1c(Br)cccc1-c1nc2cc(CO)cc(Cl)c2o1]

II-1a

323. The process of embodiment 321 or 322, wherein the borylating agent for the reacting with the compound of formula II-1, or the salt thereof, is 4,4,4',4',5,5,5',5'-octamethyl-2,2'-bi(1,3,2-dioxaborolane).

324. The process of any one of embodiments 321-323, wherein the catalyst, present in the reacting of the compound of formula II-1, or the salt thereof, with a borylating agent, is a palladium catalyst.

325. The process of embodiment 324, wherein the catalyst, present in the reacting of the compound of formula II-1, or the salt thereof, with a borylating agent, is selected from RuPhos Pd G4, CataCXium® Pd G4 ((2'-(methylamino)-[1,1'-biphenyl]-2-yl)((methylsulfonyl)oxy)palladium di(1-adamantyl)-n-butylphosphine complex), Pd(PPh₃)₄, Pd(dppf)₂Cl₂, dichlorobis[di-tert-butyl(p-dimethylaminophenyl)phosphino]palladium and PdCl₂(dtbpf) (Pd-118).

326. The process of any one of embodiments 321-325, wherein the base, present in the reacting of the compound of formula II-1, or the salt thereof, with a borylating agent, is selected from cesium acetate, lithium acetate, sodium acetate and potassium acetate.

327. The process of any one of embodiments 321-326, wherein the compound of formula II-1, or the salt thereof, is prepared by a process comprising:
reducing a compound of formula VII-5:

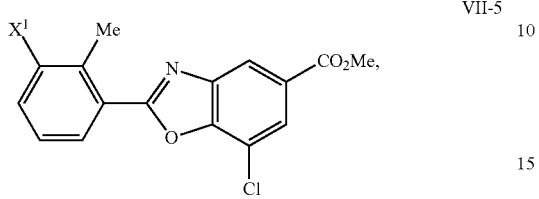

or a salt thereof, to form the compound of formula II-1, or the salt thereof, wherein $X^1$ is halo.

328. The process of embodiment 327, wherein $X^1$ is bromo.

329. The process of embodiment 327, wherein the compound of formula VII-5, or a salt thereof, is a compound of formula VII-5a:

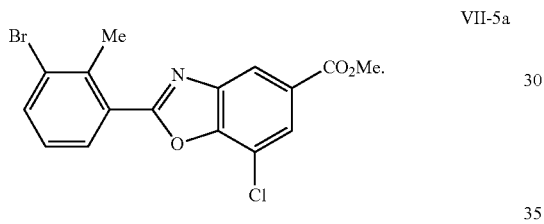

330. The process of any one of embodiments 327-329, wherein the reducing of the compound of formula VII-5, or the salt thereof, is accomplished by a process comprising reacting the compound of formula VII-5, or the salt thereof, with diisobutylaluminium hydride.

331. The process of any one of embodiments 327-330, wherein the compound of formula VII-5, or the salt thereof, is prepared by a process comprising:
reacting a compound of formula VII-3:

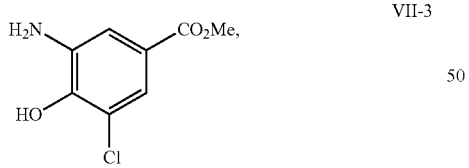

or a salt thereof, with a compound of formula VII-4:

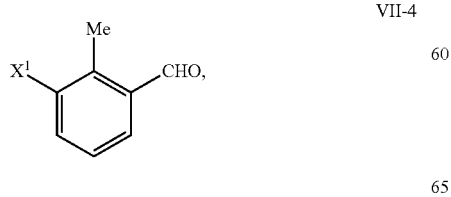

in the presence of an oxidant to form the compound of formula VII-5, or the salt thereof, wherein $X^1$ is halo.

332. The process of embodiment 331, wherein $X^1$ is bromo.

333. The process of embodiment 331, wherein the compound of formula VII-4 is a compound of formula VII-4a:

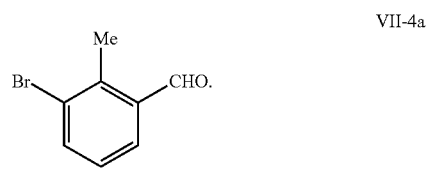

334. The process of any one of embodiments 331-333, wherein the compound of formula VII-3, or the salt thereof, is prepared by a process comprising:
reducing a compound of formula VII-2:

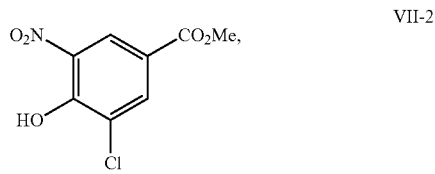 [SMILES: COC(=O)c1cc(Cl)c(O)c([N+](=O)[O-])c1]

to form the compound of formula VII-3, or the salt thereof.

335. The process of embodiment 334, wherein the reducing of the compound of formula VII-2 is carried out in the presence of hydrogen and a catalyst.

336. The process of embodiment 334 or 335, wherein the compound of formula VII-2 is prepared by a process comprising:
reducing a compound of formula VII-1:

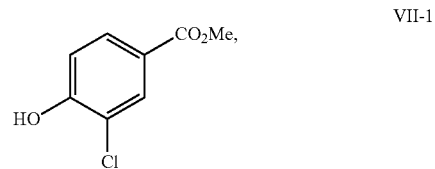 [SMILES: COC(=O)c1ccc(O)c(Cl)c1]

with nitric acid to form the compound of formula VII-2.

337. The process of any one of embodiments 42-63 and 294-307, wherein the compound of formula V-1, or the salt thereof, is prepared by a process comprising:
reacting a compound of formula VIII-8:

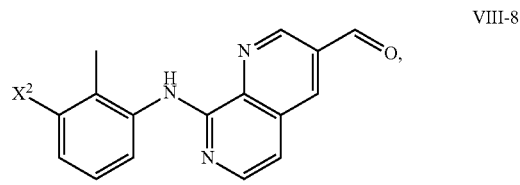

or a salt thereof, with a compound of formula III-2:

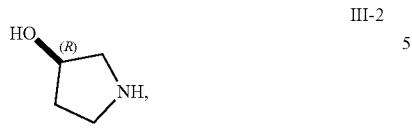

or a salt thereof, in the presence of a reducing agent to form the compound of formula V-1, or the salt thereof, wherein $X^2$ is halo.

338. The process of embodiment 337, wherein $X^2$ is bromo.
339. The process of embodiment 337, wherein the compound of formula VIII-8, or the salt thereof, is a compound of formula VIII-8a:

340. The process of any one of embodiments 337-339, wherein the compound of formula VIII-8, or the salt thereof, is prepared by a process comprising:
oxidizing a compound of formula VIII-7:

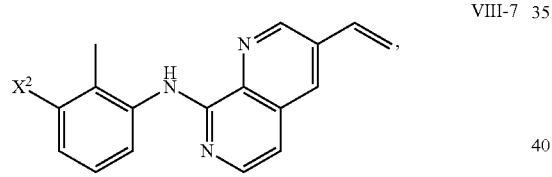

or a salt thereof, to form the compound of formula VIII-8, or the salt thereof, wherein $X^2$ is halo.

341. The process of embodiment 340, wherein $X^2$ is bromo.
342. The process of embodiment 340, wherein the compound of formula VIII-7 is a compound of formula VIII-7a:

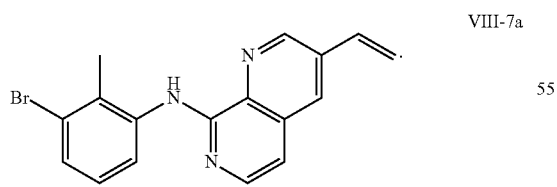

343. The process of any one of embodiments 340-342, wherein the oxidizing the compound of formula VIII-7, or the salt thereof, is carried out in the presence of a catalyst.
344. The process of embodiment 343, wherein the catalyst, present for the oxidizing the compound of formula VIII-7, or the salt thereof, is osmium tetroxide.

345. The process of any one of embodiments 340-344, wherein the oxidizing of the compound of formula VIII-7, or the salt thereof, is carried out in the presence of an oxidizing agent.
346. The process of any one of embodiments 340-345, wherein the compound of formula VIII-7, or the salt thereof, is prepared by a process comprising:
reacting a compound of formula VIII-6:

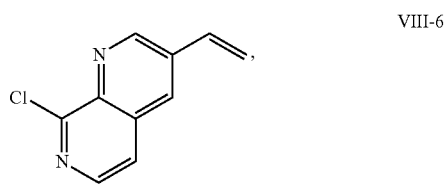

or a salt thereof, with a compound of formula XIV-1:

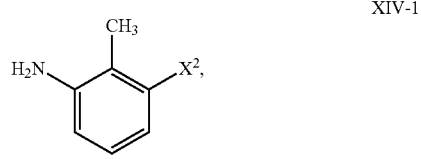

or a salt thereof, to form a compound of formula VIII-7, or the salt thereof, wherein $X^2$ is halo.

347. The process of embodiment 346, wherein $X^2$ is bromo.
348. The process of embodiment 346, wherein the compound of formula XIV-1 is a compound of formula XIV-1a:

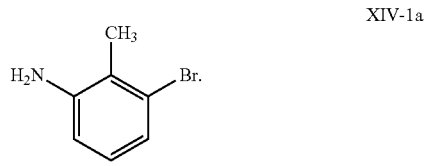

349. The process of any one of embodiments 346-348, wherein the reacting of the compound of formula VIII-6, or the salt thereof, with a compound of formula XIV-1, or the salt thereof, is carried out in the presence of an acid.
350. The process of embodiment 349, wherein the acid, present in the reacting of the compound of formula VIII-6, or the salt thereof, with the compound of formula XIV-1, or the salt thereof, is a strong organic acid.
351. The process of any one of embodiments 346-350, wherein the compound of formula VIII-6, or the salt thereof, is prepared by a process comprising:

reacting a compound of formula VIII-5:

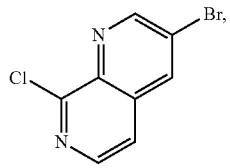

VIII-5 or a salt thereof, with 4,4,5,5-tetramethyl-2-vinyl-1,3,2-dioxaborolane in the presence of a catalyst and a base to form a compound of formula VIII-6, or the salt thereof.

352. The process of embodiment 351, wherein the catalyst, present in the reacting of the compound of formula VIII-5, or the salt thereof, with the 4,4,5,5-tetramethyl-2-vinyl-1,3,2-dioxaborolane, is a palladium catalyst.

353. The process of embodiment 352, wherein the catalyst, present in the reacting of the compound of formula VIII-5, or the salt thereof, with the 4,4,5,5-tetramethyl-2-vinyl-1,3,2-dioxaborolane, is selected from RuPhos Pd G4, CataCXium® Pd G4 ((2'-(methylamino)-[1,1'-biphenyl]-2-yl)((methylsulfonyl)oxy)palladium di(1-adamantyl)-n-butylphosphine complex), $Pd(PPh_3)_4$, $Pd(dppf)_2Cl_2$, dichlorobis[di-tert-butyl(p-dimethylaminophenyl)phosphino]palladium and $PdCl_2(dtbpf)$ (Pd-118).

354. The process of any one of embodiments 351-353, wherein the compound of formula VIII-5, or the salt thereof, is prepared by a process comprising:

reacting a compound of formula VIII-4:

VIII-4 or a salt thereof, with a chlorinating agent to form a compound of formula VIII-5, or the salt thereof.

355. The process of embodiment 354, wherein the compound of formula VIII-4, or the salt thereof, is prepared by a process comprising:

(i) reacting a compound of formula VIII-2:

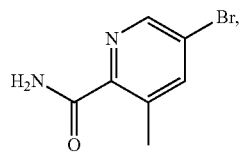

VIII-2 or a salt thereof, with N,N-dimethylformamide dimethyl acetal to form a compound of formula VIII-3:

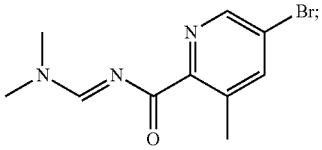

VIII-3 and (ii) treating the compound of formula VIII-3 with a strong base to form the compound of formula VIII-4, or the salt thereof.

356. The process of embodiment 355, wherein the compound of formula VIII-2, or the salt thereof, is prepared by a process comprising:

(i) reacting a compound of formula VIII-1:

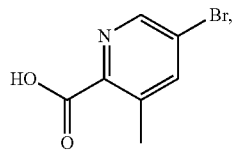

VIII-1 or a salt thereof, with a chlorinating agent to form a compound of formula VIII-1a:

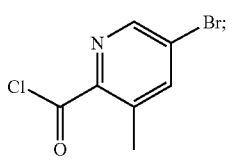

VIII-1a and (ii) reacting the compound of formula VIII-1a with an ammonia agent to form the compound of formula VIII-2, or the salt thereof.

357. The process of embodiment 356, wherein the reacting of the compound of formula VIII-1, or the salt thereof, is carried out in the presence of a catalyst.

358. The process of embodiment 356 or 357, wherein the chlorinating agent, for reacting with the compound of formula VIII-1, or the salt thereof, is selected from oxalyl chloride, phosphorus oxychloride, diphosgene, thionyl chloride, sulfuryl chloride, and phosphorus pentachloride.

359. The process of any one of embodiments 356-358, wherein the ammonia agent is ammonium hydroxide.

360. The process of any one of embodiments 25-40, 61-72, 85-94 and 215-226, wherein the compound of formula IV-1, or the salt thereof, is prepared by a process comprising:

reacting a compound of formula X-7:

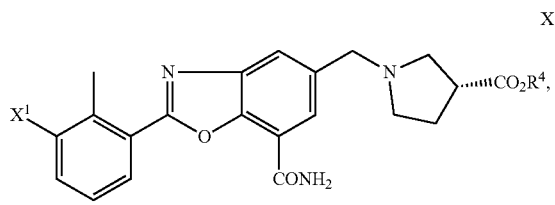

or a salt thereof, with a dehydrating agent to form the compound of formula IV-1, or the salt thereof, wherein $X^1$ is halo; and $R^4$ is $C_{1-6}$ alkyl.

361. The process of embodiment 360, wherein $X^1$ is bromo.
362. The process of embodiment 360 or 361, wherein $R^4$ is t-butyl.
363. The process of embodiment 360, wherein the compound of formula X-7 is a compound of formula X-7a:

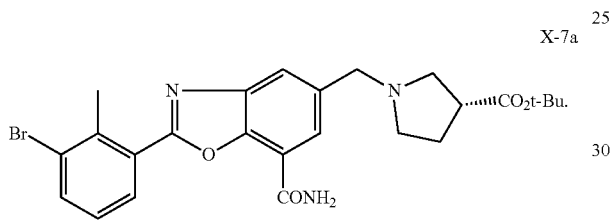

364. The process of any one of embodiments 360-363, wherein the reacting of the compound of formula X-7, or the salt thereof, is carried out in the presence of a base.
365. The process of any one of embodiments 360-364, wherein the compound of formula X-7, or the salt thereof, is prepared by a process comprising:
reacting a compound of formula X-6:

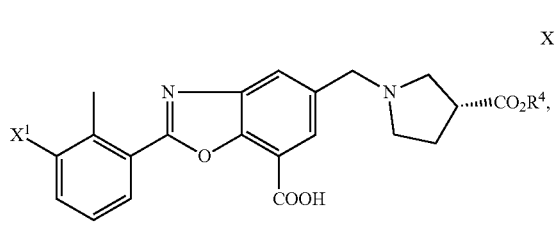

or a salt thereof, with an $C_{1-6}$ alkyl chloroformate; and
reacting the product of said reacting of the compound of formula X-6, or the salt thereof, with ammonium hydroxide to form the compound of formula X-7, or the salt thereof, wherein $X^1$ is halo; and $R^4$ is $C_{1-6}$ alkyl.
366. The process of embodiment 365, wherein $X^1$ is bromo.
367. The process of embodiment 365 or 366, wherein $R^4$ is t-butyl.
368. The process of embodiment 366, wherein the compound of formula X-6 is a compound of formula X-6a:

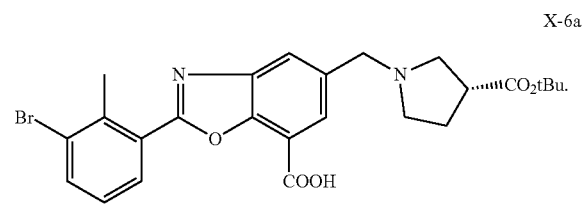 [SMILES: Cc1c(Br)cccc1-c1nc2cc(CN3CC[C@@H](C(=O)OC(C)(C)C)C3)cc(C(=O)O)c2o1]

369. The process of any one of embodiments 365-368, wherein the reacting of the compound of formula X-6, or the salt thereof, with the $C_{1-6}$ alkyl chloroformate is carried out in the presence of a base.
370. The process of any one of embodiments 365-369, wherein the compound of formula X-6, or the salt thereof, is prepared by a process comprising:
reacting a compound of formula X-4:

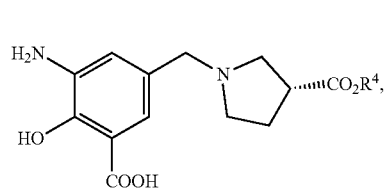

or a salt thereof, with a compound of formula X-5:

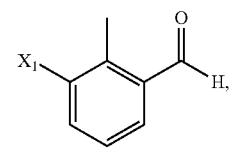

to form a compound of formula X-44:

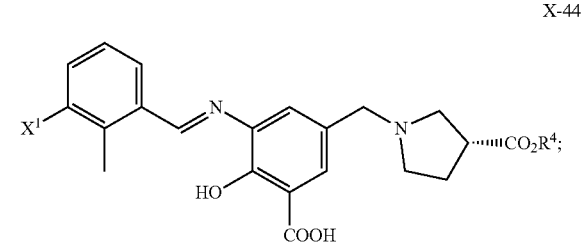

and
reacting the compound of formula X-44 with a dehydrogenating agent to form the compound of formula X-6, or the salt thereof, wherein $X^1$ is halo; and $R^4$ is $C_{1-6}$ alkyl.
371. The process of embodiment 370, wherein $X^1$ is bromo.
372. The process of embodiment 370 or 371, wherein $R^4$ is t-butyl.
373. The process of embodiment 370, wherein the compound of formula X-4 is a compound of formula X-4a:

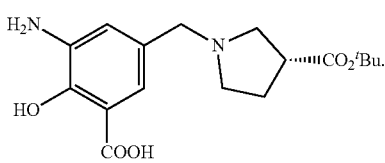

X-4a

374. The process of any one of embodiments 370, 372 and 373, wherein the compound of formula X-5 is a compound of formula X-5a:

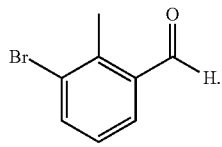

X-5a

375. The process of any one of embodiments 370-374, wherein the compound of formula X-4, or the salt thereof, is prepared by a process comprising:
reducing a compound of formula X-3:

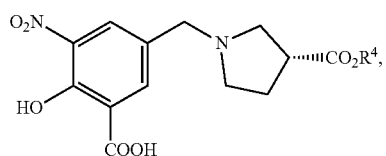

X-3 or a salt thereof, to form the compound of formula X-4, or the salt thereof, wherein $R^4$ is $C_{1-6}$ alkyl.

376. The process of embodiment 375, wherein $R^4$ is t-butyl.
377. The process of embodiment 375, wherein the compound of formula X-3 is a compound of formula X-3a:

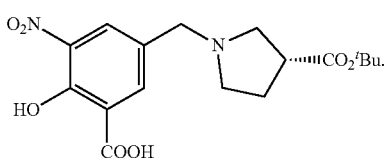

X-3a

378. The process of any one of embodiments 375-377, wherein the reducing of the compound of formula X-3, or a salt thereof, is carried out in the presence of hydrogen and a catalyst.
379. The process of any one of embodiments 375-378, wherein the compound of formula X-3, or the salt thereof, is prepared by a process comprising:
reacting a compound of formula X-2:

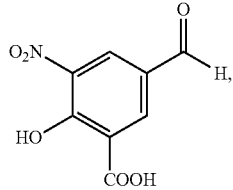

X-2 or a salt thereof, with a compound of formula XV-4:

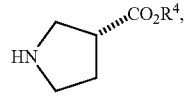

XV-4 or a salt thereof, in the presence of a reducing agent to form the compound of formula X-3, or the salt thereof, wherein $R^4$ is $C_{1-6}$ alkyl.

380. The process of embodiment 379, wherein $R^4$ is t-butyl.
381. The process of embodiment 379, wherein the compound of formula XV-4, or the salt thereof, is a compound of formula XV-4a:

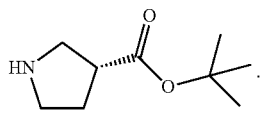

XV-4a

382. The process of embodiment 379, wherein the compound of formula XV-4, or the salt thereof, is a salt of formula XV-4b:

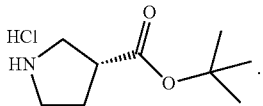

XV-4b

383. The process of any one of embodiments 379-382, wherein the compound of formula X-2, or the salt thereof, is prepared by a process comprising:
reducing a compound of formula X-1:

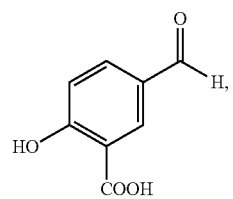

X-1 or a salt thereof, with nitric acid to form the compound of formula X-2, or the salt thereof.

384. The process of any one of embodiments 241-252, 283-290 and 379-382, wherein the compound of formula XV-4, or the salt thereof, is prepared by a process comprising:
reacting a chiral salt of the compound of formula XV-4:

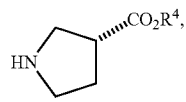

with a base to form the compound of formula XV-4, or the salt thereof, wherein $R^4$ is $C_{1-6}$ alkyl.

385. The process of embodiment 384, wherein $R^4$ is t-butyl.

386. The process of embodiment 384 or 385, wherein the chiral salt of the compound of formula XV-4 is the L-tartrate salt of formula XV-3:

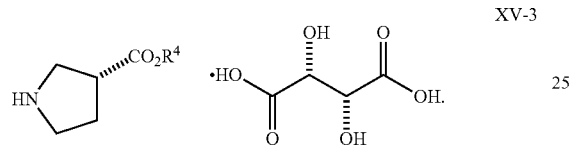

387. The process of embodiment 386, wherein the L-tartrate salt of formula XV-3 has formula XV-3a:

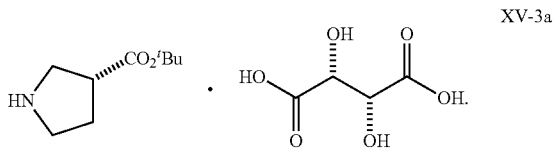 [SMILES: CC(C)(C)OC(=O)[C@@H]1CCNC1 ; O=C(O)[C@H](O)[C@@H](O)C(=O)O]

388. The process of embodiment 386 or 387, wherein the L-tartrate salt of formula XV-3 is prepared by a process comprising:
reacting the compound of formula XV-4 with L-(+)-tartaric acid to form the L-tartrate salt of formula XV-3.

389. The process of embodiment 388, wherein the compound of formula XV-4 is prepared by a process comprising:
reducing the compound of formula XV-2:

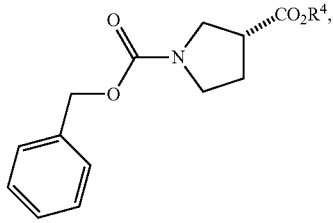

to form the compound of formula XV-4, wherein $R^4$ is $C_{1-6}$ alkyl.

390. The process of embodiment 389, wherein $R^4$ is t-butyl.

391. The process of embodiment 389, wherein the compound of formula XV-2 has formula XV-2a:

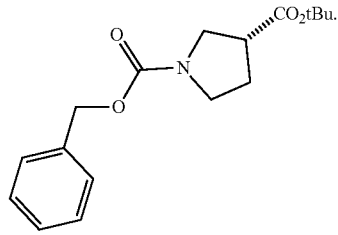

392. The process of any one of embodiments 389-391, wherein reducing of the compound of formula XV-2 is carried out in the presence of hydrogen and a catalyst.

393. The process of any one of embodiments 389-392, wherein the compound of formula XV-2 is prepared by a process comprising:
esterifying the compound of formula XV-1:

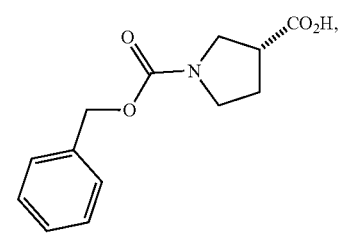

to form the compound of formula XV-2.

394. The process of embodiment 393, wherein the esterifying of the compound of formula XV-1 is performed in the presence of an esterification agent.

395. The process of embodiment 394, wherein the esterification agent, for the esterifying of the compound of formula XV-1, is tert-butyl 2,2,2-trichloroacetimidate.

396. The process of any one of embodiments 393-395, wherein the compound of formula XV-1 is prepared by a process comprising:
reacting the compound of formula XV-0:

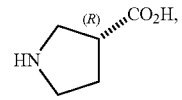

or a salt thereof, with benzyl chloroformate to form the compound of formula XV-1.

397. The process of embodiment 396, wherein the reacting of the compound of formula XV-0, or the salt thereof, with the benzyl chloroformate is carried out in the presence of a base.

398. The process of any one of embodiments 241-252, 283-290 and 379-383, wherein the compound of formula XV-4, or the salt thereof, is prepared by a process comprising:

reducing the compound of formula XV-2:

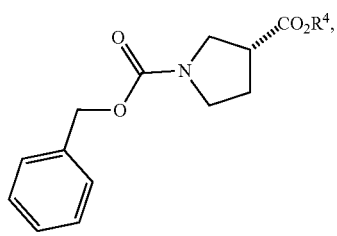
XV-2 to form the compound of formula XV-4, or the salt thereof, wherein $R^4$ is $C_{1-6}$ alkyl.

399. The process of embodiment 398, wherein $R^4$ is t-butyl.

400. The process of embodiment 398, wherein the compound of formula XV-2 has formula XV-2a:

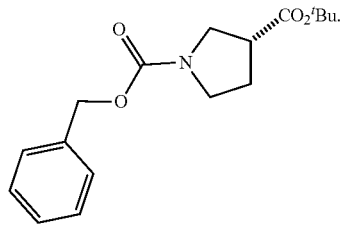
XV-2a

401. The process of any one of embodiments 398-400, wherein the reducing of the compound of formula XV-2 is carried out in the presence of hydrogen and a catalyst.

402. The process of any one of embodiments 398-401, wherein the compound of formula XV-2 is prepared by a process comprising:

esterifying the compound of formula XV-1:

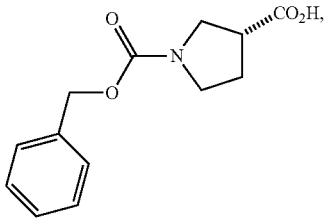
XV-1 to form the compound of formula XV-2.

403. The process of any one of embodiments 241-252, 283-290 and 379-383, wherein the compound of formula XV-4 is prepared by a process comprising:
esterifying the salt of formula XV-0a:

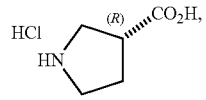
XV-0a to form the compound of formula XV-4.

404. A compound of formula IV-1b:

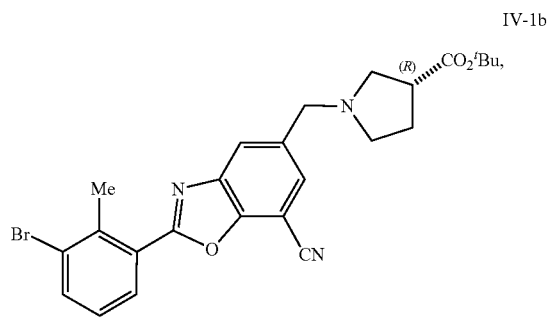
IV-1b or a salt thereof.

405. A compound of formula IV-2a:

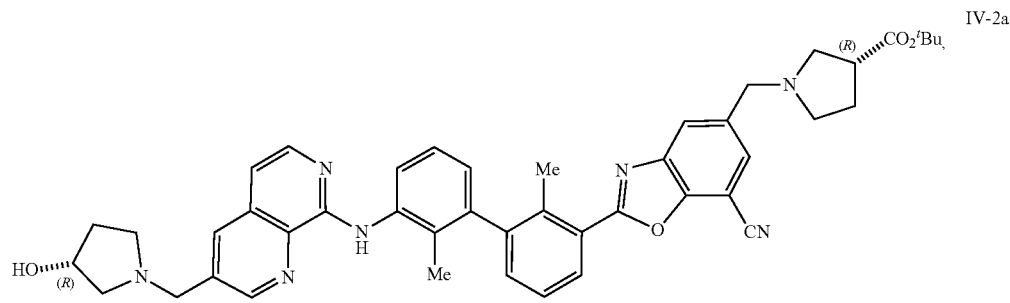
IV-2a or a salt thereof.

406. A compound of formula III-5:

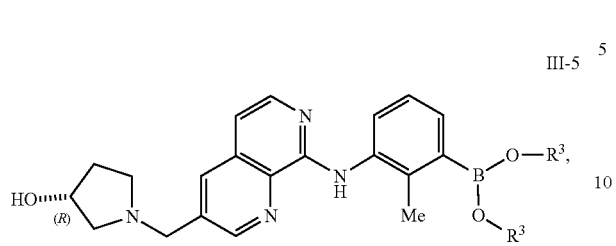

or a salt thereof, wherein:
each $R^3$ is independently selected from H and $C_{1-6}$ alkyl; or
each $R^3$ together form an $C_{2-3}$ alkylene linker, which is optionally substituted by 1, 2, 3, or 4 independently selected $C_{1-4}$ alkyl groups.

407. A compound of formula III-5a:

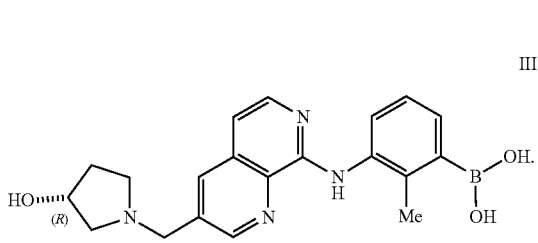

408. A compound of formula III-5c:

409. A compound of formula III-6a:

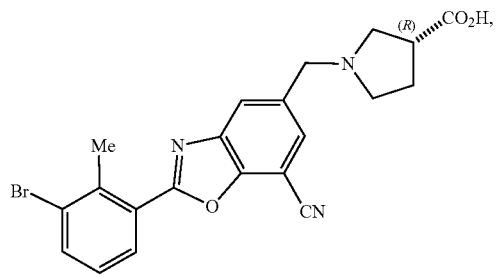

or a salt thereof.

410. A compound of formula III-6b:

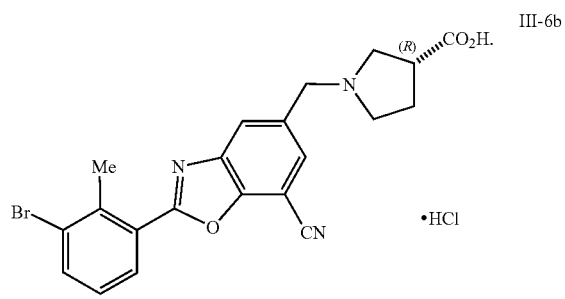

411. A compound of formula V-2:

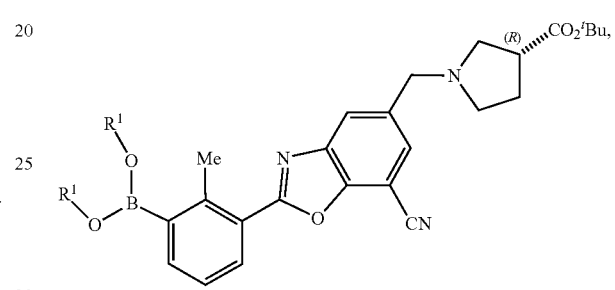

or a salt thereof, wherein:
each $R^1$ is independently selected from H and $C_{1-6}$ alkyl; or
each $R^1$ together form an $C_{2-3}$ alkylene linker, which is optionally substituted by 1, 2, 3, or 4 independently selected $C_{1-4}$ alkyl groups.

412. A compound of formula V-2b:

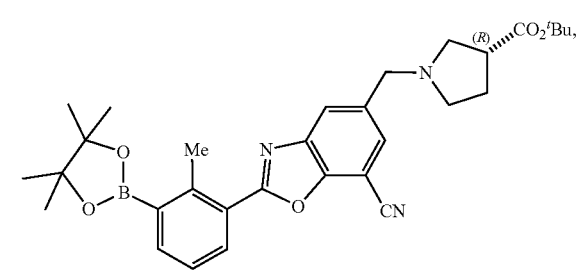

or a salt thereof.

413. A compound of formula VI-1a:

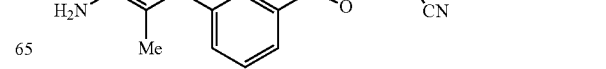

or a salt thereof.

414. A compound of formula IX-4a:
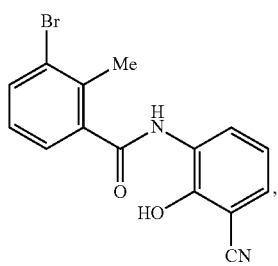
or a salt thereof.
415. A compound of formula IX-5a:
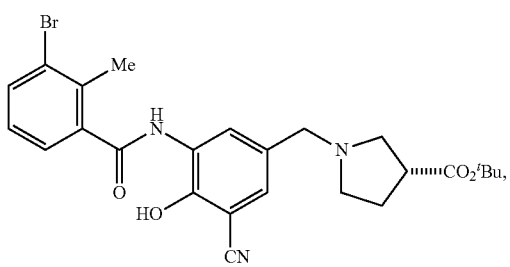
or a salt thereof.
416. A compound of formula X-3a:
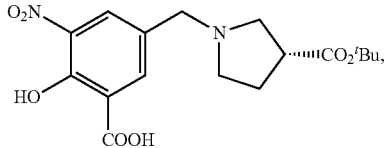
or a salt thereof.
417. A compound of formula X-4:
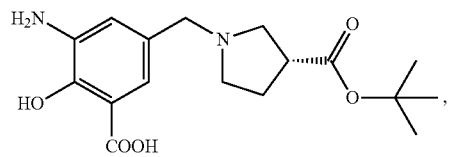
or a salt thereof.
418. A compound of formula X-44a:
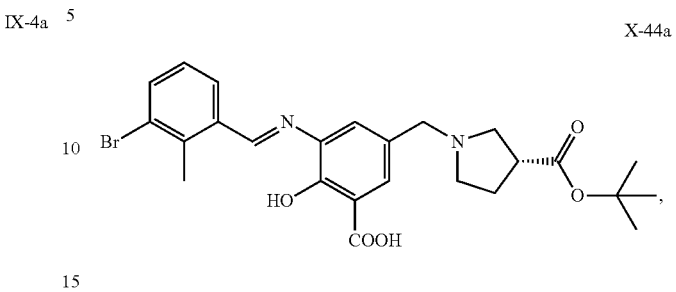
or a salt thereof.
419. A compound of formula X-6a:
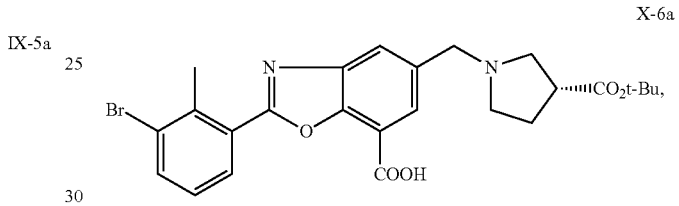
or a salt thereof.
420. A compound of formula X-7a:
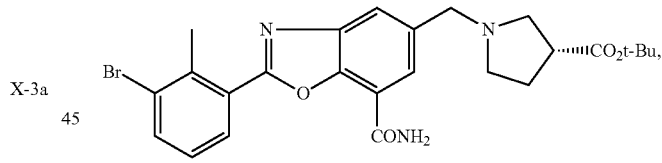
or a salt thereof.
421. A compound of formula XI-4:
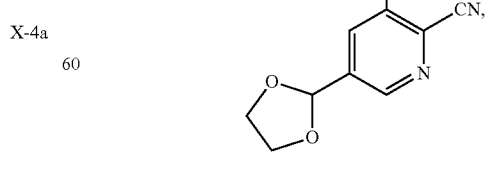
or a salt thereof.

422. A compound of formula XI-5:
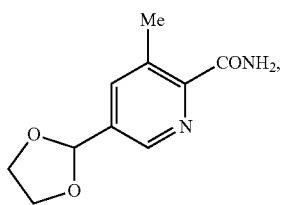
or a salt thereof.
423. A compound of formula XI-6:
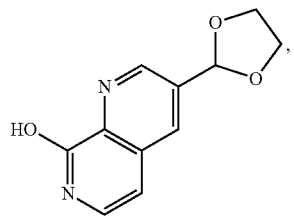
or a salt thereof.
424. A compound of formula XI-7a:
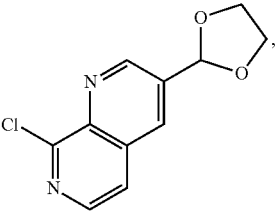
or a salt thereof.
425. A compound of formula XV-3a:
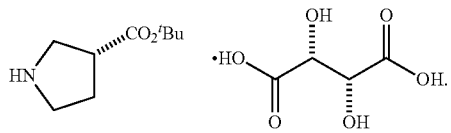
EXAMPLES
Example 1. Synthesis of Compound A-1 by the Reductive Amination Reaction with Pyrrolidine-3-Carboxylic Acid tert-Butyl Ester XV-4a
Scheme 1.
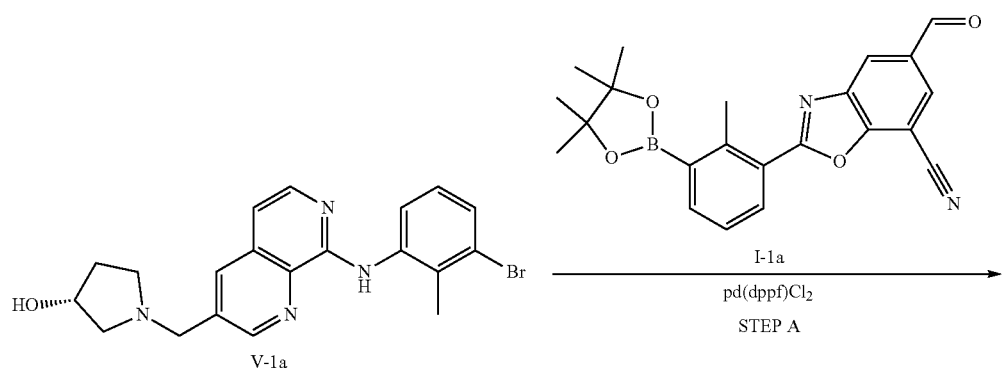
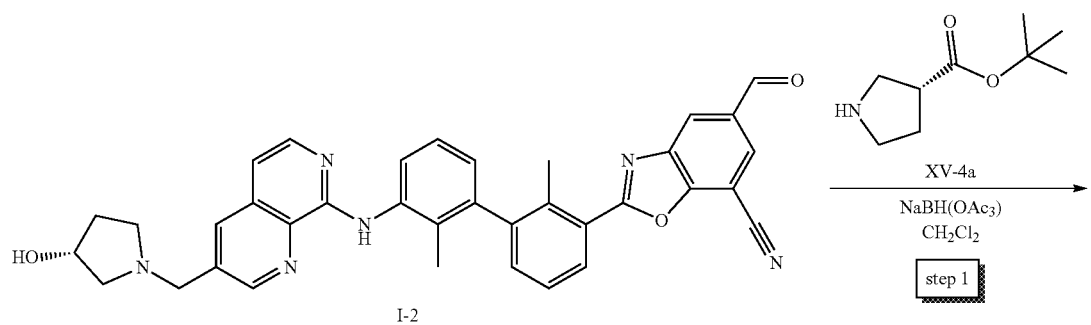

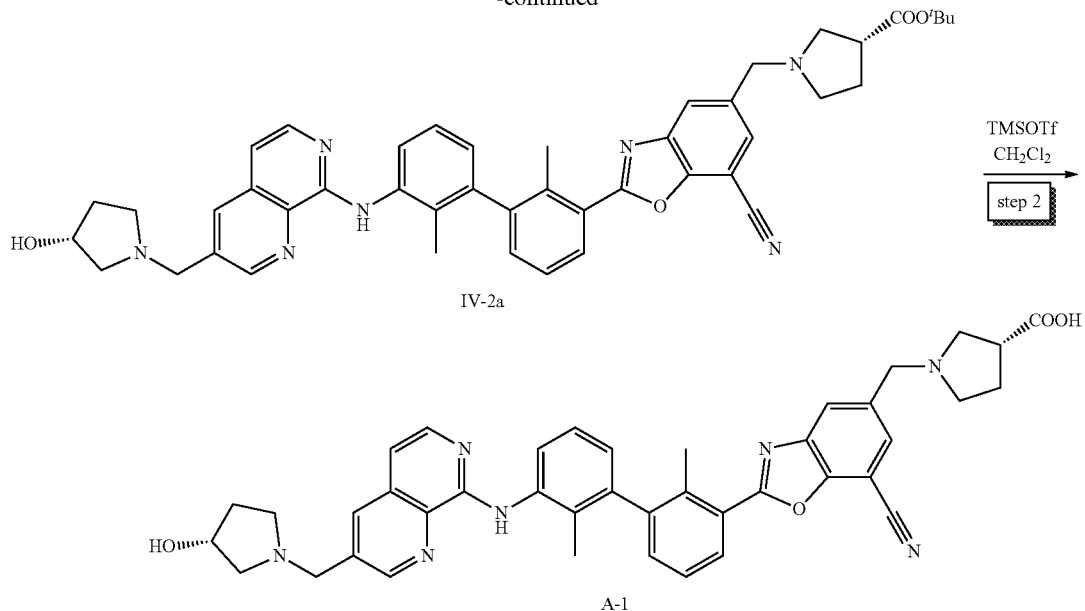

Step A: (R)-5-Formyl-2-(3'-(3-((3-hydroxypyrrolidin-1-yl)methyl)-1,7-naphthyridin-8-ylamino)-2,2'-dimethylbiphenyl-3-yl)benzo[d]oxazole-7-carbonitrile (I-2)

A mixture of 5-formyl-2-(2-methyl-3-(4,4,5,5-tetramethyl-1,3,2-dioxaborolan-2-yl)phenyl)benzo[d]oxazole-7-carbonitrile (I-1a, 9.50 g, 23.8 mmol, 1.02 equiv), (R)-1-((8-((3-bromo-2-methylphenyl)amino)-1,7-naphthyridin-3-yl)methyl)pyrrolidin-3-ol (V-1a, 10.0 g, 23.4 mmol), dichloro[1,1'-bis(dicyclohexylphosphino)ferrocene]palladium(II) dichloromethane adduct (Pd(dppf)Cl$_2$, 0.273 g, 0.351 mmol, 0.015 equiv) and potassium phosphate (K$_3$PO$_4$, 14.88 g, 70.1 mmol, 3.0 equiv) in 1,4-dioxane (70.1 mL) and water (23.37 mL) was heated to 80° C. and stirred at 80° C. for 1.5 hours. When HPLC analysis showed that the coupling reaction was complete, the reaction mixture was cooled to room temperature before DCM (100 mL) and water (100 mL) were added. The two phases were separated and the aqueous phase was extracted with DCM (100 mL). The combined organic extracts was washed with brine (100 mL), dried over MgSO$_4$, filtered, and concentrated under the reduced pressure. The residue was then purified by the silica gel (SiO$_2$) column chromatography eluting with 1-8% of MeOH in DCM to afford the desired product, (R)-5-formyl-2-(3'-(3-((3-hydroxypyrrolidin-1-yl)methyl)-1,7-naphthyridin-8-ylamino)-2,2'-dimethylbiphenyl-3-yl)benzo[d]oxazole-7-carbonitrile (1-2, 13.13 g, 13.91 g theoretical, 94.4%), as a thick oil, which was solidified upon standing under vacuum at ambient temperature. For 1-2: $^1$H NMR (500 MHz, DMSO-d$_6$) δ 10.13 (s, 1H), 9.32 (s, 1H), 8.86 (d, J=2.0 Hz, 1H), 8.69 (d, J=1.4 Hz, 1H), 8.53 (d, J=1.4 Hz, 1H), 8.49 (dd, J=8.2, 1.3 Hz, 1H), 8.21 (dd, J=7.9, 1.4 Hz, 1H), 8.18 (d, J=2.0 Hz, 1H), 8.07 (d, J=5.8 Hz, 1H), 7.59 (t, J=7.7 Hz, 1H), 7.49 (dd, J=7.5, 1.4 Hz, 1H), 7.37 (t, J=7.8 Hz, 1H), 7.19 (d, J=5.8 Hz, 1H), 6.93 (dd, J=7.5, 1.3 Hz, 1H), 4.72 (d, J=4.5 Hz, 1H), 4.26-4.19 (m, 1H), 3.85 (d, J=13.8 Hz, 1H), 3.79 (d, J=13.7 Hz, 1H), 2.75 (dd, J=9.7, 6.1 Hz, 1H), 2.70-2.62 (m, 1H), 2.51 (s, 3H), 2.49-2.46 (m, 1H), 2.39 (dd, J=9.6, 3.6 Hz, 1H), 2.10 (s, 3H), 2.07-1.98 (m, 1H), and 1.58 (dddd, J=13.0, 7.9, 5.4, 3.3 Hz, 1H) ppm; $^{13}$C NMR (125 MHz, DMSO-d$_6$) δ 191.36, 165.60, 153.91, 153.24, 150.74, 144.08, 143.35, 142.41, 141.44, 139.01, 137.66, 137.46, 134.31, 133.99, 132.95, 131.38, 130.15, 126.90, 126.84, 126.56, 126.43, 125.32, 124.22, 121.18, 114.22, 111.06, 96.10, 73.98, 69.89, 62.99, 57.32, 52.87, 34.97, 25.43, 18.64, and 14.96 ppm; C$_{36}$H$_{30}$N$_6$O$_3$ (MW 594.66), LCMS (EI) m/z 595.5 (M$^+$+H).

Step 1: tert-Butyl (R)-1-((7-cyano-2-(3'-((3-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylate (IV-2a)

A solution of (R)-5-formyl-2-(3'-((3-((3-hydroxypyrrolidin-1-yl)methyl)-1,7-naphthyridin-8-yl)amino)-2,2'-dimethyl-[1,1'-biphenyl]-3-yl)benzo[d]oxazole-7-carbonitrile (1-2, 43.10 g, 72.5 mmol) in dichloromethane (DCM, 600 mL) was added a solution of tert-butyl (R)-pyrrolidine-3-carboxylate (XV-4a, 14.90 g, 87 mmol, 1.20 equiv) in DCM (50 mL) at room temperature. Triethylamine (TEA, 33.1 mL, 238 mmol, 3.28 equiv) and sodium triacetoxyborohydride (NaB(OAc)$_3$H, STAB, 32.0 g, 151 mmol, 2.08 equiv) were then sequentially added and the resulting reaction mixture was stirred at room temperature for 5 hours. When HPLC analysis showed the reductive amination reaction was complete, the reaction mixture was quenched by adding a solution of sodium bicarbonate (NaHCO$_3$, 30 g) in water (250 mL). Two phases were separated and the organic phase was washed by water (250 mL) and brine (5%, 250 mL) before being concentrated under the reduced pressure. The residue was then purified by the silica gel (SiO$_2$) column chromatography eluting with 0-5% of MeOH in DCM to afford the desired product, tert-butyl (R)-1-((7-cyano-2-(3'-((3-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylate (IV-2a, 49.0 g, 54.37 g theoretical, 90.1%), as a light yellow amorphous powder. For IV-2a: $^1$H NMR (400 MHz, DMSO-d$_6$) δ 9.32 (s, 1H), 8.85 (d, J=2.0 Hz, 1H), 8.49 (dd, J=8.2, 1.3 Hz, 1H), 8.17 (t, J=2.2 Hz, 1H), 8.15 (dd, J=8.2, 1.4 Hz, 1H), 8.10 (d, J=1.5 Hz, 1H), 8.06 (d, J=5.8 Hz, 1H), 7.55 (t, J=7.7 Hz, 1H), 7.45 (dd, J=7.6, 1.5 Hz, 1H), 7.36 (t, J=7.8 Hz, 1H), 7.18 (d, J=5.8 Hz, 1H), 6.92 (dd, J=7.5, 1.3 Hz, 1H), 4.72 (d, J=4.5 Hz, 1H), 4.23 (tq, J=7.5, 3.7 Hz, 1H), 3.91-3.74 (m, 3H), 3.69 (d, J=13.6 Hz, 1H), 3.32 (s, 2H), 3.03-2.83 (m, 1H), 2.74 (dd, J=9.6, 6.1 Hz, 1H), 2.67 (p, J=8.1, 7.3 Hz, 3H), 2.61-2.53 (m, 2H), 2.47 (s, 3H), 2.39 (dd, J=9.6, 3.7 Hz, 1H), 2.10 (s, 3H), 2.07-1.88 (m, 3H), 1.58 (dddd, J=13.1, 8.1, 5.5, 3.0 Hz, 1H), and 1.39 (s, 9H) ppm; $^{13}$C NMR (101 MHz, DMSO-d$_6$) δ 174.03, 164.40, 153.23, 150.73, 149.45, 143.98, 142.84, 142.41, 141.55, 139.00, 137.71, 137.69, 137.11, 134.29, 133.52, 132.96, 131.37, 129.87, 129.60, 126.78 (two carbons), 126.40, 125.80, 125.45, 124.21, 121.09, 114.98, 111.05, 94.57, 80.18, 69.90, 63.00, 58.14, 57.33, 56.34, 53.50, 52.87, 42.92, 34.97, 28.16, 27.57, 18.60, and 14.94 ppm; $C_{45}H_{47}N_7O_4$ (MW 749.9), LCMS (EI) m/z 750.7 (M$^+$+H).

Step 2: (R)-1-((7-Cyano-2-(3'-((3-(((R)-3-hydroxy-pyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid (A-1)

A solution of tert-butyl (R)-1-((7-cyano-2-(3'-((3-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylate (IV-2a, 55.0 g, 73.3 mmol) in DCM (550 mL) was cooled to 0-5° C. in an ice bath, and the cooled solution was treated with TMSOTf (54.0 mL, 299 mmol, 4.1 equiv) at 0-5° C. The resulting reaction mixture was gradually warmed to ambient temperature and stirred at ambient temperature for 13 hours. When HPLC showed the deprotection reaction was complete, the reaction mixture was cooled to 0-5° C. before being transferred to a cooled aqueous solution of ammonium hydroxide (NH$_4$OH, 29%, 40.1 mL, 299 mmol, 4.1 equiv) in water (82 mL). The mixture was gradually warmed to ambient temperature and stirred at ambient temperature for 30 minutes. Two phases were separated, and aqueous phase was discarded. The organic phase was concentrated under the reduced pressure and the residual sticky oil was then directly purified by the silica gel (SiO$_2$) column chromatography eluting with 0-25% of methanol (MeOH) in dichloromethane (DCM) to afford the desired product, (R)-1-((7-Cyano-2-(3'-((3-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid (A-1, 43.74 g, 50.85 g theoretical, 86%), as a light yellow oil, which was solidified upon standing under vacuum at ambient temperature. For A-1: $^1$H NMR (500 MHz, DMSO-d$_6$) δ 9.31 (s, 1H), 8.84 (d, J=2.0 Hz, 1H), 8.46 (dd, J=8.2, 1.0 Hz, 1H), 8.17 (d, J=2.0 Hz, 1H), 8.14 (dd, J=7.9, 1.3 Hz, 1H), 8.09 (d, J=1.4 Hz, 1H), 8.05 (d, J=5.8 Hz, 1H), 7.86 (d, J=1.3 Hz, 1H), 7.54 (dd, J=7.7, 7.7 Hz, 1H), 7.43 (dd, J=7.5, 1.3 Hz, 1H), 7.34 (dd, J=7.8, 7.9 Hz, 1H), 7.17 (d, J=5.8 Hz, 1H), 6.91 (dd, J=7.5, 1.1 Hz, 1H), 4.21 (m, 1H), 3.82 & 3.77 (d & d, J=13.9 & 13.8 Hz, 2H), 3.75 & 3.71 (d & d, J=13.5 & 13.5 Hz, 2H), 2.92 (m, 1H), 2.73 & 2.64 (m, 2H), 2.72 & 2.37 (m & dd, J=9.8, 3.7 Hz, 2H), 2.64 & 2.46 (m & m, 2H), 2.53 (m, 2H), 2.45 (s, 3H), 2.08 (s, 3H), 2.00 & 1.56 (m & m, 2H), and 1.96 (m, 2H) ppm; 13C NMR (125 MHz, DMSO-d$_6$) δ 175.9, 163.9, 152.8, 150.3, 149.0, 143.5, 142.3, 141.9, 141.1, 138.5, 137.2 (two carbons), 136.6, 133.8, 133.0, 132.5, 130.9, 129.4, 129.3, 126.3 (two carbons), 125.9, 125.3, 125.1, 123.8, 120.7, 114.5, 110.6, 94.1, 69.4, 62.5, 57.9, 56.8, 56.0, 53.1, 52.4, 41.7, 34.5, 27.2, 18.1, and 14.5 ppm; $C_{41}H_{39}N_7O_4$ (MW 693.79), LCMS m/z 694.2 (M$^+$+H); $C_{41}H_{39}N_7O_4$, cald C, 70.98; H, 5.67; and N, 14.13. found C, 70.59; H, 5.49; and N, 14.16.

Example 2: Synthesis of Compound A-1 by the Reductive Amination Reaction with Pyrrolidine-3-Carboxylic Acid XV-0

Scheme 2.

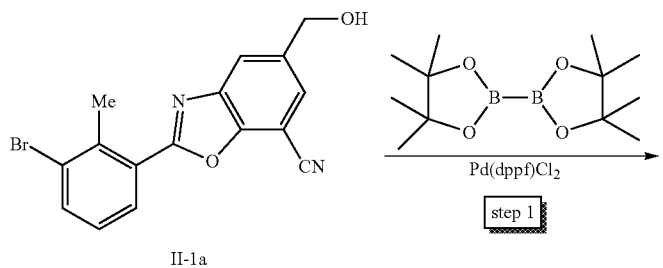

II-1a

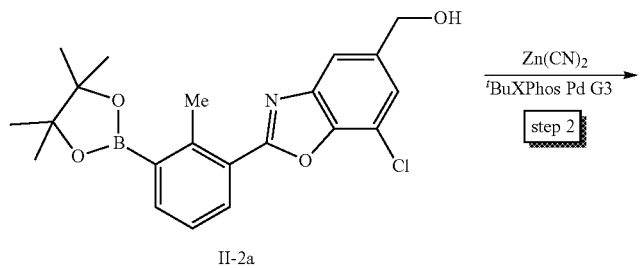

II-2a

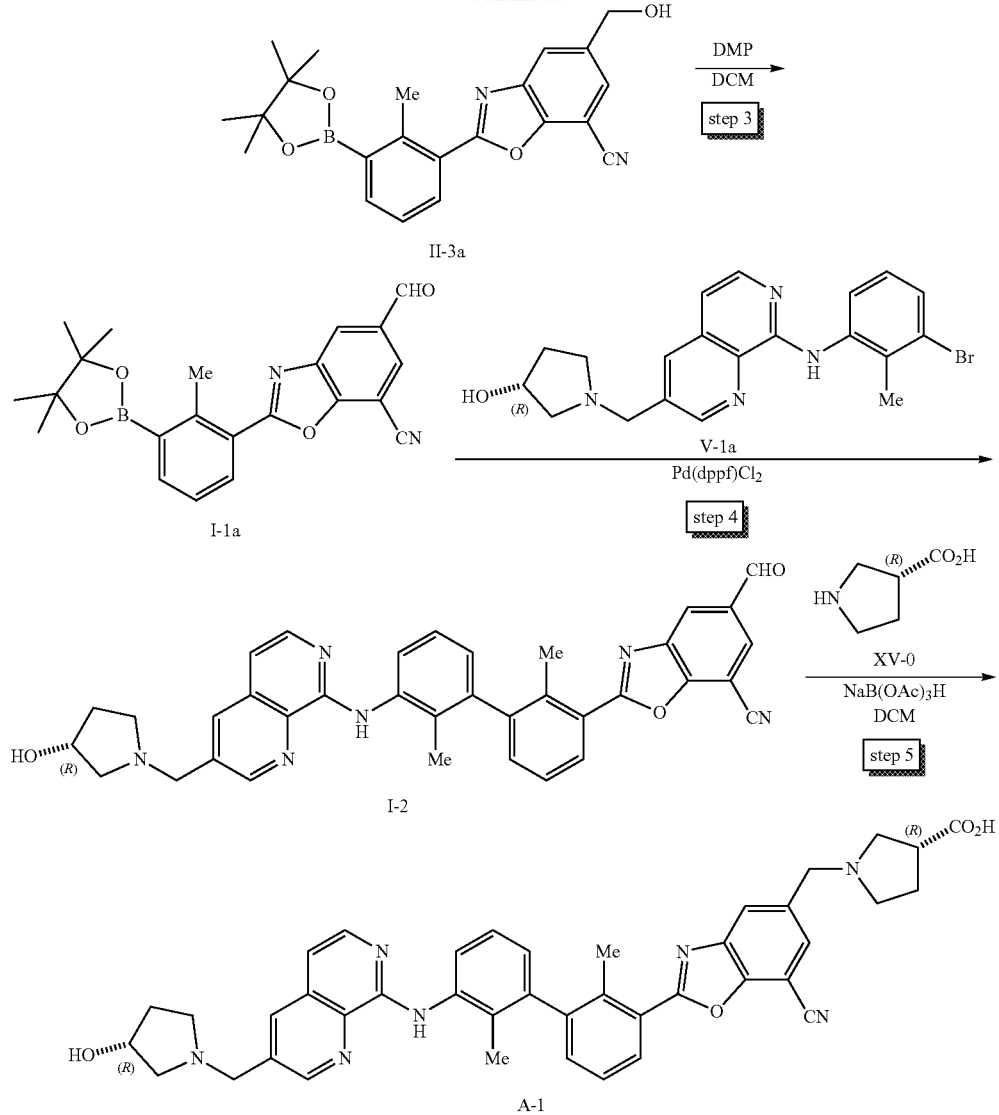

Step 1: (7-Chloro-2-(2-methyl-3-(4,4,5,5-tetramethyl-1,3,2-dioxaborolan-2-yl)phenyl)benzo[d]oxazol-5-yl)methanol (II-2a)

A mixture of (2-(3-bromo-2-methylphenyl)-7-chlorobenzo[d]oxazol-5-yl)methanol (II-1a, 4.10 g, 11.63 mmol), 4,4,4',4',5,5,5',5'-octamethyl-2,2'-bi(1,3,2-dioxaborolane) (B₂(pin)₂, 3.84 g, 15.12 mmol, 1.3 equiv), dichloro[1,1'-bis(diphenylphosphino)ferrocene]palladium (II) dichloromethane adduct (Pd(dppf)Cl₂, 0.950 g, 1.163 mmol, 0.1 equiv) and KOAc (2.054 g, 20.93 mmol, 1.8 equiv) in 1,4-dioxane (25 mL) was degassed three times before being heated to 100° C. The reaction mixture was stirred at 100° C. for 1 hour. When HPLC analysis showed the coupling reaction was complete, the reaction mixture was cooled to ambient temperature, diluted with DCM, and filtered through Celite. The filtrate was concentrated under the reduced pressure and the residue was purified by the silica gel (SiO₂) column chromatography eluting with 20-50% of EtOAc in hexanes to give the desired product, (7-chloro-2-(2-methyl-3-(4,4,5,5-tetramethyl-1,3,2-dioxaborolan-2-yl)phenyl)benzo[d]oxazol-5-yl)methanol (II-2a, 3.58 g, 4.65 g theoretical, 77%), as an off-white powder. For II-2a: $C_{21}H_{23}BClNO_4$ (MW 399.68), LCMS (EI) m/z 400.2 (M$^+$+H).

Step 2: 5-(Hydroxymethyl)-2-(2-methyl-3-(4,4,5,5-tetramethyl-1,3,2-dioxaborolan-2-yl)phenyl)benzo[d]oxazole-7-carbonitrile (II-3a)

A mixture of (7-chloro-2-(2-methyl-3-(4,4,5,5-tetramethyl-1,3,2-dioxaborolan-2-yl)phenyl)benzo[d]oxazol-5-yl)methanol (II-2a, 32.0 g, 78 mmol), zinc cyanide (Zn(CN)₂, 7.91 g, 66.0 mmol, 1.85 equiv) and ᵗBuXPhos Pd G3 (3.15 g, 3.88 mmol, 0.04 equiv) in 1,4-dioxane (311 mL) was stirred at 80° C. for 3 hours and 85° C. for 3 hours. When HPLC analysis showed the coupling reaction was complete, the reaction mixture was cooled to room temperature and diluted with THF (640 mL). The resulting mixture was filtered through a Celite pad and the filtrate was concentrated under the reduced pressure. The residue was treated with acetonitrile (640 mL) and the resulting slurry was stirred at ambient temperature for 30 minutes. The solids were collected by filtration and dried to give the crude desired product, 5-(hydroxymethyl)-2-(2-methyl-3-(4,4,5,5-tetramethyl-1,3,2-dioxaborolan-2-yl)phenyl)benzo[d]oxazole-7-carbonitrile (II-3a, 25.8 g, 30.44 g theoretical, 84.8%), as an off-white powder, which was used in the subsequent reaction without further purification. For II-3a: $^1$H NMR (400 MHz, CDCl$_3$) δ 8.21 (dd, J=7.9, 1.5 Hz, 1H), 8.03-7.99 (m, 1H), 7.94 (dd, J=7.4, 1.5 Hz, 1H), 7.70-7.65 (m, 1H), 7.36 (t, J=7.6 Hz, 1H), 4.86 (s, 2H), 2.97 (s, 3H), 1.96 (br s, 1H), and 1.39 (s, 12H) ppm; $C_{22}H_{23}BN_2O_4$(MW 390.25), LCMS (EI) m/z 391.2 (M$^+$+H).

Step 3: 5-Formyl-2-(2-methyl-3-(4,4,5,5-tetramethyl-1,3,2-dioxaborolan-2-yl)phenyl)benzo[d]oxazole-7-carbonitrile (I-1a)

1,1,1-Triacetoxy-1,1-dihydro-1,2-benziodoxl-3(1H)-one (Dess-Martin periodinane, 39.2 g, 92 mmol, 1.3 equiv) was added to a solution of 5-(hydroxymethyl)-2-(2-methyl-3-(4,4,5,5-tetramethyl-1,3,2-dioxaborolan-2-yl)phenyl)benzo[d]oxazole-7-carbonitrile (II-3a, 27.7 g, 70.3 mmol) in DCM (351 mL) at ambient temperature. The mixture was stirred at ambient temperature for 3 hours before being quenched with a saturated aqueous Na$_2$S$_2$O$_3$ solution (120 mL) and a saturated aqueous NaHCO$_3$ solution (350 mL). After quenching, the solution pH was adjusted to 9. The two layers were separated, and the aqueous layer was extracted with DCM. The combined organic phase was dried over sodium sulfate (Na$_2$SO$_4$), filtered and concentrated under the reduced pressure. The residue was then treated with MTBE (350 mL) to form a slurry. The resulting slurry was stirred at ambient temperature for 30 minutes before the solids were collected by filtration. The wet cake was dried to afford the crude desired product, 5-formyl-2-(2-methyl-3-(4,4,5,5-tetramethyl-1,3,2-dioxaborolan-2-yl)phenyl)benzo[d]oxazole-7-carbonitrile (I-1a, 25.9 g, 27.29 g theoretical, 94.9%), as an off-white powder. For I-1a: $^1$H NMR (400 MHz, CDCl$_3$) δ 10.11 (s, 1H), 8.52 (d, J=1.5 Hz, 1H), 8.25 (dd, J=7.9, 1.5 Hz, 1H), 8.21 (d, J=1.4 Hz, 1H), 7.99 (dd, J=7.5, 1.5 Hz, 1H), 7.39 (t, J=7.7 Hz, 1H), 3.00 (s, 3H), and 1.40 (s, 12H) ppm; $C_{22}H_{21}BN_2O_4$(MW 388.23), LCMS m/z 389.2 (M$^+$+H).

Step 4: (R)-5-Formyl-2-(3'-(3-((3-hydroxypyrrolidin-1-yl)methyl)-1,7-naphthyridin-8-ylamino)-2,2'-dimethylbiphenyl-3-yl)benzo[d]oxazole-7-carbonitrile (1-2)

A mixture of 5-formyl-2-(2-methyl-3-(4,4,5,5-tetramethyl-1,3,2-dioxaborolan-2-yl)phenyl)benzo[d]oxazole-7-carbonitrile (I-1a, 9.50 g, 23.8 mmol, 1.02 equiv), (R)-1-((8-((3-bromo-2-methylphenyl)amino)-1,7-naphthyridin-3-yl)methyl)pyrrolidin-3-ol (V-1, 10.0 g, 23.4 mmol), dichloro[1,1'-bis(dicyclohexylphosphino)ferrocene]palladium(II) dichloromethane adduct (Pd(dppf)Cl$_2$, 0.273 g, 0.351 mmol, 0.015 equiv) and potassium phosphate (K$_3$PO$_4$, 14.88 g, 70.1 mmol, 3.0 equiv) in 1,4-dioxane (70.1 mL) and water (23.37 mL) was stirred at 80° C. for 1.5 hours. When HPLC analysis showed the coupling reaction was complete, the reaction mixture was cooled to ambient temperature and the cooled reaction mixture was treated with DCM (100 mL) and water (100 mL). The two layers were separated, and the aqueous layer was extracted with DCM (3×100 mL). The combined organic phase was washed with brine (100 mL), dried over sodium sulfate (Na$_2$SO$_4$), filtered, and concentrated under the reduced pressure. The residue was then purified by the silica gel (SiO$_2$) column chromatography eluting with 1-8% of MeOH in DCM to afford the desired product, (R)-5-formyl-2-(3'-(3-((3-hydroxypyrrolidin-1-yl)methyl)-1,7-naphthyridin-8-ylamino)-2,2'-dimethylbiphenyl-3-yl)benzo[d]oxazole-7-carbonitrile (1-2, 13.13 g, 13.92 g theoretical, 94.3%), as an off-white to light-yellow powder, which is identical in every comparable aspect to the compound prepared by Example 1, Step A.

Step 5: (R)-1-((7-Cyano-2-(3'-((3-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid (A-1)

A mixture of (R)-5-formyl-2-(3'-((3-((3-hydroxypyrrolidin-1-yl)methyl)-1,7-naphthyridin-8-yl)amino)-2,2'-dimethyl-[1,1'-biphenyl]-3-yl)benzo[d]oxazole-7-carbonitrile (1-2, 50.0 g, 84 mmol) and (R)-pyrrolidine-3-carboxylic acid (XV-0, 16.0 g, 139 mmol, 1.655 equiv) in anhydrous dichloromethane (DCM, 383 mL) was stirred at room temperature for 30 minutes before being concentrated under the reduced pressure to dryness. Anhydrous dichloromethane (DCM, 250 mL) was then added to the residue to give a slurry. Sodium triacetoxyborohydride (NaB(OAc)$_3$H, STAB, 35.5 g, 168 mmol, 2.0 equiv) was then added to the slurry in three portions over a period of 10 minutes. The resulting reaction mixture was stirred at room temperature for 1.5 hours. When HPLC analysis showed the reductive amination reaction was complete, dichloromethane (DCM, 282 mL), water (500 mL), and MeOH (279 mL) were added to the reaction mixture at ambient temperature. An aqueous sodium hydroxide solution (NaOH, 1.0 N, 238.9 mL, 239 mmol) was then added to the quenched reaction mixture to adjust pH to 7.5. The bottom organic phase and oil layer were separated and combined. The aqueous phase was extracted with DCM three times (280 mL, 194 mL and 170 mL). The organic extracts were combined with the original organic phase and oil layer and concentrated under the reduced pressure. The residue (crude A-1, 65.5 g) was then purified by the silica gel (SiO$_2$) column chromatography eluting with 5-25% of MeOH in DCM to afford the purified desired product, (R)-1-((7-cyano-2-(3'-((3-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid (A-1, 55.3 g, 58.3 g theoretical, 94.9%; 99.6% pure by HPLC), as a light yellow oil, which was solidified upon standing under vacuum at ambient temperature and is identical in every comparable aspect to the compound prepared by Example 1, Step 2.

Example 3 Synthesis of Compound A-1 by the Suzuki Coupling Reaction Between III-5b and III-6b (Process 2)
Scheme 3.
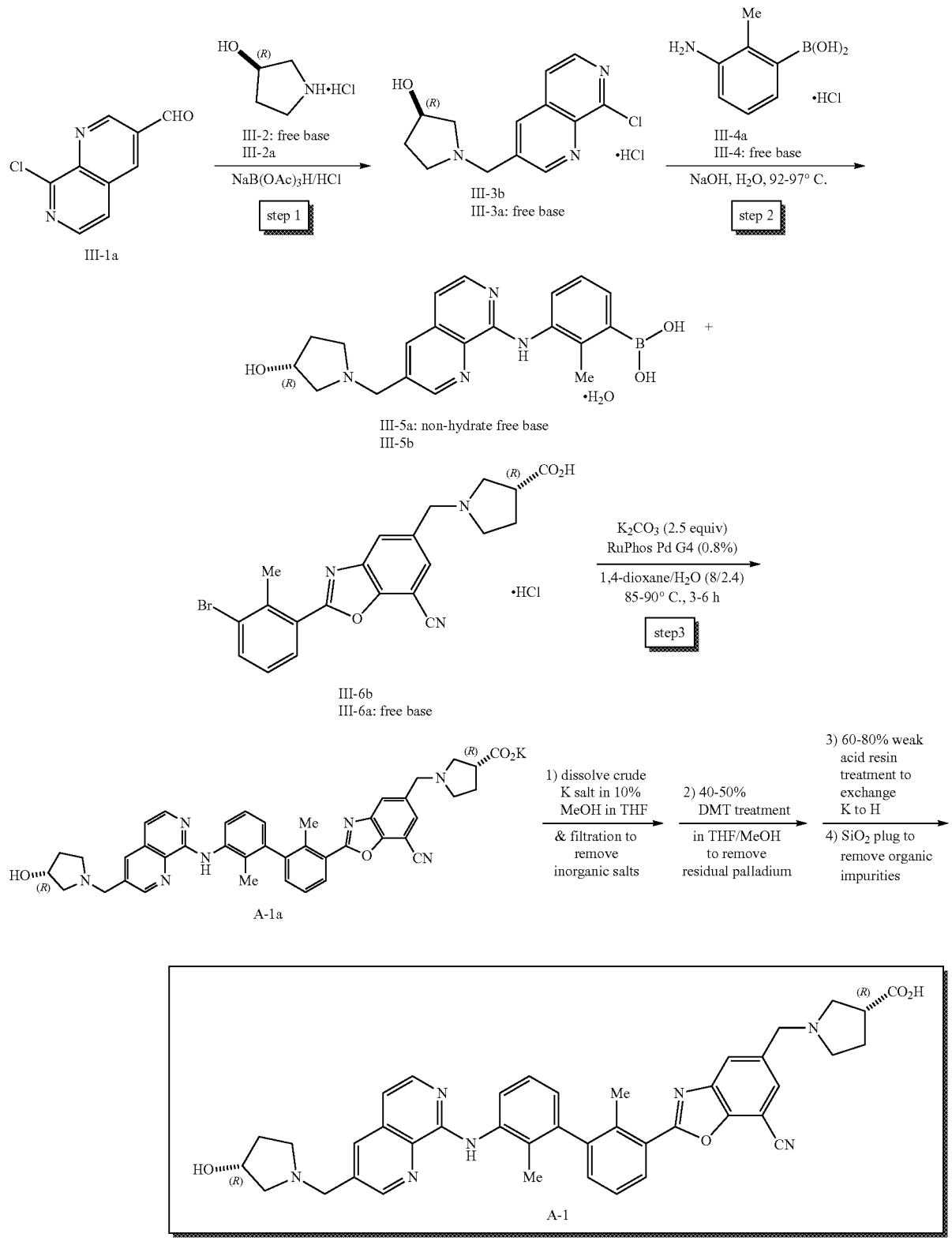

Step 1 Method A: (R)-1-((8-Chloro-1,7-naphthyridin-3-yl)methyl)pyrrolidin-3-ol Hydrochloride (III-3b)

A suspension of (R)-pyrrolidin-3-ol hydrochloride (III-2a, 7.7 g, 62.3 mmol, 1.2 equiv) in MeOH (35 mL) and DCM (35 mL) was agitated at ambient temperature. Sodium hydroxide (NaOH, 2.49 g, 62.3 mmol, 1.2 equiv) was added to the suspension at ambient temperature and the resulting mixture was agitated at ambient temperature for no less than (NLT) 1 hour before DCM (35 mL) was charged to the mixture. The mixture was continued to agitate at ambient temperature for 10 minutes. The solids (NaCl) were removed by filtration and the wet cake was washed with DCM (2×20 mL). The combined filtrates and wash solution was concentrated under the reduced pressure to remove most of the solvents. During concentration, DCM was charged to the concentrated residue for a total three times (3×50 mL) to remove most of the MeOH in the mixture. The concentrated residue, which contained MeOH in a range of 2.3-3.2% by weight, was then dissolved in DCM (100 mL) before 8-chloro-1,7-naphthyridine-3-carbaldehyde (III-1a, 10.0 g, 51.9 mmol) was charged at ambient temperature. The resulting mixture was cooled to 10-20° C. and sodium triacetoxyborohydride (NaB(OAc)$_3$H, STAB, 12.97 g, 62.3 mmol, 1.2 equiv) was added to the cooled mixture portion wise at 10-20° C. The resulting reaction mixture was then agitated at 10-20° C. until the completion of the reductive amination reaction was confirmed by the HPLC analysis. An aqueous NaOH solution (2 N, 31.2 mL, 62.4 mmol, 1.2 equiv) was charged to the reaction mixture with agitation at 10-20° C. to quench the reductive amination reaction before an aqueous hydrochloric acid solution (4 N HCl, 40 mL, 160 mmol, 3.08 equiv) was charged at 10-20° C. to adjust pH to 3-4. The resulting mixture was stirred at 10-20° C. for not longer than 30 minutes. Two phases were separated, and aqueous phase was extracted with DCM (2×50 mL). The organic phase, which contained the undesired process impurities, was discarded and the aqueous phase, which contained the desired product (III-3a) was kept for the subsequent process steps. The aqueous phase was added MeOH (10 mL) and DCM (90 mL) and the resulting mixture was then treated with an aqueous NaOH solution (2 N, 93.5 mL, 187 mmol, 3.6 equiv) at 10-25° C. to adjust the pH to 8.5-9.5. The resulting mixture was agitated at 10-25° C. for not longer than 20 minutes before two phases were separated. The aqueous phase was extracted with a mixture of MeOH and DCM (1 to 9 by volume) twice (2×100 mL). The combined organic phase was then concentrated under the reduced pressure to remove the organic solvents. During concentration, additional amount of DCM (100 mL) was charged to the residue to remove most of methanol (MeOH). The residue was then dissolved in DCM (70 mL) and the methanol (MeOH) content in the solution was adjusted to 4-6%. If MeOH is below 4% by volume, charge more MeOH and if MeOH is over 6% by volume, continue the concentration under the reduced pressure with addition of DCM until the criterion set for the methanol content was met. A solution of 5-6 N HCl in IPA (9.44 mL, 1.0 equiv) was slowly charged to the solution at 15-30° C. and the resulting mixture was charged MTBE (150 mL) at 15-30° C. The resulting mixture was agitated at 15-30° C. for NLT 2 hours. The solids were collected by filtration, washed with MTBE (3×25 mL), and dried under vacuum at 40-45° C. to constant weight (weight loss ≤1.0% within two hours) to afford the desired product, (R)-1-((8-chloro-1,7-naphthyridin-3-yl)methyl)pyrrolidin-3-ol hydrochloride (III-3b, 13.7 g, 15.58 g theoretical, 87.9%; 99.5% pure by HPLC), as a white to off-white powder, which was used for the subsequent reaction without further purification. For III-3b: $^1$H NMR (500 MHz, DMSO-d$_6$) δ 12.03 & 11.43 (s, 1H), 9.41 & 9.35 (s, 1H), 8.84 & 8.79 (s, 1H), 8.47 (d, J=5.5 Hz, 1H), 7.98 (m, 1H), 5.63 & 5.47 (s, 1H), 4.72 (m, 2H), 4.47 & 4.42 (s, 1H), 3.58, 3.36, 3.33 & 3.08 (m, 2H), 3.58, 3.47, 3.33 & 3.29 (m, 2H), and 2.32, 2.03, 1.96 & 1.87 (m, 2H); $^{13}$C NMR (125 MHz, DMSO-d$_6$) δ 155.2, 152.5, 143.3, 139.6, 138.7, 138.6, 132.7, 130.6 & 130.5, 121.9, 68.7, 61.1 & 60.4, 55.6 & 54.6, 52.4, and 33.7 & 33.0 ppm; $C_{13}H_{15}Cl_2N_3O$ (MW 300.18; $C_{13}H_{14}ClN_3O$ for III-3a, MW 263.73), LCMS m/z 264.1 and 266.0 (M$^+$+H).

Step 1 Method B

A suspension of 8-chloro-1,7-naphthyridine-3-carbaldehyde (III-1a, 10.0 g, 98.2% pure, 51.9 mmol) and (R)-pyrrolidin-3-ol hydrochloride (III-2a, 6.98 g, 99.36% pure, 56.1 mmol, 1.1 equiv) in a mixture of DCM (50 mL) and acetonitrile (10 mL) was treated with diisopropylethylamine (Hunig's base, DIEA, 56.1 mmol, 1.1 equiv) at ambient temperature. The resulting mixture was stirred at ambient temperature for 0.5-1 hour until it became a clear solution. Trimethyl borate (B(OMe)$_3$, 5.3 g, 51 mmol, 1.0 equiv) was added and the resulting solution (Solution A) was stirred at ambient temperature for 0.5-1 hour before being used for the subsequent reductive amination reaction. In another flask, sodium triacetoxyborohydride (NaB(OAc)$_3$H, STAB, 12.97 g, 61.2 mmol, 1.2 equiv) was suspended in DCM (50 mL) and the resulting suspension (Solution B) was cooled to 0-10° C. in an ice-bath. Solution A was then slowly added (dropwise) into Solution B while the internal temperature was kept at 0-10° C. After completion of adding Solution A, the additional funnel and flask were rinsed with DCM three times (3×20 mL) to make sure all Solution A was rinsed down to the reaction mixture. The ice-bath was removed, the reaction temperature was gradually warmed to 10-25° C., and the resulting reaction mixture was agitated at ambient temperature for 0.5 to 1 hour. When HPLC analysis showed the reductive amination reaction was complete, a 1 N aqueous NaOH solution (153 mmol, 153 mL, 3.0 equiv) was charged to quench the reaction at 10-25° C. followed by addition of MeOH (10 mL). Two phases were separated and the aqueous phase was extracted with a solution of 10% MeOH in DCM (3×50 mL). The combined organic extracts was then treated with the activated carbon (charcoal, 3 g) and Celite (3 g) and the resulting mixture was stirred at ambient temperature for NLT 2 hours. The mixture was filtered through a Celite pad (5 g) and the Celite bed was washed with a solution of 10% MeOH in DCM (3×30 mL). The combined filtrate and wash solution was concentrated under the reduced pressure to remove the organic solvents. The oily residue (crude III-3a) was dissolved in DCM (60 mL) to afford a solution. A solution of the first half of 5-6 N HCl in IPA (12.16/2 mL, 66.3/2 mmol, 1.3/2 equiv) was slowly charged to the solution of the crude III-3a in a mixture of MeOH and DCM at 15-30° C. with agitation. The solution became cloudy, solid formed, and the HCl vapor subsided. The resulting suspension was then charged MTBE (80 mL) to help induce the precipitation of III-3b salt. The second half of a solution of 5-6 N HCl in IPA (12.16/2 mL, 66.3/2 mmol, 1.3/2 equiv) was then added to the suspension at ambient temperature with agitation before additional amount of MTBE (80 mL) was charged into the mixture. The resulting mixture was stirred at 15-30° C. for NLT 2 hours. The solids were collected by filtration, washed with MTBE (3×25 mL), and dried under vacuum at 40-45° C. to the constant weight (weight loss ≤1.0% within two hours) to afford the desired product, (R)-1-((8-chloro-1,7-naphthyridin-3-yl)methyl)pyrrolidin-3-ol hydrochloride (III-3b, 13.94 g, 15.31 g theoretical, 91%; 99.5% pure by HPLC), as a white to off-white crystalline powder, which is identical in every comparable aspect to the compound obtained by Example 3, Step 1 Method A and was used for the subsequent reaction without further purification.

Step 2: (R)-(3-((3-((3-Hydroxypyrrolidin-1-yl)methyl)-1,7-naphthyridin-8-yl)amino)-2-methylphenyl)boronic acid Hydrate (III-5b)

To a 2000 mL four-neck round bottom flask equipped with a mechanic stirrer, a thermocouple, and a nitrogen inlet was charged ((R)-1-((8-chloro-1,7-naphthyridin-3-yl)methyl)pyrrolidin-3-ol hydrochloride (III-3b, 100 g, 90% by weight, 300 mmol), 3-amino-2-methylphenylboronic acid hydrochloride (III-4a, 57.7 g, 97.4% by weight, 300 mmol, 1.0 equiv), and water (200 mL). The mixture was then treated with a 1 N aqueous NaOH solution (300 mL, 300 mmol, 1.0 equiv) at ambient temperature before being heated to 92-97° C. The reaction mixture was then stirred at 92-97° C. for 4-6 hours until the nucleophilic substitution reaction completion was indicated by HPLC analysis. The reaction mixture was cooled to 35-45° C. before being polish filtered through a 3-5 cm thick of Celite pad. The Celite bed was washed with water (3×100 mL) and the combined filtrate and wash solution was charged THF (200 mL). The resulting mixture was then treated with 70% of a total 2 equivalents of 6 N aqueous NaOH solution (70 mL, 420 mmol, 1.4 equiv) at 35-45° C. until the clear solution becomes cloudy. The crystalline III-5b seed (100 mg, 0.1 wt %) was then added to the cloudy mixture at 35-45° C. and solids was gradually formed within 20-40 minutes. The resulting suspension was stirred at 35-45° C. for NLT 1 hour before the remaining 30% of a total 2 equivalents of 6 N aqueous NaOH solution (30 mL, 180 mmol, 0.6 equiv) was added to the suspension at 35-45° C. The mixture was agitated at 35-45° C. for NLT 15 minutes before being cooled to ambient temperature. The pH value of the suspension was adjusted to 7.5-8.5 by addition of 1 N aqueous NaOH solution or 1 N aqueous HCl solution at ambient temperature. Water (200 mL) was charged into the suspension at ambient temperature and the mixture was agitated at ambient temperature for NLT 2 hours. The solids were collected by filtration, washed with a mixture of THF and water (10%, 3×300 mL) and MTBE (2×300 mL), and dried under vacuum at 40-45° C. to constant weight (weight loss ≤1.0% within two hours) to afford the desired product, (R)-(3-((3-((3-hydroxypyrrolidin-1-yl)methyl)-1,7-naphthyridin-8-yl)amino)-2-methylphenyl)boronic acid hydrate (III-5b, 118 g, 129.68 g theoretical, 91.0%; 99.6% pure by HPLC), as a white to off-white crystalline powder. For III-5b: $^1$H NMR (500 MHz, DMSO-$d_6$) δ 9.20 (s, 1H), 8.88 (s, 1H), 8.31 (d, J=7.8 Hz, 1H), 8.18 (s, 1H), 8.12 (s, 2H), 8.01 (d, J=5.9 Hz, 1H), 7.20 (dd, J=7.7, 7.4 Hz, 1H), 7.15 (d, J=7.4 Hz, 1H), 7.13 (d, J=5.7 Hz, 1H), 4.77 (s, 1H), 4.25 (m, 1H), 3.86 (s, 2H), 2.79 & 2.54 (m, 2H), 2.71 & 2.54 (m, 2H), 2.44 (s, 3H), and 2.04 & 1.61 (M, 2h); $^{13}$C NMR (125 MHz, DMSO-$d_6$) δ 153.3, 150.7, 142.5, 138.6, 138.2, 137.4, 134.5, 133.0, 131.7, 131.5, 127.9, 125.6, 122.4, 110.5, 62.9, 57.2, 52.8, 34.9, 17.8, and 6.98 ppm; $C_{20}H_{25}BN_4O_4$(MW 396.25; $C_{20}H_{23}BN_4O_3$ for anhydrous III-5a, MW 378.24), LCMS m/z 379.1 (M$^+$+H).

Step 3: (R)-1-((7-Cyano-2-(3'-((3-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic Acid Potassium Salt (A-1a)

In a 3 L three-neck round bottom flask equipped with a reflux condenser, a mechanical stirrer, a thermal couple and a nitrogen inlet and nitrogen outlet was charged (R)-1-((2-(3-bromo-2-methylphenyl)-7-cyanobenzo[d]oxazol-5-yl)methyl)pyrrolidine-3-carboxylic acid hydrochloride (III-6b, 136.5 g, 285 mmol, 1.014 equiv), (R)-(3-((3-((3-hydroxypyrrolidin-1-yl)methyl)-1,7-naphthyridin-8-yl)amino)-2-methylphenyl)boronic acid (III-5b, 87 wt %, 122.0 g, 281 mmol), potassium carbonate ($K_2CO_3$, 98 g, 712 mmol, 2.53 equiv), 1,4-dioxane (1200 mL), and water (360 mL) at room temperature. Nitrogen was bubbled through the mixture for 30 minutes at room temperature before the catalyst (RuPhos Pd G4, 1.939 g, 2.28 mmol, 0.008 equiv) was added to at room temperature under nitrogen atmosphere. The resulting reaction mixture was then heated to 88° C. and stirred at 87-89° C. for 4-6 hours. When HPLC analysis showed the coupling reaction was complete, the reaction mixture was cooled to 50° C. The bottom aqueous phase was separated and discarded. The top organic phase was added to a cold solution of acetonitrile (3400 mL) and water (200 mL) at 0-5° C. in 30 minutes. After stirred at 0-5° C. for 30 minutes, the solids were collected by filtration. The wet cake was washed with acetonitrile (1460 mL) and dried on the filter funnel for 16 hours at room temperature under house vacuum to provide the crude desired product, (R)-1-((7-cyano-2-(3'-((3-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid potassium salt (A-1a, 237.1 g, 205.66 g theoretical, 115.2%), as a yellow to brown amorphous powder, which contained inorganic salts and water and was used for the subsequent step without further purification. For A-1a: $^1$H NMR (400 MHz, DMSO-$d_6$) δ 9.30 (s, 1H), 8.83 (d, J=2.0 Hz, 1H), 8.49 (dd, J=8.3, 1.3 Hz, 1H), 8.20-8.10 (m, 2H), 8.06 (s, 1H), 8.04 (d, J=5.7 Hz, 1H), 7.82 (d, J=1.4 Hz, 1H), 7.53 (t, J=7.7 Hz, 1H), 7.43 (dd, J=7.6, 1.5 Hz, 1H), 7.34 (t, J=7.9 Hz, 1H), 7.16 (d, J=5.8 Hz, 1H), 6.91 (dd, J=7.6, 1.3 Hz, 1H), 4.98 (br.s., 1H), 4.22 (dp, J=9.7, 3.5 Hz, 1H), 3.88-3.73 (m, 2H), 3.73-3.59 (m, 2H), 3.41 (br.s., 2H), 2.73 (dd, J=9.6, 6.1 Hz, 1H), 2.66 (t, J=7.9 Hz, 2H), 2.60-2.53 (m, 3H), 2.45 (s, 3H), 2.38 (dd, J=9.7, 3.5 Hz, 2H), 2.09 (s, 3H), 2.06-1.94 (m, 2H), 1.75 (ddt, J=12.3, 9.8, 7.2 Hz, 1H), and 1.58 (dddd, J=13.1, 8.1, 5.4, 3.3 Hz, 1H) ppm; $^{13}$C NMR (101 MHz, DMSO-$d_6$) δ 177.44, 164.30, 153.19, 150.70, 149.32, 143.95, 142.73, 142.37, 141.54, 138.98, 138.38, 137.68, 137.08, 134.26, 133.46, 132.94, 131.34, 129.85, 129.75, 126.73, 126.67, 126.38, 125.83, 125.55, 124.16, 120.97, 115.02, 111.04, 94.41, 69.85, 63.02, 59.25, 58.66, 57.35, 54.49, 52.88, 46.08, 34.95, 29.14, 18.60, and 14.91 ppm; $C_{41}H_{38}KN_7O_4$(MW 731.90; $C_{41}H_{39}N_7O_4$ for free carboxylic acid, MW 693.79), LCMS (EI) m/z 694.6 (M$^+$+H).

Step 4: (R)-1-((7-Cyano-2-(3'-((3-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid (A-1)

In a 5 L three-neck round bottom flask equipped with a reflux condenser, a mechanical stirrer, a thermal couple and a nitrogen inlet and nitrogen outlet was charged crude (R)-1-((7-cyano-2-(3'-((3-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid potassium salt (A-1a, 254.0 g, 347 mmol), THF (2300 mL), and MeOH (254 mL) at room temperature. The resulting suspension was then charged Celite (50 g) before being stirred at room temperature for 2 hours. The mixture was filtered and the filter cake was washed with a mixture of THF (225 mL) and MeOH (25 mL). The filtrate was treated with SiliaMetS® DMT (125 g) and the resulting mixture was heated to 55-60° C. and stirred at 55-60° C. for 24 hours. After cooling to room temperature, the mixture was filtered and the filter cake was washed with a mixture of THF (450 mL) and MeOH (50 mL). Ion exchange resin (Dowex MAC-3 hydrogen form, 200 g) was then added to the filtrate and the resulting mixture was stirred at ambient temperature for 24 hours. The mixture was filtered and the filter cake was washed with a mixture of THF (225 mL) and MeOH (25 mL). Most of the solvents were removed by concentration under the reduced pressure and the residue was dissolved in THF (2000 mL) at room temperature to generate a solution. The solution was concentrated under the reduced pressure to about 700 grams and the resulting concentrated solution was then charged to methyl tert-butyl ether (MTBE, 5000 mL) at 0-5° C. to induce the precipitation of the crude desired product (A-1). After stirred at 0-5° C. for 1 hour, the solids were collected by filtration, washed with MTBE (1000 mL), and dried on the filter under house vacuum to afford the crude desired product (crude A-1). The crude product was purified by the silica gel ($SiO_2$) column chromatography eluting with 10-25% of MeOH in DCM to provide the desired product, (R)-1-((7-cyano-2-(3'-((3-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid (A-1, 202 g, 240.5 g theoretical, 84.0%; 96.6% pure by HPLC), as a light yellow amorphous powder, which is identical in every comparable aspect to the compound obtained by Example 1, Step 2 and Example 2, Step 5 described previously.

Example 4. Synthesis of A-1 by the Suzuki Coupling Reaction Between IV-1b and III-5c (Process 2)

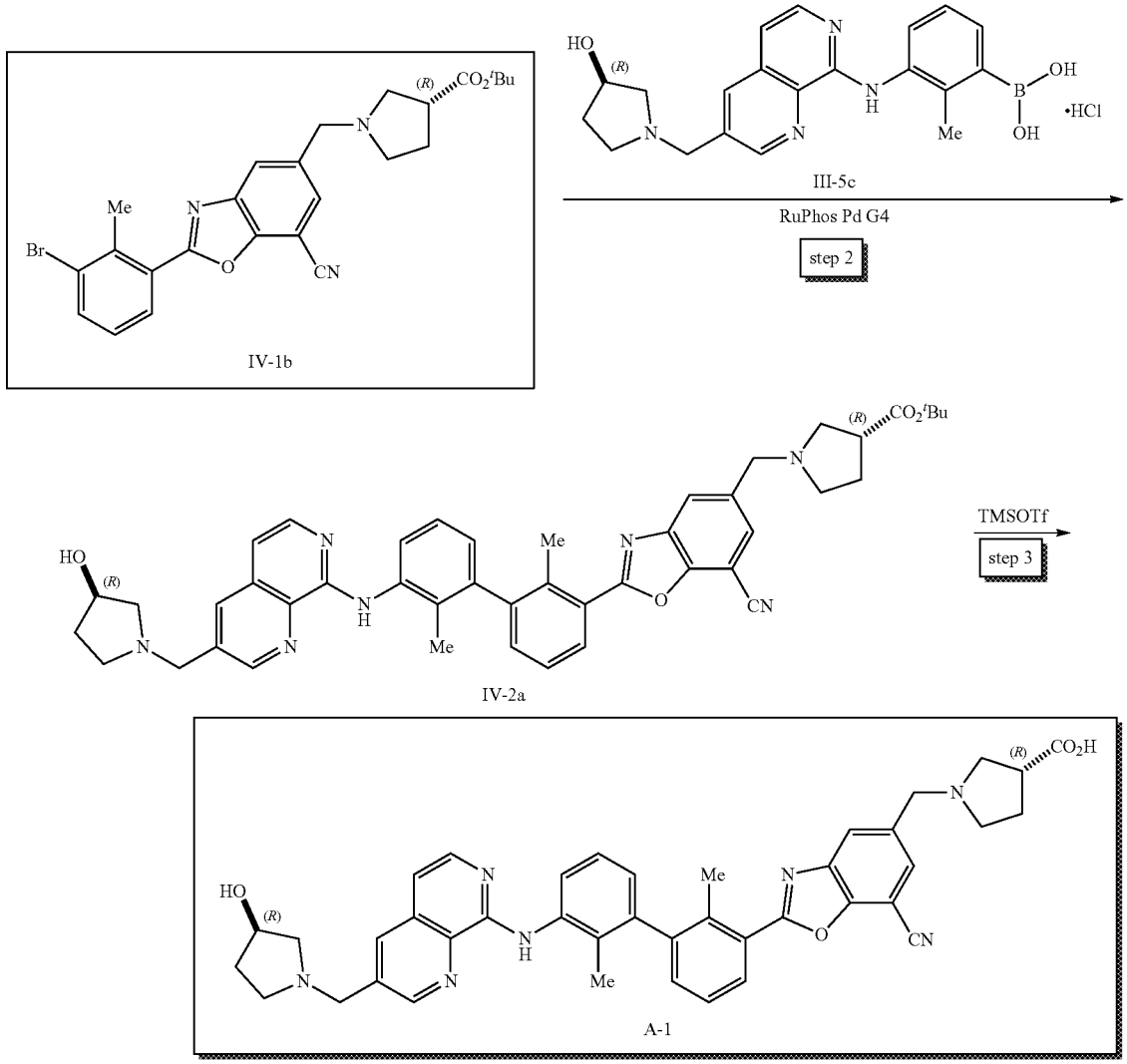

Step 1: tert-Butyl (R)-1-((7-cyano-2-(3'-((3-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylate (IV-2a)

In a 1 L three-neck round bottom flask equipped with a reflux condenser, a magnetic stirring bar, a thermal couple and a nitrogen inlet and nitrogen outlet was placed tert-butyl (R)-1-((2-(3-bromo-2-methylphenyl)-7-cyanobenzo[d]oxazol-5-yl)methyl)pyrrolidine-3-carboxylate (IV-1b, 7.86 g, 15.83 mmol), potassium carbonate ($K_2CO_3$, 5.90 g, 42.7 mmol, 2.7 equiv), tert-butanol (78 mL), and water (48 mL) at room temperature. The mixture was then charged a solution of (R)-(3-((3-(((3-hydroxypyrrolidin-1-yl)methyl)-1,7-naphthyridin-8-yl)amino)-2-methylphenyl)boronic acid hydrochloride (III-5c, 6.89 g, 16.6 mmol, 1.05 equiv) in water (30 mL) at room temperature. The resulting mixture was degassed by bubbling nitrogen under the liquid surface for 10 minutes before the catalyst RuPhos Pd G4 (154 mg, 0.1805 mmol, 0.0114 equiv) was added. The reaction mixture was then heated to reflux and stirred at reflux for 4 hours. When HPLC analysis showed the coupling reaction was complete, the reaction mixture was cooled to room temperature. Two phases were separated and the organic phase was added to cold water (510 mL) at 0-5° C. over a period of 15 minutes. The solids were collected by filtration, washed with water, and dried at 50° C. under the house vacuum with a gentle nitrogen sweeping to provide the crude desired product, tert-butyl (R)-1-((7-cyano-2-(3'-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylate (IV-2a, 11.4 g, 11.87 g theoretical, 96%), as a yellow powder, which is identical to the compound manufactured by Example 1, Step 1 and was used in Example 1, Step 2 without further purification to produce Compound A-1.

Example 5. Synthesis of Compound A-1 by the Suzuki Coupling Reaction Between V-2b and V-1a (Process 2)

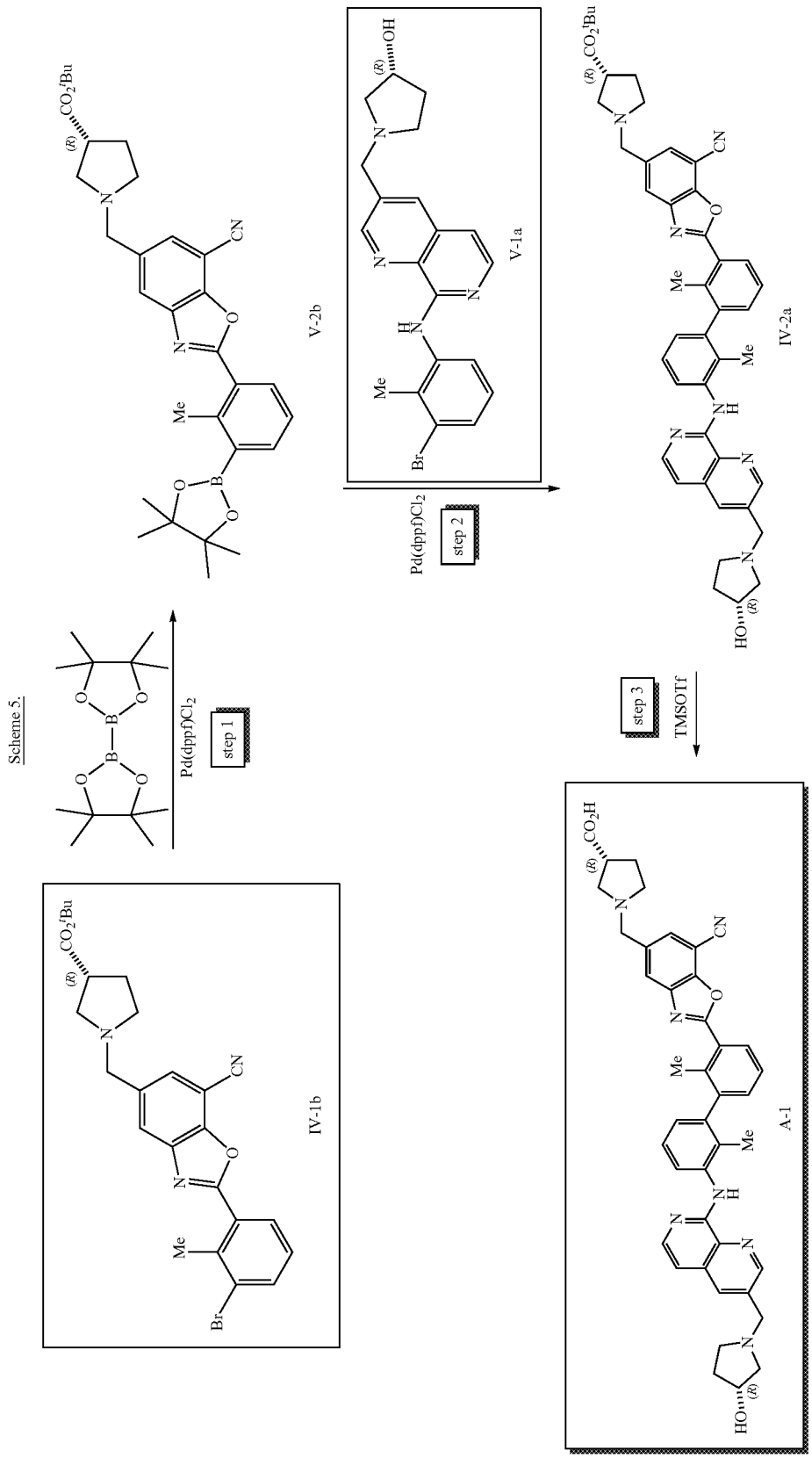

Step 1: (R)-tert-Butyl 1-((7-cyano-2-(2-methyl-3-(4,4,5,5-tetramethyl-1,3,2-dioxaborolan-2-yl)phenyl)benzo[d]oxazol-5-yl)methyl)pyrrolidine-3-carboxylate (V-2b)

A stirred mixture of tert-butyl (R)-1-((2-(3-bromo-2-methylphenyl)-7-cyanobenzo[d]oxazol-5-yl)methyl)pyrrolidine-3-carboxylate (IV-1b, 0.750 g, 1.511 mmol), 4,4,4',4',5,5,5',5'-octamethyl-2,2'-bi(1,3,2-dioxaborolane) ($B_2(pin)_2$, 0.465 g, 1.813 mmol, 1.2 equiv), potassium acetate (KOAc, 0.286 ml, 4.53 mmol, 3.0 equiv) and dichloro[1,1'-bis(diphenylphosphino)ferrocene]palladium(II) dichloromethane adduct ($Pd(dppf)Cl_2$, 0.025 g, 0.030 mmol, 0.02 equiv) in anhydrous 1,4-dioxane (8 mL) was degassed and refilled with $N_2$. The degassed reaction mixture was heated at 100° C. for 4 hours under $N_2$. When HPLC analysis showed the coupling reaction was complete, the reaction mixture was cooled to room temperature before being filtered through a Celite pad and the Celite bed was washed with EtOAc. The filtrate was concentrated and the residue was purified by the silica gel ($SiO_2$) column chromatography eluting with 0-60% of EtOAc in n-hexane to afford the desired product, (R)-tert-butyl 1-((7-cyano-2-(2-methyl-3-(4,4,5,5-tetramethyl-1,3,2-dioxaborolan-2-yl)phenyl)benzo[d]oxazol-5-yl)methyl)pyrrolidine-3-carboxylate (V-2b, 755.5 mg, 821.2 mg theoretical, 92%), as a viscous yellow oil. For V-2b: $C_{31}H_{38}BN_3O_5$ (MW 543.47), LCMS (EI) m/z 544.2 ($M^++H$).

Step 2: (R)-tert-Butyl 1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylate (IV-2a)

A mixture of tert-butyl (R)-1-((7-cyano-2-(2-methyl-3-(4,4,5,5-tetramethyl-1,3,2-dioxaborolan-2-yl)phenyl)benzo[d]oxazol-5-yl)methyl)pyrrolidine-3-carboxylate (V-2b, 722 mg, 1.209 mmol, 1.03 equiv), (R)-1-((8-((3-bromo-2-methylphenyl)amino)-1,7-naphthyridin-3-yl)methyl)pyrrolidin-3-ol (V-1a, 490 mg, 1.174 mmol), dichloro[1,1'-bis(dicyclohexylphosphino)ferrocene]palladium(II) dichloromethane adduct ($Pd(dppf)Cl_2$, 22.87 mg, 0.029 mmol, 0.025 equiv) and potassium phosphate ($K_3PO_4$, 747 mg, 3.52 mmol, 3.0 equiv) in 1,4-dioxane (3.52 mL) and water (1.174 mL) was stirred at 80° C. for 8 hours. When HPLC analysis showed that the coupling reaction was complete, the reaction mixture was cooled to ambient temperature before being treated with water and ethyl acetate. Two layers were separated, and the aqueous layer was extracted with ethyl acetate. The combined organic phase was dried over sodium sulfate ($Na_2SO_4$), filtered and concentrated under the reduced pressure. The residue was purified by the silica gel ($SiO_2$) column chromatography eluting with 2-10% of MeOH in DCM to afford the desired product, (R)-tert-butyl 1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylate (IV-2a, 864 mg, 880.4 mg theoretical, 98.1%), as a light yellow powder, which is identical to the compound prepared by Example 1, Step 1 and Example 4, Step 1 in every comparable aspect. Compound IV-2a was used in Example 1, Step 2 without further purification to produce Compound A-1.

Example 6. Synthesis of Compound A-1 by the Nucleophilic Substitution Reaction Between VI-1a and III-3b (Process 3)

Scheme 6.

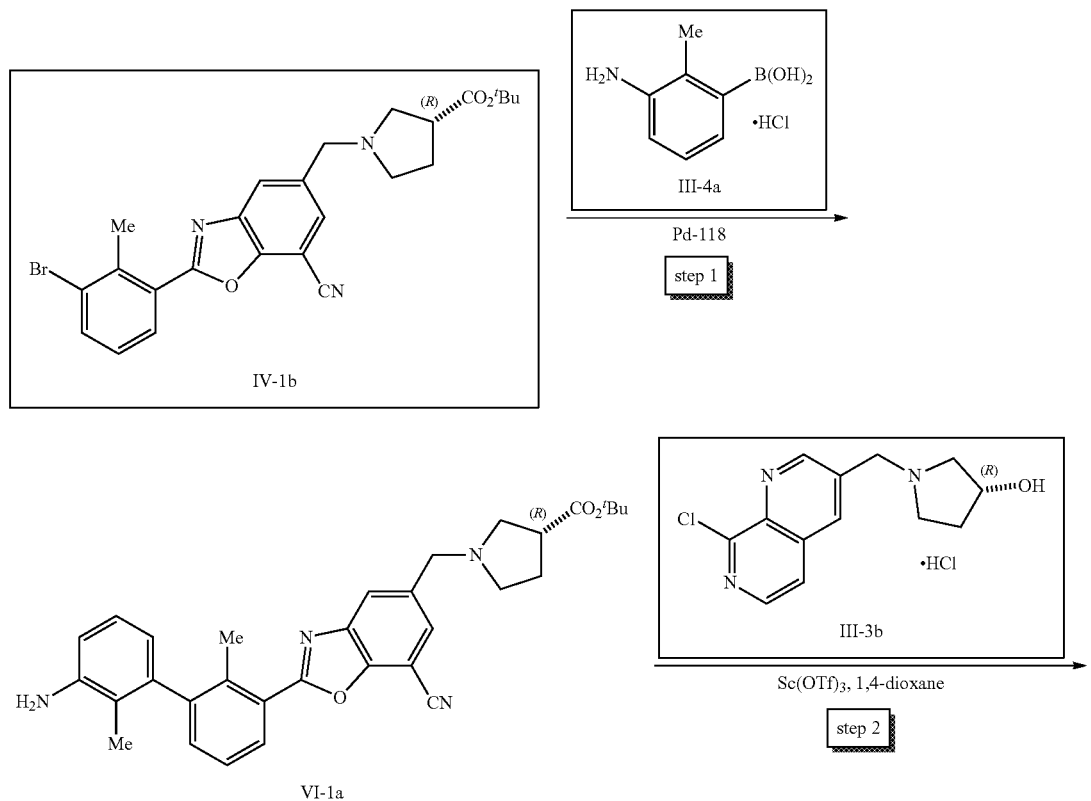

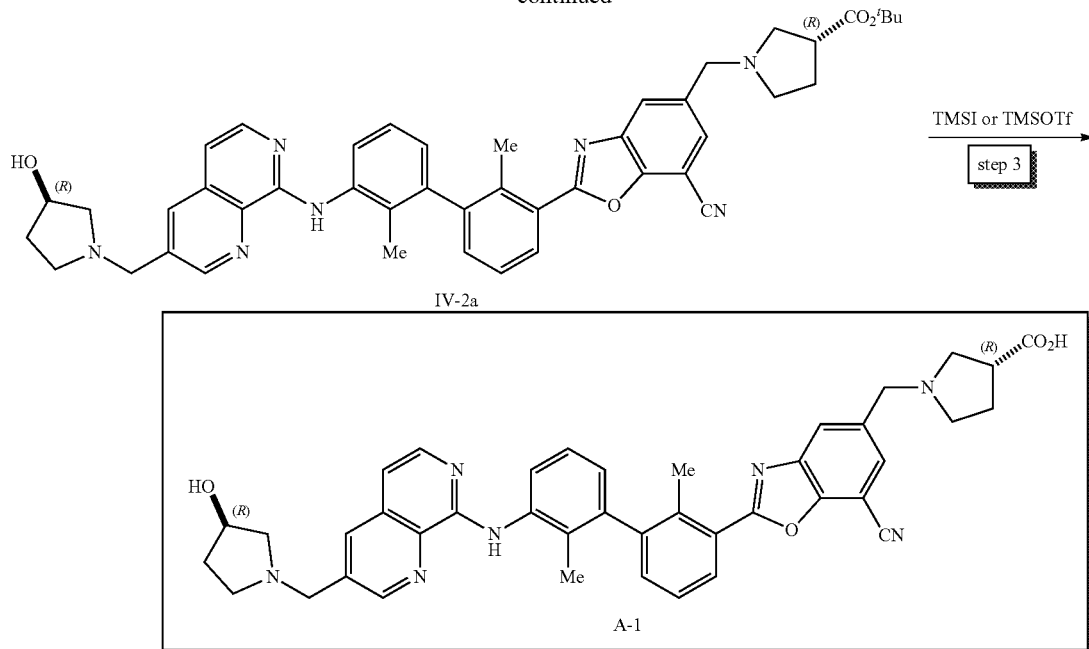

Step 1: tert-Butyl (R)-1-((2-(3'-amino-2,2'-dimethyl-[1,1'-biphenyl]-3-yl)-7-cyanobenzo[d]oxazol-5-yl)methyl)pyrrolidine-3-carboxylate (VI-1a)

In a 3 L three-neck round bottom flask equipped with a reflux condenser, a magnetic stirring bar, a thermal couple and a nitrogen inlet and nitrogen outlet was placed tert-butyl (R)-1-((2-(3-bromo-2-methylphenyl)-7-cyanobenzo[d]oxazol-5-yl)methyl)pyrrolidine-3-carboxylate (IV-1b, 30.00 g, 60.4 mmol), (3-amino-2-methylphenyl)boronic acid hydrochloride (III-4a, 13.59 g, 72.5 mmol, 1.2 equiv), dibasic potassium phosphate ($K_2HIPO_4$, 42.1 g, 242 mmol, 4.0 equiv), tert-butanol (300 mL), and water (300 mL) at room temperature. The mixture was degassed by bubbling nitrogen under the liquid surface for 30 minutes before the catalyst 1,1'-bis(di-tert-butylphosphino)ferrocene palladium dichloride (Pd-118, 0.335 g, 0.514 mmol, 0.0086 equiv) was added. The resulting reaction mixture was heated to reflux and stirred at reflux for 1-2 hours. When HPLC analysis showed the reaction was complete, the reaction mixture was cooled to room temperature. Two phases were separated and the organic phase was added to water (750 mL) over a period of 30 minutes at room temperature. The resulting slurry was cooled to 0-5° C. and stir at 0-5° C. for 1 hour. The solids were collected by filtration and washed with water (2×250 mL) and n-heptane (2×250 mL). The wet cake was then dissolved in dichloromethane (DCM, 900 mL) and the resulting solution was concentrated under the reduced pressure and dried under vacuum to provide the crude desired product, tert-butyl (R)-1-((2-(3'-amino-2,2'-dimethyl-[1,1'-biphenyl]-3-yl)-7-cyanobenzo[d]oxazol-5-yl)methyl)pyrrolidine-3-carboxylate (VI-1a, 27.5 g, 31.57 g theoretical, 87%), as a yellow foam, which was used in the subsequent reaction without further purification. For VI-1a: $^1$H NMR (400 MHz, DMSO-$d_6$) δ 8.12 (s, 1H), 8.10 (d, J=6.1 Hz, 1H), 7.86 (s, 1H), 7.49 (t, J=7.7 Hz, 1H), 7.35 (d, J=7.5 Hz, 1H), 6.98 (t, J=7.6 Hz, 1H), 6.69 (d, J=8.0 Hz, 1H), 6.35 (d, J=7.4 Hz, 1H), 4.96 (s, 2H), 3.97-3.51 (m, 2H), 2.93 (t, J=7.5 Hz, 1H), 2.76-2.62 (m, 2H), 2.41 (s, 3H), 1.96 (q, J=7.5, 6.9 Hz, 2H), 1.76 (s, 3H), and 1.40 (s, 9H) ppm; $^{13}$C NMR (100 MHz, DMSO-$d_6$) δ 173.97, 164.47, 149.36, 147.29, 144.78, 142.83, 141.29, 137.63, 137.00, 133.37, 129.45, 129.38, 126.46, 126.40, 125.47, 125.32, 119.29, 117.60, 114.90, 113.91, 94.52, 80.14, 58.15, 56.34, 53.50, 42.93, 28.14, 27.56, 18.50, and 14.37 ppm; $C_{32}H_{34}N_4O_3$ (MW 522.6), LCMS (EI) m/z 523.5 ($M^+$+H).

Step 2: tert-Butyl (R)-1-((7-cyano-2-(3'-((3-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylate (IV-2a)

A mixture of tert-butyl (R)-1-((2-(3'-amino-2,2'-dimethyl-[1,1'-biphenyl]-3-yl)-7-cyanobenzo[d]oxazol-5-yl)methyl)pyrrolidine-3-carboxylate (VI-1a, 51 mg, 0.098 mmol) and (R)-1-((8-chloro-1,7-naphthyridin-3-yl)methyl)pyrrolidin-3-ol hydrochloride (III-3b, 31 mg, 0.103 mmol, 1.05 equiv) in 1,4-dioxane (0.5 mL) was treated with scandium trifluoromethanesulfonate (Sc(OTf)$_3$, 78 mg, 0.158 mmol, 1.62 equiv) at ambient temperature. The resulting reaction mixture was then warmed to 80° C. and agitated at 80° C. for 20-24 hours. Once the nucleophilic substitution reaction was complete as indicated by HPLC analysis, the reaction mixture was concentrated under the reduced pressure. The residue was purified by the silica gel (SiO$_2$) column chromatography eluting with 0-10% of MeOH in DCM to afford the desired product, tert-butyl (R)-1-((7-cyano-2-(3'-((3-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylate (IV-2a, 46 mg, 73.5 mg theoretical, 62%), as a light-yellow powder, which is identical to the compound prepared by Example 1, Step 1; Example 4, Step 1; and Example 5, Step 2 in every comparable aspect. Compound IV-2a was used in Example 1, Step 2 without further purification to produce Compound A-1.

Example 7. Synthesis of the Example 2 Starting Material II-1

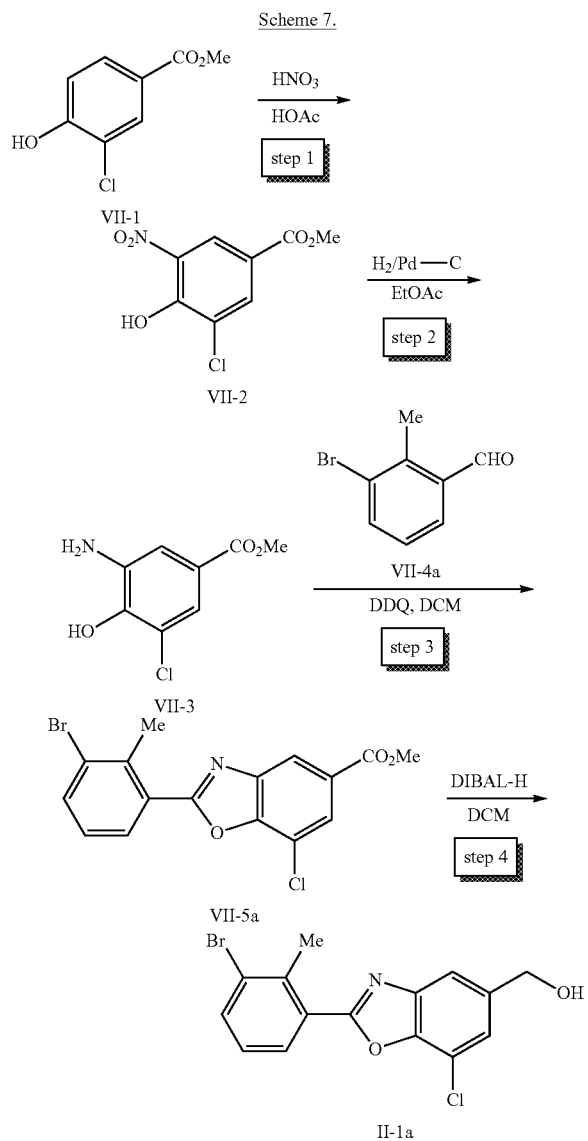

Scheme 7.

Step 1: Methyl 3-chloro-4-hydroxy-5-nitrobenzoate (VII-2)

To a solution of methyl 3-chloro-4-hydroxybenzoate (VII-1, 10.0 g, 53.6 mmol) in acetic acid (HOAc, 20.0 mL) was added a solution of nitric acid (HNO$_3$, 4.72 mL, 112 mmol) in acetic acid (HOAc, 20.0 mL) dropwise at 0° C. The ice bath was removed and the thick reaction mixture was gradually warmed to ambient temperature and stirred at ambient temperature for 2 hours. When the nitration reaction was complete, the reaction mixture was treated with water (20 mL) before the mixture was cooled to 0-5° C. The mixture was stirred at 0-5° C. for an addition 1 hour before the solids were collected by filtration. The cake was washed with cold water and dried under vacuum to afford the crude desired product, methyl 3-chloro-4-hydroxy-5-nitrobenzoate (12.02 g, 12.41 g theoretical, 96.9%), as a yellow powder, which was used directly in the subsequent reaction without further purification. For VII-2: C$_8$H$_6$ClNO$_5$ (MW 231.59), LCMS (EI) m/z 232.0 and 234.0 (M$^+$+H).

Step 2: Methyl 3-amino-5-chloro-4-hydroxybenzoate (VII-3)

Methyl 3-chloro-4-hydroxy-5-nitrobenzoate (VII-2, 2.08 g, 8.98 mmol) was hydrogenated under 1 atmosphere pressure of hydrogen (H$_2$) using the palladium on carbon (Pd/C, 0.57 g) as a catalyst in ethyl acetate (15 mL) for 1 hour. The reaction mixture was filtered through a celite pad and the pad was washed with EtOAc. The filtrate was concentrated under the reduced pressure to remove the solvent. The residue was purified by the silica gel (SiO$_2$) column chromatography eluting with 0-10% of MeOH in DCM to afford the desired product, methyl 3-amino-5-chloro-4-hydroxybenzoate (1.65 g, 1.81 g theoretical, 91.1%), as a light yellow powder. For VII-3: C$_8$H$_8$ClNO$_3$ (MW 201.61), LCMS (EI) m/z 202.0 and 204.0 (M$^+$+H).

Step 3: Methyl 2-(3-bromo-2-methylphenyl)-7-chlorobenzo[d]oxazole-5-carboxylate (VII-5a)

A mixture of methyl 3-amino-5-chloro-4-hydroxybenzoate (VII-3, 1.04 g, 5.16 mmol, 1.05 equiv) and 3-bromo-2-methylbenzaldehyde (VII-4a, 0.98 g, 4.92 mmol) in EtOH (25 mL) was stirred at room temperature for 1 hour. The mixture was then concentrated under the reduced pressure and the residue was dissolved in DCM (25 mL). Dichlorodicyanoquinone (DDQ, 1.12 g, 4.92 mmol, 1.0 equiv) was added to the solution at room temperature and the resulting reaction mixture was stirred at room temperature for 30 minutes. When HPLC showed the cyclization reaction was complete, the reaction mixture was diluted with DCM and the resulting solution was washed with the aqueous Na$_2$S$_2$O$_3$ solution and the aqueous NaHCO$_3$ solution. The organic phase was dried over MgSO$_4$, filtered, and concentrated under the reduced pressure. The residue, which contained the crude desired product, methyl 2-(3-bromo-2-methylphenyl)-7-chlorobenzo[d]oxazole-5-carboxylate, was used in the subsequent reaction directly without further purification. For VII-5a: C$_{16}$H$_{11}$BrClNO$_3$ (MW 380.62), LCMS (EI) m/z 379.9 and 381.9 (M$^+$+H).

Step 4: (2-(3-Bromo-2-methylphenyl)-7-chlorobenzo[d]oxazol-5-yl)methanol (II-1a)

To a solution of methyl 2-(3-bromo-2-methylphenyl)-7-chlorobenzo[d]oxazole-5-carboxylate (VII-5a, 395.0 mg, 1.04 mmol) in DCM (10.0 mL) was added a solution of diisobutylaluminum hydride (DIBAL-H) in DCM (1.0 M, 2.08 mL, 2.08 mmol, 2.0 equiv) dropwise at −78° C. The reaction mixture was then slowly warmed up to 0° C. When the reduction reaction was complete as indicated by HPLC analysis, the reaction mixture was added DCM and quenched with the aqueous Rochell's salt solution. The mixture was stirred vigorously at room temperature for 1 hour. Two phases were separated and the organic phase was dried over MgSO$_4$ before being filtered through a short pad of Celite to remove solids. The filtrate was concentrated under the reduced pressure and the residue was purified by the silica gel (SiO$_2$) column chromatography eluting with 0-5% of MeOH in DCM to afford the desired product, (2-(3-bromo-2-methylphenyl)-7-chlorobenzo[d]oxazol-5-yl)methanol (II-1a, 328 mg, 366.7 mg theoretical, 89.4%), as a light yellow to off-white powder. For II-1a: C₁₅HnBr ClNO₂ (MW 352.61), LCMS (EI) m/z 352.0 and 354.0 (M⁺+H).

Example 8. Synthesis of Starting Material V-1a

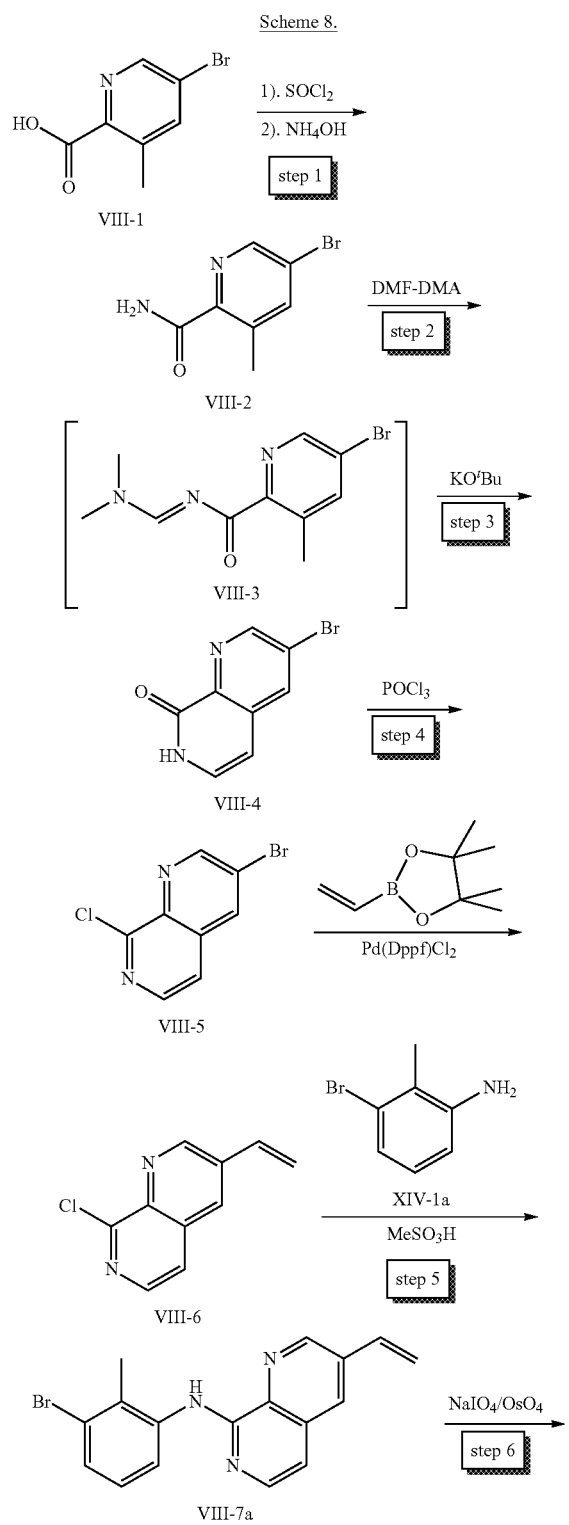

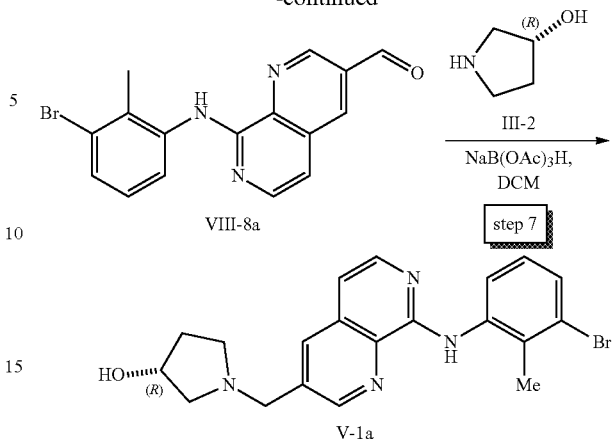

Step 1: 5-Bromo-3-methylpicolinamide (VIII-2)

A suspension of 5-bromo-3-methylpicolinic acid (VIII-1, 6.0 Kg, 27.89 mol) in toluene (30.0 L) was charged DMF (15 mL) and thionylchloride (SOCl₂, 4.0 Kg, 33.47 mol, 1.2 equiv) at ambient temperature. The resulting reaction mixture was then warmed to reflux and agitated at reflux for 2 hours. When HPLC analysis showed the acyl chloride formation reaction was complete, the reaction mixture was cooled to ambient temperature and the cooled reaction mixture was slowly added to an aqueous solution of ammonium hydroxide (NH₄OH, 36.0 L) while maintaining the internal temperature at below 40 aC. The reaction mixture was then agitated at below 40° C. for 2 hours. The solids were collected by filtration, washed with water (5.0 L), and dried under vacuum to afford the crude desired product, 5-bromo-3-methylpicolinamide (5.5 Kg, 6.04 Kg theoretical, 91%; 99% pure by HPLC) as an off-white powder, which was used in the subsequent reaction without further purification. For VIII-2: ¹H NMR (300 MHz, CDCl₃) δ 8.47 (s, 1H), 7.79 (d, 2H), 5.61 (m, 1H), and 2.74 (s, 3H) ppm.

Step 2: 3-Bromo-1,7-naphthyridin-8(7H)-one (VIII-4)

A suspension of 5-bromo-3-methylpicolinamide (VIII-2, 5.5 Kg, 25.57 mol) in toluene (27.5 L) was added DMF-DMA (4.0 Kg, 33.24 mol, 1.3 equiv) at ambient temperature. The mixture was warmed to reflux and then stirred at reflux for 2 hours. The mixture was gradually cooled to ambient temperature before being charged slowly to a suspension of potassium tert-butoxide (ᵗBuOK, 4.3 Kg, 38.36 mol, 1.5 equiv) in toluene (55.0 L) in another reactor at ambient temperature. The resulting reaction mixture was then warmed to reflux (110° C.) and stirred at reflux (110° C.) for 3 hours. When HPLC analysis showed that the cyclization reaction was complete, the reaction mixture was cooled to 50-60° C. before the pH of the reaction mixture was adjusted to 7 with the concentrated aqueous hydrochloric acid (HCl) solution. The quenched reaction mixture was concentrated under the reduced pressure to remove solvent and the residue was treated with water (30.0 Kg). The resulting mixture was stirred at ambient temperature for 1 hour. The solids were collected by filtration and dried under vacuum to afford the crude desired product, 3-bromo-1,7-naphthyridin-8(7H)-one (5.2 Kg, 5.78 Kg theoretical, 90%; 87% pure by HPLC), as an off-white to brown powder, which was used in the subsequent reaction without further purification. For VIII-4: $^1$H NMR (300 MHz, DMSO-d$_6$) δ 11.65 (br s, 1H), 8.81 (d, 1H), 8.48 (d, 1H), 7.32 (dd, 1H), and 6.51 (d, 1H) ppm.

Step 3: 3-Bromo-8-chloro-1,7-naphthyridine (VIII-5)

POCl$_3$ (15.3 Kg, 99.99 mol, 3.0 equiv) was slowly added to a suspension of 3-bromo-1,7-naphthyridin-8(7H)-one (VIII-4, 7.5 Kg, 33.33 mol) in toluene (75.0 L) at ambient temperature. The mixture was then treated with N,N-dimethylaniline (14.9 Kg, 99.99 mol, 3.0 equiv) dropwise before being heated to 130° C. The reaction mixture was stirred at 130° C. for 5 hours. When HPLC analysis showed that the reaction was complete, the reaction mixture was cooled to ambient temperature before being concentrated under the reduced pressure. The residue was then charged water (55.0 Kg) and the resulting mixture was stirred at ambient temperature for 1 hour. The solids were collected by filtration and dried under vacuum to afford the crude desired product, 3-bromo-8-chloro-1,7-naphthyridine (4.5 Kg, 8.04 Kg theoretical, 56%; 98% pure by HPLC), as a yellow to brown powder, which was used in the subsequent reaction without further purification. For VIII-5: $^1$H NMR (300 MHz, DMSO-d$_6$), Q 9.21 (d, 1H), 8.93 (d, 1H), 8.47 (d, 1H), and 7.93 (d, 1H) ppm.

Step 4: 8-Chloro-3-vinyl-1,7-naphthyridine (VIII-6)

A solution of 3-bromo-8-chloro-1,7-naphthyridine (VIII-5, 4.0 Kg, 16.43 mol) in 1,4-dioxane (40.0 L) and water (16.0 L) was charged sodium carbonate (Na$_2$CO$_3$, 5.2 Kg, 49.29 mol, 3.0 equiv). The resulting mixture was degasses three times before Pd(dppf)Cl$_2$ (724 g, 0.99 mol, 0.06 equiv) and 4,4,5,5-tetramethyl-2-vinyl-1,3,2-dioxaborolane (3.3 Kg, 21.36 mol, 1.3 equiv) were charged under nitrogen (N$_2$) atmosphere. The reaction mixture was then degassed three times before being heated to 90° C. The reaction mixture was stirred at 90° C. for 2 hours under a nitrogen (N$_2$) atmosphere. When the Suzuki coupling reaction was complete as indicated by HPLC analysis, the reaction mixture was cooled to ambient temperature before ice water (25.0 Kg) and ethyl acetate (25.0 L) were charged. The resulting mixture was stirred at ambient temperature for 30 minutes and the insoluble material was removed by filtration. Two layers of the filtrate were separated, and the aqueous layer was extracted with ethyl acetate (12.0 L). The combined organic extracts was washed with brine (6.0 L) before being concentrated to dryness under the reduced pressure to afford the crude desired product, 8-chloro-3-vinyl-1,7-naphthyridine (1.5 Kg, 3.13 Kg theoretical, 48%; 93% pure by HPLC), which was used in the subsequent reaction without further purification. For VIII-6: $^1$H NMR (300 MHz, CDCl$_3$) Q 9.20 (s, 1H), 8.37 (d, 1H), 8.07 (d, 1H), 7.60 (d, 1H), 6.92 (dd, 1H), 6.12 (d, 1H), and 5.66 (d, 1H) ppm.

Step 5: N-(3-Bromo-2-methylphenyl)-3-vinyl-1,7-naphthyridin-8-amine (VIII-7a)

A solution of 8-chloro-3-vinyl-1,7-naphthyridine (VIII-6, 1.5 Kg, 7.87 mol) and 3-bromo-2-methylaniline (XIV-1a, 1.5 Kg, 7.87 mol, 1.0 equiv) in IPA (15.0 L) was added methanesulfonic acid (MeSO$_3$H, 756 g, 7.87 mol, 1.0 equiv) at ambient temperature. The resulting reaction mixture was warmed to 60° C. and agitated at 60° C. for 7 hours. When HPLC analysis showed the reaction was complete, the reaction mixture was cooled to ambient temperature before the pH was adjusted to 8-9 with a 20% aqueous sodium hydroxide (NaOH) solution. The neutralized reaction mixture was stirred at ambient temperature for 30 minutes and the solids were collected by filtration. The wet cake was then purified by reslurrying in a mixture of MTBE (9.0 L) and water (6.0 L) at ambient temperature for 2 hours. The solids were collected by filtration and dried under vacuum to afford the crude desired product, N-(3-bromo-2-methylphenyl)-3-vinyl-1,7-naphthyridin-8-amine (3.5 Kg, 5.3 Kg theoretical, 66%; 93% pure by HPLC), as a light yellow powder, which was used in the subsequent reaction without further purification. For VIII-7a: $^1$H NMR (300 MHz, DMSO-d$_6$) δ 9.33 (s, 1H), 9.09 (s, 1H), 8.31 (d, 1H), 8.16 (d, 1H), 7.99 (d, 1H), 7.39 (d, 1H), 7.18 (m, 2H), 7.13 (dd, 1H), 6.25 (d, 1H), 5.60 (d, 1H), and 2.51 (s, 3H) ppm.

Step 6: 8-((3-Bromo-2-methylphenyl)amino)-1,7-naphthyridine-3-carbaldehyde (VIII-8a)

A solution of N-(3-bromo-2-methylphenyl)-3-vinyl-1,7-naphthyridin-8-amine (VIII-7a, 1.0 Kg, 2.94 mol) and 2,6-dimethylpyridine (629 g, 5.88 mol, 2.0 equiv) in THE (20.0 L) and water (6.0 L) was charged OsO$_4$ (31 g, 0.04 equiv) at ambient temperature. The mixture was stirred at ambient temperature for 1 hour before NaIO$_4$ (1.3 Kg, 5.88 mol, 2.0 equiv) was added. The resulting reaction mixture was then warmed to 30-35° C. and stirred at 30-35° C. for 15 hours. When HPLC analysis showed the reaction was complete, water (14.0 L) was charged into the reaction mixture. The resulting mixture was stirred at ambient temperature for 1 hour before being concentrated under the reduced pressure at 40-45° C. The solids were collected by filtration and the wet cake was suspended in water (20.0 L). The suspension was heated to 50° C. and stirred at 50° C. for 1 hour. The solids were then collected by filtration and the wet cake was further purified by reslurrying in MTBE (6.2 L). The suspension was heated to 50° C. and stirred at 50° C. for 1 hour before being filtered. The collected solids were dried under vacuum to afford the desired product, 8-((3-bromo-2-methylphenyl)amino)-1,7-naphthyridine-3-carbaldehyde (VIII-8a, 715 g, 1007 g theoretical, 71%; 97% pure by HPLC), as a light yellow to brown powder. For VIII-8a: $^1$H NMR (300 MHz, DMSO-d$_6$) Q D 10.28 (s, 1H), 9.51 (s, 1H), 9.27 (s, 1H), 8.83 (s, 1H), 8.07 (d, 1H), 7.97 (d, 1H), 7.41 (d, 1H), 7.30 (d, 1H), 7.18 (d, 1H), and 2.36 (s, 3H) ppm; $^{13}$C NMR (75 MHz, DMSO-d$_6$) Q 192.7, 157.3, 148.2, 143.5, 140.8, 138.9, 135.2, 132.5, 131.4, 131.1, 128.5, 127.8, 126.8, 124.2, 111.8, and 18.6 ppm.

Step 7. (R)-1-((8-((3-Bromo-2-methylphenyl)amino)-1,7-naphthyridin-3-yl)methyl)pyrrolidin-3-ol (V-1a)

A mixture of 8-((3-bromo-2-methylphenyl)amino)-1,7-naphthyridine-3-carbaldehyde (VIII-8a, 500 g, 1.46 moles), (R)-pyrrolidin-3-ol hydrochloride (III-2, 298 g, 2.41 moles, 1.65 equiv) and triethylamine (TEA, 336 mL, 244 g, 2.41 moles, 1.65 equiv) in dichloromethane (DCM, 5.8 L) was stirred at room temperature for two hours. Sodium triacetoxyborohydride (NaB(OAc)$_3$H, STAB, 625 g, 2.94 moles, 2 equiv) was added portion-wise to the mixture at ambient temperature over 30 minutes. A water bath was used as the heat sink to maintain the temperature of the reaction between 25 and 30° C. The reaction mixture was stirred at 25-30° C. for one hour. When LCMS indicated the reductive amination reaction was complete, the reaction mixture was cooled to 0-5° C. before being quenched with a 10% aqueous sodium bicarbonate (NaHCO$_3$) solution (10.3 L) The quenched reaction mixture was then gradually warmed to room temperature and stirred at room temperature for overnight. The resulting solids were collected by filtration and the collected solids were washed sequentially with dichloromethane (DCM, 3 L), water (3 L) and heptanes (3 L). The wet cake was dried under vacuum at 40° C. to give the first crop of the crude desired product, (R)-1-((8-((3-bromo-2-methylphenyl)amino)-1,7-naphthyridin-3-yl) methyl)pyrrolidin-3-ol (V-1a, 418 g, 69.3%; 96% purity by HPLC). The filtrates were transferred into a separatory funnel, the organic layer was separated, and the aqueous layer was extracted with dichloromethane (DCM, 2 L). The combined organic phase was concentrated under the reduced pressure and the residue was added dichloromethane (DCM, 500 mL). The resulting slurry was agitated at ambient temperature for two hours. The resulting solids were filtered, washed with dichloromethane (DCM, 200 mL) and n-heptane (200 mL). The wet cake were dried under vacuum at 40° C. to afford the second crop of the crude desired product, (R)-1-((8-((3-bromo-2-methylphenyl)amino)-1,7-naphthyridin-3-yl)methyl)pyrrolidin-3-ol (V-1a, 112 g, 18.6%; 96% purity by HPLC). The combined isolated crude desired product, (R)-1-((8-((3-bromo-2-methylphenyl)amino)-1,7-naphthyridin-3-yl)methyl)pyrrolidin-3-ol (V-1a, 530 g, 603 g theoretical, 87.9%), was suspended in acetonitrile (5.3 L) and the suspension was warmed to 60° C. and stirred at 60° C. for two hours before being cooled to room temperature and stirred at ambient temperature for overnight. The solids were collected by filtration and the wet cake was washed sequentially with acetonitrile (2×1.8 L) and n-heptane (2×1.3 L) and dried under vacuum at 40° C. to afford the purified the desired product, (R)-1-((8-((3-bromo-2-methylphenyl)amino)-1,7-naphthyridin-3-yl)methyl)pyrrolidin-3-ol (V-1a, 523 g, 603 g theoretical, 86.7%; 97.7% purity by HPLC), as an off-white to tan powder. For V-1a: $^1$H NMR (300 MHz, DMSO-d$_6$) δ 9.35 (s, 1H), 8.85 (s, 1H), 8.15 (m, 2H), 7.98 (m, 1H), 7.37 (m, 1H), 7.15 (m, 2H), 4.72 (s, 1H), 4.22 (s, 1H), 3.80 (m, 2H), 2.75 (m, 1H), 2.65 (m, 1H), 2.45 (m, 1H), 2.38 (s, 3H), 2.35 (m, 1H), 2.00 (m, 1H), and 1.57 (m, 1H) ppm; C$_{20}$H$_{21}$BrN$_4$O (MW 412.09), LCMS (EI) m/z 413.1 and 415.1 (M$^+$+H).

Example 9. Synthesis of the Example 3 Starting Material III-6b

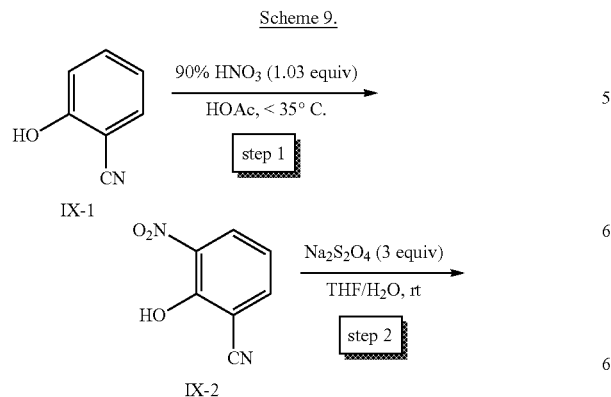

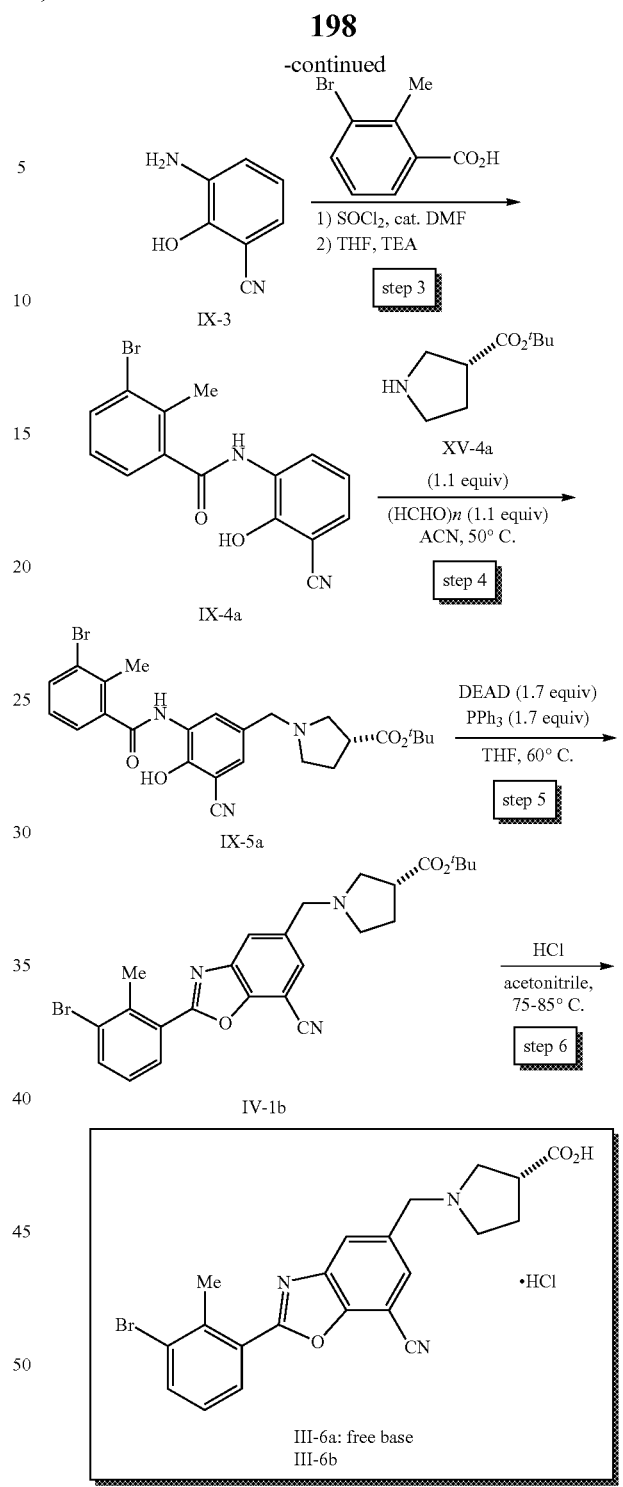

Step 1: 2-Hydroxy-3-nitrobenzonitrile (IX-2)

A mixture of acetic acid (HOAc, 2000 Kg) and salicylic nitrile (IX-1, 400 Kg) in a reactor was warmed to 30-35° C. The resulting mixture in the reactor was agitated at 30-35° C. until a solution was obtained. In an addition tank, a mixture of acetic acid (HOAc, 800 Kg) and fuming nitric acid (HNO$_3$, 250 Kg) was mixed well. The solution of nitric acid in acetic acid was then added from the addition tank to the reactor while maintaining the internal temperature at 35

45° C. After addition, the reaction mixture was kept at 35-45° C. for 30 minutes. When HPLC analysis indicated the reaction was complete, the reaction content was added slowly to water (4200 L). The resulting mixture was then heated to 70-75° C. until a clear solution was formed. The solution was then slowly cool to 25° C. at a rate of 10-12° C. per hour. the solids were then collected by centrifugation and the wet cake was washed with cold water (0° C., 140 Kg) and dried under vacuum at ≤75° C. for NLT 12 h (water content control by KF) to afford the crude desired product, 2-hydroxy-3-nitrobenzonitrile (IX-2, 100.3 Kg, 400 Kg theoretical, 25.08%; 99.4% pure by HPLC), as a yellow crystalline powder, which was used in the subsequent reaction without further purification.

Step 2: 3-Amino-2-hydroxybenzonitrile (IX-3)

To a reactor was charged 2-hydroxy-3-nitrobenzonitrile (IX-2, 139 Kg) and ethanol (EtOH, 1086.7 Kg). The agitation started and water (1390 Kg) was pumped into the reactor. The mixture was heated to 40° C. under nitrogen. The temperature was controlled at 40-60° C. when sodium hydrosulfite (sodium dithionite, $Na_2S_2O_4$, 516 Kg) was added in portions. After sodium hydrosulfite addition, the reaction mixture was checked by HPLC for completion. When HPLC analysis showed the reduction reaction was complete, the reaction mixture was cooled to 30° C. and the solvent was removed under the reduced pressure. Water (1390 Kg) was then introduced into the reactor, and the mixture was cooled slowly to 8° C. The solids were collected by centrifugation. The wet cake was washed with cold water (0-5° C., 459 Kg) and dried under vacuum of P≤−0.095 MPa at a jacket temperature of ≤75° C. for 24 hours to afford the desired product, 3-amino-2-hydroxybenzonitrile (IX-3, 91.16 Kg, 113.6 Kg theoretical, 80.24%; 94.7% pure by HPLC), as a dark brown powder, which was used in the subsequent reaction without further purification. For IX-3: $C_7H_6N_2O$ (MW 134.14), LCMS (EI) m/z 134.9 (M$^+$+H).

Step 3: 3-Bromo-N-(3-cyano-2-hydroxyphenyl)-2-methylbenzamide (IX-4a)

To a reactor flushed with nitrogen was charged thionylchloride ($SOCl_2$, 202.5 Kg, 2.5 equiv). 3-Bromo-2-methylbenzoic acid (146.1 Kg, 1.0 equiv) and a catalytical amount of DMF (633 g) were added. The mixture was heated to 70-75° C. with stirring and agitated at 70-75° C. under nitrogen for 2-6 hours. When HPLC analysis showed the acyl chloride formation reaction was complete, excess amount of thionylchloride ($SOCl_2$) was removed by distillation under the reduced pressure. The residue was co-evaporated with toluene (91.2 Kg) once to ensure complete removal of the residual thionylchloride ($SOCl_2$). To another reactor was added tetrahydrofuran (THF, 897.7 Kg), triethylamine (TEA, 137.5 Kg, 2.0 equiv), and 3-amino-2-hydroxybenzonitrile (IX-3, 91.16 Kg) and the resulting solution was cooled to 0-5° C. The acyl chloride prepared was added slowly to the solution of 3-amino-2-hydroxybenzonitrile (IX-3) while maintaining the internal temperature at 0-5° C. After addition, the reaction mixture was gradually heated to 25-30° C. and agitated at 25-30° C. for 4-12 hours. When HPLC analysis showed the amide formation reaction was complete, the reaction mixture was cooled to 0-5° C. before an aqueous sodium hydroxide solution (NaOH, 128 Kg) was added slowly to the cooled reaction mixture to adjust the pH to 10~11 at 0-5° C. The resulting mixture was further stirred at 0-5° C. for 60 minutes until HPLC analysis showed the completion of the hydrolysis reaction. To an addition tank were charged the concentrated hydrochloric acid (HCl, 146.1 Kg) and water (730.5 Kg) to obtain a solution. The aqueous hydrochloric acid solution from the addition tank was then slowly added into the reactor to adjust the pH of the reaction mixture to 5-6 at room temperature. The resulting mixture was further stirred at room temperature for no less than 2 hours. The solids were collected by centrifugation and washed with water (292.2 Kg) and petroleum ether (974.2 Kg). The wet cake was then dried under vacuum of P≤−0.09 MPa at a jacket temperature of 70-75° C. for 12 hours to afford the desired product, 3-bromo-N-(3-cyano-2-hydroxyphenyl)-2-methylbenzamide (IX-4a, 151.43 Kg, 225 Kg theoretical, 67.3%; 99.8% pure by HPLC), as an off-white powder. For IX-4a: $^1$H NMR (400 MHz, DMSO-d$_6$) δ 10.71 (s, 1H), 10.24 (s, 1H), 7.80 (dd, J=8.0, 1.4 Hz, 1H), 7.77 (dd, J=8.0, 1.4 Hz, 1H), 7.66-7.60 (m, 1H), 7.55 (dd, J=7.7, 1.6 Hz, 1H), 7.29 (t, J=7.8 Hz, 1H), 7.04 (t, J=7.9 Hz, 1H) and 2.45 (s, 3H) ppm; $^{13}$C NMR (101 MHz, DMSO-d$_6$) δ 168.66, 153.00, 138.80, 135.32, 134.30, 130.87, 130.54, 128.03, 127.54, 127.51, 125.93, 120.81, 117.17, 102.21 and 20.37 ppm; $C_{15}H_{11}BrN_2O_2$ (MW 331.17), LCMS (EI) m/z 332.1 (M$^+$+H).

Step 4: tert-Butyl (R)-1-(3-(3-bromo-2-methylbenzamido)-5-cyano-4-hydroxybenzyl)pyrrolidine-3-carboxylate (IX-5a)

To a reactor was charged acetonitrile (639 Kg), 3-bromo-N-(3-cyano-2-hydroxyphenyl)-2-methylbenzamide (IX-4a, 98 Kg) and paraformaldehyde ((HCHO)$_n$, 10.6 Kg, 1.2 equiv). The mixture was protected with nitrogen before a solution of tert-butyl pyrrolidin-3-carboxylate (XV-4a, 55.5 Kg, 1.1 equiv, 99.6% ee) in acetonitrile was added. The resulting reaction mixture was heated to 50-55° C. and maintained at this temperature for 2 hours. When the reaction completion was confirmed by HPLC analysis, the reaction mixture was cooled to 0-5° C. The precipitate was removed by filtration and the filter cake was rinsed with acetonitrile (49 Kg). The filtrate was concentrated under the reduced pressure and the solvent was swapped with MTBE (200 Kg). The residue was added MTBE (300 Kg) with agitation at 35° C. and petroleum ether (PE, 150 Kg) was then added. The agitation was continued for 30 minutes to give a fine slurry. The solids were collected by centrifugation. The filter cake was rinsed with a mixture of MTBE (50 Kg) and petroleum ether (50 Kg) before being dried under vacuum of P≤−0.095 MPa at ≤75° C. (jacket temperature) for 6 hours until water content by KF met the requirement. The crude desired product, tert-butyl (R)-1-(3-(3-bromo-2-methylbenzamido)-5-cyano-4-hydroxybenzyl)pyrrolidine-3-carboxylate (IX-5a, 135 Kg, 152.2 Kg, 88.7%; 93.3% pure by HPLC), was obtained as an off-white powder, which was used in the subsequent reaction without further purification. For IX-5a: $C_{25}H_{28}BrN_3O_4$ (MW 514.42), LCMS (EI) m/z 514.0 and 516.0 (M$^+$+H).

Step 5: tert-Butyl (R)-1-((2-(3-bromo-2-methylphenyl)-7-cyanobenzo[d]oxazol-5-yl)methyl)pyrrolidine-3-carboxylate (IV-1b)

Into a reactor was pumped tetrahydrofuran (THF, 810 L) and the reactor was purged with nitrogen. tert-Butyl (R)-1-(3-(3-bromo-2-methylbenzamido)-5-cyano-4-hydroxybenzyl)pyrrolidine-3-carboxylate (IX-5a, 135 Kg) and triphenylphosphine (PPh$_3$, 113.6 Kg, 1.7 equiv) were then charged into the reactor. The reaction mixture was cooled to 10° C. before diethyl azodicarboxylate (DEAD, 75.4 Kg, 1.7 equiv) from the addition tank was slowly added to reactor while maintaining the internal temperature at 10-20° C. After addition, the reaction mixture was heated to 50-55° C. and maintained at this temperature for 2 hours. When the completion of the cyclization reaction was confirmed by HPLC, the reaction mixture was cooled to about 20° C. The reaction mixture was then concentrated under vacuum of P≤−0.090 MPa at a jacket temperature of 40-50° C. until no flow of distillate. MTBE (63.45 Kg) was pumped into the reactor and the resulting mixture was heated to 50° C. to form a suspension. Petroleum ether (675 Kg) was added from the addition tank to the suspension in the reactor, and the resulting mixture was further stirred for 1 h at 50° C. The mixture was cooled with agitation to 10° C. at a rate of 20° C. per hour. The solids were collected by centrifugation, and the wet cake was rinsed twice with a one to one mixture (v/v) of MTBE and petroleum ether (100 Kg). The Filter cake was discarded, and the filtrate was diluted with MTBE (594 Kg) before being washed with water (2×148.5 Kg). The organic phase was separated and dried over anhydrous sodium sulfate (Na$_2$SO$_4$, 100 Kg). The solid mass was filtered off and the filter cake was washed with MTBE (20.25 Kg). The filtrate was then concentrated under the reduced pressure (P≤−0.090 MPa) at a jacket temperature of 35-50° C. to dryness to afford the crude desired product, tert-butyl (R)-1-((2-(3-bromo-2-methylphenyl)-7-cyanobenzo[d]oxazol-5-yl)methyl)pyrrolidine-3-carboxylate (IV-1b, 68.6% pure by HPLC), which contaminated with the byproducts from the Mitsunobu reaction and was used directly in the subsequent reaction without further purification. An analytically pure sample of IV-1b was obtained by the silica gel (SiO$_2$) column purification. For IV-1b: $^1$H NMR (400 MHz, DMSO-d$_6$) δ 8.20-8.07 (m, 2H), 7.99-7.86 (m, 2H), 7.42 (dd, J=7.9, 7.9 Hz, 1H), 3.82 (d, J=13.5 Hz, 1H), 3.71 (d, J=13.6 Hz, 1H), 3.01-2.87 (m, 1H), 2.82 (s, 3H), 2.74-2.62 (m, 2H), 2.61-2.53 (m, 2H), 2.08-1.88 (m, 2H), and 1.41 (s, 9H) ppm; C$_{25}$H$_{26}$BrN$_3$O$_3$(MW 496.41), LCMS (EI) m/z 496.0 and 498.0 (M$^+$+H).

Step 6: (R)-1-((7-Cyano-2-(2-methyl-3-(4,4,5,5-tetramethyl-1,3,2-dioxaborolan-2-yl)phenyl)benzo[d]oxazol-5-yl)methyl)pyrrolidine-3-carboxylic acid Hydrochloride (III-6a)

A solution of crude IV-1b (200 Kg) in acetonitrile (400 Kg) was charged into a reactor and the solution was then cooled to 10-15° C. A solution of HCl in 1,4-dioxane (4.8 M, 280 Kg, 5.0 equiv) was added slowly to the reactor while maintaining the internal temperature at 10-30° C. After addition, the reaction mixture was warmed to 36-39° C. and kept at this temperature for 12 hours. When the deprotection reaction was complete as indicated by HPLC analysis, the reaction mixture was cooled down to 5-10° C. at a rate of 10-15° C. per hour. The solids were collected by centrifugation and the wet cake was rinsed twice with acetonitrile (2×20 Kg). The wet cake was dried under vacuum of P≤−0.095 MPa and at a jacket temperature of 50-55° C. for 10 hours to afford the crude desired product, (R)-1-((7-cyano-2-(2-methyl-3-(4,4,5,5-tetramethyl-1,3,2-dioxaborolan-2-yl)phenyl)benzo[d]oxazol-5-yl)methyl)pyrrolidine-3-carboxylic acid Hydrochloride (III-6b, 114.09 Kg, 125.09 g theoretical, 91.2% for two steps; 98.7% pure by HPLC), as a white powder, which was further purified as described below.

To a reactor were charged acetonitrile (344.2 Kg) and water (36 Kg). Agitation was started and crude III-6b (114.09 Kg) was added. The resulting slurry was heated to 75-85° C. and agitated at 75-85° C. for 2 hours. The batch was cooled to 20-25° C. at a rate of 10-15° C. per hour. The solids were collected by filtration and the wet cake was rinsed twice with acetonitrile (2×20 Kg). The wet cake was dried under vacuum of P≤−0.095 MPa at a jacket temperature of 60-65° C. for 12 hours to afford the purified desired product, (R)-1-((7-cyano-2-(2-methyl-3-(4,4,5,5-tetramethyl-1,3,2-dioxaborolan-2-yl)phenyl)benzo[d]oxazol-5-yl) methyl)pyrrolidine-3-carboxylic acid hydrochloride (III-6b, 99.4 Kg, 87.2%; 99.4% pure by HPLC), as a white crystalline powder. For III-6b: $^1$H NMR (400 MHz, DMSO-d$_6$) δ 12.88 (s, 1H), 11.63 (broad, two peaks, 11.63 and 11.28, 1H), 8.53 (d, J=1.6 Hz, 1H), 8.25 (d, J=1.6 Hz, 1H), 8.14 (dd, J=7.9, 1.3 Hz, 1H), 7.96 (dd, J=8.0, 1.3 Hz, 1H), 7.44 (t, J=7.9 Hz, 1H), 4.58 (s, 2H), 3.61-3.24 (m, 5H), 2.83 (s, 3H), and 2.35-2.09 (m, 2H) ppm; $^{13}$C NMR (101 MHz, DMSO-d$_6$) δ 173.42, 163.71, 150.60, 142.63, 138.27, 136.60, 132.59, 130.35, 129.48, 128.58, 128.51, 127.21, 126.91, 114.45, 95.15, 55.88, 54.01, 52.49, 41.12, 26.99, and 21.38 ppm; C$_{21}$H$_{19}$BrClN$_3$O$_3$(MW 476.76; C$_{21}$H$_{18}$BrN$_3$O$_3$ for III-6a free base, MW 440.30), LCMS (EI) m/z 440.0 and 442.0 (M$^+$+H).

Example 10. An Alternate Synthesis of the Example 4 Starting Material IV-1

Scheme 10.

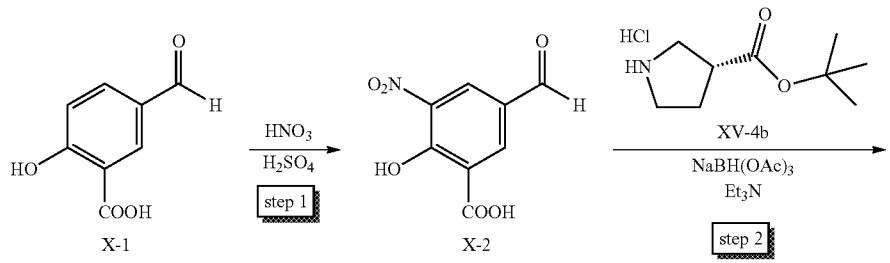

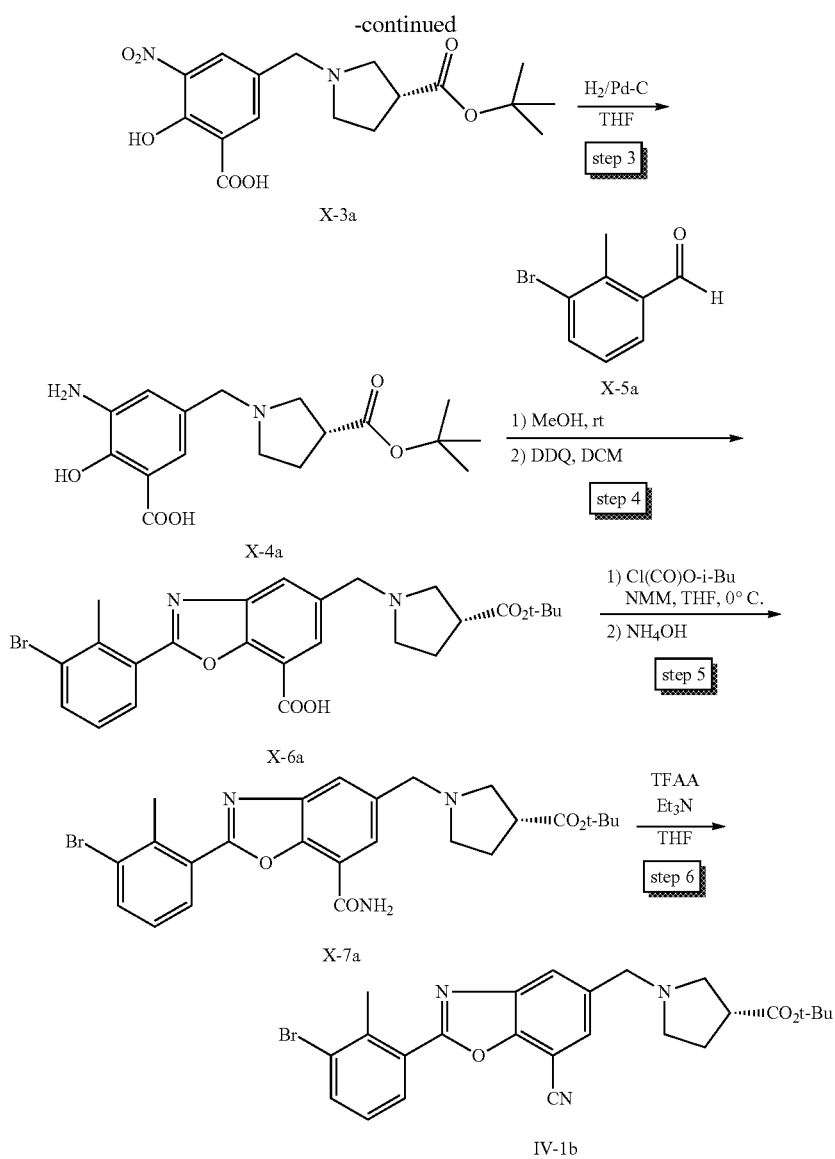

Step 1: 5-Formyl-2-hydroxy-3-nitrobenzoic acid (X-2)

5-Formyl-2-hydroxybenzoic acid (X-1, 50.00 g, 301 mmol) was added to concentrated sulfuric acid (H$_2$SO$_4$, 180.0 mL) portion wise at ambient temperature. During addition, the internal temperature was increased from 20.9° C. to 23.9° C. The suspension was then cooled to 0-5° C. in an ice bath before nitric acid (HNO$_3$, 14.94 ml, 301 mmol, 1.0 equiv) was added at below 10° C. The reaction mixture was agitated at 0-10° C. for an additional 1 hour before being poured into an ice water (750 g) with caution. The quenched reaction mixture was agitated for another 30 minutes before the solids were collected by filtration. The wet cake was washed with water (2×400 mL) and dried under vacuum to afford the crude desired product, 5-formyl-2-hydroxy-3-nitrobenzoic acid (X-2, 62.32 g, 63.5 g theoretical, 98%; 94.3% pure by HPLC), as a light yellow powder, which was used in the subsequent reaction without further purification.

Step 2: (R)-5-((3-(tert-Butoxycarbonyl)pyrrolidin-1-yl)methyl)-2-hydroxy-3-nitrobenzoic acid (X-3a)

To a stirred solution of 5-formyl-2-hydroxy-3-nitrobenzoic acid (X-2, 20.00 g, 89 mmol, 94.3% pure by HPLC) in DMF (200 mL) at ambient temperature was added tert-butyl (R)-pyrrolidine-3-carboxylate hydrochloride (XV-4b, 20.27 g, 94 mmol, 1.05 equiv) and trimethylamine (TEA, 13.12 ml, 94 mmol, 1.05 equiv). The orange mixture was stirred at ambient temperature for 30 minutes before sodium triacetoxyborohydride (NaB(OAc)$_3$H, STAB, 39.0 g, 178 mmol, 2.0 equiv) was added portion wise. The resulting reaction mixture was stirred at ambient temperature for 90 minutes. When HPLC analysis showed the reaction was complete, the reaction mixture was quenched with water (500 mL). The resulting slurry was stirred at ambient temperature for 1 hour. The solids were collected by filtration, washed with water, and dried at 50° C. under vacuum for overnight to give the crude desired product, (R)-5-((3-(tert-butoxycarbonyl)pyrrolidin-1-yl)methyl)-2-hydroxy-3-nitrobenzoic acid (29.9 g, 34 g theoretical, 88%; 96.43% pure by HPLC), as a yellow powder, which was used in the subsequent reaction without further purification. For X-3a: $C_{17}H_{22}N_2O_7$ (MW 366.37), LCMS (EI) m/z 367.1 (M$^+$+H).

Step 3: (R)-3-Amino-5-((3-(tert-butoxycarbonyl)pyrrolidin-1-yl)methyl)-2-hydroxybenzoic acid (X-4a)

To a stirred suspension of (R)-5-((3-(tert-butoxycarbonyl)pyrrolidin-1-yl)methyl)-2-hydroxy-3-nitrobenzoicacid (X-3a, 1.000 g, 2.63 mmol, 96.43% pure by HPLC) in THF (10 mL) and MeOH (10 mL) at ambient temperature was added palladium (Pd) on carbon (Pd/C, 108 mg) and palladium acetate (Pd(OAc)$_2$, 0.012 g, 0.053 mmol, 0.02 equiv). The mixture was degassed three times and refilled with hydrogen gas each time. The reaction mixture was then stirred at ambient temperature under hydrogen pressure (1 atm) for 6 hours. When HPLC analysis showed the reaction was complete, the reaction mixture was diluted with MeOH (10 mL), filtered through a pad of Celite and the Celite pad was washed with MeOH. The filtrate was then concentrated under the reduced pressure to afford the crude desired product, (R)-3-amino-5-((3-(tert-butoxycarbonyl)pyrrolidin-1-yl)methyl)-2-hydroxybenzoic acid (943 mg, 943 mg theoretical, 100%; 93.86% pure by HPLC), as a brown foamy solid. For X-4a: $C_{17}H_{24}N_2O_5$ (MW 336.39), LCMS (EI) m/z 337.0 (M$^+$+H).

Step 4: (R)-2-(3-bromo-2-methylphenyl)-5-((3-(tert-butoxycarbonyl)pyrrolidin-1-yl)methyl)benzo[d]oxazole-7-carboxylic acid (X-6a)

A stirred solution of (R)-3-amino-5-((3-(tert-butoxycarbonyl)pyrrolidin-1-yl)methyl)-2-hydroxybenzoic acid (X-4a, 0.943 g, 2.63 mmol, 93.86% pure by HPLC) and 3-bromo-2-methylbenzaldehyde (X-5a, 0.606 g, 2.89 mmol, 1.1 equiv) in anhydrous methanol (MeOH, 10 mL) was stirred at ambient temperature for overnight. The mixture slowly became a suspension. When HPLC analysis showed the imine formation reaction was complete, the reaction mixture was concentrated under the reduced pressure to remove MeOH. The residue (yellow solid) was dissolved in anhydrous dichloromethane (DCM, 15 mL). 2,3-Dichloro-5,6-dicyano-p-benzoquinone (DDQ, 0.792 g, 3.42 mmol, 1.3 equiv) was then added. The resulting reaction mixture was stirred at ambient temperature for 3 hours. When HPLC analysis showed the cyclization reaction was complete, the reaction mixture was diluted with THF (20 mL) before being treated with a saturated aqueous NaHCO$_3$ solution (20 mL) and water (20 mL). Two phases were separated and the aqueous layer was extracted with DCM twice (60 mL and 40 mL). The combined organic layers was washed with brine (30 mL) and water (10 mL), dried over Na$_2$SO$_4$, filtered, and concentrated under the reduced pressure. The residue was purified by the silica gel (SiO$_2$) column chromatography eluting with 0-25% of MeOH in DCM to give the desired product, (R)-2-(3-bromo-2-methylphenyl)-5-((3-(tert-butoxycarbonyl)pyrrolidin-1-yl)methyl)benzo[d]oxazole-7-carboxylic acid (896 mg, 1.391 g theoretical, 64.4% for two steps; 97.4% pure by HPLC), as a brown foamy solid. For X-6a: $C_{25}H_{27}BrN_2O_5$ (MW 515.40), LCMS (EI) m/z 514.8 and 516.7 (M$^+$+H).

Step 5: tert-Butyl (R)-1-((2-(3-bromo-2-methylphenyl)-7-carbamoylbenzo[d]oxazol-5-yl)methyl)pyrrolidine-3-carboxylate (X-7a)

To a stirred solution of (R)-2-(3-bromo-2-methylphenyl)-5-((3-(tert-butoxycarbonyl)pyrrolidin-1-yl)methyl)benzo[d]oxazole-7-carboxylic acid (X-6a, 0.840 g, 1.599 mmol, 98.10% pure by HPLC) in anhydrous THF (17 mL) at 0° C. was added 4-methylmorpholine (NMM, 0.972 ml, 8.79 mmol, 5.5 equiv) and isobutyl chloroformate (0.635 ml, 4.80 mmol, 3 equiv). The mixture was stirred at 0° C. for 30 minutes. An ammonium hydroxide aqueous solution (NH$_4$OH, 14.8 M, 0.864 mL, 12.79 mmol, 8.0 equiv) was then added dropwise to the mixture via a syringe. The resulting reaction mixture was stirred at 0° C. for 1 hour and it became a suspension. When HPLC analysis showed the amide formation reaction was complete, the reaction mixture was diluted with water (34 mL). The resulting slurry was stirred at ambient temperature for 30 minutes. The solids were collected by filtration, washed with water, and dried at 50° C. in a vacuum oven for overnight to afford the crude desired product, tert-butyl (R)-1-((2-(3-bromo-2-methylphenyl)-7-carbamoylbenzo[d]oxazol-5-yl)methyl)pyrrolidine-3-carboxylate (718 mg, 835 mg theoretical, 86%; 98.23% pure by HPLC), as a light yellow powder, which was used in the subsequent reaction without further purification. For X-7a: $C_{25}H_{28}BrN_3O_4$ (MW 514.42), LCMS (EI) m/z 513.8 and 515.8 (M$^+$+H).

Step 6: tert-Butyl (R)-1-((2-(3-bromo-2-methylphenyl)-7-cyanobenzo[d]oxazol-5-yl)methyl)pyrrolidine-3-carboxylate (IV-1b)

To a stirred suspension of tert-butyl (R)-1-((2-(3-bromo-2-methylphenyl)-7-carbamoylbenzo[d]oxazol-5-yl)methyl)pyrrolidine-3-carboxylate (X-7a, 0.630 g, 1.154 mmol, 94.21% pure by HPLC) in anhydrous THF (20 mL) at 0° C. was added triethylamine (TEA, 0.808 ml, 5.77 mmol, 5.0 equiv) followed by dropwise addition of trifluoroacetic anhydride (TFAA, 0.329 mL, 2.308 mmol, 2.0 equiv). The resulting clear solution was stirred at 0° C. for 1 hour. When HPLC analysis showed the reaction was complete, the reaction mixture was quenched with the saturated aqueous NaHCO$_3$ solution (15 mL) and water (5 mL). The mixture was then extracted with DCM (50 mL). The organic layer was dried over Na$_2$SO$_4$, filtered and concentrated under the reduced pressure. The residue was purified by the silica gel (SiO$_2$) column chromatography eluting with 0-60% of EtOAc in n-hexane to afford the desired product, tert-butyl (R)-1-((2-(3-bromo-2-methylphenyl)-7-cyanobenzo[d]oxazol-5-yl)methyl)pyrrolidine-3-carboxylate (IV-1b, 530 mg, 576 mg theoretical, 92%; 99.71% pure by HPLC), as a light yellow viscous oil, which was solidified under vacuum at ambient temperature and is identical in every comparable aspect to the compound prepared by Example 9, Step 5 described previously.

Example 11. Synthesis of the Example 3 Starting Material III-1a

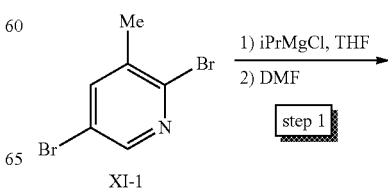

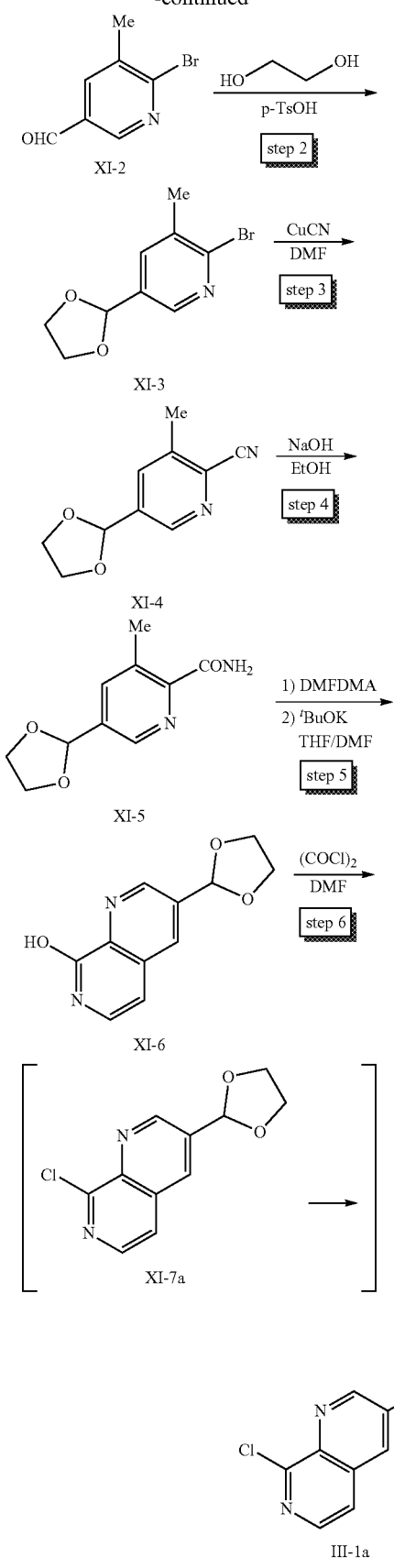

Step 1: 6-Bromo-5-methylnicotinaldehyde (XI-2)

To a reactor was charged THF (1200 L) and 2,5-dibromo-3-methylpyridine (XI-1, 400 Kg, 1.0 equiv). The resulting solution was cooled to 0° C. before a 2 M solution of i-PrMgCl (1200 L, 1.5 equiv) in THF was introduced at 0-10° C. The mixture was agitated at 0-10° C. for 30 minutes and then at 25-35° C. for 2 hours. After HPLC analysis confirmed the starting material was consumed, the reaction mixture was cooled to 0-10° C. before DMF (348.3 Kg, 3.0 equiv) was added dropwise at 0-10° C. After the mixture was kept at 0-10° C. for 30 minutes and then at 20-25° C. for 2 hours, the reaction mixture was discharged to a mixed solution of citric acid monohydrate (400 Kg, 1.2 equiv) in water (1200 L) and MTBE (1200 L), making sure that the temperature during the addition did not exceed 15° C. After addition, the batch was stirred at ambient temperature for 15 minutes and then allowed to stand at ambient temperature for 15 minutes for phase separation. Two phases were separated and the aqueous phase was extracted once with MTBE (1200 L). The combined organic phases was washed with water (2×800 L) and brine (2×800 L), dried over anhydrous sodium sulfate ($Na_2SO_4$), and concentrated under the reduced pressure to dryness. The crude desired product, 6-bromo-5-methylnicotinaldehyde (crude XI-2, 323.1 Kg, 103%; 88.7% pure by HPLC), was dissolved in toluene, assayed for its weight amount, and used directly for the next step without further purification.

Step 2: 2-Bromo-5-(1,3-dioxolan-2-yl)-3-methylpyridine (XI-3)

To a reactor containing a solution of 6-bromo-5-methylnicotinaldehyde (XI-2, 319 Kg) in toluene (1105 Kg, 1276 L) was introduced ethylene glycol (296.3 Kg, 3.0 equiv) and p-toluenesulfonic acid (13.7 Kg, 0.05 equiv). The reaction mixture was heated to reflux and agitated at reflux for twelve hours while water was being continuously removed. After HPLC analysis confirmed the acetal formation reaction was complete, the batch was cooled to 30° C. and discharged into a saturated aqueous solution of sodium hydrogen carbonate ($NaHCO_3$, 26.8 Kg, 0.1 equiv). Two phases were separated and the aqueous phase was extracted with toluene (552.5 Kg, 638 L). The combined organic phases was washed with half-saturated brine, dried over anhydrous $Na_2SO_4$ and concentrated under the reduced pressure to dryness. The crude desired product, 2-bromo-5-(1,3-dioxolan-2-yl)-3-methylpyridine (crude XI-3, 351.0 Kg, 90.2%; 82.3% pure by HPLC), was used directly for next step without further purification. For XI-3: $^1$H NMR (600 MHz, DMSO-$d_6$) δ 8.35 (s, 1H), 7.76 (s, 1H), 5.78 (s, 1H), 4.04 (m, 4H), and 2.52 (s, 3H) ppm; $C_9H_{10}BrNO_2$ (MW 244.09), LCMS (EI) m/z 244.0 and 246.0 (M$^+$+H).

Step 3: 5-(1,3-Dioxolan-2-yl)-3-methylpicolinonitrile (XI-4)

To a reactor containing crude 2-bromo-5-(1,3-dioxolan-2-yl)-3-methylpyridine (XI-3, 330 Kg) was charged DMF (990 L). Agitation was started and cuprous cyanide (CuCN, 145.2 Kg, 1.2 equiv) was added. The resulting reaction mixture was heated to 110-120° C. and stirred at 110-120° C. for 2 hours. After HPLC analysis confirmed the cyanation reaction was complete, the batch was cooled to room temperature and discharged into a mixed solution of aqueous ammonia ($NH_4OH$, 25%, 1650 L) and ethyl acetate (EtOAc, 2640 L). The mixture was stirred at ambient temperature for

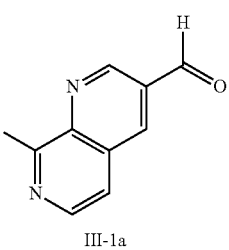

30 minutes before being filtered. Two phases of the filtrates were separated and the aqueous phase was extracted once with ethyl acetate (EtOAc, 1320 L). The combined organic phases was washed sequentially with aqueous ammonia (NH$_4$OH, 990 L) half-saturated brine (660 L) and brine (660 L), dried over anhydrous sodium sulfate (Na$_2$SO$_4$, 100 Kg), and concentrated under the reduced pressure to dryness. The crude desired product, 5-(1,3-dioxolan-2-yl)-3-methylpicolinonitrile (crude XI-4, 237.1 Kg, 92.3%; 83.2% pure by HPLC), was used directly for the next step without further purification. For XI-4: $^1$H NMR (400 MHz, DMSO-d$_6$) δ 8.61 (d, 1H), 7.98 (m, 1H), 5.91 (s, 1H), 4.03 (m, 4H), and 2.52 (s, 3H) ppm; C$_{10}$H$_{10}$N$_2$O$_2$(MW 190.20), LCMS (EI) m/z 191.2 (M$^+$+H).

Step 4: 5-(1,3-Dioxolan-2-yl)-3-methylpicolinamide (XI-5)

A solution of crude 5-(1,3-dioxolan-2-yl)-3-methylpicolinonitrile (XI-4, 468.2 Kg) in ethanol (EtOH, 1872 L) was treated with sodium hydroxide (NaOH, 118 Kg, 1.2 equiv) at ambient temperature. The reaction mixture was heated to 50° C. and agitated at this temperature for 8 hours. After HPLC analysis confirmed that the hydrolysis reaction was complete, the batch was cooled to room temperature and glacial acetic acid (HOAc, 162.5 Kg, 1.1 equiv) was added while the internal temperature was controlled at below 35° C. during the addition of glacial acetic acid. After the pH of the reaction mixture was confirmed to be neutral or weakly acidic, the batch was concentrated under the reduced pressure and the residue was dissolved in dichloromethane (DCM, 2341 L). The DCM solution was washed with a saturated aqueous solution of sodium hydrogen carbonate (NaHCO$_3$, 1872 L) and the aqueous phase was extracted with DCM (936 L). The combined organic phase was washed with saturated brine (1404 L), dried over anhydrous sodium sulfate (Na$_2$SO$_4$, 93.5 Kg), and concentrated under the reduced pressure. After solvent swap with MTBE, fresh MTBE (702.3 L) was added. The resulting slurry was agitated at ambient temperature for 1 hour and the solids were collected by centrifugation. The filter cake was washed with MTBE and dried under vacuum to afford the crude desired product, 5-(1,3-dioxolan-2-yl)-3-methylpicolinamide (XI-5, 297.4 Kg, 58.0%; 99.3% pure by HPLC), as a yellow to brown powder, which was used in the subsequent reaction without further purification. For XI-5: $^1$H NMR (400 MHz, DMSO-d$_6$) δ 8.46 (d, 1H), 7.96 (s, 1H), 7.75 (m, 1H), 7.49 (s, 1H), 5.85 (s, 1H), 4.03 (m, 4H), and 2.53 (s, 3H) ppm; C$_{10}$H$_{12}$N$_2$O$_3$ (MW 208.22), LCMS (EI) m/z 209.1 (M$^+$+H).

Step 5: 3-(1,3-Dioxolan-2-yl)-1,7-naphthyridin-8-ol (XI-6)

A solution of 5-(1,3-dioxolan-2-yl)-3-methylpicolinamide (XI-5, 150 Kg) in tetrahydrofuran (THF, 600 L) was treated with DMF-DMA (128.7 Kg, 1.5 equiv) at ambient temperature. The resulting reaction mixture was heated to 60-65° C. and stirred at 60-65° C. for 2 hours. After HPLC analysis confirmed the complete consumption of the starting material, the reaction mixture was concentrated under the reduced pressure and co-evaporated with toluene (2×150 Kg). The residue was dissolved in DMF (900 L) and the solution was added to another reactor containing an agitated solution of potassium tert-butoxide (KO$^t$Bu, 121.1 Kg, 1.5 equiv) in THF (450 L) while the internal temperature was maintained at 60-68° C. After addition, the mixture was kept under reflux (60 to 65° C.) for two hours. When HPLC analysis confirmed the cyclization reaction was complete, the batch was cooled to room temperature and diluted with MTBE (2700 L). To the resulting slurry was added a solution of 30% hydrochloric acid (HCl) in EtOH (197.4 Kg, 2.25 equiv) to adjust the pH of the batch to neutral. The mixture was then agitated at ambient temperature for 2 hours before the solids were collected by centrifugation. The wet cake was slurry-washed with MTBE (900 L) and dried under vacuum to afford the crude desired product, 3-(1,3-dioxolan-2-yl)-1,7-naphthyridin-8-ol (XI-6, 246.7 Kg, 157.1%; 89.6% pure by HPLC), which contained inorganic salts and was used in the subsequent reaction without further purification. For XI-6: $^1$H NMR (400 MHz, DMSO-d$_6$) δ 8.83 (s, 1H), 8.47 (d, 1H), 8.12 (s, 1H), 7.41 (d, 1H), 6.77 (d, 1H), 6.02 (s, 1H), and 4.04 (m, 4H) ppm; C$_{11}$H$_{10}$N$_2$O$_3$(MW 218.21), LCMS (EI) m/z 219.1 (M$^+$+H).

Step 6: 8-Chloro-1,7-naphthyridine-3-carbaldehyde (III-1a)

A solution of DMF (246.7 L) in 1,2-dichloroethane (1480 L) was cooled to 0° C. before oxalyl chloride ((COCl)$_2$, 358.1 Kg, 2.5 equiv) was introduced at 0° C. The mixture was agitated at 0-10° C. for 15 minutes and then at 25° C. for 15 minutes to generate the corresponding Vilsmeier reagent. 3-(1,3-Dioxolan-2-yl)-1,7-naphthyridin-8-ol (XI-6, 246.7 Kg) was then charged into the in-situ generated Vilsmeier reagent at room temperature with stirring. The resulting reaction mixture was agitated at ambient temperature for 15 minutes and then at 58-62° C. for 2 hours. After HPLC analysis confirmed the both chlorination and deacetalization reactions were complete, the batch was cooled to room temperature before being discharged into a mixture of sodium carbonate (Na$_2$CO$_3$, 322.9 Kg, 2.7 equiv), water (1233 L) and dichloromethane (DCM 1233 L). During addition, the internal temperature was controlled at 10-25° C. The mixture was agitated at 10-25° C. for 30 minutes and the batch was filtered with the aid of a diatomaceous earth bed. Two phases of the filtrate were separated and the aqueous phase was extracted with DCM (494 L). The combined organic phase was washed with water (2×987 L and 494 L), dried over anhydrous sodium sulfate (Na$_2$SO$_4$, 100 Kg), and concentrated under the reduced pressure to dryness. The residue was charged MTBE (246.7 L) and petroleum ether (PE, 246.7 L) and the resulting mixture was agitated at ambient temperature for 1 hour. The solids were collected by filtration to afford batch A of the crude desired product (III-1a) as a wet cake. In the next, batch B of the crude desired product (III-1a) was similarly produced from 276.7 Kg of 3-(1,3-dioxolan-2-yl)-1,7-naphthyridin-8-ol (XI-6a). The combined wet cake from batch A and batch B was dissolved in dichloromethane (DCM, 5234 L) at 35° C. Silica gel (SiO$_2$, 209.4 Kg) was added and the mixture was agitated at 35° C. for 2 hours before being cooled to room temperature and filtrated through a pad of silica gel (SiO$_2$, 104.7 Kg). The filter cake was washed with DCM and discarded. The filtrate was concentrated under the reduced pressure and the residue was slurried with MTBE (1047 L) and PE (1047 L). The solids were collected by filtration. The wet cake was washed with PE and MTBE and dried under vacuum to afford the desired product, 8-chloro-1,7-naphthyridine-3-carbaldehyde (III-1a, 117.07 Kg, 288.3 Kg theoretical, 40.6%; 99.2% pure by HPLC), as a light yellow to tan crystalline powder. For III-1a: $^1$H NMR (600 MHz, DMSO-d$_6$) δ 10.32 (s, 1H), 9.48 (d, J=2.0 Hz, 1H), 9.10 (d, J=2.0 Hz, 1H), 8.54 (d, J=5.5 Hz, 1H), and 8.18 (d, J=5.5 Hz, 1H) ppm. $^{13}$C NMR (150 MHz, DMSO-d$_6$) δ 192.36, 152.57, 151.82, 143.76, 141.27, 139.95, 132.95, 132.46, and 122.79 ppm; C$_9$H$_5$ClN$_2$O (MW 192.60), LCMS (EI) m/z 192.9 and 194.9 (M$^+$+H).

Example 12. An Alternate Synthesis of the Example 3 Starting Material III-1a

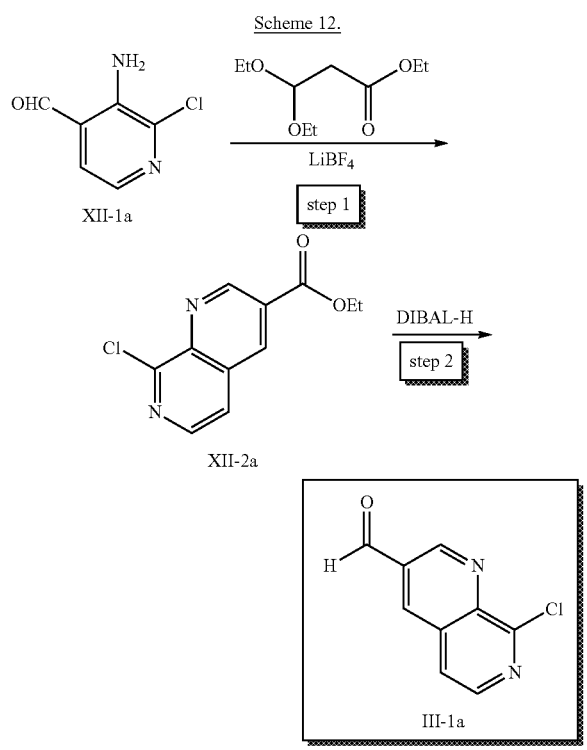

Step 1: Ethyl 8-chloro-1,7-naphthyridine-3-carboxylate (XII-2a)

Lithium tetrafluoroborate (LiBF$_4$, 7.55 g, 79 mmol, 1.30 equiv) was added to the solution of 3-amino-2-chloroisonicotinaldehyde (XII-1a, 10.00 g, 60.7 mmol) and ethyl 3,3-diethoxypropanoate (15.66 mL, 79 mmol, 1.30 equiv) in acetonitrile (80 mL) at ambient temperature. The resulting reaction mixture was then warmed to 60° C. and stirred at 60° C. for 3 hours. When HPLC analysis showed the reaction was complete, the reaction mixture was cooled to ambient temperature before a saturated aqueous NaHCO$_3$ solution (80 mL) was added. The quenched reaction mixture was extracted with DCM (3×80 mL) and the combined organic extracts was dried over MgSO$_4$, filtered, and concentrated under the reduced pressure. A mixture of MTBE and pentane (3:1 in volume, 70 mL) was then added to the residue to form a slurry. The slurry was stirred at room temperature for overnight. The solids were collected by filtration and dried under vacuum to afford the desired product, ethyl 8-chloro-1,7-naphthyridine-3-carboxylate (11.81 g, 14.37 g theoretical, 82.1%; 99.2% pure by HPLC) as a white powder, which was used in the subsequent reaction without further purification. For XII-2a: $^1$H NMR (400 MHz, CDCl$_3$) δ 9.66 (d, J=2.0 Hz, 1H), 8.88 (d, J=2.0 Hz, 1H), 8.50 (d, J=5.5 Hz, 1H), 7.76 (d, J=5.5 Hz, 1H), 4.55 (q, J=7.2 Hz, 2H), and 1.51 (t, J=7.1 Hz, 3H) ppm; $^{13}$C NMR (100 MHz, CDCl$_3$) δ 164.01, 153.68, 152.08, 143.26, 141.57, 137.71, 131.98, 127.81, 120.84, 62.30, and 14.27 ppm.

Step 2: 8-Chloro-1,7-naphthyridine-3-carbaldehyde (III-1a)

A 1.0 M solution of DIBAL-H in DCM (38.2 mL, 38.2 mmol, 1.20 equiv) was added dropwise over 30 minutes to the solution of ethyl 8-chloro-1,7-naphthyridine-3-carboxylate (XII-2a, 7.53 g, 31.8 mmol) in DCM (80 mL) at −78° C. During addition, the internal temperature was maintained between −78° C. and −72° C. The reaction mixture was stirred at −78° C. for 2 hours. When HPLC analysis showed the reduction reaction was not complete, an additional amount of DIBAL-H (9.55 mL, 9.55 mmol, 0.3 equiv) was added dropwise to the reaction mixture at −78° C. to −72° C. The resulting reaction mixture was continued to stir at −78° C. to −72° C. for another one hour. The cooling bath was removed and a 1 M aqueous hydrochloric acid solution (HCl, 12.73 mL, 12.73 mmol) was slowly added to the reaction mixture. The quenched reaction mixture was then slowly warmed to room temperature and the pH of the aqueous solution was measured to be approximately 8. The mixture was then filtered to remove the solids and the filtrate was diluted with DCM (40 mL). Two layers of the filtrate were separated and the organic layer was washed with water (2×25 mL) and dried over MgSO$_4$. The drying reagent was removed by the filtration and the filtrate was concentrated under the reduced pressure to afford the crude desired product (III-1a, 6.00 g). The crude product was then purified by slurrying in IPA (48 mL) at ambient temperature for overnight. The solids were collected by filtration, washed with IPA (10 mL), and dried under vacuum to afford the desired product, 8-chloro-1,7-naphthyridine-3-carbaldehyde (III-1a, 4.61 g, 6.12 g theoretical, 75.3%; 99.1% pure by HPLC) as a light yellow crystalline powder, which is identical in every comparable aspect to the compound manufactured by Example 11, Step 6.

Example 13. An Alternate Synthesis of the Example 3 Starting Material III-1a

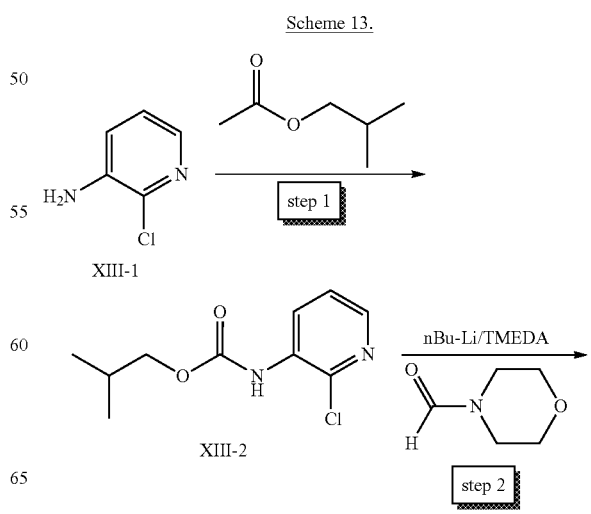

213

-continued

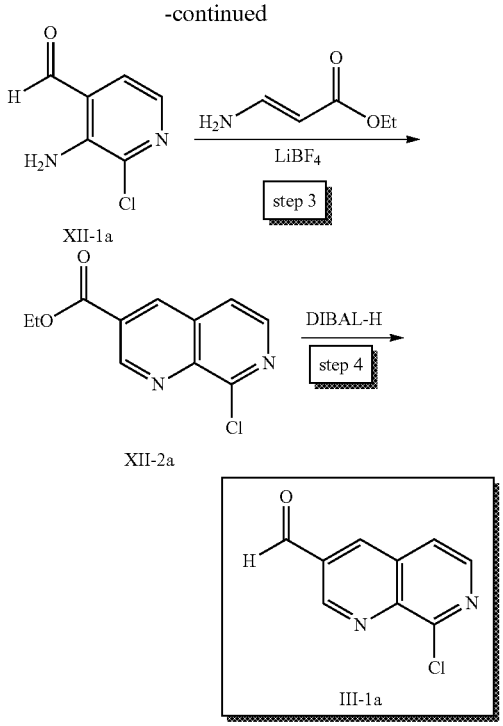

Step 1: Isobutyl (2-chloropyridin-3-yl)carbamate (XIII-2)

Under the protection of nitrogen ($N_2$), 2-chloro-3-aminopyridine (XIII-1, 208 Kg, 1618 moles), sodium carbonate ($Na_2CO_3$, 343.0 kg of, 3236 moles, 2.0 equiv) and water (2080 Kg) were charged into a reactor at ambient temperature. While the mixture in the reactor was agitated at ambient temperature, isobutyl chloroformate (441.9 Kg, 3804 moles, 2.35 equiv) was introduced. During addition of isobutyl chloroformate, the internal temperature was controlled at 25-35° C. The resulting reaction mixture was then agitated at 25-35° C. for 3-4 hours. When HPLC analysis showed the carbamate protection reaction was complete, n-heptane (2000 L) was charged into the reactor at ambient temperature. The resulting mixture was agitated at ambient temperature for an additional 1 hour before being filtered. The filter cake was washed with n-heptane (2×200 L) before being discarded. Two layers of the filtrate were separated and the aqueous layer was discarded. The organic phase was gradually cooled to 0-5° C. to induce crystallization of the desired product and the resulting suspension was agitated at 0-5° C. for 2-4 hours. The solids were collected by filtration, and the wet cake was washed with n-heptane (200 L) to afford the first crop of the desired product (wet cake 1). The filtrate was then concentrated under the reduced pressure to remove some of n-heptane, the concentrated solution was then cooled to 0-5° C., and the resulting suspension was agitated at 0-5° C. for 2-4 hours.

The solids were collected by filtration, and the wet cake was washed with n-heptane (150 L) to afford the second crop of the desired product (wet cake 2). The combined wet cake was dried under vacuum to afford the desired product, isobutyl (2-chloropyridin-3-yl)carbamate (XIII-2, 305.6 Kg, 370 Kg theoretical, 82.6%), as a pale-yellow powder, which was used in the subsequent reaction without further purification.

214

Step 2: 3-Amino-2-chloroisonicotinaldehyde (XII-1a)

Under the protection of nitrogen ($N_2$), tetrahydrofuran (THF, 267.0 Kg), isobutyl (2-chloropyridin-3-yl)carbamate (XIII-2, 60.0 Kg, 262.3 moles), and tetramethylethylenediamine (TMEDA, 42.7 Kg, 367.4 moles, 1.4 equiv) were sequentially charged into a reactor at ambient temperature. The mixture in the reactor was then cooled to −55 to −45° C. before a solution of n-butyl lithium in n-hexane (168.7 Kg) was slowly charged at −55 to −45° C. After addition of the solution of n-butyl lithium in n-hexane, the mixture in the reactor was agitated at −55 to −45° C. for 30 minutes before a solution of N-formylmorpholine (45.3 Kg, 393.4 moles, 1.5 equiv) in THF (45 Kg) was added at −55 to −45° C. The resulting reaction mixture was agitated at −55 to −45° C. for an additional 30 minutes before being gradually warmed to 0-5° C. The reaction mixture was agitated at 0-5° C. until the completion of the formylation reaction was indicated by HPLC analysis. A diluted aqueous hydrochloric acid solution (HCl, 357 Kg prepared from 27 Kg of the concentrated hydrochloric acid and 330 Kg of water) was then charged into the reactor at 0-5° C. to quench the reaction. After quenching, the mixture in the reactor was agitated at 0-5° C. for 30 minutes. Two layers were separated and the aqueous layer was extracted with MTBE (400 Kg). The combined organic phases was then washed with brine (20%, 200 Kg) and concentrated under the reduced pressure. The concentrated solution was then added n-heptane (100 Kg) and the resulting solution was filtered through a silica gel ($SiO_2$) pad. The silica gel ($SiO_2$) pad was eluted with a mixture of MTBE and n-heptane. The combined filtrate was concentrated to a certain volume under the reduced pressure and the concentrated solution was then cooled to 0-5° C. to induce the crystallization of the desired product. The resulting suspension was agitated at 0-5° C. for 2-4 hours before the solids were collected by filtration. The wet cake was washed with a mixture of MTBE and n-heptane and dried under vacuum to afford the desired product, 3-amino-2-chloroisonicotinaldehyde (XII-1a, 26.7 Kg, 41.06 Kg theoretical, 65%), as a light-yellow powder, which was directly used in the subsequent reaction without further purification.

Step 3: Ethyl 8-chloro-1,7-naphthyridine-3-carboxylate (XII-2a)

Under the protection of nitrogen ($N_2$), acetonitrile (450 Kg), lithium tetrafluoroborate ($LiBF_4$, 78 Kg, 832 moles, 1.3 equiv), and 3-amino-2-chloroisonicotinaldehyde (XII-1a, 100 Kg, 638.7 moles) were charged into a reactor at ambient temperature. The resulting solution was then warmed to 50-70° C. before a solution of N,N-dimethylaminoacrylate (128 Kg, 1112 moles, 1.74 equiv) in acetonitrile (50 Kg) was added at 50-70° C. The resulting reaction mixture was agitated at 50-70° C. for 4-6 hours. When HPLC analysis showed the cyclization reaction was complete, the reaction mixture was gradually cooled to ambient temperature before an aqueous solution of the diluted hydrochloric acid (HCl, prepared from 62.8 Kg of the concentrated hydrochloric acid and 1000 Kg of water) was charged. The quenched reaction mixture was subsequently cooled to 0-5° C. to induce the crystallization of the desired product. The resulting suspension was agitated at 0-5° C. for 2-4 hours. The solids were collected by filtration and the wet cake was washed with MTBE (2×100 Kg) and dried under vacuum to afford the desired product, ethyl 8-chloro-1,7-naphthyridine-3-carboxylate (XII-2a, 113.4 Kg, 151.2 Kg theoretical, 75%), as an off-white powder, which is identical in every comparable aspect to the compound manufactured by Example 12, Step 1 and was used in Example 12, Step 2 without further purification to form III-1a.

Example 14. Synthesis of the Example 3 Starting Material III-4a

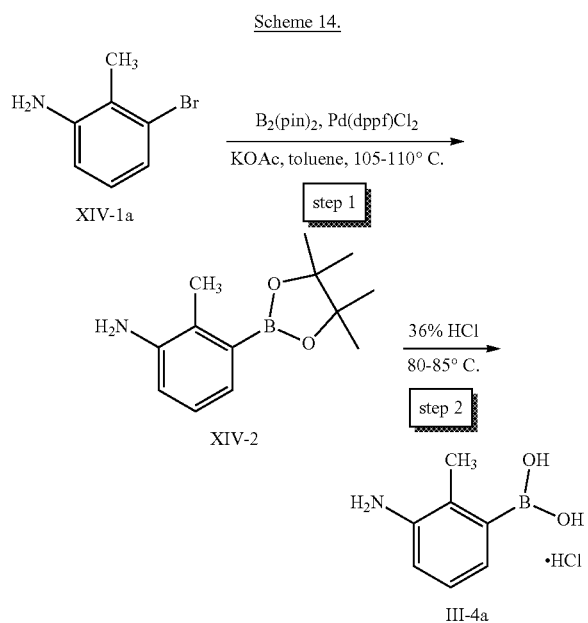

Step 1: 2-Methyl-3-(4,4,5,5-tetramethyl-1,3,2-dioxaborolan-2-yl)aniline (XIV-2)

Under the protection of nitrogen (N₂), 2-methyl-3-bromoaniline (XIV-1a, 93 Kg, 500 moles), toluene (930 Kg), potassium acetate (KOAc, 147 Kg, 1500 moles, 3.0 equiv), 4,4,4',4',5,5,5',5'-octamethyl-2,2'-bi(1,3,2-dioxaborolane) (B₂(pin)₂, 190.5 Kg, 750 moles, 1.5 equiv), and [1,1'-bis(diphenylphosphine) ferrocene]dichloropalladium (II) complex with dichloromethane (1:1) (Pd(dppf)Cl₂, 6.124 Kg, 7.5 moles, 0.015 equiv) were sequentially charged into a 2000 L glass-lined reactor. The resulting reaction mixture was heated to 105-110° C. and agitated at 105-110° C. for 2-4 hours. When HPLC analysis showed the coupling reaction was complete, the reaction mixture was gradually cooled to ambient temperature. The mixture was filtered and the wet cake was suspended in toluene (500 Kg). The resulting suspension was agitated at ambient temperature for 1 hour before being filtered. The wet cake was washed with toluene (100 Kg) before being discarded. The combined filtrates and wash solution was then washed sequentially with water (2×500 Kg) and a 25% aqueous sodium chloride (NaCl) solution (500 Kg) before being concentrated under the reduced pressure. The concentrated solution was then charged n-heptane (500 Kg) to induce the crystallization of the desired product. The resulting suspension was cooled to 0-5° C. and agitated at 0-5° C. for 2 hours. The solids were collected by filtration and the wet cake was washed with a mixture of toluene and n-heptane and dried under vacuum to afford the desired product, 2-methyl-3-(4,4,5,5-tetramethyl-1,3,2-dioxaborolan-2-yl)aniline (XIV-2, 94.3 Kg, 116.56 Kg theoretical, 80.9%), as a yellow to brown powder, which was used in the subsequent reaction without further purification.

Step 2: (3-Amino-2-methylphenyl)boronic acid Hydrochloride (III-4a)

Under the protection of nitrogen (N₂), 2-methyl-3-(4,4,5,5-tetramethyl-1,3,2-dioxaborolan-2-yl)aniline (46.6 Kg, 200 moles) and a 8 N hydrochloric acid (HCl) aqueous solution (300 Kg) were charged into a 500 L glass-lined reactor at ambient temperature. The resulting mixture was heated to 80-85° C. and agitated at 80-85° C. for 2-4 hours. When HPLC analysis showed the hydrolysis reaction was complete, the reaction mixture was gradually cooled to ambient temperature and subsequent to 0-5° C. to induce the crystallization of the crude desired product. The resulting suspension was agitated at 0-5° C. for 1-2 hours before the solids were collected by filtration and washed with cold water (50 Kg). The wet cake was then charged back into a clean reactor followed by water (300 Kg). The resulting mixture was agitated at ambient temperature to generate a clear solution. The solution was then polish-filtered through a polish filter before being concentrated under the reduced pressure. The concentrated aqueous solution was then cooled to 0-5° C. before acetonitrile (400 Kg) was charged at 0-5° C. The mixture was agitated at 0-5° C. for 2-4 hours to induce the crystallization of the desired product. The solids were collected by filtration, washed with acetonitrile (2×50 Kg), and dried under vacuum to afford the purified desired product, (3-amino-2-methylphenyl)boronic acid hydrochloride (III-4a, 32.25 Kg, 37.5 Kg theoretical, 86%; 99.9% by HPLC), as an off-white to tan crystalline powder. For III-4a: ¹H NMR (500 MHz, D₂O) δ 7.5 (s, 1H), 7.3 (m, 2H), and 2.38 (s, 3H) ppm; ¹³C NMR (125 MHz, D₂O) δ 138.0, 133.7, 132.8, 128.9, 126.9, 124.0, and 16.5 ppm; C₇H₁₁BClNO₂ (MW 187.43; C₇H₁₀BNO₂ for III-4, MW 150.97), LCMS (EI) m/z 152.1 (M⁺+H).

Example 15. Synthesis of the Synthetic Starting Material tert-Butyl (R)-Pyrrolidine-3-Carboxylate (XV-4)

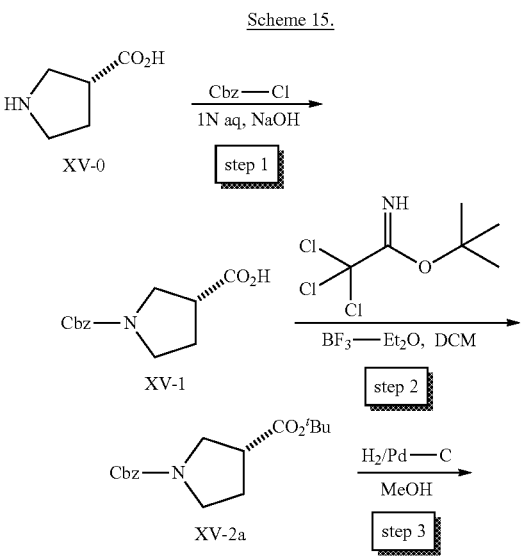

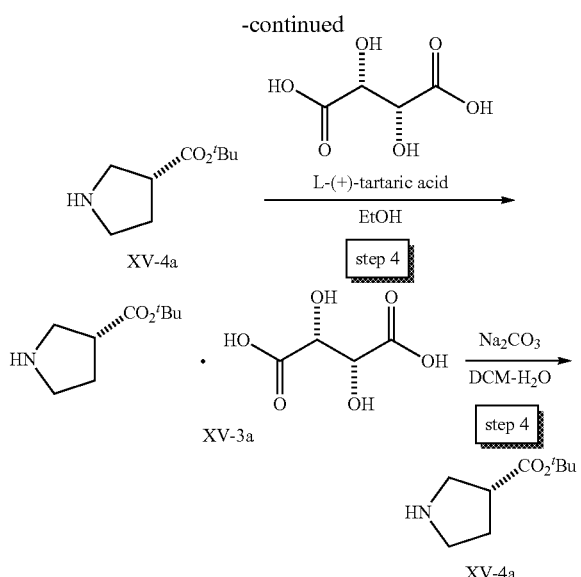

Step 1: (R)-1-((Benzyloxy)carbonyl)pyrrolidine-3-carboxylic acid (XV-1)

A solution of (R)-pyrrolidine-3-carboxylic acid (XV-0, 48.1 g, 417.8 mmol; chiral purity: 99.6% by chiral GC) in a 1.0 N aqueous sodium hydroxide solution (456 mL, 456 mmol, 1.1 equiv) was treated with Cbz-Cl (62.3 mL, 437 mmol, 1.05 equiv) at 0-5° C. The resulting reaction mixture was then gradually warmed to ambient temperature and stirred at ambient temperature for overnight. When HPLC analysis showed the reaction was complete, the reaction mixture was cooled to 0-5° C. before a 1.0 N aqueous sodium hydroxide solution (250 mL) was added to the reaction mixture with stirring to adjust the solution pH to 12.5. This mixture was allowed to warm up to room temperature before being extracted with MTBE three times (3×450 mL). The organic phase was discarded and the aqueous layer was cooled down to 0-5° C. before a 3.0 N aqueous hydrochloric acid (HCl) solution was added to adjust the pH to 2-3. The aqueous layer was extracted with DCM (3×500 mL). The combined organic extracts was washed with water (100 mL), dried over sodium sulfate ($Na_2SO_4$), filtered, and concentrated under the reduced pressure to afford the crude desired product, (R)-1-((benzyloxy)carbonyl)pyrrolidine-3-carboxylic acid (XV-1, 78.1 g, 104.2 g theoretical, 75%), which was used in the subsequent reaction without further purification.

Step 2: 1-Benzyl 3-(tert-butyl) (R)-pyrrolidine-1,3-dicarboxylate (XV-2a)

A solution of (R)-1-(benzyloxy)carbonyl)pyrrolidine-3-carboxylic acid (XV-1, 78.1 g, 313.3 mmol) in DCM (800 mL) was charged tert-butyl 2,2,2-trichloroacetimidate (112 mL, 627 mmol, 2.0 equiv) and boron trifluoride etherate ($BF_3$-$Et_2O$, 5.16 mL, 40.7 mmol, 0.13 equiv) at 0-5° C. The resulting reaction mixture was gradually warmed to room temperature and agitated at ambient temperature for 2 hours. When HPLC analysis showed the reaction was complete, the reaction mixture was diluted with DCM (800 mL) before being quenched with a saturated sodium bicarbonate aqueous solution (960 mL). The bi-phase mixture was filtered and the solid was washed with DCM (2×100 mL). Two layers of the filtrate were separated, and the aqueous layer was extracted with DCM (2×800 mL). The combined organic phases was concentrated under the reduced pressure and the residue was added MTBE (160 mL) and hexanes (640 mL). The resulting mixture was stirred at ambient temperature for 30 minutes. The solids were removed by filtration and the cake was washed with a mixture of MTBE and hexanes (1 to 4 by volume, 100 mL). The filtrate was then concentrated under the reduced pressure and the residue was purified by the silica gel ($SiO_2$) column chromatography eluting with 0-40% of EtOAc in n-hexane to afford the desired product, 1-benzyl 3-(tert-butyl) (R)-pyrrolidine-1,3-dicarboxylate (XV-2a, 83 g, 95.67 g theoretical, 86.8%), which still contaminated with some 2,2,2-trichloroacetamide and was used in the subsequent step without further purification.

Step 3: tert-Butyl (R)-pyrrolidine-3-carboxylate (2R,3R)-2,3-dihydroxysuccinic acid (XV-3a)

A solution of 1-benzyl 3-(tert-butyl) (R)-pyrrolidine-1,3-dicarboxylate (XV-2a, 43 g, 141 mmol) in methanol (MeOH, 220 mL) was added 10% of palladium on carbon (Pd/C, 4.3 g) at ambient temperature. The resulting mixture was degassed three times and each time was filled with hydrogen gas. The degassed reaction mixture was put into a par shaker for the hydrogenolysis reaction at 32 psi at ambient temperature. Once the reaction was complete as confirmed by HPLC analysis, the catalyst was removed by filtration through a Celite bed and the bed was washed with MeOH (50 mL). The filtrate was then concentrated under the reduced pressure to afford the crude desired product, tert-butyl (R)-pyrrolidine-3-carboxylate (XV-4a, 21.73 g, 24.14 g theoretical, 90%; chiral purity: 93.0% by chiral GC) as a colorless oil, which was purified in the subsequent steps.

In a 2 L round bottom flask equipped with a magnetic stirring bar and a thermal couple was placed tert-butyl (R)-pyrrolidine-3-carboxylate (XV-4a, 34.65 g, 202 mmol; chiral purity: 93% by chiral GC) in ethanol (EtOH, 700 mL) at room temperature. The resulting solution was then treated with L-(+)-tartaric acid (28.2 g, 188 mmol, 0.93 equiv) at ambient temperature. The mixture was stirred at room temperature for 4 hours. The solids were collected by filtration and dried on the filter to provide the desired product, tert-butyl (R)-pyrrolidine-3-carboxylate (2R,3R)-2,3-dihydroxysuccinate (XV-3a, 49.0 g, 65.33 g theoretical, 75%; chiral purity: 99.9% by chiral GC), as a white crystalline powder. For XV-3a: $^1$H NMR (400 MHz, DMSO-$d_6$) δ 8.47 (br.s, 5H), 4.03 (s, 2H), 3.41 (dd, J=11.5, 8.5 Hz, 1H), 3.26 (dd, J=11.5, 7.1 Hz, 1H), 3.21-3.09 (m, 3H), 2.19 (dt, J=10.8, 10.8 Hz, 1H), 2.02 (dt, J=10.8, 10.8 Hz, 1H), and 1.42 (s, 9H) ppm; $^{13}$C NMR (101 MHz, DMSO-d6) δ 175.34, 171.84, 81.38, 72.65, 46.43, 44.82, 43.02, 28.34, and 28.08 ppm; $C_9H_{17}NO_2$ for (R)-tert-butyl pyrrolidine-3-carboxylate (XV-4a, MW 171.24), LCMS (EI) m/z 172.2 ($M^+$+H).

Step 4: tert-Butyl (R)-pyrrolidine-3-carboxylate (XV-4a)

In a 2 L round bottom flask equipped with a magnetic stirring bar and a thermal couple was placed tert-butyl (R)-pyrrolidine-3-carboxylate (2R,3R)-2,3-dihydroxysuccinate (XV-3a, 47.8 g, 149 mmol; 99.9% pure by chiral GC) in DCM (700 mL) at room temperature. The resulting suspension was charged a solution of sodium carbonate (Na₂CO₃, 23.65 g, 223 mmol, 1.5 equiv) in water (700 mL) at ambient temperature. The resultant slurry was stirred at room temperature for 3 hours to obtain a clear two phases mixture. After phase split, the aqueous phase was extracted with DCM (2×500 mL). The combined organic phases was washed with 5% brine, dried with anhydrous MgSO₄, filtered, and concentrated under the reduced pressure to afford the desired product, tert-butyl (R)-pyrrolidine-3-carboxylate (XV-4a, 22.95 g, 25.5 g theoretical, 90%; chiral purity: 99.9% by chiral GC), as a colorless oil. For XV-4a: ¹H NMR (400 MHz, CDCl₃) δ 3.02 (m, 3H), 2.79 (m, 2H), 1.95 (m, 3H), and 1.41 (s, 9H) ppm; C₉H₁₇NO₂ (MW 171.2), LCMS (EI) m/z 172.1 (M⁺+H).

Example 16. An Alternate Synthesis of the Synthetic Starting Material tert-Butyl (R)-Pyrrolidine-3-Carboxylate (XV-4a)

Scheme 16.

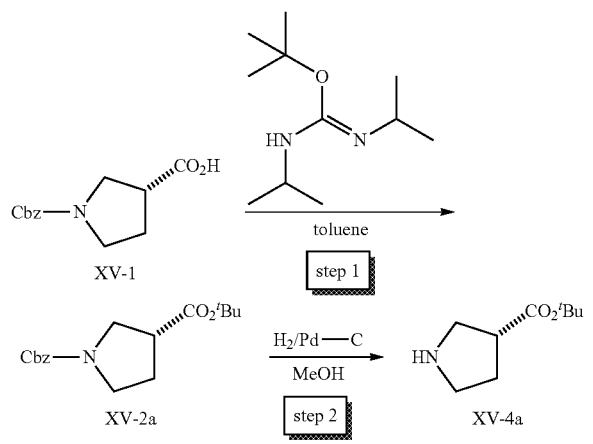

Step 1: 1-Benzyl 3-(tert-butyl) (R)-pyrrolidine-1,3-dicarboxylate (XV-2a)

A solution of tert-butyl N,N'-diisopropylcarbamimidate (36.4 g, 75% pure, 136 mmol, 1.7 equiv) in toluene (44.6 mL) was added dropwise (20 drops in 90 seconds) using an addition funnel to the suspension of (R)-1-((benzyloxy)carbonyl)pyrrolidine-3-carboxylic acid (XV-1, 20.0 g, 80 mmol; chiral purity: 99.6% by chiral GC) in toluene (89 mL) at 50° C. The addition took 90 minutes. The resulting reaction mixture was stirred at 50° C. for an additional 90 minutes (total 3 hours). When the reaction was complete as confirmed by HPLC analysis, H₂O (1.445 mL, 80 mmol, 1.0 equiv) was added to the reaction mixture at 50° C. The mixture was stirred at 50° C. for 30 minutes before being gradually cooled to room temperature. The cooled mixture was then diluted with hexanes (134 mL), and the resulting diluted mixture was filtered through a silica gel (SiO₂, 8.0 g) pad to remove most of the urea by-product. The pad was rinsed with hexanes (50 mL). The filtrate was concentrated under the reduced pressure to afford the crude desired product, 1-benzyl 3-(tert-butyl) (R)-pyrrolidine-1,3-dicarboxylate (XV-2, 24.2 g, 24.42 g theoretical, 99.0%), which was used for the next step without further purification.

Step 2: tert-Butyl (R)-pyrrolidine-3-carboxylate

A solution of 1-benzyl 3-(tert-butyl) (R)-pyrrolidine-1,3-dicarboxylate (XV-2a: 24.0 g, 79 mmol) in MeOH (121 mL) was treated with 10% of palladium on carbon (Pd/C, 2.425 g, 10 wt %) at ambient temperature. The resulting mixture was degassed three times and each time was filled with hydrogen gas. The degassed reaction mixture was put into a par shaker for the hydrogenolysis reaction at 35 psi at ambient temperature. Once the reaction was complete as confirmed by HPLC analysis, the catalyst was removed by filtration through a Celite bed and the bed was washed with MeOH (60 mL). The filtrate was then concentrated under the reduced pressure to afford the desired product, tert-butyl (R)-pyrrolidine-3-carboxylate (XV-4a, 13.25 g, 13.52 g theoretical, 98%; chiral purity: 99.6% pure by chiral GC), as a colorless oil, which is identical to the compound prepared by Example 15, Step 4 and was used in the subsequent synthesis without further purification.

Example 17. An Alternate Synthesis of the Starting Material tert-Butyl (R)-Pyrrolidine-3-Carboxylate (XV-4a)

Scheme 17.

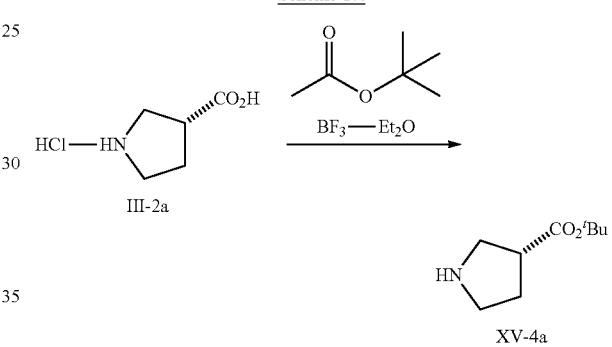

tert-Butyl (R)-pyrrolidine-3-carboxylate (XV-4a)

In a 500 mL 3-neck round bottle flask equipped with a thermocouple, (R)-pyrrolidine-3-carboxylic acid hydrochloride (III-2a, 20.36 g, 128 mmol; chiral purity: 99.6% by chiral GC) was slurried in tert-butyl acetate (180 ml, 1333 mmol, 10.4 equiv) under a nitrogen atmosphere. The mixture was cooled to 0° C. before boron trifluoride etherate (BF₃-Et₂O, 97 ml, 766 mmol, 6.0 equiv) was added dropwise over 10 minutes. The mixture was stirred at 0-5° C., solids were gradually dissolved, and a clear solution was obtained after 45 minutes. When LC-MS showed the esterification reaction was complete, the reaction mixture was transferred into water (180 mL) with a cannula at 0° C. over 25 minutes. During quenching, the internal temperature was maintained at below 5° C. The biphasic mixture was separated, the organic layer was discarded, the aqueous layer was charged back to the flask, and DCM (400 mL) was added to the aqueous solution in the flask. An 8.0 N aqueous sodium hydroxide (NaOH, 207 mL, 1659 mmol) solution was then added dropwise to the mixture over approximately 45 minutes to neutralize the solution to pH to 9-10. During addition of the aqueous NaOH solution, the internal temperature was maintained at below 25° C. Two layers were separated and the aqueous layer was extracted with DCM (400 mL). The combined organic extracts were dried over MgSO₄ before being concentrated under the reduced pressure to afford the crude desired product, tert-butyl (R)-pyrrolidine-3-carboxylate (XV-4a, 16.4 g, 21.85 g theoretical, 75%; 97.6 wt % by $^1$H NMR analysis; chiral purity: 99.3% by chiral GC) as a yellow to brown oil, which is identical to the compound manufactured by example 14, Step 4 and Example 16, Step 2 and was used in the subsequent reaction without further purification.

Example A. PD-1/PD-L1 Homogeneous Time-Resolved Fluorescence (HTRF) Binding Assay The assays were conducted in a standard black 384-well polystyrene plate with a final volume of 20 μL. Inhibitors were first serially diluted in DMSO and then added to the plate wells before the addition of other reaction components. The final concentration of DMSO in the assay was 1%. The assays were carried out at 25° C. in the PBS buffer (pH 7.4) with 0.05% Tween-20 and 0.1% BSA. Recombinant human PD-L1 protein (19-238) with a His-tag at the C-terminus was purchased from AcroBiosystems (PD1-H5229). Recombinant human PD-1 protein (25-167) with Fc tag at the C-terminus was also purchased from AcroBiosystems (PD1-H5257). PD-L1 and PD-1 proteins were diluted in the assay buffer and 10 μL was added to the plate well. Plates were centrifuged and proteins were preincubated with inhibitors for 40 minutes. The incubation was followed by the addition of 10 μL of HTRF detection buffer supplemented with Europium cryptate-labeled anti-human IgG (PerkinElmer-AD0212) specific for Fc and anti-His antibody conjugated to SureLight®-Allophycocyanin (APC, PerkinElmer-AD0059H). After centrifugation, the plate was incubated at 25° C. for 60 min. before reading on a PHER-Astar FS plate reader (665 nm/620 nm ratio). Final concentrations in the assay were ~3 nM PD1, 10 nM PD-L1, 1 nM europium anti-human IgG and 20 nM anti-His-Allophycocyanin. IC$_{50}$ determination was performed by fitting the curve of percent control activity versus the log of the inhibitor concentration using the GraphPad Prism 5.0 software.

Compound 1 of the present disclosure, showed IC$_{50}$ (nM) value in the range of ≤10 nM using the PD-1/PD-L1 homogenous time-resolved fluorescence (HTFR) binding assay.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A process of preparing (R)-1-((7-cyano-2-(3'-((3-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid, or a salt thereof, comprising:

reacting a compound of formula III-5:

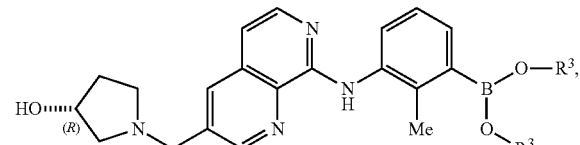

or a salt thereof, with a compound of formula IV-1:

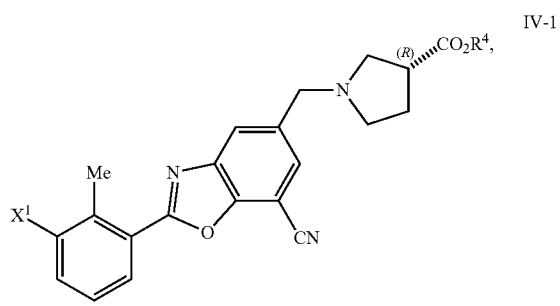

or a salt thereof, in the presence of a Suzuki catalyst and a base to form a compound of formula IV-2:

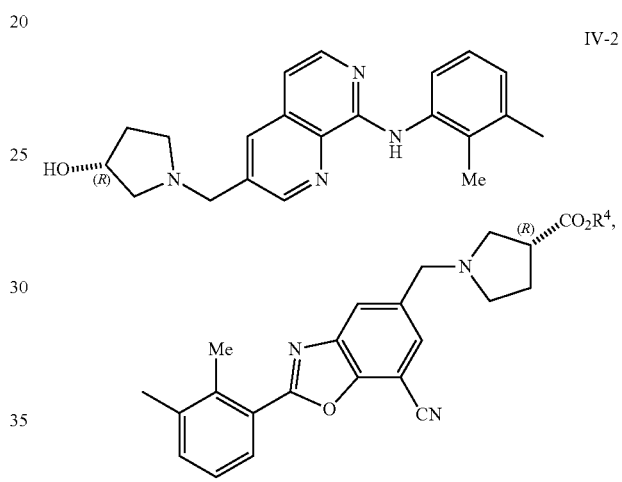

or a salt thereof, wherein:
each R$^3$ is independently selected from H and C$_{1-6}$ alkyl; or
each R$^3$ together form an C$_{2-3}$ alkylene linker, which is optionally substituted by 1, 2, 3, or 4 independently selected C$_{1-4}$ alkyl groups; and
R$^4$ is C$_{1-6}$ alkyl; and
X$^1$ is halo.

2. The process of claim 1, further comprising deprotecting the compound of formula IV-2, or the salt thereof, to form (R)-1-((7-cyano-2-(3'-((3-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid, or the salt thereof.

3. The process of claim 1, wherein the process comprises:
reacting a salt of formula III-5c:

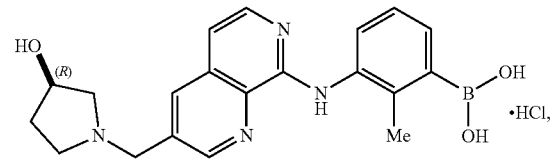

with a compound of formula IV-1b:

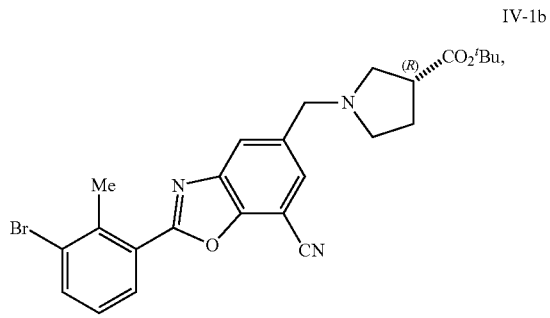

or a salt thereof, in the presence of a Suzuki catalyst and a base to form a compound of formula IV-2a:

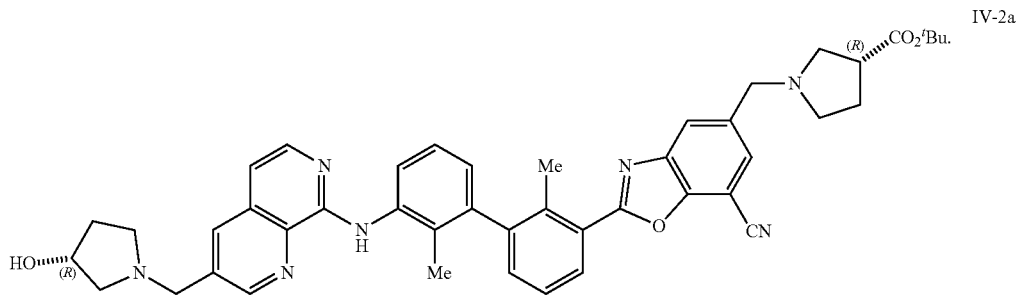

4. The process of claim 1, wherein the compound of formula IV-1, or the salt thereof, is prepared by a process comprising:
reacting a compound of formula X-7:

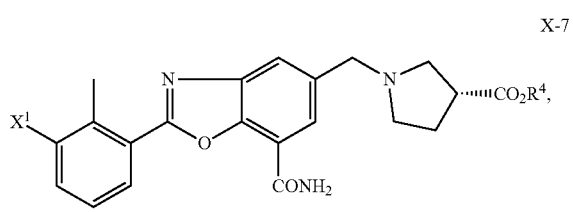

or a salt thereof, with a dehydrating agent to form the compound of formula IV-1, or the salt thereof, wherein $X^1$ is halo; and $R^4$ is $C_{1-6}$ alkyl.

5. The process of claim 4, wherein the compound of formula X-7, or the salt thereof, is prepared by a process comprising:
reacting a compound of formula X-6:

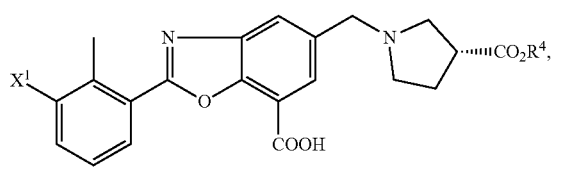

or a salt thereof, with an $C_{1-6}$ alkyl chloroformate; and reacting the product of said reacting of the compound of formula X-6, or the salt thereof, with ammonium hydroxide to form the compound of formula X-7, or the salt thereof, wherein $X^1$ is halo; and $R^4$ is $C_{1-6}$ alkyl.

6. The process of claim 5, wherein the compound of formula X-6, or the salt thereof, is prepared by a process comprising:
reacting a compound of formula X-4:

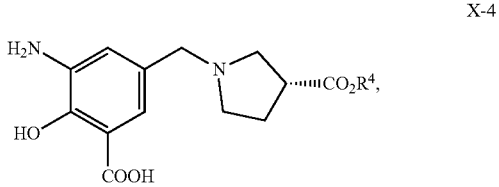

or a salt thereof, with a compound of formula X-5:

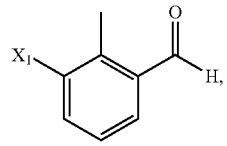

to form a compound of formula X-44:

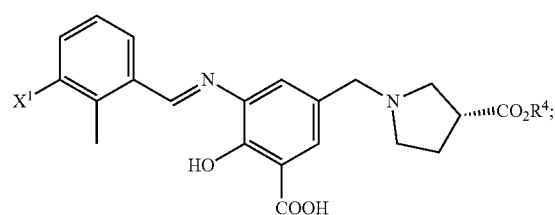

and
reacting the compound of formula X-44 with a dehydrogenating agent to form the compound of formula X-6, or the salt thereof, wherein $X^1$ is halo; and $R^4$ is $C_{1-6}$ alkyl.

7. The process of claim 6, wherein the compound of formula X-4, or the salt thereof, is prepared by a process comprising:

reducing a compound of formula X-3:

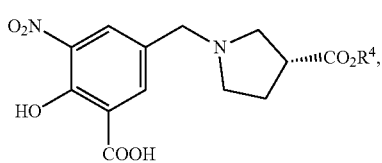

X-3 or a salt thereof, to form the compound of formula X-4, or the salt thereof, wherein $R^4$ is $C_{1-6}$ alkyl.

8. The process of claim 7, wherein the compound of formula X-3, or the salt thereof, is prepared by a process comprising:

reacting a compound of formula X-2:

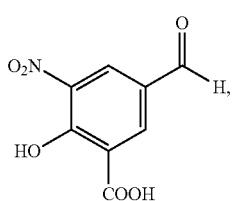

X-2 or a salt thereof, with a compound of formula XV-4:

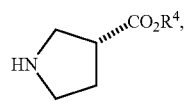

XV-4 or a salt thereof, in the presence of a reducing agent to form the compound of formula X-3, or the salt thereof, wherein $R^4$ is $C_{1-6}$ alkyl.

9. The process of claim 8, wherein the compound of formula X-2, or the salt thereof, is prepared by a process comprising:

reducing a compound of formula X-1:

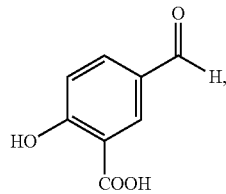

X-1 or a salt thereof, with nitric acid to form the compound of formula X-2, or the salt thereof.

* * * * *